(12) United States Patent
Luo et al.

(10) Patent No.: US 10,532,986 B2
(45) Date of Patent: Jan. 14, 2020

(54) CYCLIC COMPOUND ACTING AS PDE4 INHIBITOR

(71) Applicant: MEDSHINE DISCOVERY INC., Nanjing, Jiangsu (CN)

(72) Inventors: Yunfu Luo, Shanghai (CN); Chundao Yang, Shanghai (CN); Maoyi Lei, Shanghai (CN); Lanbao Sun, Shanghai (CN); Guoping Hu, Shanghai (CN); Jian Li, Shanghai (CN); Shuhui Chen, Shanghai (CN)

(73) Assignee: Medshine Discovery Inc., Nanjing (CN)

( * ) Notice: Subject to any disclaimer, the term of this patent is extended or adjusted under 35 U.S.C. 154(b) by 0 days.

(21) Appl. No.: 16/325,626

(22) PCT Filed: Aug. 22, 2017

(86) PCT No.: PCT/CN2017/098462
§ 371 (c)(1),
(2) Date: Mar. 21, 2019

(87) PCT Pub. No.: WO2018/036470
PCT Pub. Date: Mar. 1, 2018

(65) Prior Publication Data
US 2019/0210975 A1 Jul. 11, 2019

(30) Foreign Application Priority Data
Aug. 22, 2016 (CN) .......................... 2016 1 0706073

(51) Int. Cl.
| | | |
|---|---|---|
| *C07D 235/26* | (2006.01) | |
| *C07D 263/58* | (2006.01) | |
| *C07D 401/04* | (2006.01) | |
| *C07D 403/04* | (2006.01) | |
| *C07D 403/06* | (2006.01) | |
| *C07D 405/04* | (2006.01) | |
| *C07D 409/04* | (2006.01) | |
| *C07D 417/04* | (2006.01) | |
| *A61P 29/00* | (2006.01) | |
| *A61K 31/423* | (2006.01) | |
| *A61P 37/00* | (2006.01) | |
| *A61K 31/4184* | (2006.01) | |
| *C07D 401/10* | (2006.01) | |
| *C07D 403/10* | (2006.01) | |
| *C07D 405/10* | (2006.01) | |
| *C07D 409/10* | (2006.01) | |
| *C07D 417/10* | (2006.01) | |

(52) U.S. Cl.
CPC ........ *C07D 235/26* (2013.01); *A61K 31/4184* (2013.01); *A61K 31/423* (2013.01); *A61P 29/00* (2018.01); *A61P 37/00* (2018.01); *C07D 263/58* (2013.01); *C07D 401/04* (2013.01); *C07D 401/10* (2013.01); *C07D 403/04* (2013.01); *C07D 403/06* (2013.01); *C07D 403/10* (2013.01); *C07D 405/04* (2013.01); *C07D 405/10* (2013.01); *C07D 409/04* (2013.01); *C07D 409/10* (2013.01); *C07D 417/04* (2013.01); *C07D 417/10* (2013.01)

(58) Field of Classification Search
CPC .. C07D 235/26; C07D 263/58; C07D 401/04; C07D 403/04; C07D 403/06; C07D 405/04; C07D 409/04; C07D 417/04
See application file for complete search history.

(56) References Cited

U.S. PATENT DOCUMENTS

2004/0192748 A1\* 9/2004 Barbosa, Jr. .......... C07D 231/12
514/394
2016/0159801 A1\* 6/2016 Quinn ................ A61K 31/4985
514/210.21

FOREIGN PATENT DOCUMENTS

WO WO-02/072576 A1 \* 9/2002 ........... C07D 403/14

\* cited by examiner

*Primary Examiner* — Laura L Stockton
(74) *Attorney, Agent, or Firm* — Harness, Dickey & Pierce, P.L.C.

(57) ABSTRACT

Provided are a phosphodiesterase-4 (PDE4) inhibitor and application thereof in preparation of a medication for treating a disease related to PDE4. Specifically disclosed is a compound as shown in formula (I) and a pharmaceutically acceptable salt thereof.

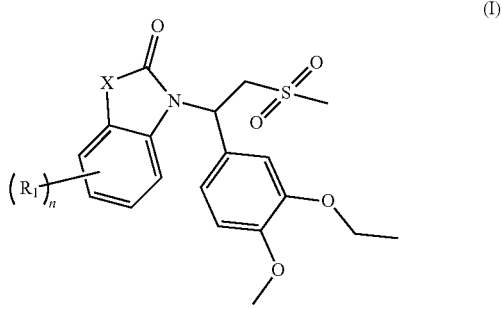

(I)

24 Claims, No Drawings

CYCLIC COMPOUND ACTING AS PDE4 INHIBITOR

CROSS REFERENCE TO RELATED APPLICATIONS

This application is a 371 National Phase of PCT/CN2017/098462 filed Aug. 22, 2017, which claims the benefit of Chinese Patent Application No. CN201610706073.1, filed on Aug. 22, 2016. The entire disclosures of the above applications are incorporated herein by reference.

FIELD OF INVENTION

The present invention relates to a class of phosphodiesterase-4 (PDE4) inhibitor and a use thereof in manufacturing a medicament for treating a disease related to PDE4. Specifically related is a compound as shown in formula (I) and a pharmaceutically acceptable salt thereof.

PRIOR ARTS

Tumor necrosis factor alpha (TNF-α) is a cytokine released primarily by mononuclear phagocytes in response to immunostimulators. TNF-α is capable of enhancing most cellular processes, such as differentiation, recruitment, proliferation, and proteolytic degradation. At low levels, TNF-α confers protection against infective agents, tumors, and tissue damage. However, excessive release of TNF-α also cause diseases, when administered to mammals or humans, TNF-α causes or aggravates inflammation, fever, cardiovascular effects, hemorrhage, coagulation, and acute responses similar to those seen during acute infections and shock states. Enhanced or uncontrolled TNF-α production in animals or humans often indicates a number of diseases, for example, endotoxemia and/or toxic shock syndrome, cachexia, adult respiratory distress syndrome, cancers such as solid tumors and hematological tumors, heart disease such as congestive heart failure; viral infection, and genetic, inflammatory, allergic, or autoimmune diseases.

Cancer is a particularly devastating disease, and the increased TNF-α levels in blood indicates cancer or a risk of cancer spreading. Normally, in healthy subjects, cancer cells fail to survive in the circulatory system, one of the reasons being that the inner wall of blood vessels acts as a barrier to tumor-cell extravasation. ELAM-1 on endothelial cells was shown to mediate the increased adhesion of colon cancer cells to endothelium treated with cytokines.

Cyclic adenosine monophosphate (cAMP) also plays a role in many diseases and conditions. It has been shown that the elevation of cAMP in inflammatory leukocytes inhibits their activation and then release inflammatory mediators, including TNF-α and nuclear factor κB (NF-κB). Increased levels of cAMP also lead to the relaxation of airway smooth muscle.

It is believed that primary cellular mechanism for the inactivation of cAMP is the breakdown of cAMP by a family of isoenzymes referred to as cyclic nucleotide phosphodiesterases (PDE). There are eleven known members of the family of PDEs. So far it has been recognized that the inhibition of PDE type IV (PDE4) is particularly effective both in inhibition of inflammatory mediators release and relaxation of airway smooth muscle. Therefore, PDE4 has become one of the most popular drug targets. The family of PDE-4 can be divided into four subtypes (PDE-4A, B, C, D) based on different genetic codes, wherein PDE-4A, PDE-4B and PDE-4D are more widely expressed in inflammatory cells (such as B cells, T cells and neutrophils) than PDE-4C. The inhibition of PDE4 leads to an increase in cAMP levels, thereby regulating TNF-α levels for therapeutic purposes.

CONTENT OF THE PRESENT INVENTION

The present invention provides a compound as shown in formula (I) and a pharmaceutically acceptable salt thereof,

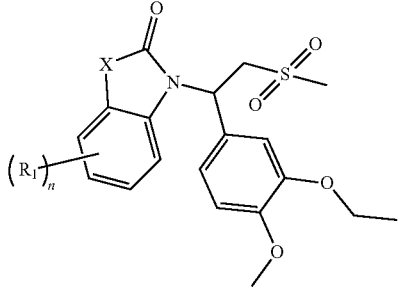

wherein,

X is O, or N($R_2$);

$R_2$ is H, F, Cl, Br, I, OH, $NH_2$, $R_3$-$L_1$-, or selected from the group consisting of $C_{1-6}$ alkyl, $C_{1-6}$ heteroalkyl, $C_{3-6}$ cycloalkyl, 3-6 membered heterocycloalkyl, phenyl and 5-6 membered heteroaryl, each of which is optionally substituted by 1, 2 or 3 R;

$R_3$ is selected from the group consisting of $C_{3-6}$ cycloalkyl, 3-6 membered heterocycloalkyl, phenyl and 5-6 membered heteroaryl, each of which is optionally substituted by 1, 2 or 3 R;

$L_1$ is —$CH_2$—, —$CH_2CH_2$—, O, S, NH, or —C(=O)—;

n is 1, 2 or 3;

$R_1$ is H, F, Cl, Br, I, OH, $NH_2$, or COOH, $R_4$-$L_2$-, or selected from the group consisting of $C_{1-6}$ alkyl, $C_{1-6}$ heteroalkyl, $C_{2-6}$ alkenyl, $C_{3-6}$ cycloalkenyl, 3-6 membered heterocycloalkenyl, $C_{3-6}$ cycloalkyl, 3-6 membered heterocycloalkyl, phenyl and 5-6 membered heteroaryl, each of which is optionally substituted by 1, 2 or 3 R;

$R_4$ is selected from the group consisting of $C_{3-6}$ cycloalkyl, 3-6 membered heterocycloalkyl, 3-6 membered heterocycloalkenyl, phenyl and 5-6 membered heteroaryl, each of which is optionally substituted by 1, 2 or 3 R;

$L_2$ is —$CH_2$—, —$CH_2CH_2$—, O, S, NH, —C(=O)NH—, —C(=O)O—, or —C(=O)—;

R is H, halogen, OH, $NH_2$, CN, or selected from the group consisting of $C_{1-6}$ alkyl, $C_{1-6}$ heteroalkyl, $C_{3-6}$ cycloalkyl, 3-6 membered heterocycloalkyl, each of which is optionally substituted by 1, 2 or 3 R';

R' is H, F, Cl, Br, I, OH, CN, $NH_2$, Me, Et, $CF_3$, $CHF_2$, $CH_2F$, $NHCH_3$, or $N(CH_3)_2$;

The "hetero" in the $C_{1-6}$ heteroalkyl, 3-6 membered heterocycloalkyl, 5-6 membered heteroaryl and 3-6 membered heterocycloalkenyl is selected from the group consisting of —C(=O)NH—, —NH—, —C(=NH)—, —S(=O)$_2$NH—, —S(=O)NH—, —O—, —S—, =O, =S, —C(=O)O—, —C(=O)—, —C(=S)—, —S(=O)—, —S(=O)$_2$— and —NHC(=O)NH—;

in any of the above cases, the number of the heteroatom or the heteroatom group is independently 1, 2 or 3.

In some embodiments of the present invention, R is H, F, Cl, Br, I, OH, CN or $NH_2$, or selected from the group consisting of $C_{1-3}$ alkyl, $C_{1-3}$ alkoxy, $C_{1-3}$ alkylthio, $C_{1-3}$ alkylamino, $C_{1-4}$-alkyl-OC(=O)—, alkyl)amino, $C_{3-6}$ cycloalkyl, each of which is optionally substituted by 1, 2 or 3 R;

In some embodiments of the present invention, R is H, F, Cl, Br, I, OH, CN, $NH_2$, Me, $CF_3$, $CHF_2$, $CH_2F$, Et,

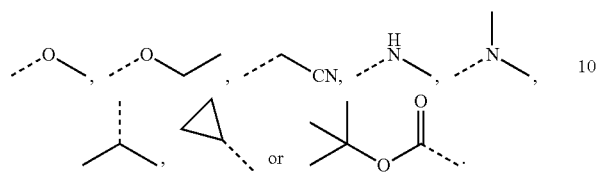

In some embodiments of the present invention, $R_3$ is selected from the group consisting of cyclopropyl, cyclobutyl, phenyl, pyridyl, pyrimidinyl, pyrazinyl, thienyl, imidazolyl, pyrazolyl, oxazolyl, thiazolyl, isoxazolyl, isothiazolyl, each of which is optionally substituted by 1, 2 or 3 R;

In some embodiments of the present invention, $R_3$ is

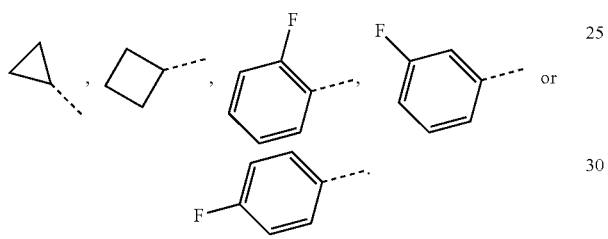

In some embodiments of the present invention, $R_3$-$L_1$- is

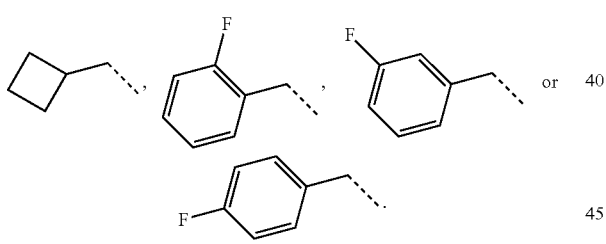

In some embodiments of the present invention, $R_2$ is H, F, Cl, Br, I, OH, $NH_2$ or $R_3$-$L_1$-, or selected from the group consisting of $C_{1-3}$ alkyl, $C_{1-3}$-alkyl-S(=O)$_2$—$C_{1-3}$ alkyl-, cyclopropyl, cyclobutyl, phenyl and 5-6 membered heteroaryl, each of which is optionally substituted by 1, 2 or 3 R.

In some embodiments of the present invention, $R_2$ is H, F, Cl, Br, I, OH, $NH_2$ or $R_3$-$L_1$-, or selected from the group consisting of Me, Et, each of which is optionally substituted by 1, 2 or 3 R.

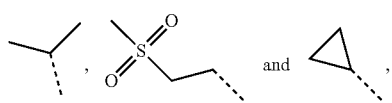

In some embodiments of the present invention, $R_2$ is H, F, Cl, Br, I, OH, CN, $NH_2$, COOH, Me, Et,

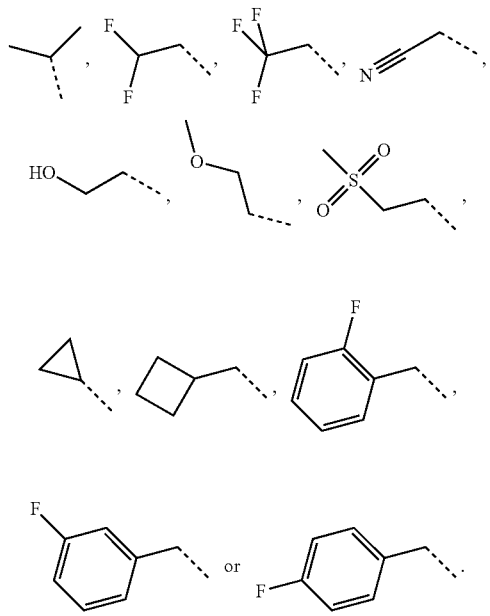

In some embodiments of the present invention, X is

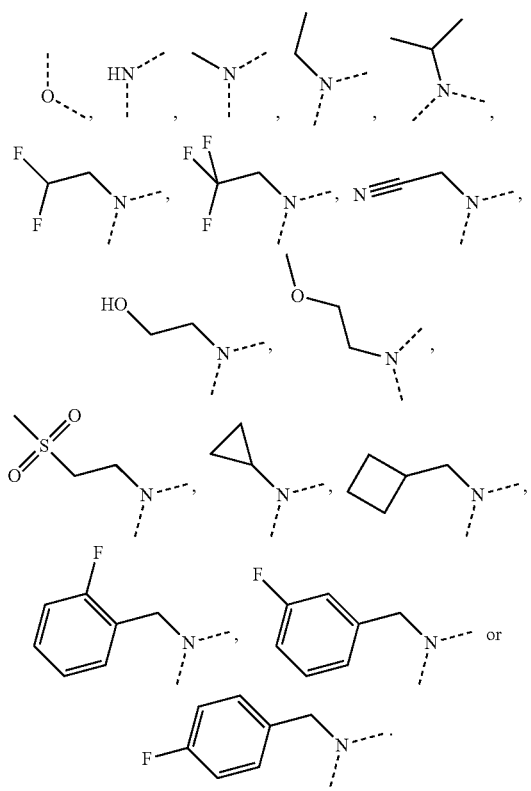

In some embodiments of the present invention, $R_4$ is selected from the group consisting of phenyl, pyrrolidinyl, pyridyl, pyrimidinyl, pyrazinyl, and pyridazinyl, each of which is optionally substituted by 1, 2 or 3 R.

In some embodiments of the present invention, $R_4$ is selected from the group consisting of

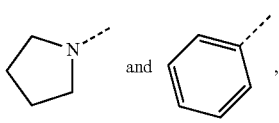

each of which is optionally substituted by 1, 2 or 3 R.

In some embodiments of the present invention, $R_4$ is

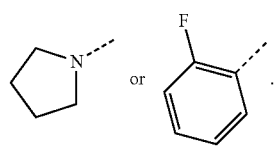

In some embodiments of the present invention, $R_4$-$L_2$- is

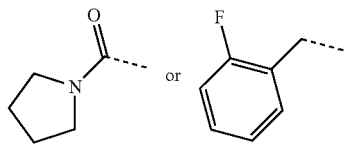

In some embodiments of the present invention, $R_1$ is H, F, Cl, Br, I, OH, $NH_2$, COOH or $R_4$-$L_2$-, or selected from the group consisting of $C_{1-3}$ alkyl, $C_{1-3}$ alkyl-C(=O)—, $C_{1-3}$ alkyl-OC(=O)—, $C_{2-4}$ alkenyl, $C_{4-6}$ cycloalkenyl, 3,6-dihydro-2H-pyranyl, $C_{3-6}$ cycloalkyl, tetrahydropyranyl, phenyl, pyridyl, pyrimidinyl, pyrazinyl, pyridazinyl, pyrazolyl, imidazolyl, thienyl, thiazolyl, isothiazolyl, oxazolyl and isoxazolyl, each of which is optionally substituted by 1, 2 or 3 R.

In some embodiments of the present invention, $R_1$ is H, F, Cl, Br, I, OH, $NH_2$, COOH or $R_4$-$L_2$-, or selected from the group consisting of Me, Et,

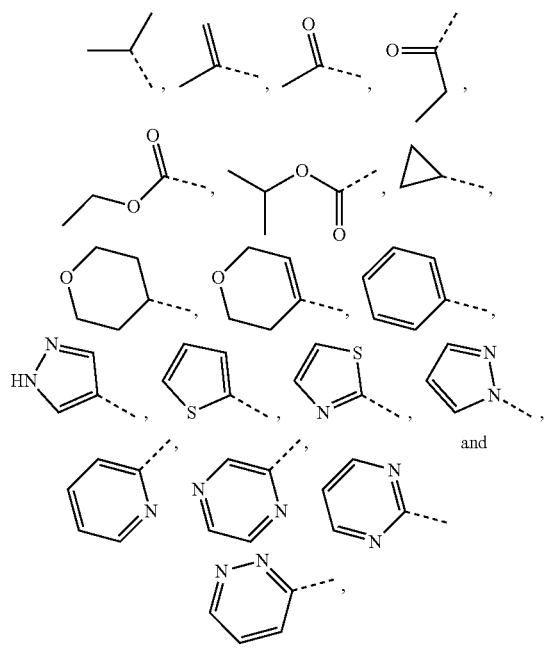

each of which is optionally substituted by 1, 2 or 3 R.

In some embodiments of the present invention, $R_1$ is H, F, Cl, Br, I, OH, $NH_2$, COOH,

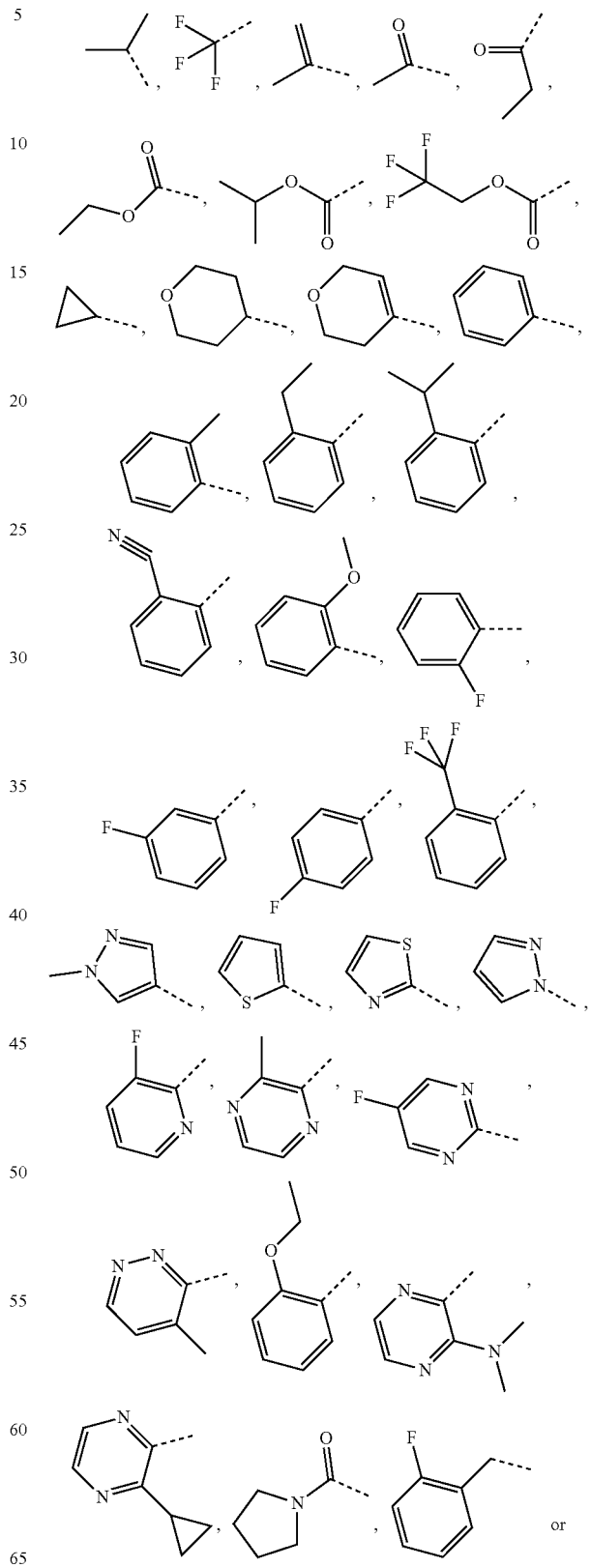

-continued

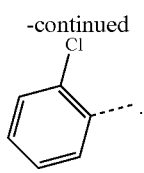

In some embodiments of the present invention, R is H, F, Cl, Br, I, OH, CN or NH$_2$, or selected from the group consisting of C$_{1-3}$ alkyl, C$_{1-3}$ alkoxy, C$_{1-3}$ alkylthio, C$_{1-3}$ alkylamino, C$_{1-4}$ alkyl-OC(=O)—, alkyl)amino, C$_{3-6}$ cycloalkyl, each of which is optionally substituted by 1, 2 or 3 R, and other variables are as defined above.

In some embodiments of the present invention, R is H, F, Cl, Br, I, OH, CN, NH$_2$, Me, CF$_3$, CHF$_2$, CH$_2$F, Et,

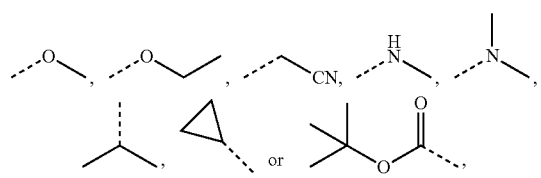

and other variables are as defined above.

In some embodiments of the present invention, R$_3$ is selected from the group consisting of cyclopropyl, cyclobutyl, phenyl, pyridyl, pyrimidinyl, pyrazinyl, thienyl, imidazolyl, pyrazolyl, oxazolyl, thiazolyl, isoxazolyl and isothiazolyl, each of which is optionally substituted by 1, 2 or 3 R, and other variables are as defined above.

In some embodiments of the present invention, R$_3$ is

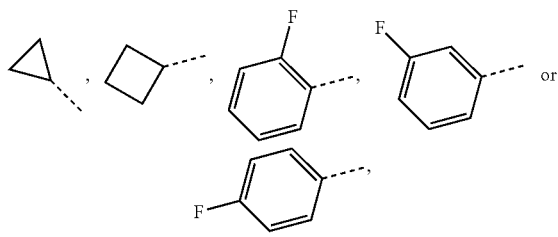

and other variables are as defined above.

In some embodiments of the present invention, R$_3$-L$_1$- is

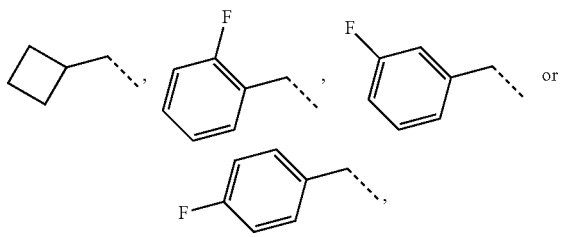

and other variables are as defined above.

In some embodiments of the present invention, R$_2$ is H, F, Cl, Br, I, OH, NH$_2$ or R$_3$-L$_1$-, or selected from the group consisting of C$_{1-3}$ alkyl, C$_{1-3}$-alkyl-S(=O)$_2$— C$_{1-3}$ alkyl-, cyclopropyl, cyclobutyl, phenyl and 5-6 membered heteroaryl, each of which is optionally substituted by 1, 2 or 3 R, and other variables are as defined above.

In some embodiments of the present invention, R$_2$ is H, F, Cl, Br, I, OH, NH$_2$ or R$_3$-L$_1$-, or selected from the group consisting of Me, Et,

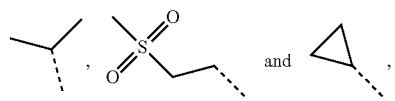

each of which is optionally substituted by 1, 2 or 3 R, and other variables are as defined above.

In some embodiments of the present invention, R$_2$ is H, F, Cl, Br, I, OH, NH$_2$, COOH, Me, Et,

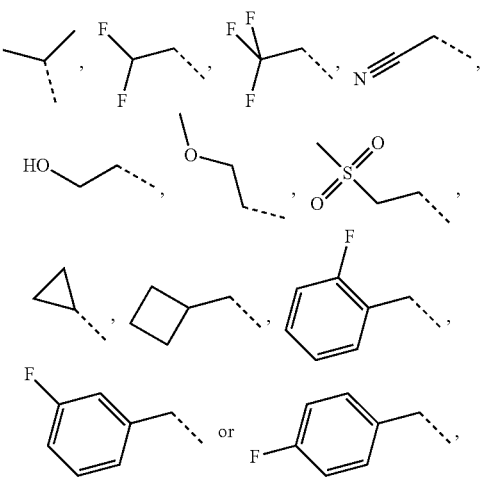

and other variables are as defined above.

In some embodiments of the present invention, X is

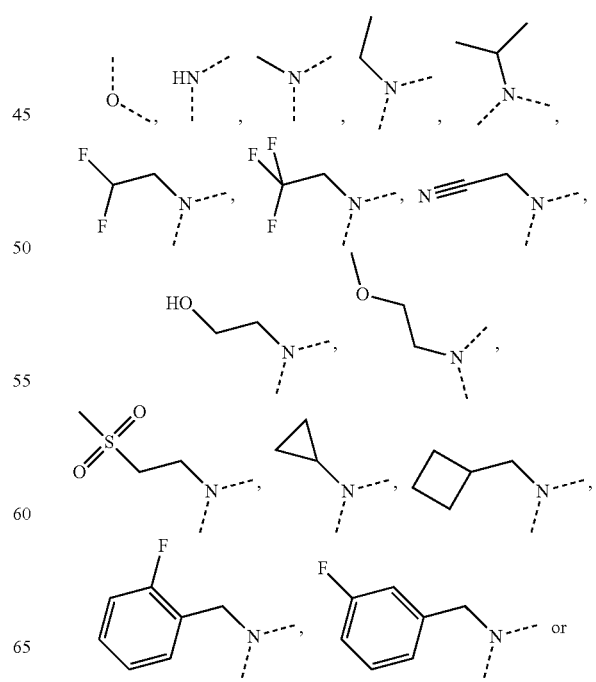

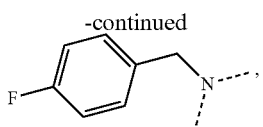

and other variables are as defined above.

In some embodiments of the present invention, $R_4$ is selected from the group consisting of phenyl, pyrrolidinyl, pyridyl, pyrimidinyl, pyrazinyl, and pyridazinyl, each of which is optionally substituted by 1, 2 or 3 R, and other variables are as defined above.

In some embodiments of the present invention, $R_4$ is selected from the group consisting of

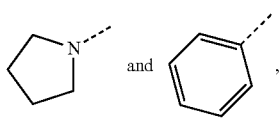

each of which is optionally substituted by 1, 2 or 3 R, and other variables are as defined above.

In some embodiments of the present invention, $R_4$ is

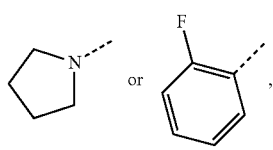

and other variables are as defined above.

In some embodiments of the present invention, $R_4$-$L_2$- is

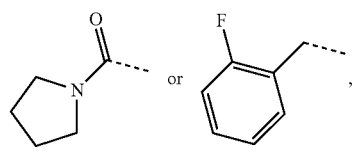

and other variables are as defined above.

In some embodiments of the present invention, $R_1$ is H, F, Cl, Br, I, OH, $NH_2$, COOH or $R_4$-$L_2$-, or selected from the group consisting of $C_{1-3}$ alkyl, $C_{1-3}$ alkyl-C(=O)—, $C_{1-3}$ alkyl-OC(=O)—, $C_{2-4}$ alkenyl, $C_{4-6}$ cycloalkenyl, 3,6-dihydro-2H-pyranyl, $C_{3-6}$ cycloalkyl, tetrahydropyranyl, phenyl, pyridyl, pyrimidinyl, pyrazinyl, pyridazinyl, pyrazolyl, imidazolyl, thienyl, thiazolyl, isothiazolyl, oxazolyl and isoxazolyl, each of which is optionally substituted by 1, 2 or 3 R, and other variables are as defined above.

In some embodiments of the present invention, $R_1$ is H, F, Cl, Br, I, OH, $NH_2$, COOH or $R_4$-$L_2$-, or selected from the group consisting of Me, Et,

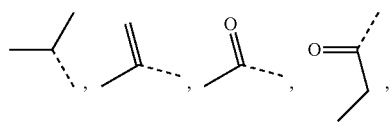

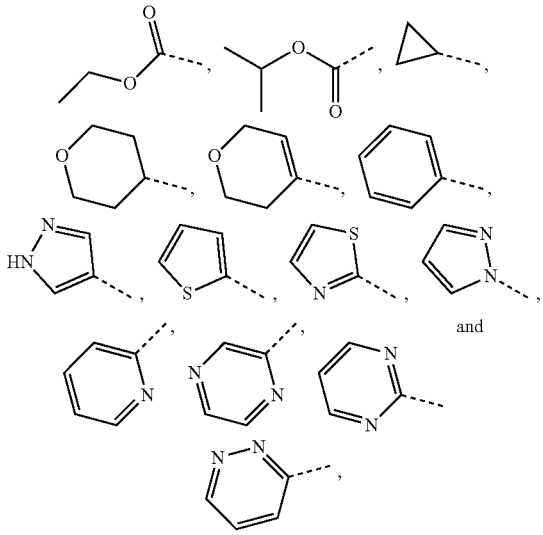

each of which is optionally substituted by 1, 2 or 3 R, and other variables are as defined above.

In some embodiments of the present invention, R, is H, F, Cl, Br, I, OH, $NH_2$, COOH,

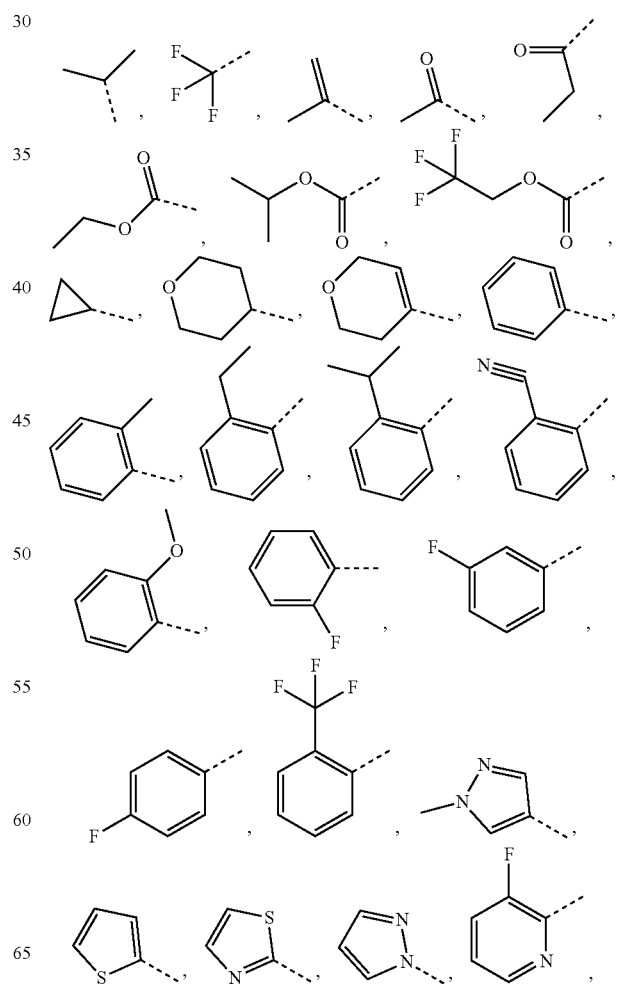

-continued
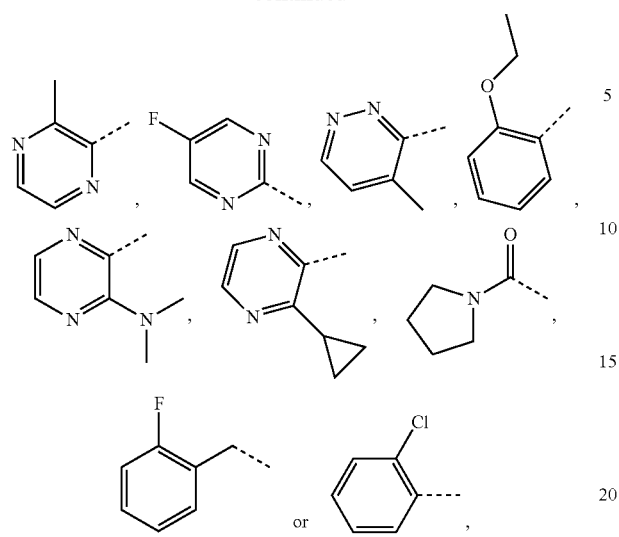
and other variables are as defined above.
In some embodiments of the present invention, the compound or the pharmaceutically acceptable salt thereof is
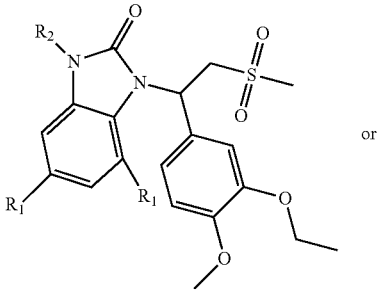
(I-1),
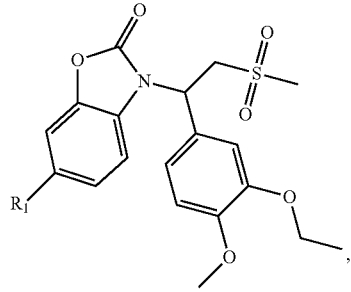
(I-4) or (I-5),
wherein, $R_1$ and $R_2$ are defined as above.
In some embodiments of the present invention, the compound or the pharmaceutically acceptable salt thereof is
(I-1A),
(I-1B), (I-2A)
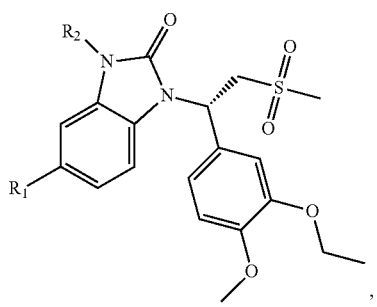
(I-2B)
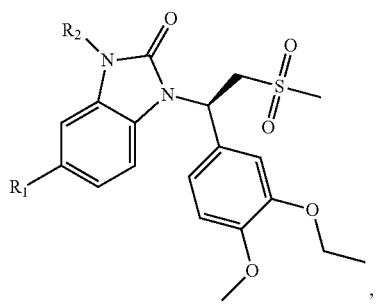
(I-3A)
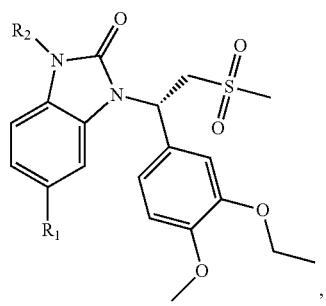
(I-3B)
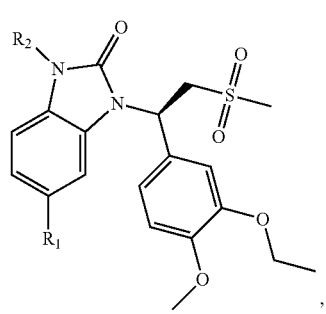
(I-4A)
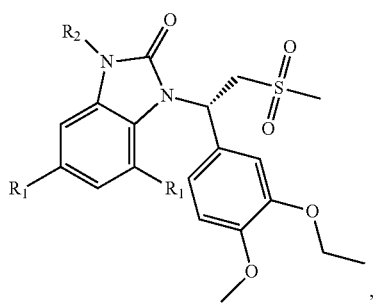
(I-4B)
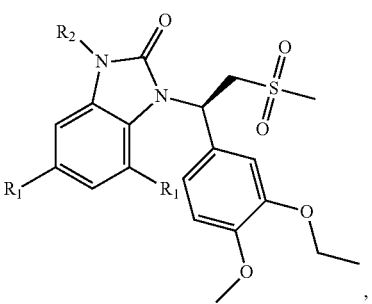
(I-5A)
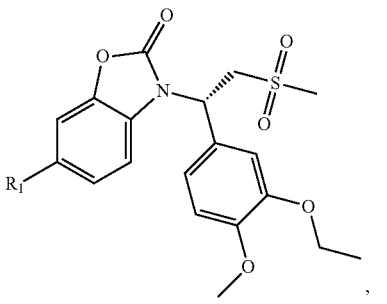
, or
(I-5B)
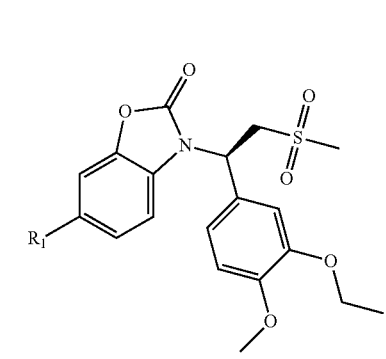
wherein, $R_1$ and $R_2$ are defined as above.
The above variables can be arbitrarily combined, then other embodiments of the present invention are obtained.
The present invention also provides a compound as shown in formula below or a pharmaceutically acceptable salt thereof, which is selected from the group consisting of
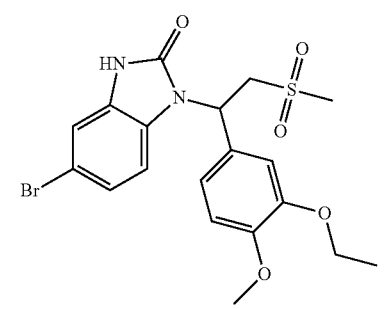

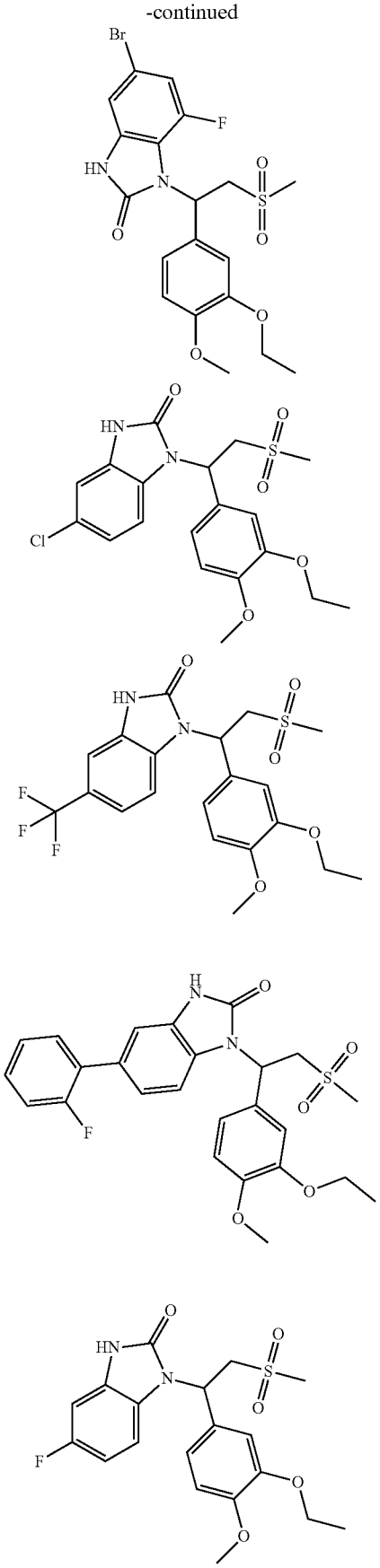
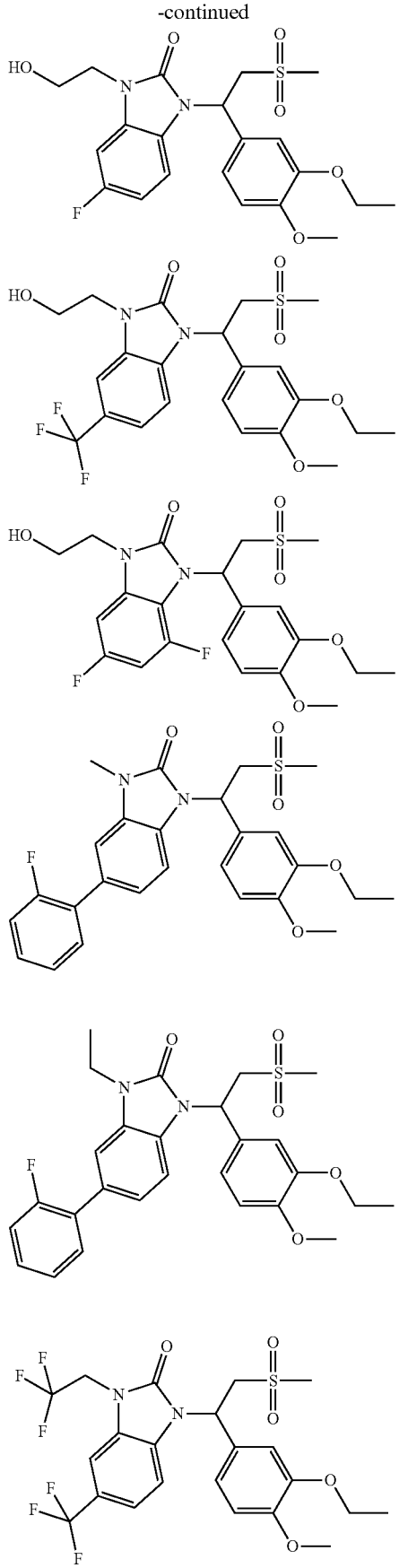

17
-continued
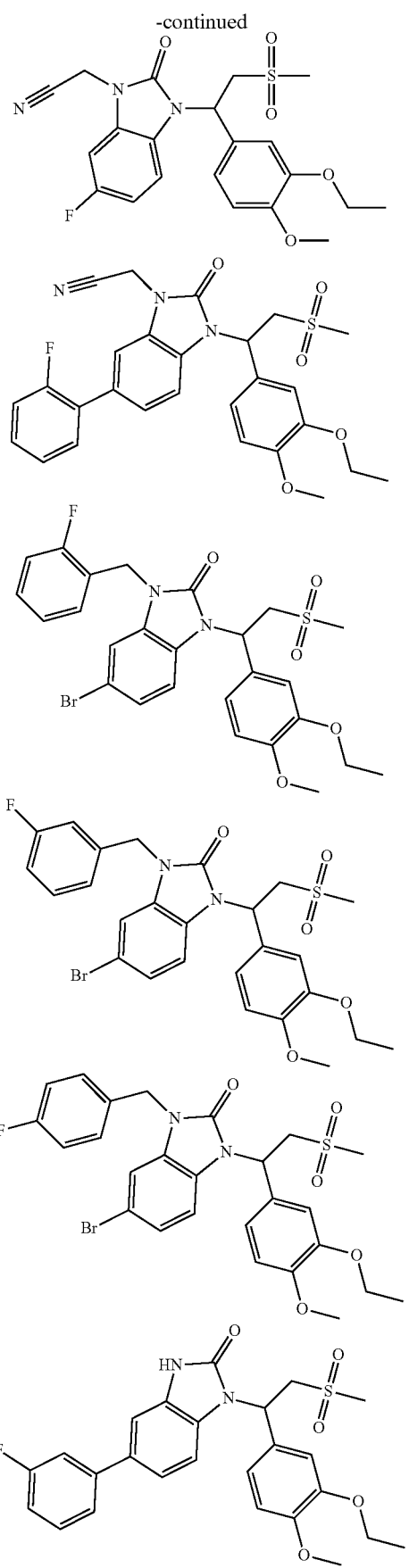
18
-continued
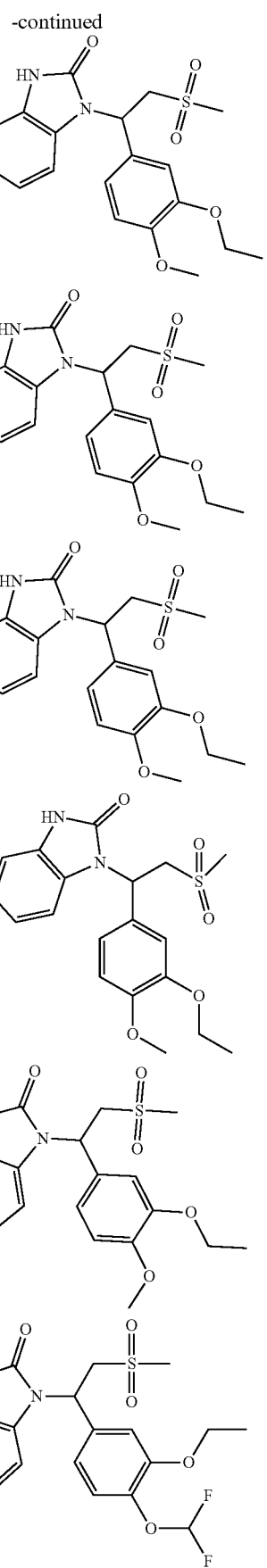

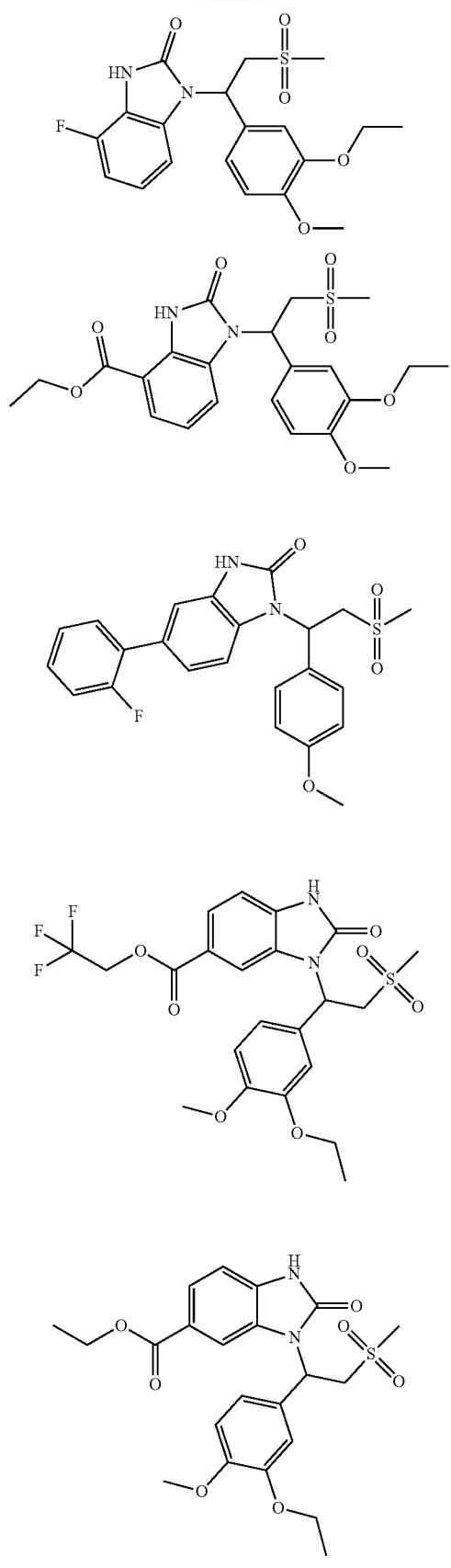
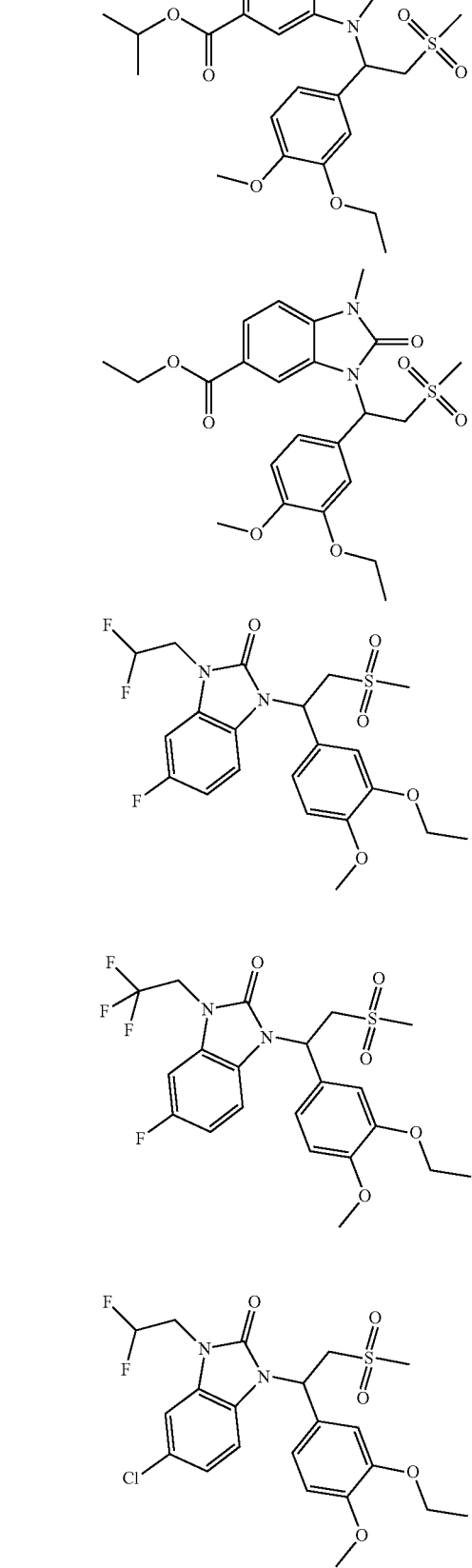

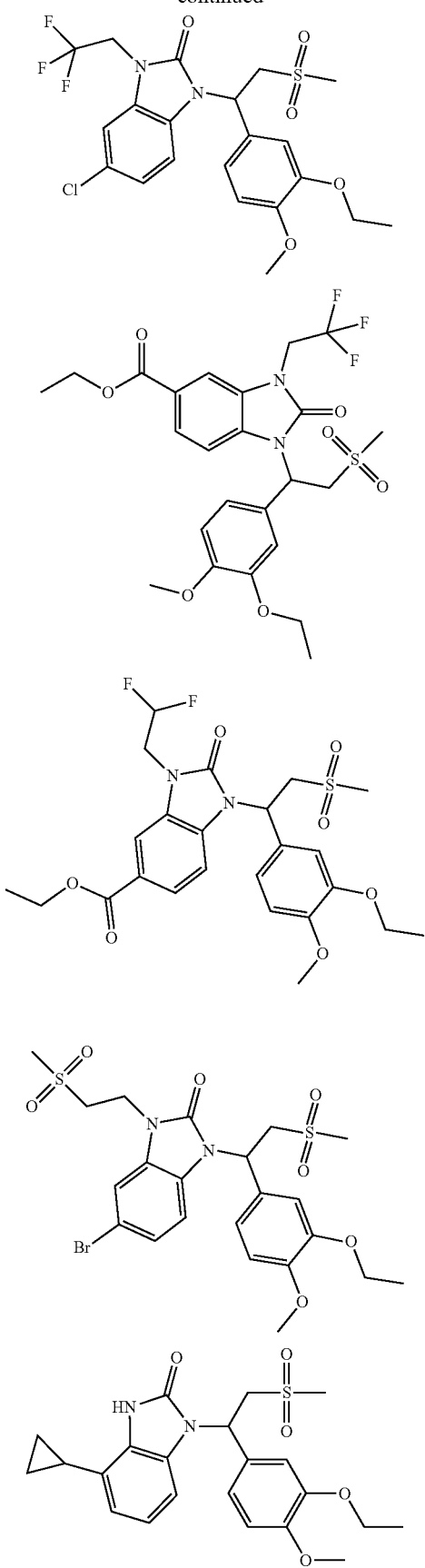
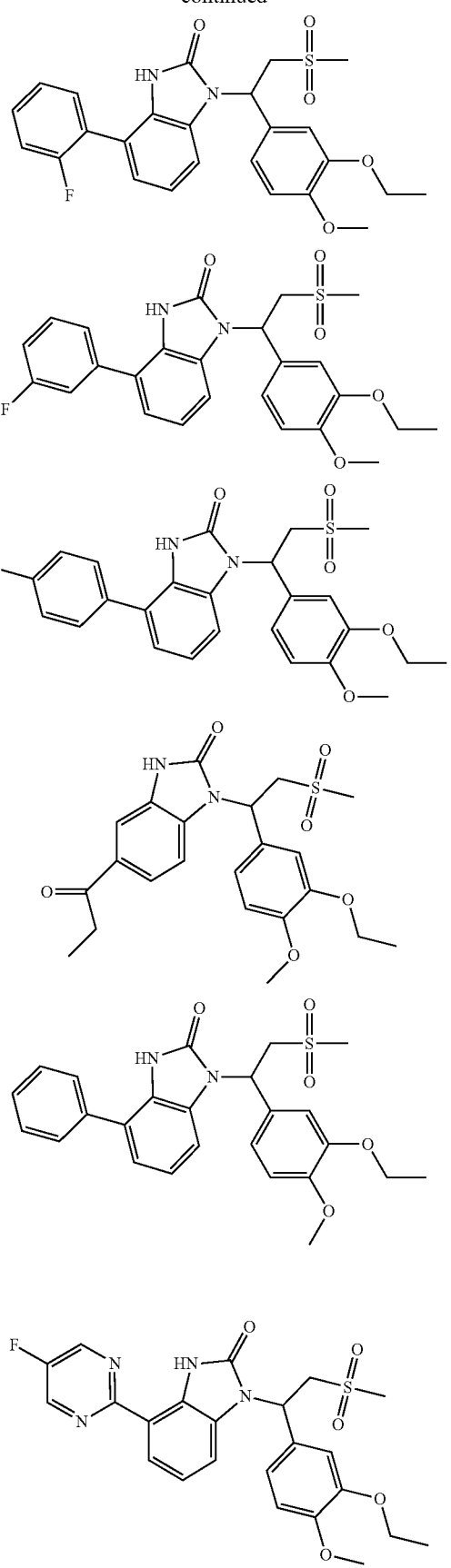

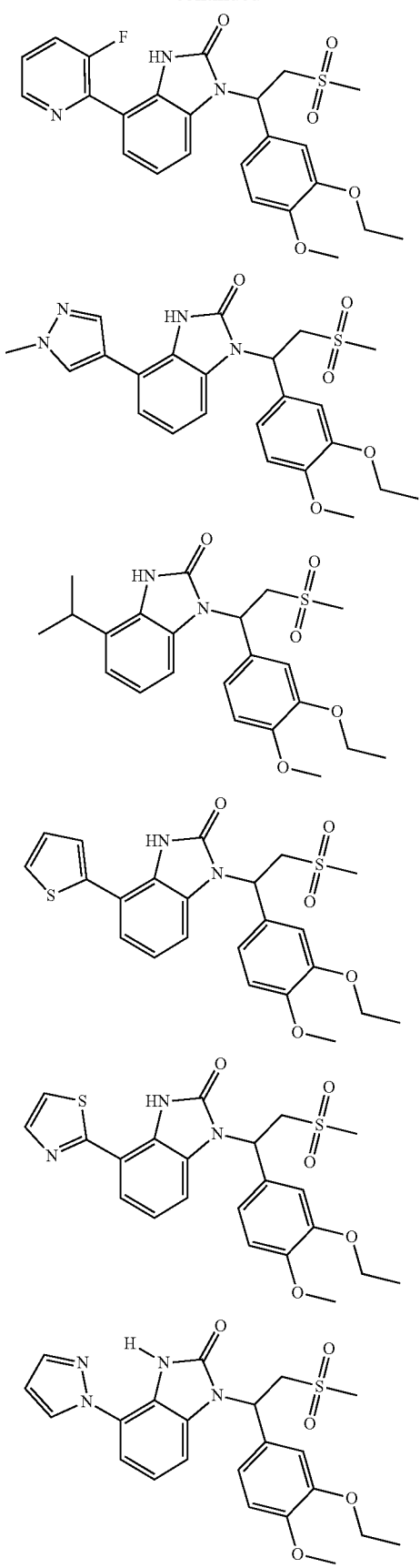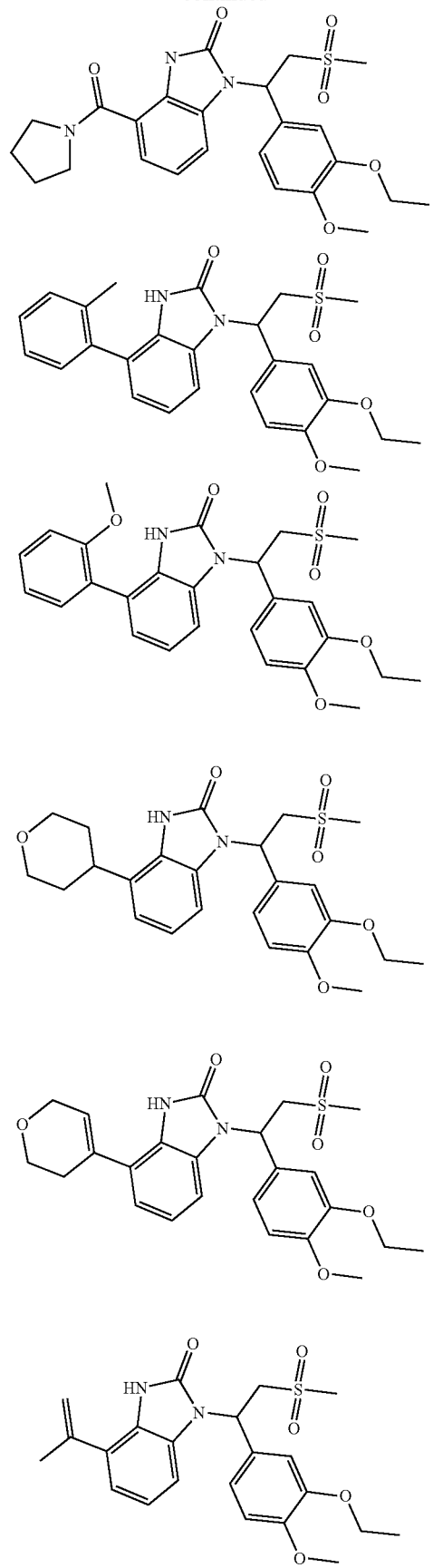

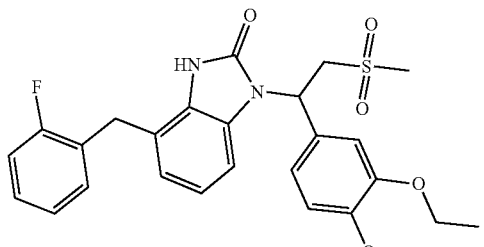
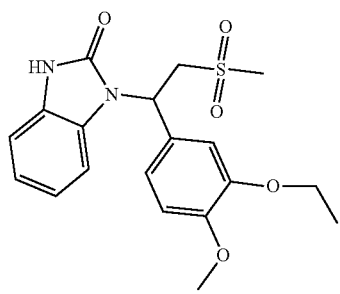
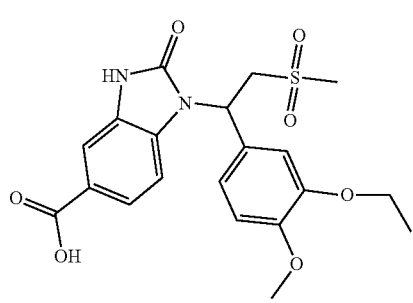
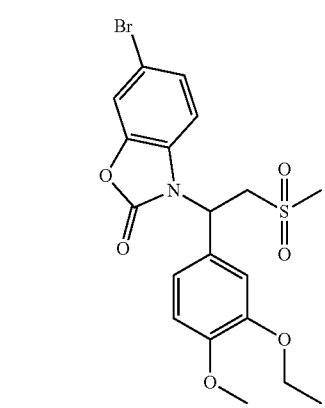
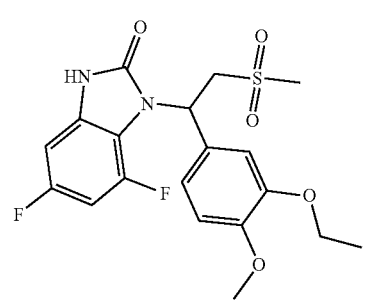
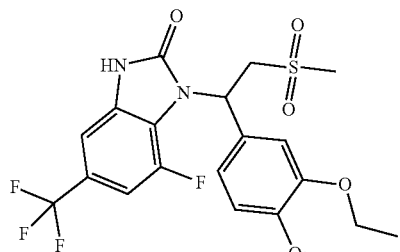
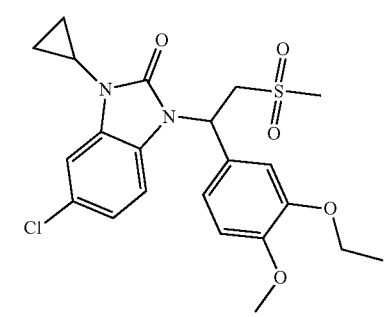
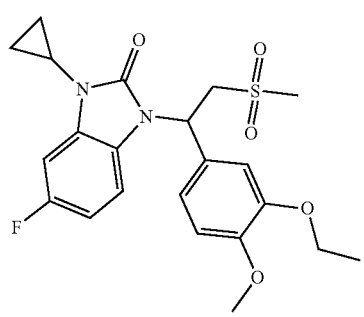
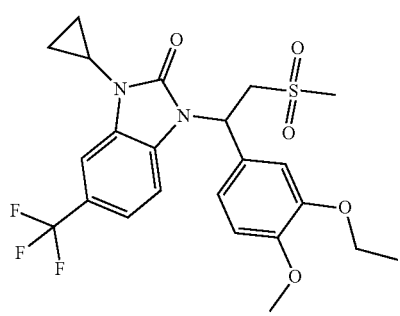
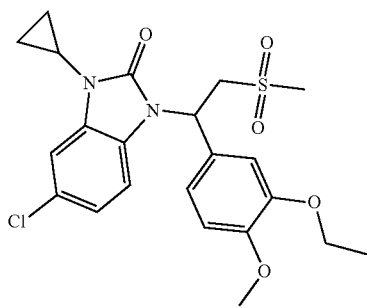

27
-continued
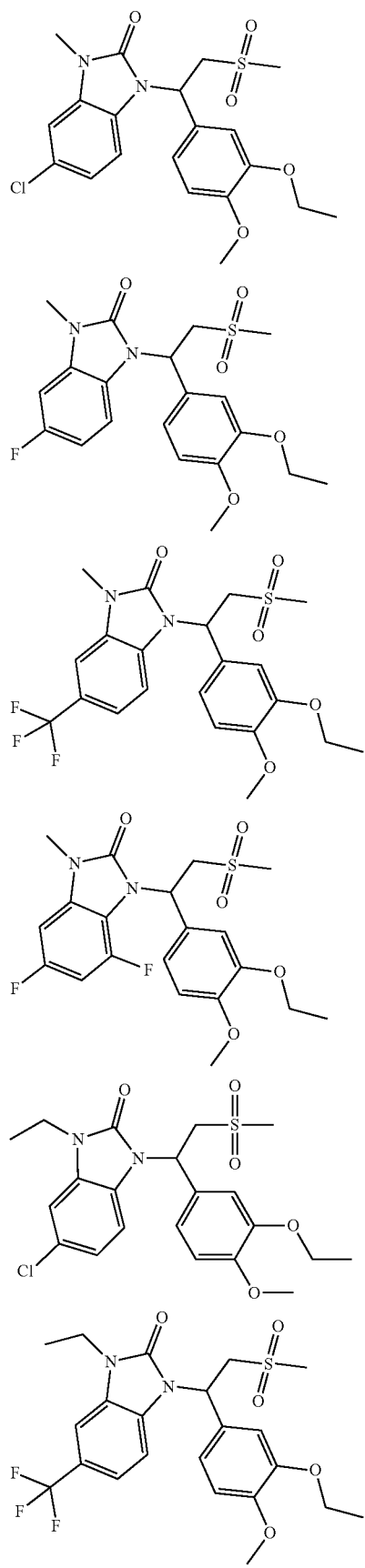
28
-continued
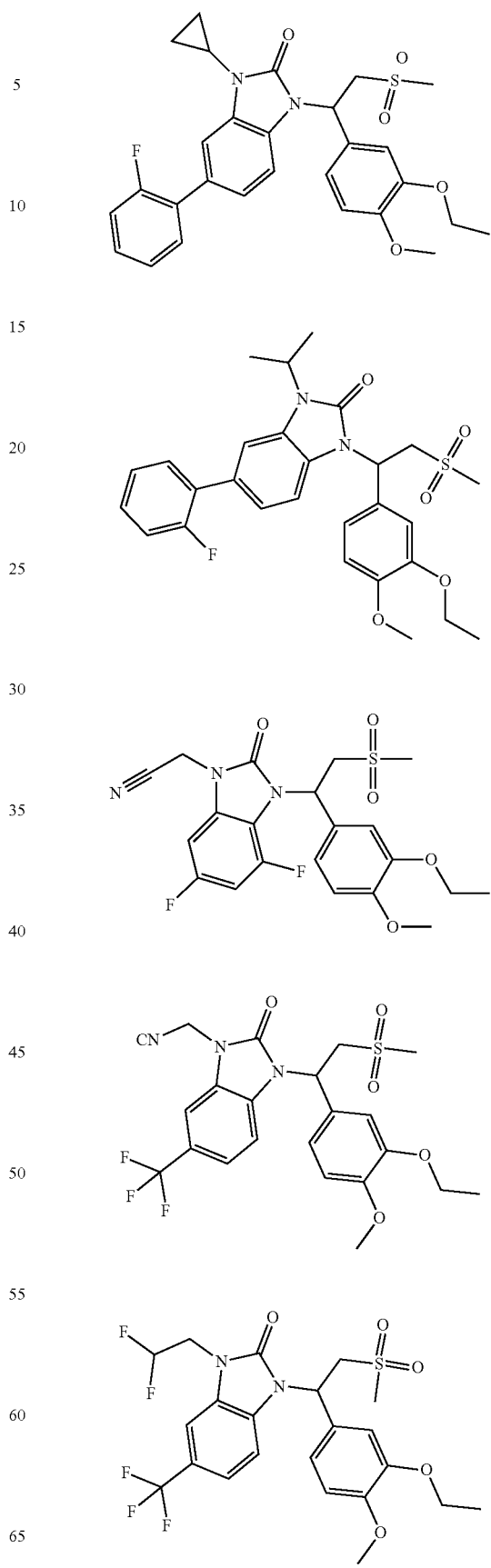

-continued
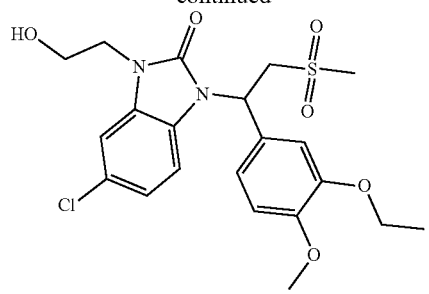
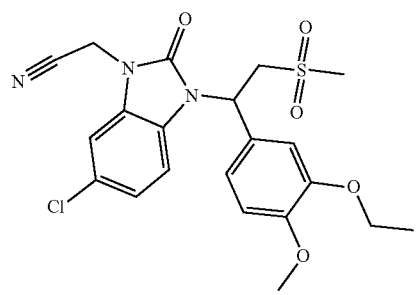
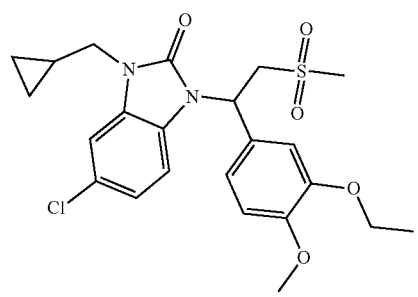
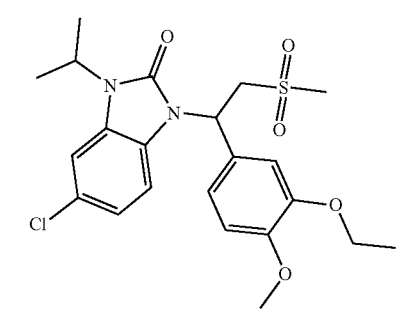
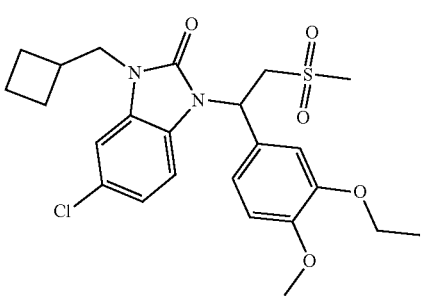
-continued
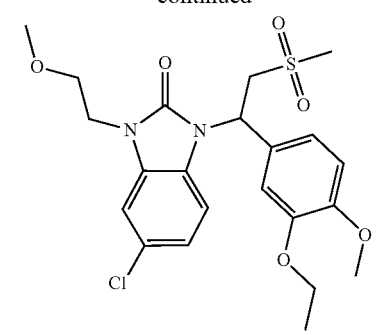
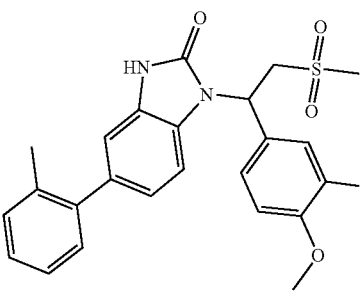
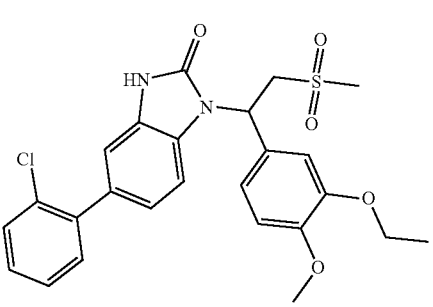
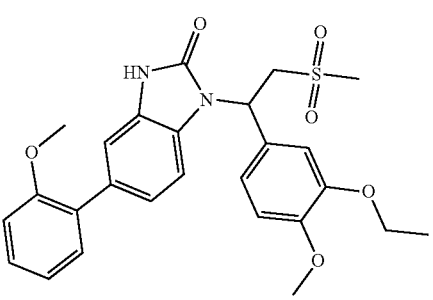
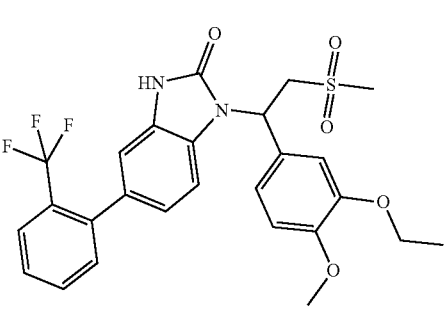

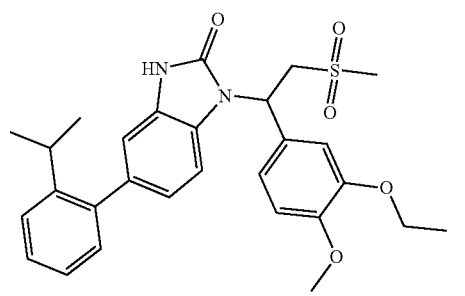
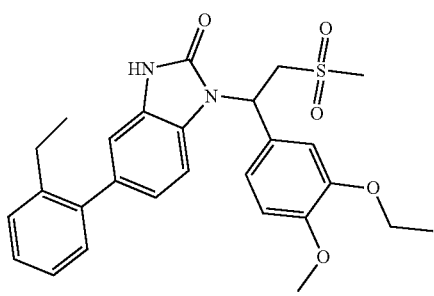
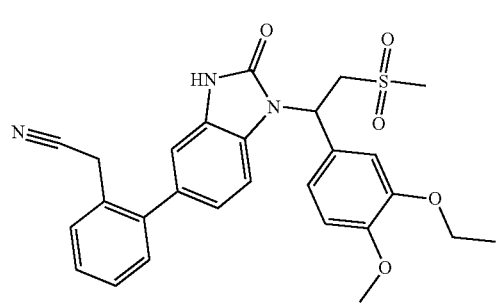
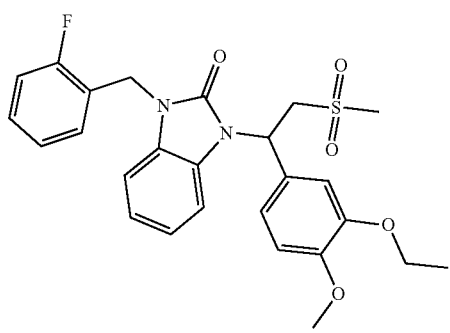
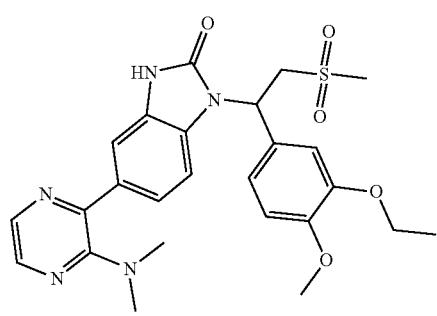
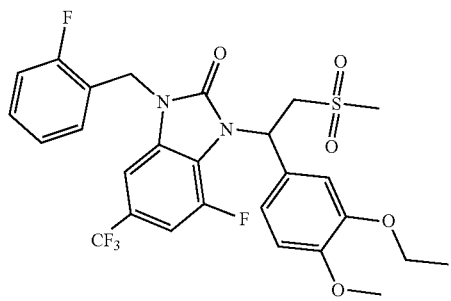
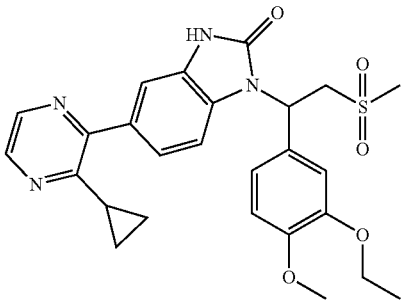
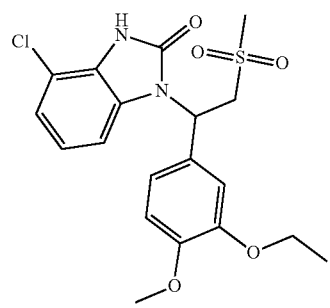
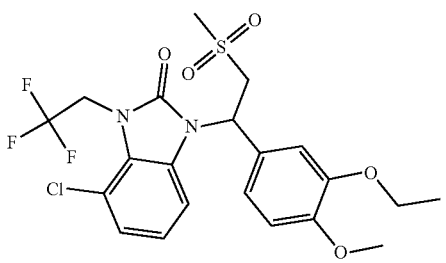
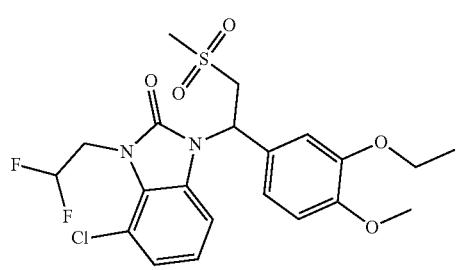
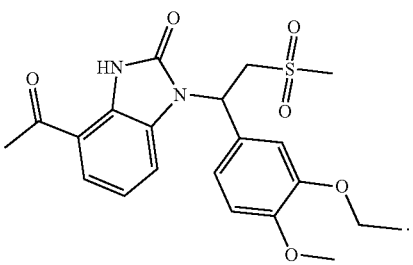
and In some embodiments of the present invention, the compound or the pharmaceutically acceptable salt thereof is selected from the group consisting of
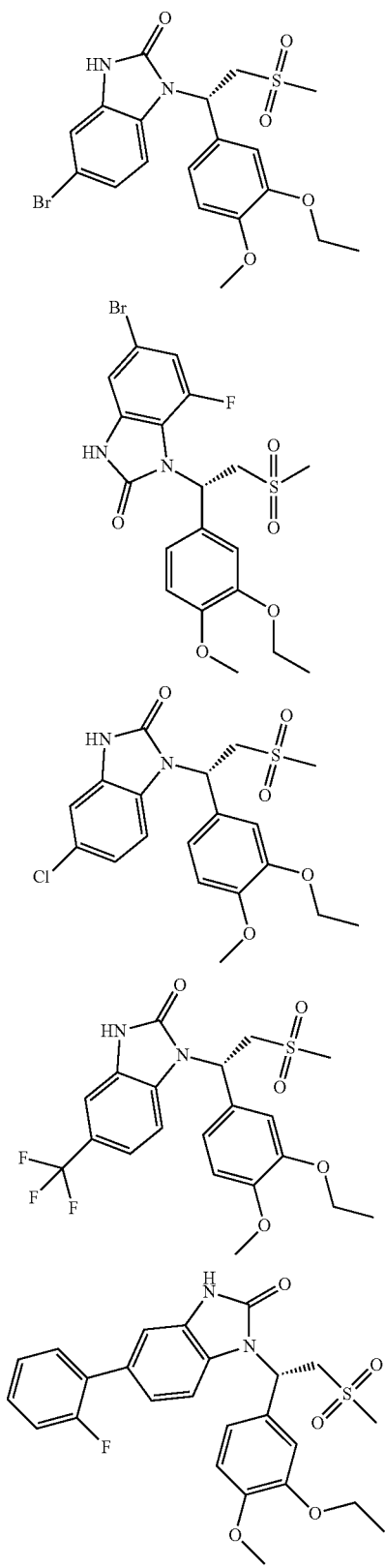
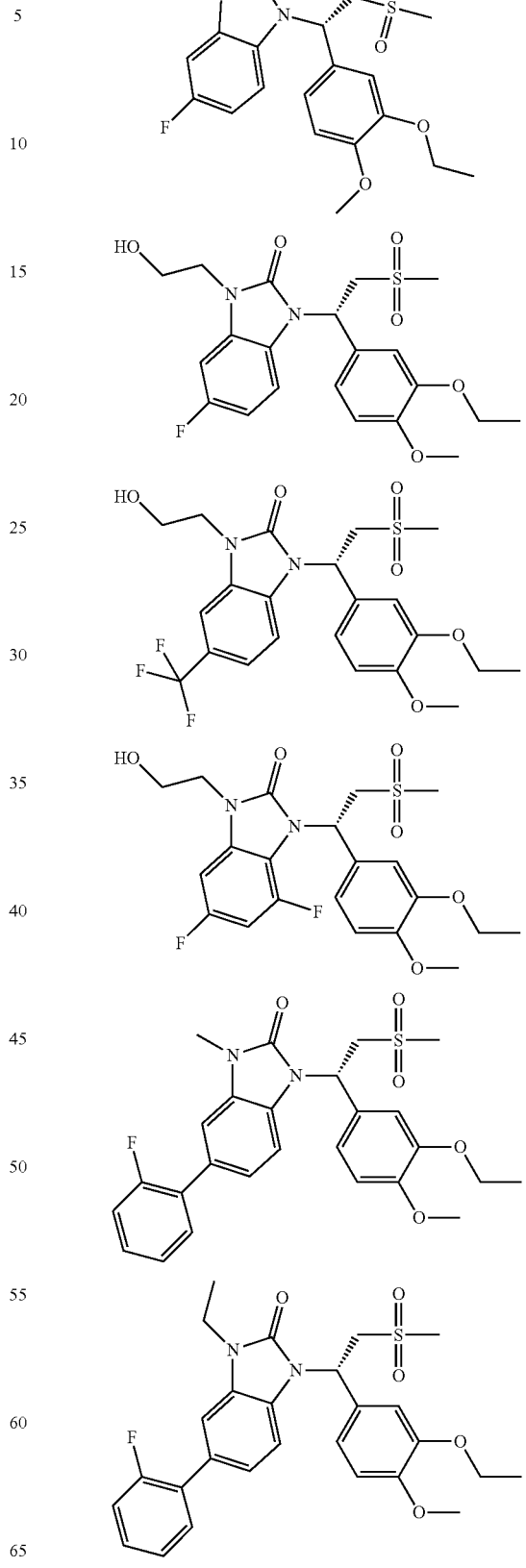

-continued
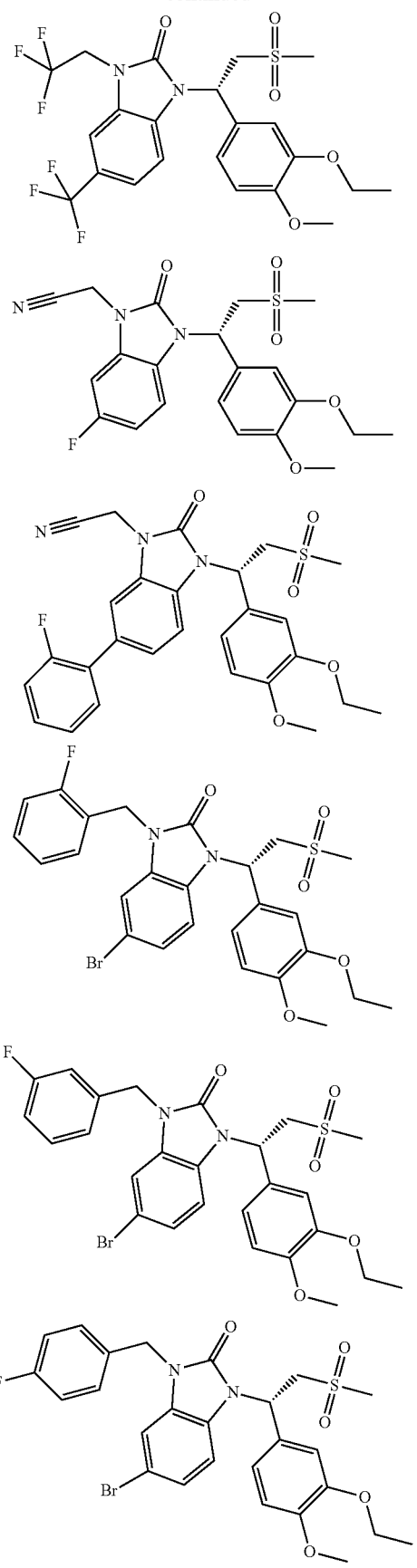
-continued
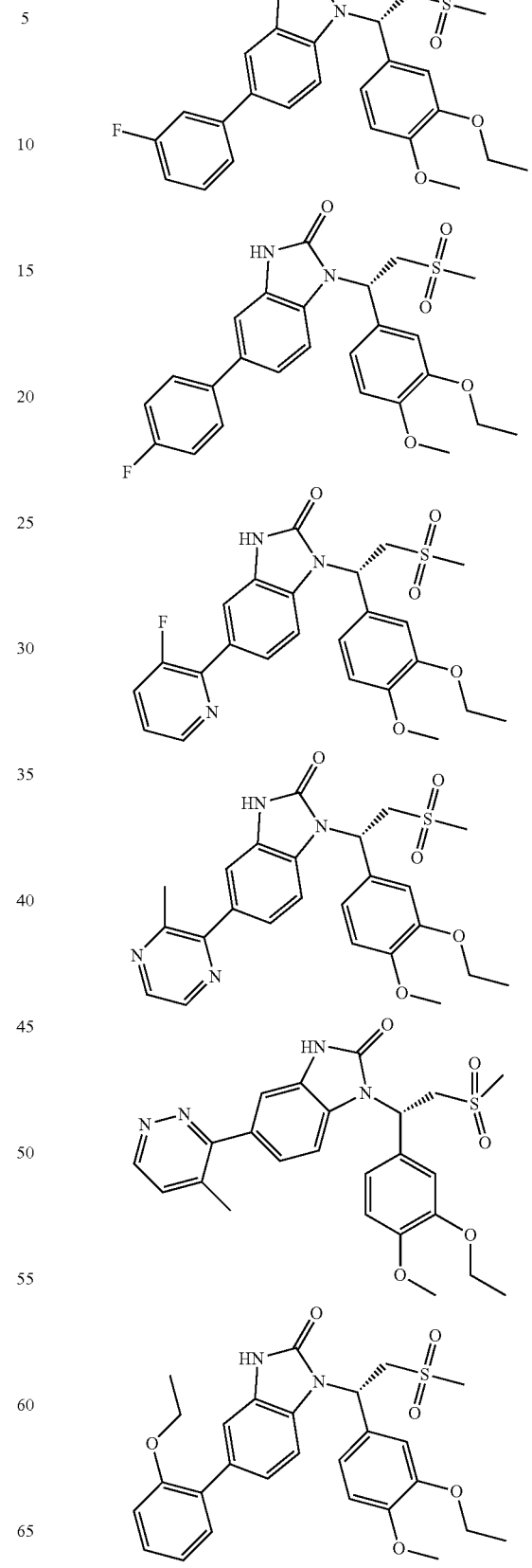

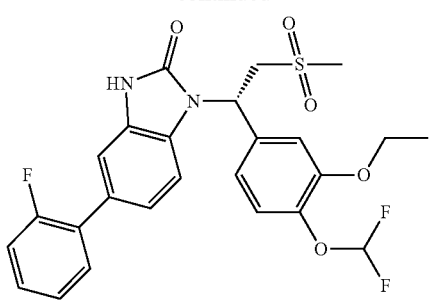
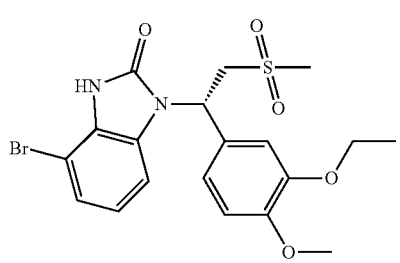
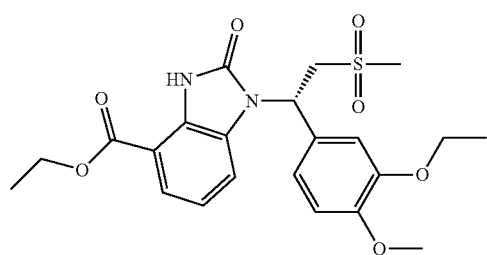
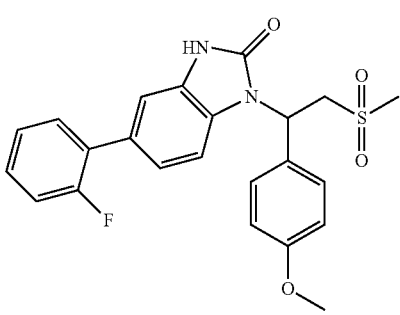
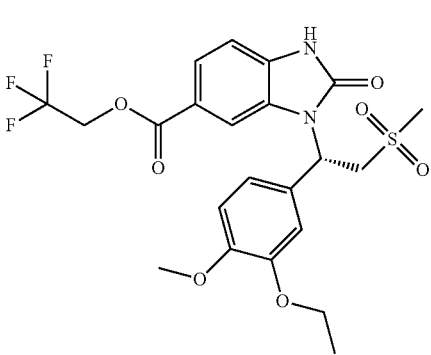
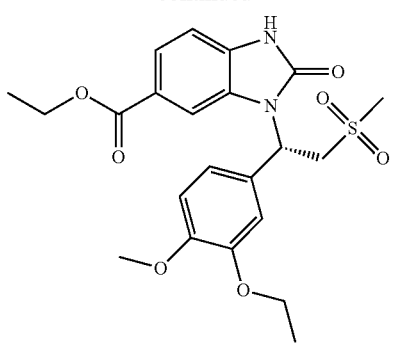
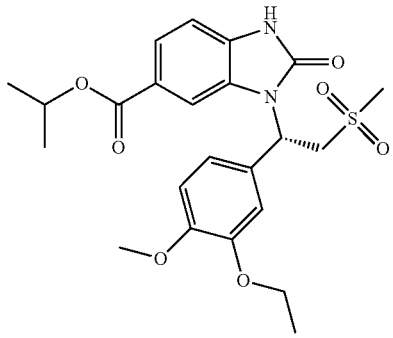
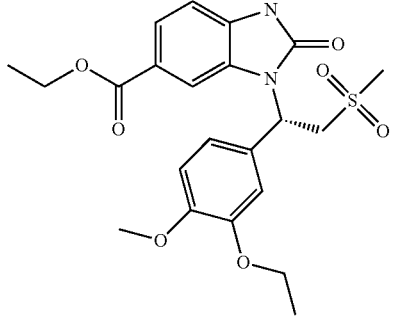
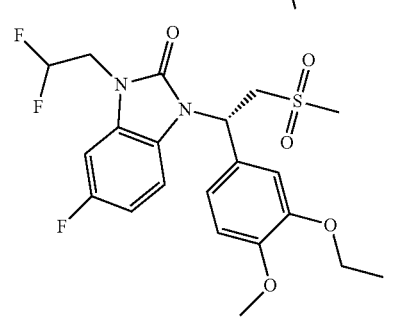
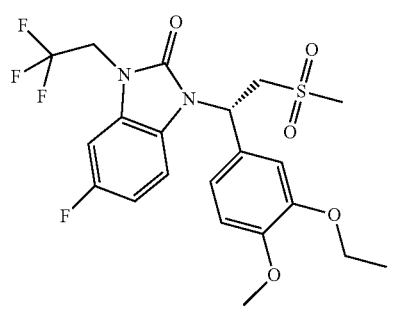

-continued
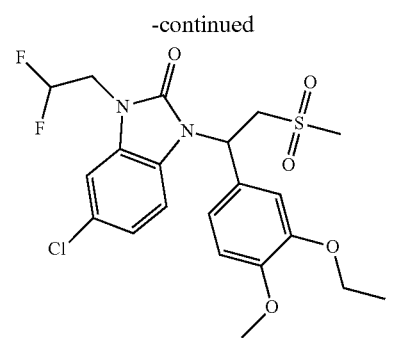
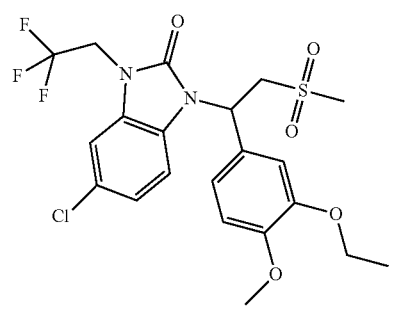
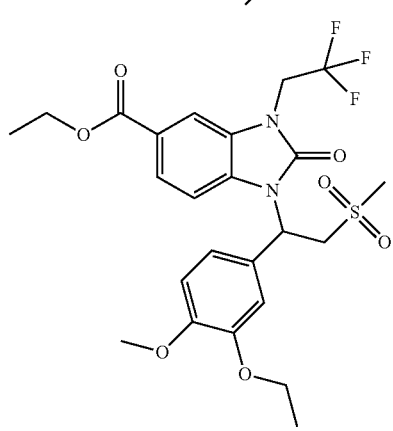
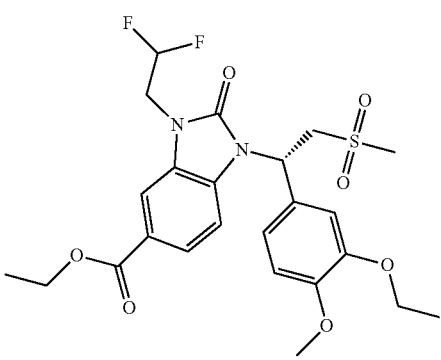
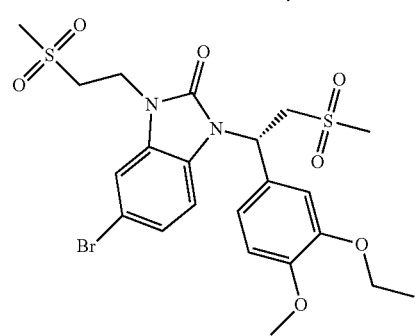
-continued
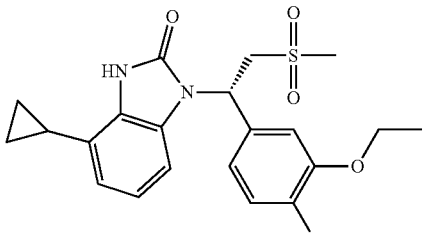
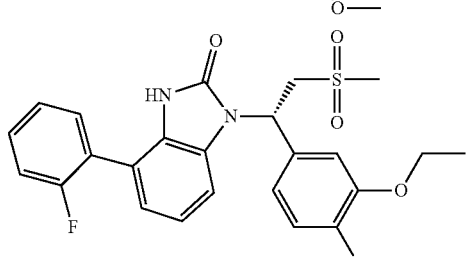
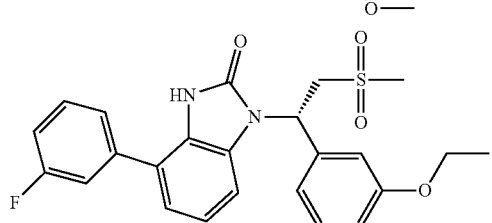
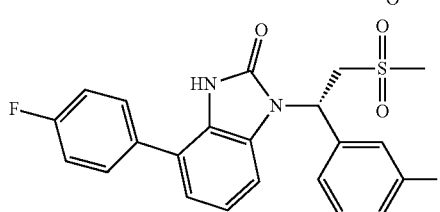
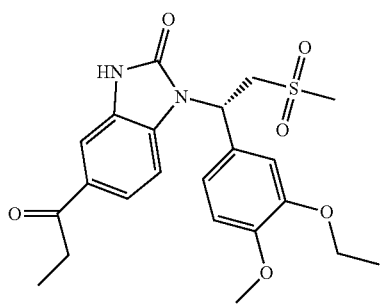
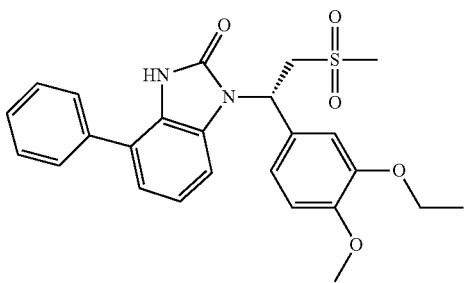

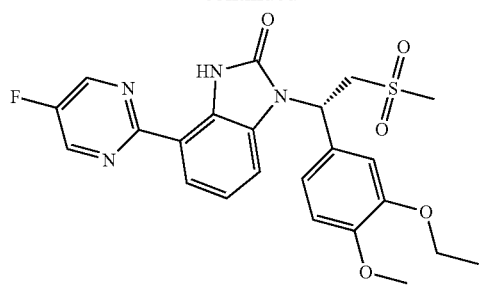
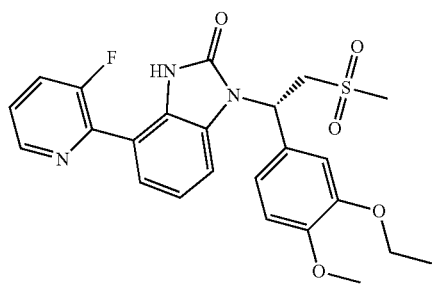
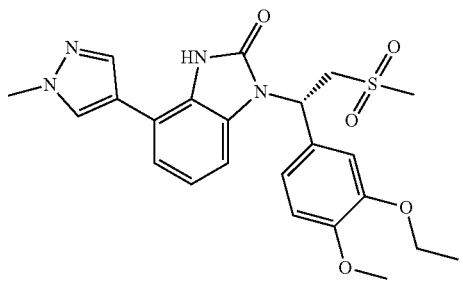
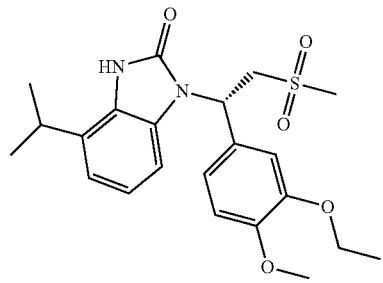
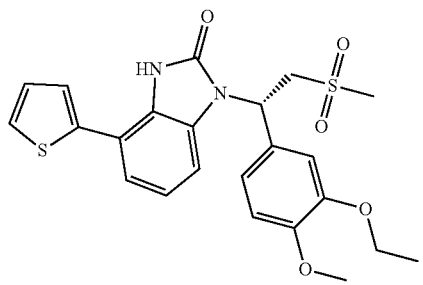
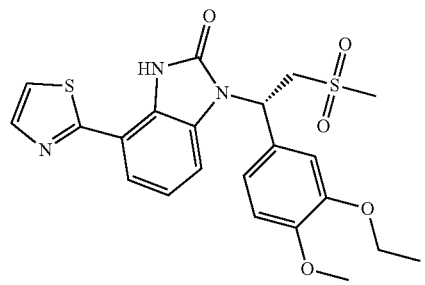
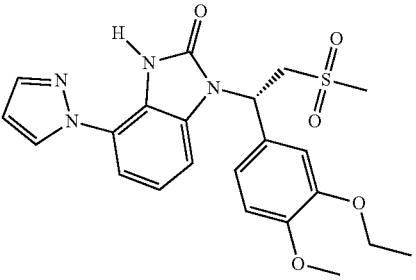
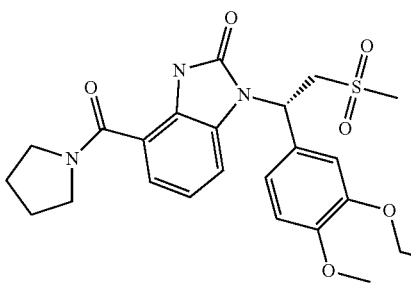
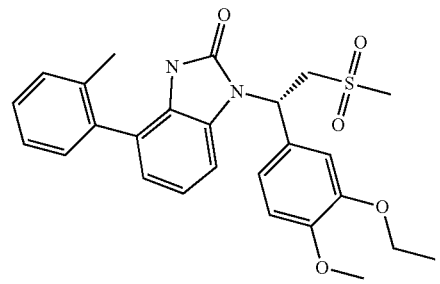
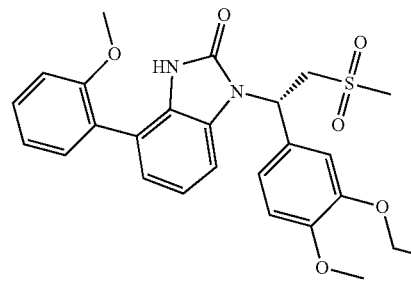
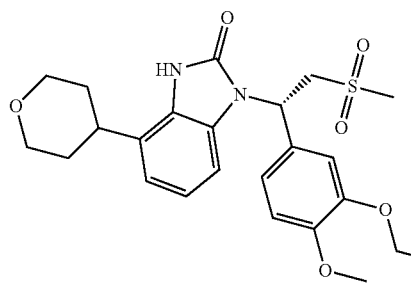
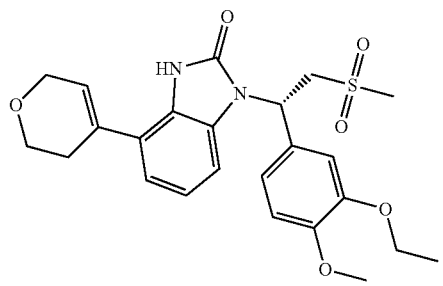

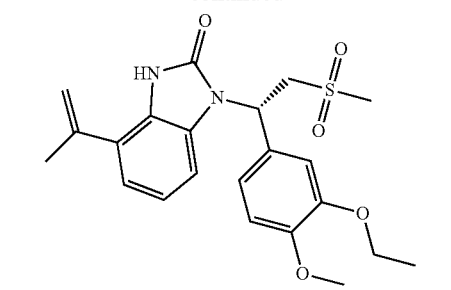
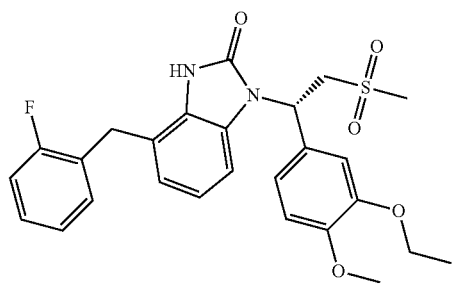
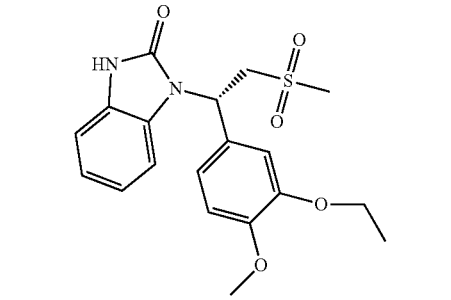
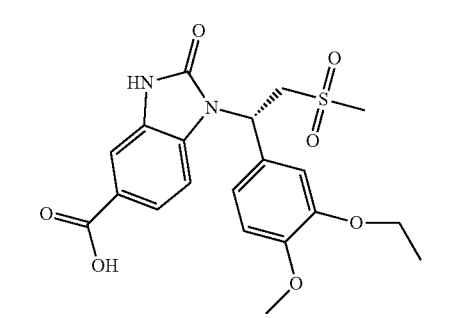
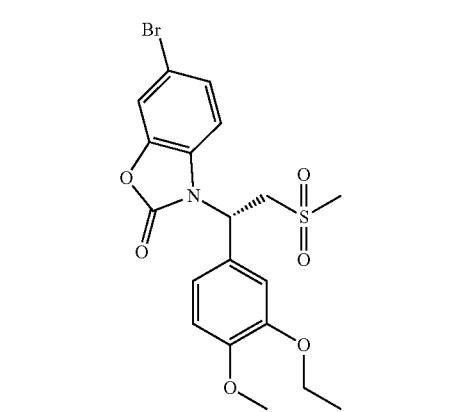
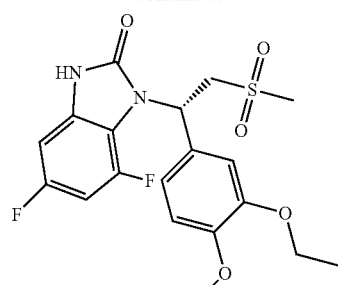
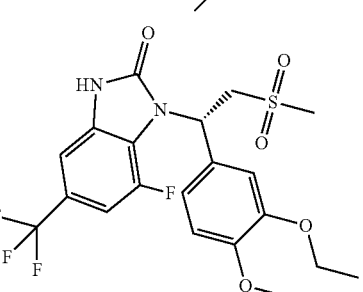
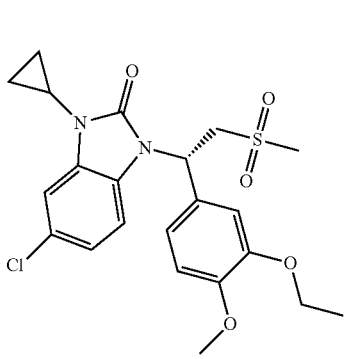
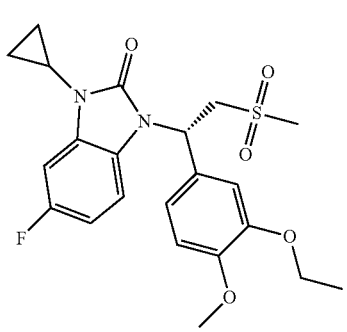
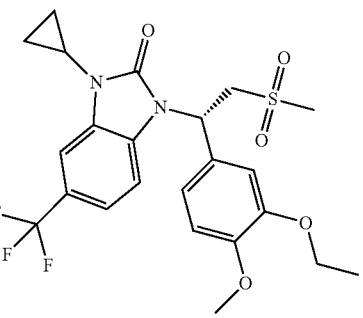

-continued
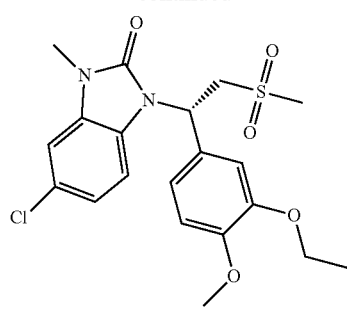
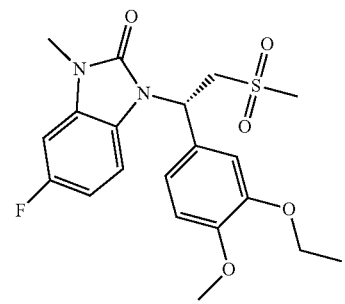
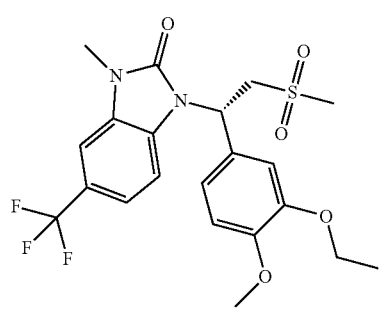
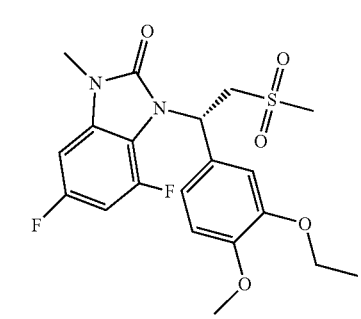
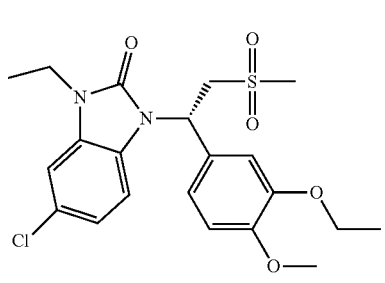
-continued
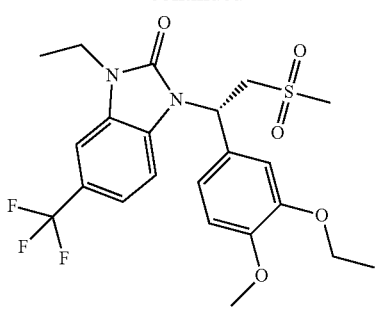
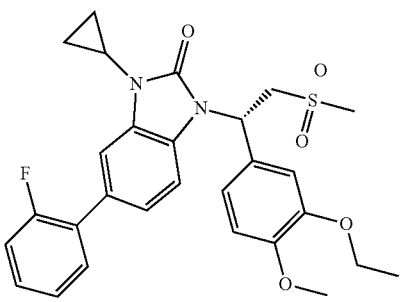
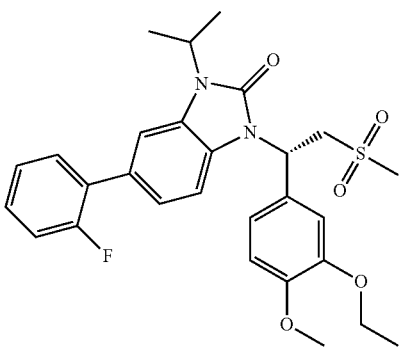
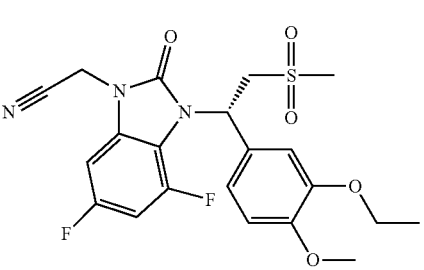
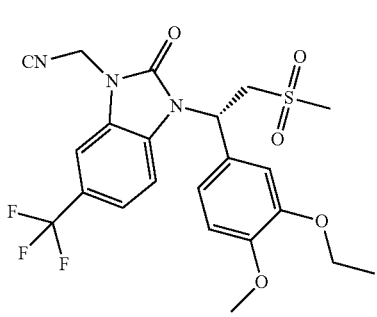

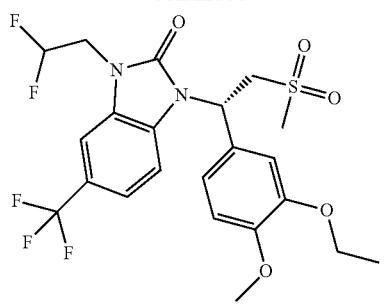
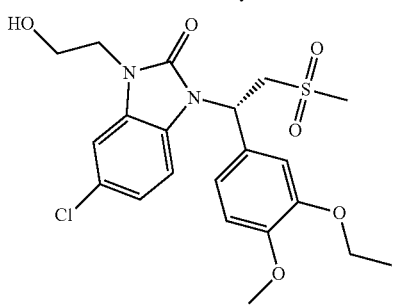
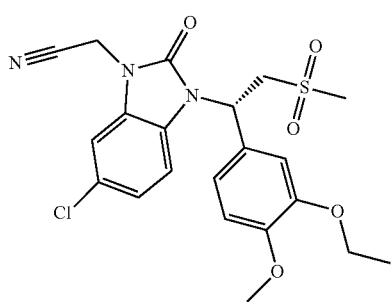
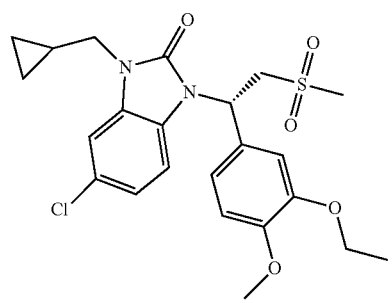
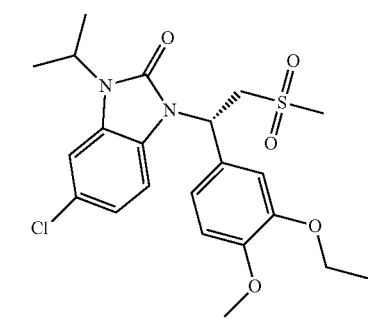
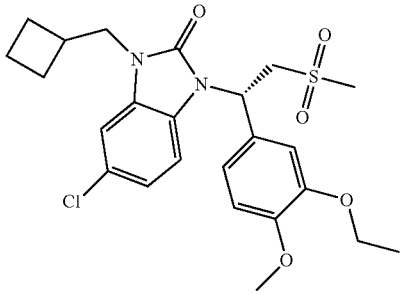
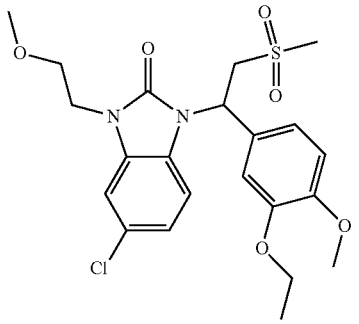
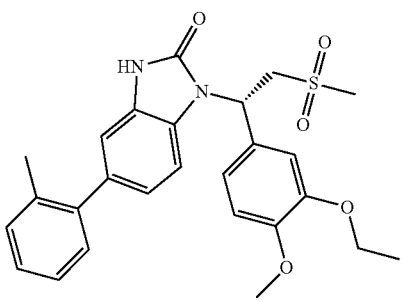
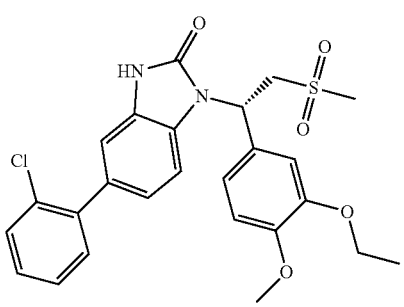
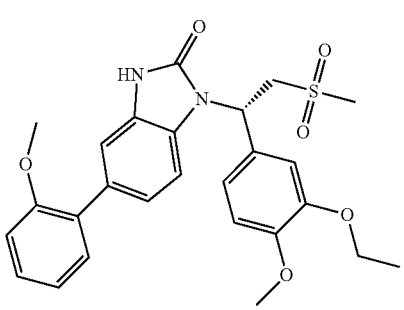

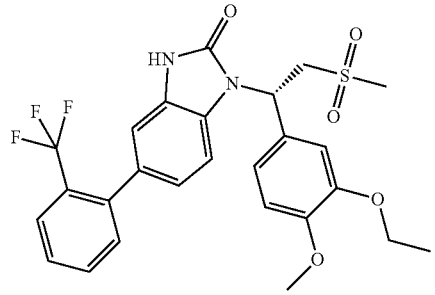
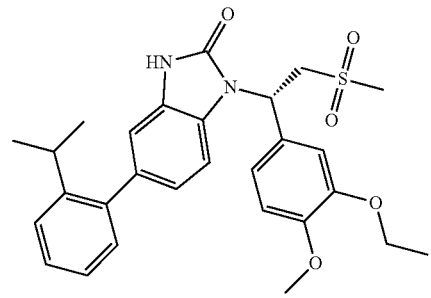
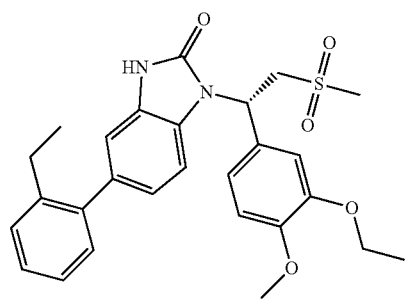
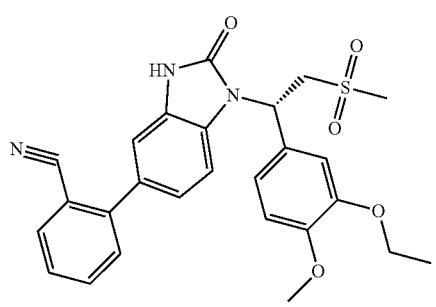
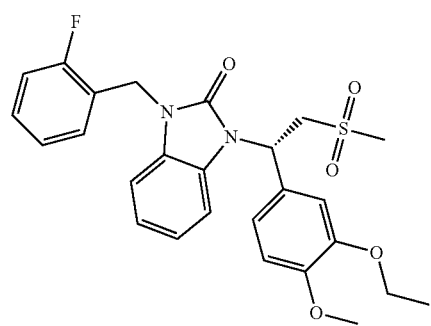
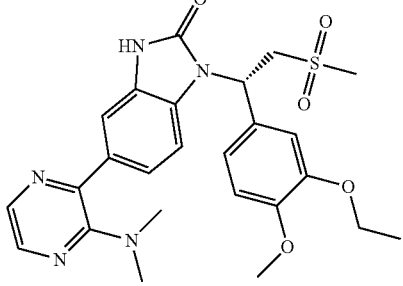
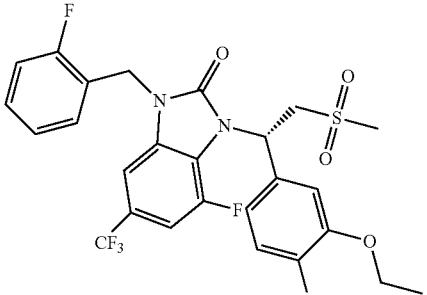
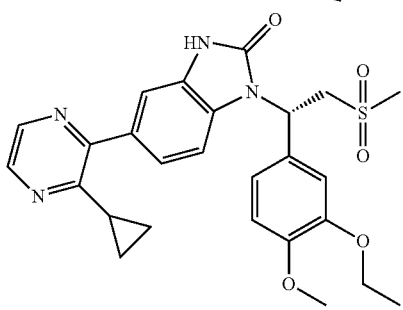
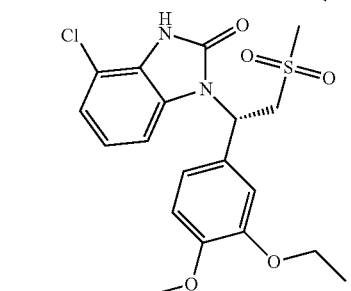
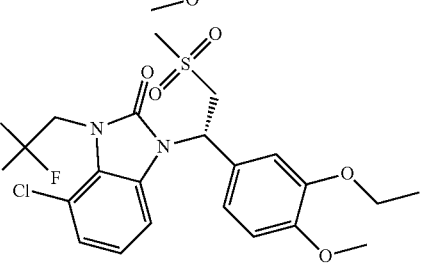
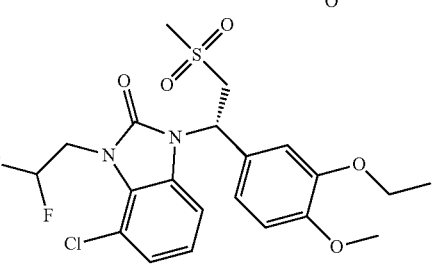

51
-continued
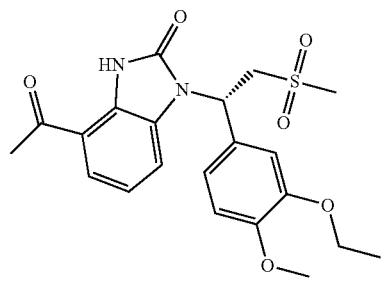
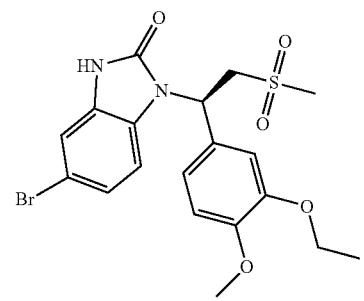
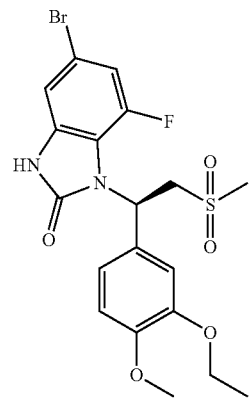
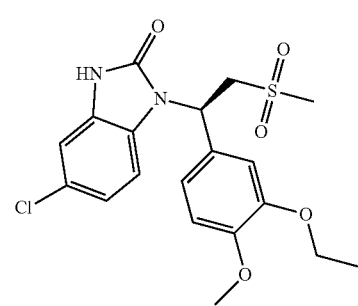
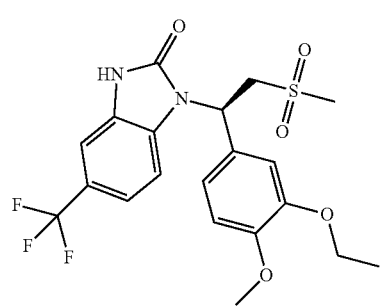
52
-continued
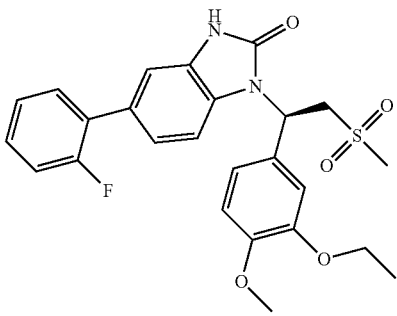
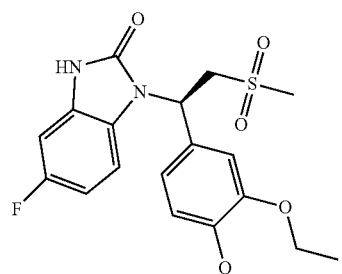
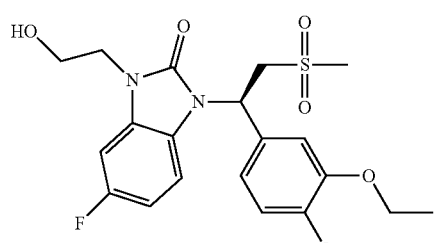
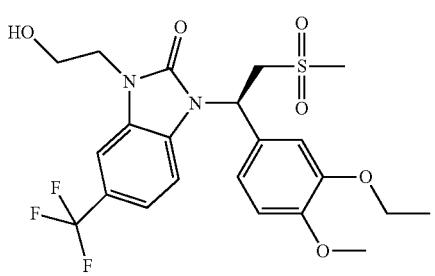
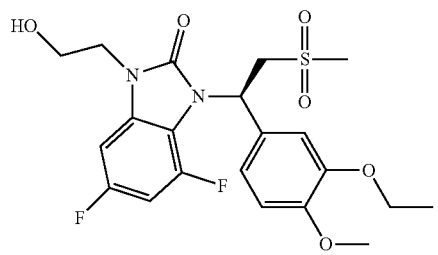
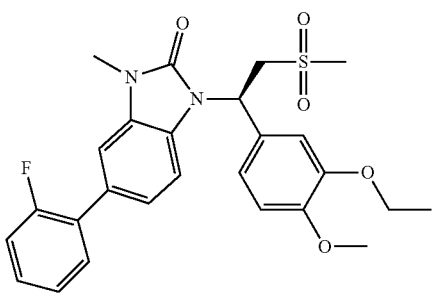

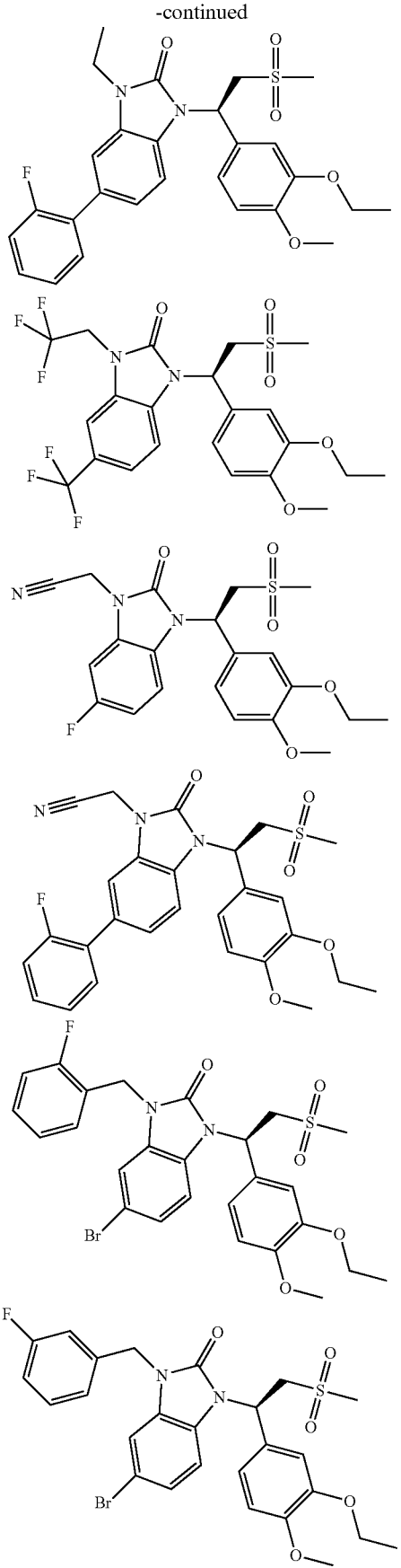
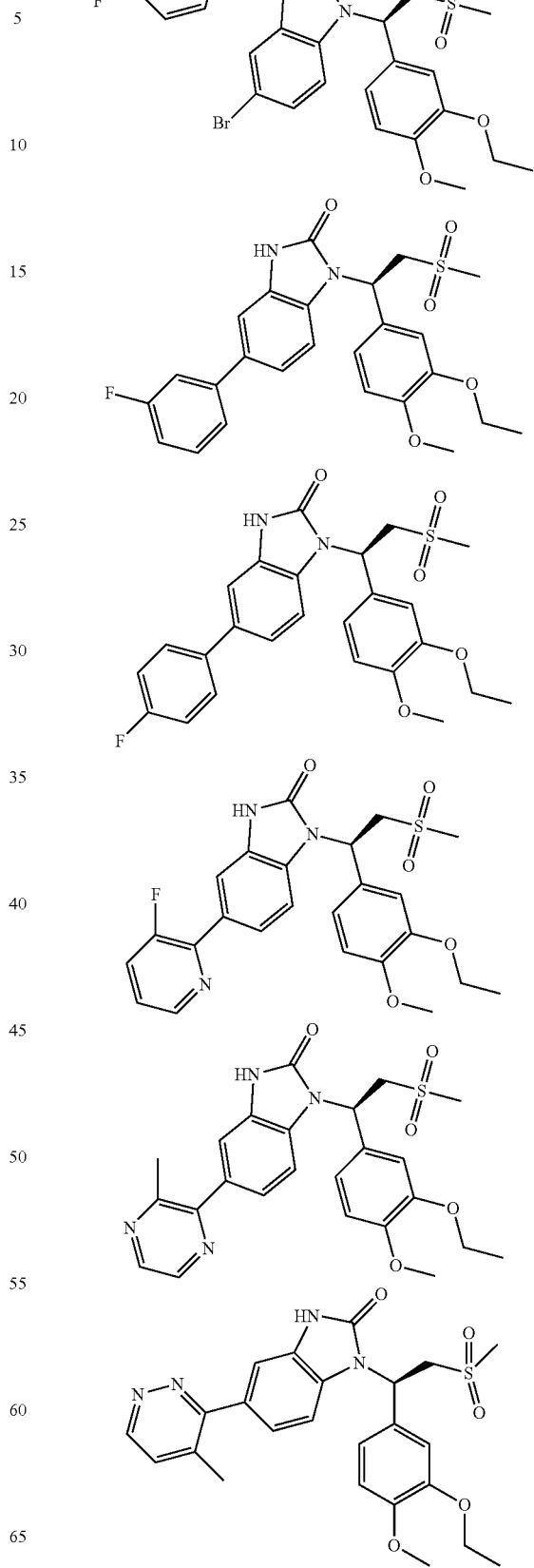

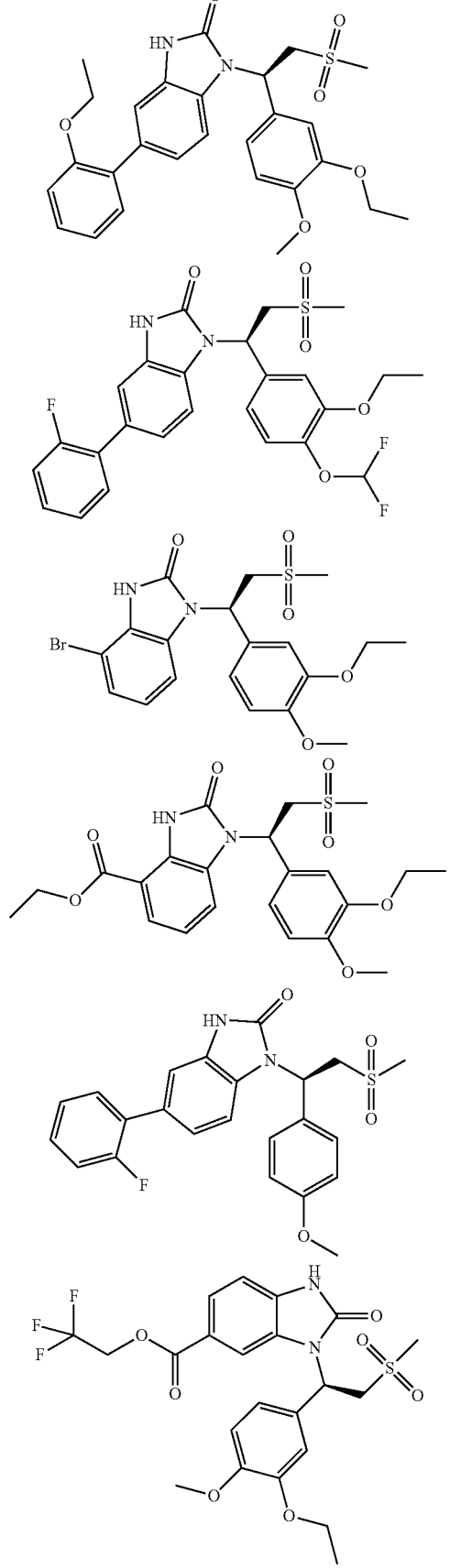
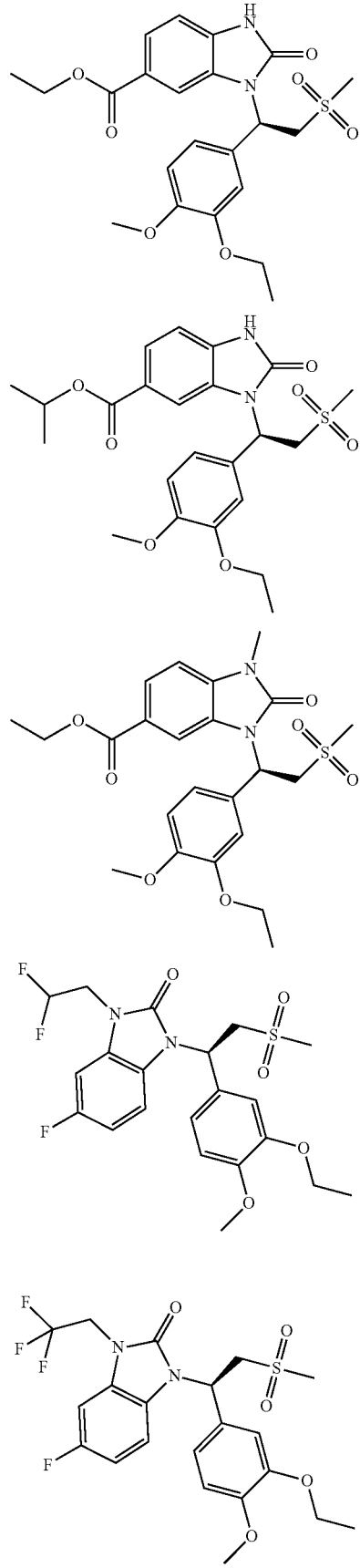

57
-continued
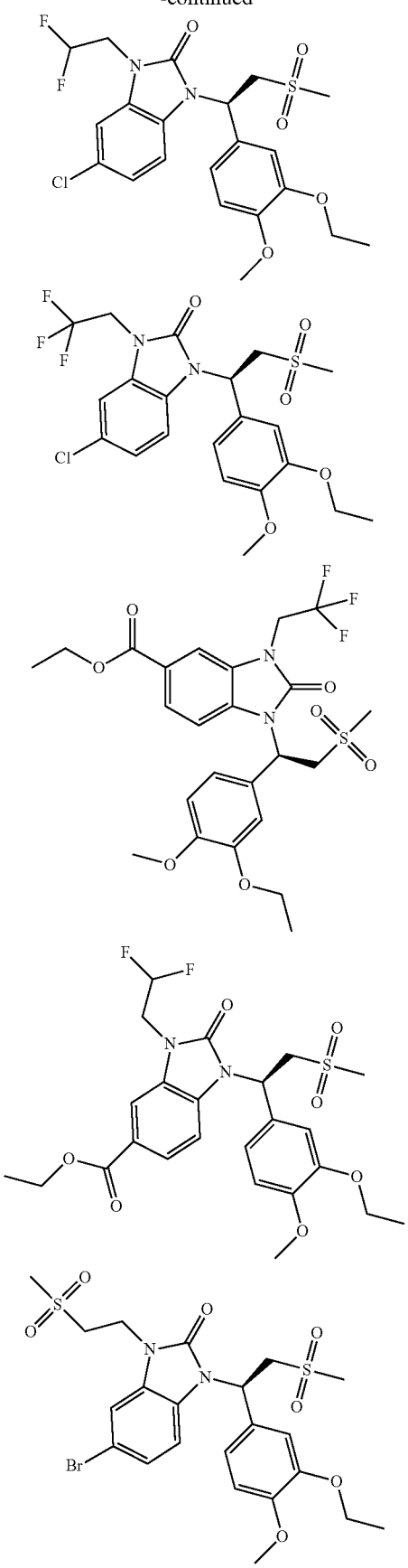
58
-continued
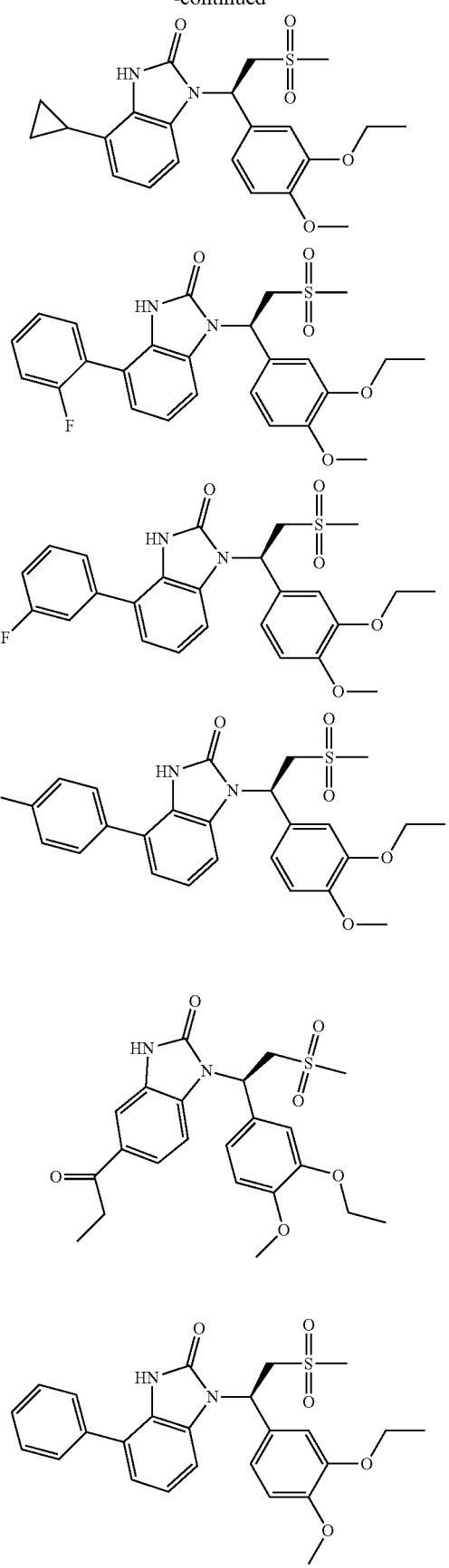

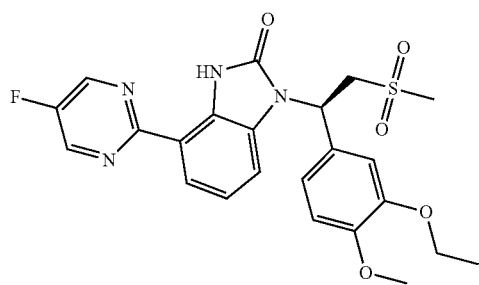
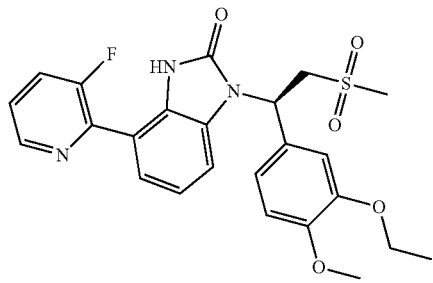
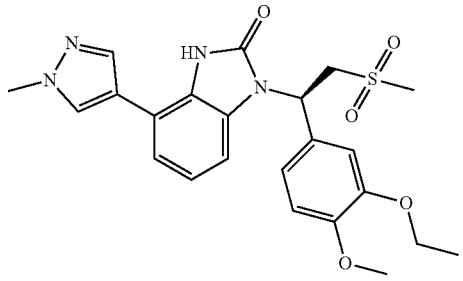
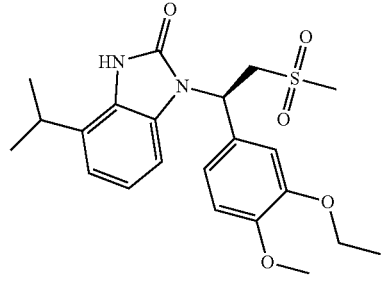
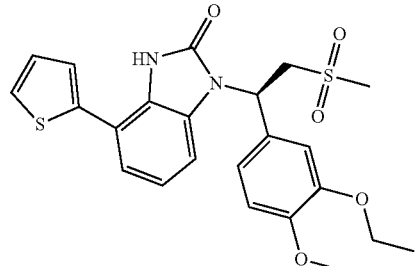
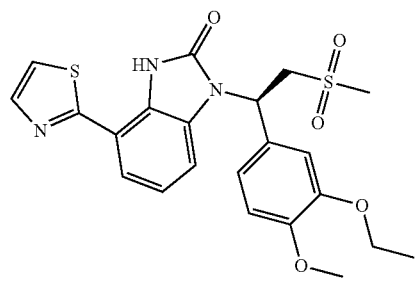
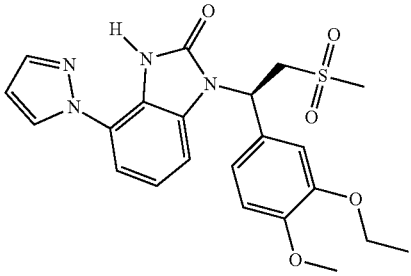
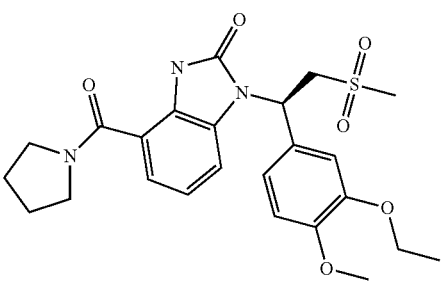
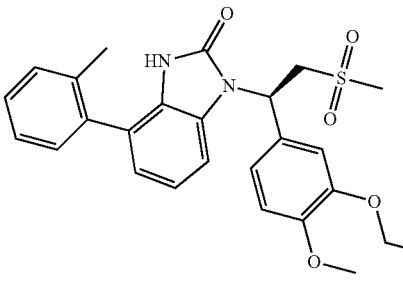
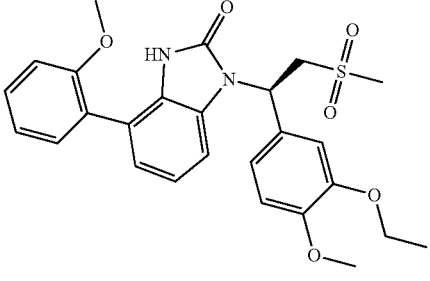
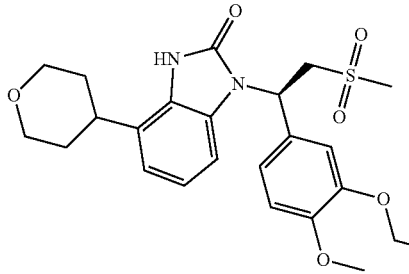
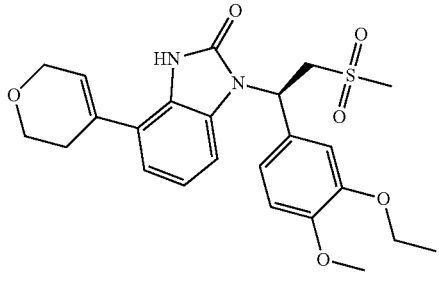

61
-continued
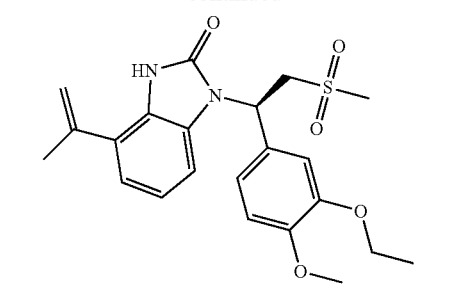
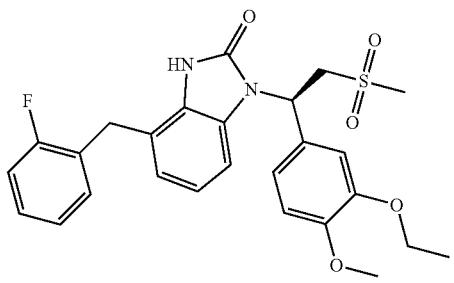
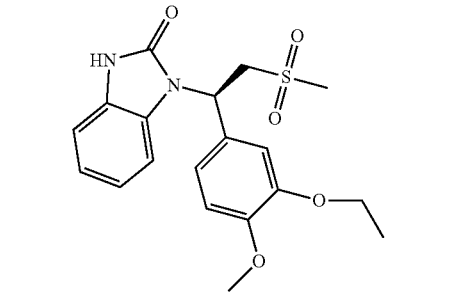
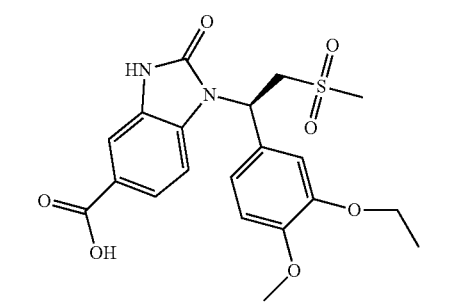
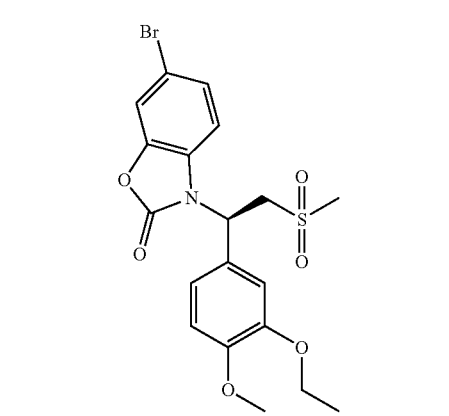
62
-continued
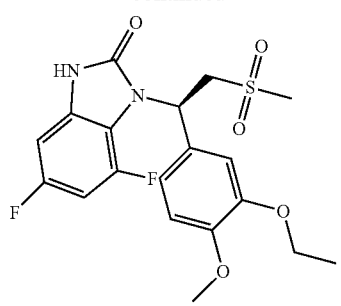
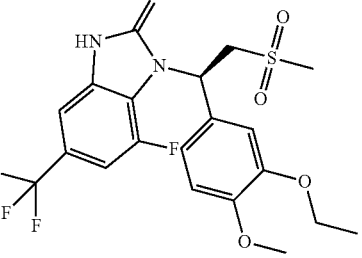
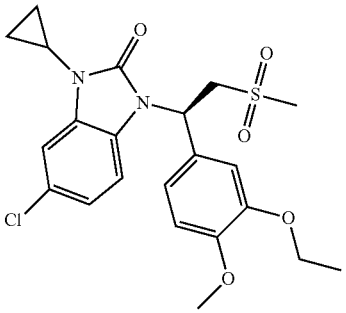
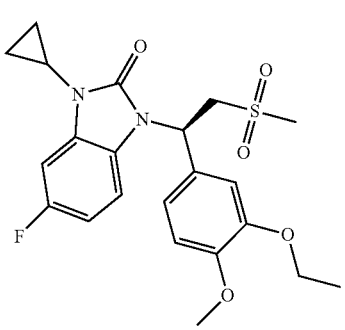
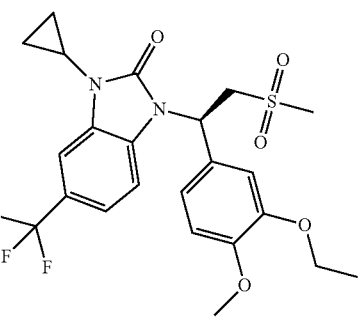

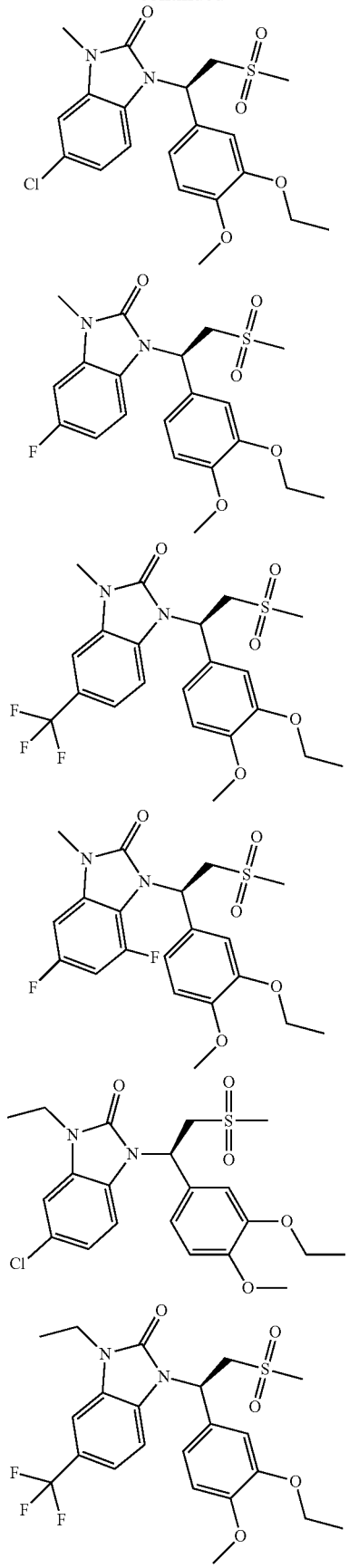
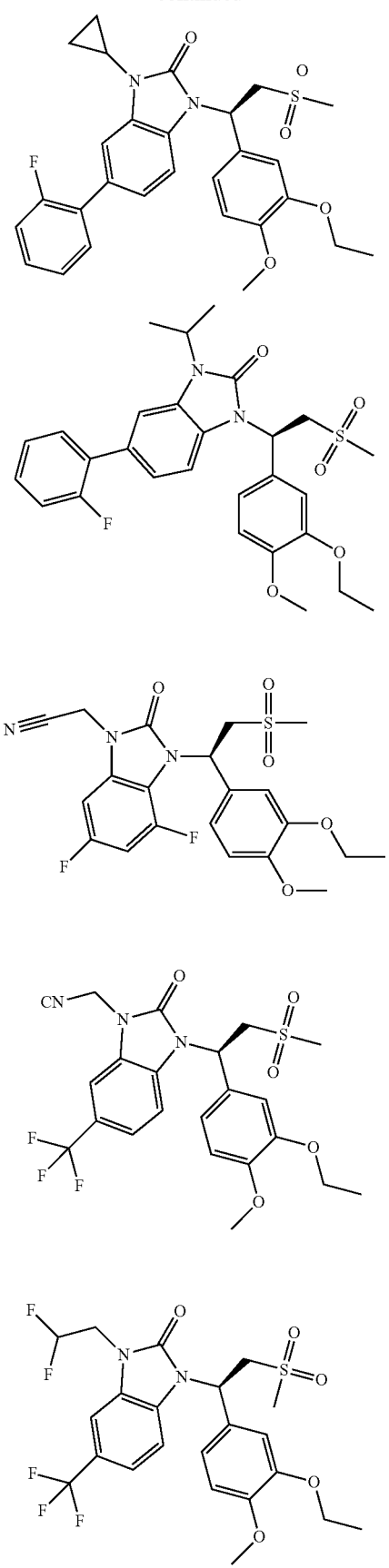

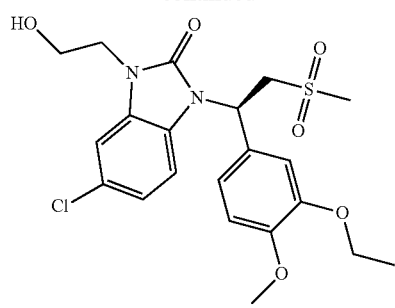
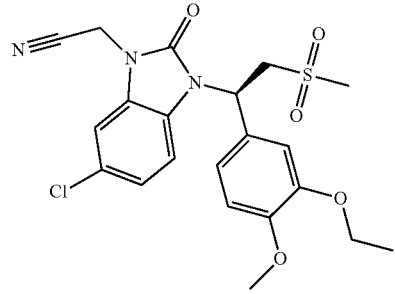
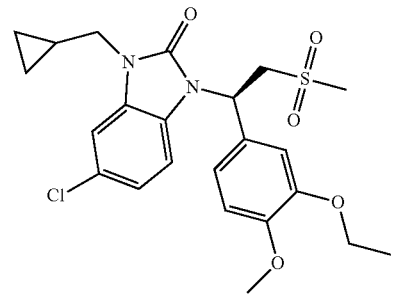
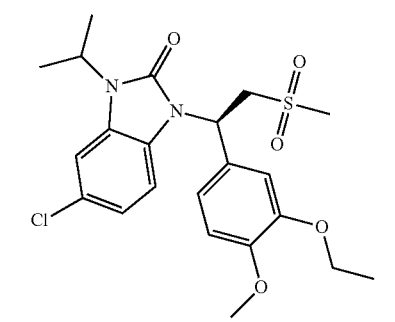
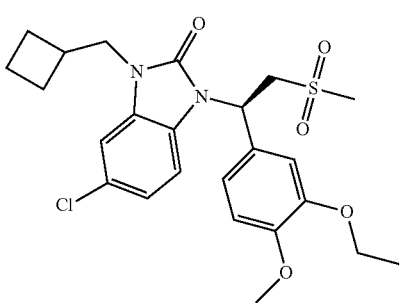
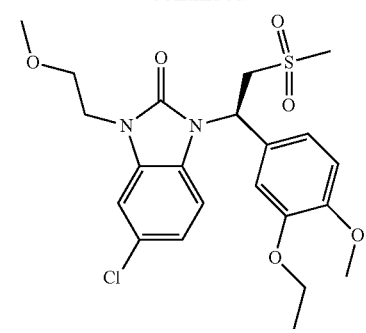
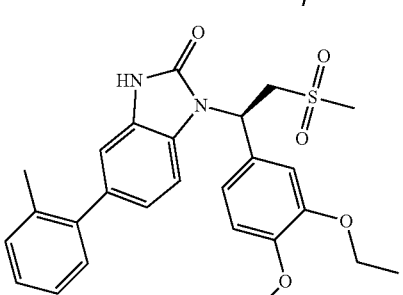
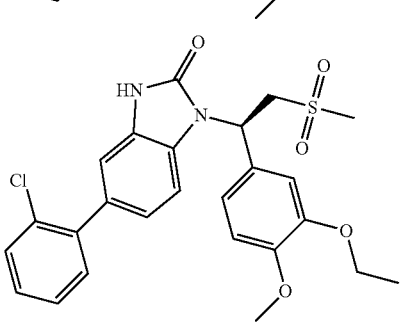
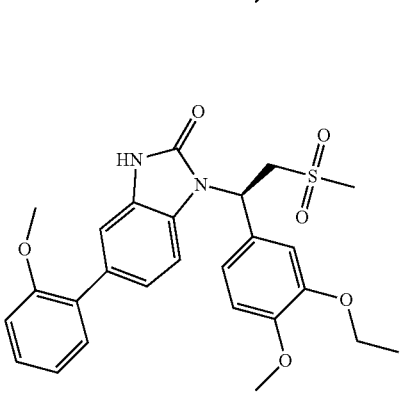
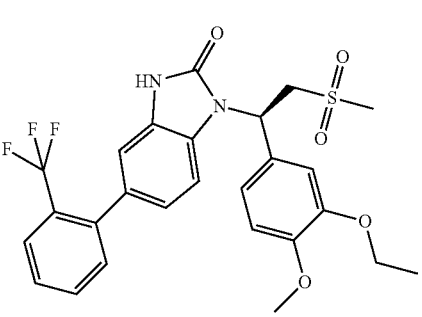

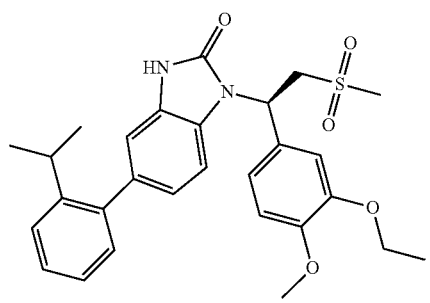
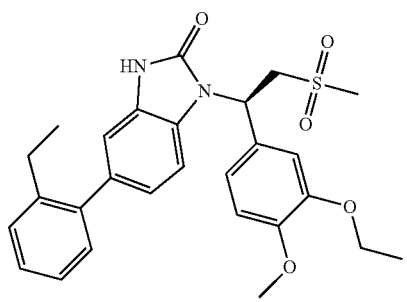
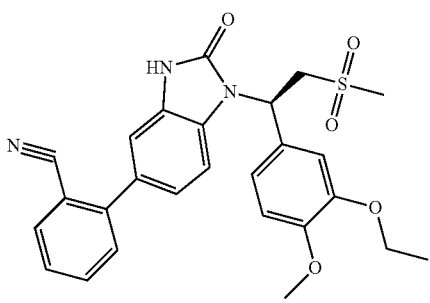
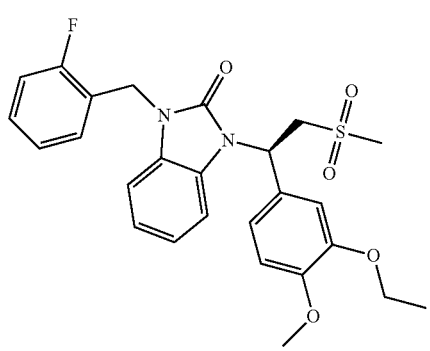
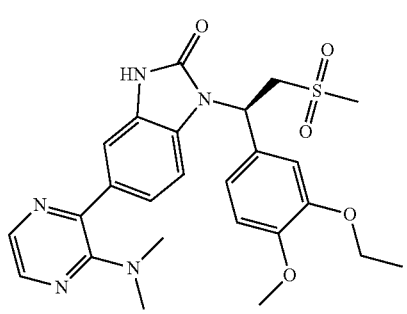
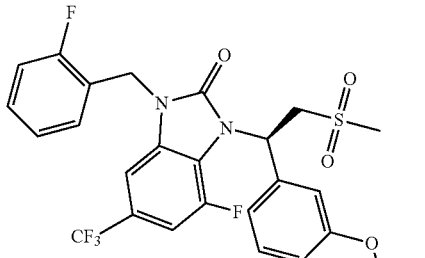
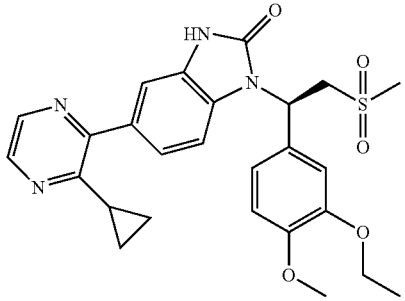
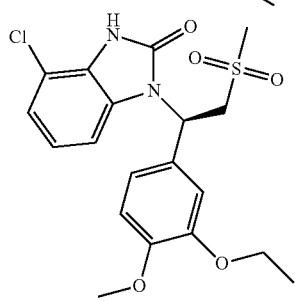
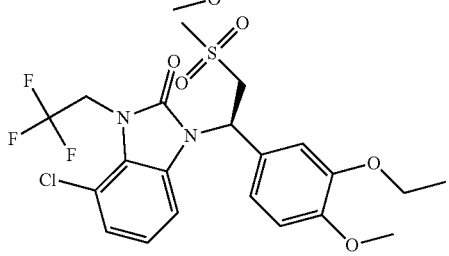
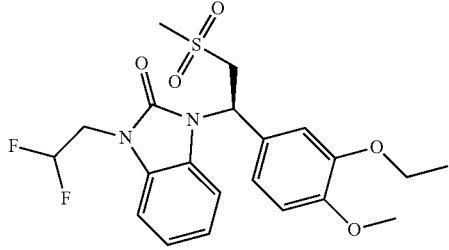
and
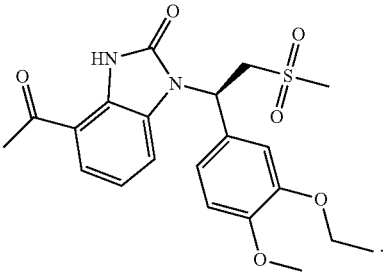

The present invention also provides a pharmaceutical composition, comprising a therapeutically effective amount of the compound or the pharmaceutically acceptable salt thereof as the active ingredient, and a pharmaceutically acceptable carrier.

The present invention also provides a use of the compound or the pharmaceutically acceptable salt thereof in manufacturing a medicament for treating a disease related to PDE4.

TECHNICAL EFFECT

Compared with Apremilast, the compound of the present invention reduces the distribution in the brain, potentially reducing vomiting and side effects associated with the brain. It significantly increases the inhibitory effect of the compound of the present invention on TNF-α in hPBMC and reduces the therapeutically effective dose in animal experiments, thereby reducing the therapeutically effective dose for human and increasing the safety factor therefor. It has improved the characteristics of pharmacokinetics and is expected to be administered to a human once a day.

DEFINITION AND DESCRIPTION

Unless otherwise indicated, the following terms when used in the descriptions and the claims of the present invention have the following meanings. A specific term or phrase should not be considered indefinite or unclear in the absence of a particular definition, but should be understood in the ordinary sense. When a trade name appears herein, it is intended to refer to its corresponding commodity or active ingredient thereof. The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, allergic reaction or other problems or complications, commensurate with a reasonable benefit/risk ratio.

The term "pharmaceutically acceptable salt" refers to a salt of the compound of the present invention that is prepared by reacting the compound having a specific substituent of the present invention with a relatively non-toxic acid or base. When the compound of the present invention contains a relatively acidic functional group, a base addition salt can be obtained by bringing the neutral form of the compound into contact with a sufficient amount of base in a pure solution or a suitable inert solvent. The pharmaceutically acceptable base addition salt includes a salt of sodium, potassium, calcium, ammonium, organic amine or magnesium or similar salts. When the compound of the present invention contains a relatively basic functional group, an acid addition salt can be obtained by bringing the neutral form of the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and an salt of amino acid (such as arginine and the like), and a salt of an organic acid such as glucuronic acid and the like (refer to Berge et al., "*Pharmaceutical Salts*", *Journal of Pharmaceutical Science* 66: 1-19 (1977)). Certain specific compounds of the present invention that contain both basic and acidic functional groups can be converted to any base or acid addition salt.

Preferably, through bringing the salt into contact with a base or an acid in a conventional manner, then separating the parent compound, the neutral form of the compound is thereby regenerated. The difference between the parent form of the compound and its various salt forms lies in specific physical properties, such as different solubility in a polar solvent.

"Pharmaceutically acceptable salt" used herein belongs to a derivative of the compound of the present invention, wherein, the parent compound is modified by forming a salt with an acid or a base. Examples of the pharmaceutically acceptable salt include but are not limited to an inorganic acid or organic acid salt of a basic moiety such as amine, an alkali metal salt or an organic salt of an acidic moiety such as carboxylic acid, and the like. The pharmaceutically acceptable salt includes conventional non-toxic salt or quaternary ammonium salt of the parent compound, such as a salt formed by a non-toxic inorganic acid or an organic acid. The conventional non-toxic salt includes but is not limited to the salt derived from an inorganic acid and an organic acid, wherein the inorganic acid or organic acid is selected from the group consisting of 2-acetoxybenzoic acid, 2-hydroxyethanesulfonic acid, acetic acid, ascorbic acid, benzenesulfonic acid, benzoic acid, bicarbonate, carbonic acid, citric acid, edetic acid, ethanedisulfonic acid, ethanesulfonic acid, fumaric acid, glucoheptose, gluconic acid, glutamic acid, glycolic acid, hydrobromic acid, hydrochloric acid, hydroiodide, hydroxyl, hydroxynaphthalene, isethionic acid, lactic acid, lactose, dodecyl sulfonic acid, maleic acid, malic acid, mandelic acid, methanesulfonic acid, nitric acid, oxalic acid, pamoic acid, pantothenic acid, phenylacetic acid, phosphoric acid, polygalactanal acid, propionic acid, salicylic acid, stearic acid, subacetic acid, succinic acid, sulfamic acid, sulfanilic acid, sulfuric acid, tannin, tartaric acid and p-toluenesulfonic acid.

The pharmaceutically acceptable salt of the present invention can be prepared from the parent compound that contains an acidic or basic moiety by conventional chemical method. Generally, such salt can be prepared by reacting the free acid or base form of the compound with a stoichiometric amount of an appropriate base or acid in water or an organic solvent or a mixture thereof. Generally, non-aqueous media such as ether, ethyl acetate, ethanol, isopropanol or acetonitrile are preferred.

In addition to the salt form, the compound provided by the present invention also exists in prodrug form. The prodrug of the compound described herein is the compound that readily undergoes chemical change under physiological condition to be converted into the compound of the present invention. Additionally, the prodrug can be converted to the compound of the present invention by a chemical or biochemical method in vivo environment.

Certain compounds of the present invention can exist in an nonsolvated form or a solvated form, including hydrated form. Generally, the solvated form is equivalent to the nonsolvated form, and both are encompassed within the scope of the present invention.

Certain compounds of the present invention can have an asymmetric carbon atom (optical center) or a double bond.

The racemate, diastereomer, geometric isomer and individual isomer are all encompassed within the scope of the present invention.

Unless otherwise specified, the absolute configuration of a stereogenic center is represented by a wedged solid bond (▰) and a wedged dashed bond (▱), and the relative configuration of a stereogenic center is represented by a straight solid bond (▰) and a straight dashed bond (▱). When the compound described herein contains an olefinic double bond or other geometric asymmetric centers, E and Z geometric isomers are included unless otherwise specified. Likewise, all tautomeric forms are encompassed within the scope of the present invention.

The compound of the present invention may have a specific geometric or stereoisomeric form. The present invention contemplates all such compounds, including cis and trans isomer, (−)- and (+)-enantiomer, (R)- and (S)-enantiomer, diastereoisomer, (D)-isomer, (L)-isomer, and racemic mixture and other mixtures, for example, an enantiomer or diastereoisomer enriched mixture, all of which are encompassed within the scope of the present invention. The substituent such as alkyl may have an additional asymmetric carbon atom. All these isomers and mixtures thereof are encompassed within the scope of the present invention.

Optically active (R)- and (S)-isomer, or D and L isomer can be prepared using chiral synthesis or chiral reagents or other conventional techniques. If one kind of enantiomer of certain compound of the present invention is to be obtained, the pure desired enantiomer can be obtained by asymmetric synthesis or derivative action of chiral auxiliary followed by separating the resulting diastereomeric mixture and cleaving the auxiliary group. Alternatively, when the molecule contains a basic functional group (such as amino) or an acidic functional group (such as carboxyl), the compound reacts with an appropriate optically active acid or base to form a salt of the diastereomeric isomer which is then subjected to diastereomeric resolution through the conventional method in the art to give the pure enantiomer. In addition, the enantiomer and the diastereoisomer are generally isolated through chromatography which uses a chiral stationary phase and optionally combines with a chemical derivative method (such as carbamate generated from amine).

The compound of the present invention may contain an unnatural proportion of atomic isotope at one or more than one atom(s) that constitute the compound. For example, the compound can be radiolabeled with a radioactive isotope, such as tritium ($^3$H), iodine-125 ($^{125}$I) or C-14 ($^{14}$C). All isotopic variations of the compound of the present invention, whether radioactive or not, are encompassed within the scope of the present invention.

The term "pharmaceutically acceptable carrier" refers to any agent or carrier medium which is capable of delivering an effective amount of the active substance of the present invention, does not interfere with the biological activity of the active substance and has no toxic side effect on the host or patient. The representative carrier includes water, oil, vegetable and mineral, cream base, lotion base, ointment base and the like. The base includes a suspending agent, a thickener, a penetration enhancer and the like. Their formulations are well known to the skilled in the cosmetic field or the topical pharmaceutical field.

The term "excipient" generally refers to a carrier, a diluent and/or a medium required for formulating an effective pharmaceutical composition.

For a medicament or a pharmacologically active agent, the term "effective amount" or "therapeutically effective amount" refers to a nontoxic but sufficient amount to achieve a desired effect of the medicament or the agent. For the oral dosage form of the present invention, an "effective amount" of the active substance in the composition refers to an amount required for achieving a desired effect when combining with another active substance in the composition. The effective amount varies from person to person and is determined depending on the age and general condition of the recipient as well as the specific active substance. The appropriate effective amount in an individual case can be determined by the skilled in the art based on routine experiment.

The term "active ingredient", "therapeutic agent", "active substance" or "active agent" refers to a chemical entity which can effectively treat the target disorder, disease or condition.

"Optional" or "optionally" means that the subsequent event or condition may occur but not requisite, that the term includes the instance in which the event or condition occurs and the instance in which the event or condition does not occur.

The term "substituted" means one or more than one hydrogen atom(s) on a specific atom are substituted with the substituent, including deuterium and hydrogen variants, as long as the valence of the specific atom is normal and the substituted compound is stable. When the substituent is a ketone (i.e. =O), it means two hydrogen atoms are substituted. Positions on an aromatic ring cannot be substituted with a ketone. The term "optionally substituted" means an atom can be substituted with a substituent or not, unless otherwise specified, the type and number of the substituent may be arbitrary as long as being chemically achievable.

When any variable (such as R) occurs in the constitution or structure of the compound more than once, the definition of the variable at each occurrence is independent. Thus, for example, if a group is substituted with 0-2 R, the group can be optionally substituted with up to two R, wherein the definition of R at each occurrence is independent. Moreover, a combination of the substituent and/or the variant thereof is allowed only when the combination results in a stable compound.

When the number of a linking group is 0, such as —(CRR)$_0$—, it means that the linking group is a single bond.

When one of the variables is selected from a single bond, it means that the two groups linked by the single bond are connected directly. For example, when L in A-L-Z represents a single bond, the structure of A-L-Z is actually A-Z.

When a substituent is vacant, it means that the substituent does not exist. For example, when X is vacant in A-X, the structure of A-X is actually A. When a bond of a substituent can be cross-linked to more than one atom on a ring, such substituent can be bonded to any atom of the ring. When an enumerative substituent does not indicate by which atom it is attached to a compound included in the general chemical formula but not specifically mentioned, such substituent can be bonded by any of its atoms. A combination of substituents and/or variants thereof is allowed only when such combination can result in a stable compound. For example, the structural unit

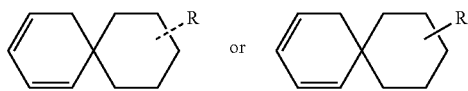

means that the substituent R can be located at any position on cyclohexyl or cyclohexadiene.

Unless otherwise specified, the term "hetero" represents a heteroatom or a heteroatom group (e.g., an atom group containing a heteroatom), including the atom except carbon (C) and hydrogen (H) and the atom group containing the above heteroatom, for example, including oxygen (O), nitrogen (N), sulfur (S), silicon (Si), germanium (Ge), aluminum (Al), boron (B), —O—, —S—, =O, =S, —C(=O)O—, —C(=O)—, —C(=S)—, —S(=O), —S(=O)$_2$—, and the group consisting of —C(=O)N(H)—, —N(H)—, —C(=NH)—, —S(=O)$_2$N(H)— and —S(=O)N(H)—, each of which is optionally substituted.

Unless otherwise specified, the term "ring" refers to a substituted or unsubstituted cycloalkyl, heterocycloalkyl, cycloalkenyl, heterocycloalkenyl, cycloalkynyl, heterocycloalkynyl, aryl or heteroaryl. The so-called ring includes a single ring, a ring assembly, a spiral ring, a fused ring or a bridged ring. The number of the atom on the ring is usually defined as the member number of the ring, for example, a "5-7 membered ring" means that 5 to 7 atoms are arranged on a ring. Unless otherwise specified, the ring optionally contains 1 to 3 heteroatoms. Therefore, a "5-7 membered ring" includes, for example, phenyl, pyridinyl and piperidinyl; on the other hand, the term "5-7 membered heterocycloalkyl ring" includes pyridyl and piperidinyl, but excluding phenyl. The term "ring" also includes a ring system containing at least one ring, wherein each ring independently meets the above definition.

Unless otherwise specified, the term "heterocycle" or "heterocyclo" refers to a stable monocyclic, bicyclic or tricyclic ring containing a heteroatom or a heteroatom group, which can be saturated, partially unsaturated or unsaturated (aromatic) and can contain carbon atoms and 1, 2, 3 or 4 ring heteroatoms independently selected from N, O and S, wherein any of the above heterocycle can be fused to a benzene ring to form a bicyclic ring. Nitrogen and sulfur heteroatoms can optionally be oxidized (i.e., NO and S(O)p, p is 1 or 2). Nitrogen atom can be substituted or unsubstituted (i.e., N or NR, wherein R is H or other substituents already defined herein). The heterocycle can be attached to the pendant group of any heteroatom or carbon atom to form a stable structure. If the resulting compound is stable, the heterocycle described herein may have a substitution at a carbon or nitrogen position. Nitrogen atom on the heterocycle is optionally quaternized. In a preferred embodiment, when the total number of S and O atom of the heterocycle is more than 1, the heteroatom is not adjacent to each other. In another preferred embodiment, the total number of S and O atom of the heterocycle is not more than 1. As used herein, the term "aromatic heterocyclic group" or "heteroaryl" refers to a stable 5-, 6- or 7-membered monocyclic or bicyclic or 7-, 8-, 9- or 10-membered bicyclic heterocyclic aromatic ring which contains carbon atoms and 1, 2, 3 or 4 ring heteroatoms independently selected from N, O and S. Nitrogen atom can be substituted or unsubstituted (i.e., N or NR, wherein R is H or other substituents already defined herein). Nitrogen and sulfur heteroatoms may optionally be oxidized (i.e., NO and S(O)p, p is 1 or 2). It is worth noting that the total number of S and O atom of an aromatic heterocycle is not more than one. The bridged ring is also included in the definition of the heterocycle. A bridged ring is formed when one or more than one atom (i.e, C, O, N or S) link two non-adjacent carbon or nitrogen atoms. A preferred bridged ring includes, but not limited to one carbon atom, two carbon atoms, one nitrogen atom, two nitrogen atoms and one carbon-nitrogen group. It is worth noting that a bridge always converts a monocyclic ring to a tricyclic ring. In a bridged ring, the substituent on the ring may also be present on the bridge.

Examples of the heterocyclic compound include, but are not limited to: acridinyl, azocinyl, benzimidazolyl, benzofuranyl, benzomercaptofuranyl, benzomercaptophenyl, benzoxazolyl, benzoxazolinyl, benzothiazolyl, benzotriazolyl, benzotetrazolyl, benzoisoxazolyl, benzoisothiazolyl, benzoimidazolinyl, carbazolyl, 4aH-carbazolyl, carbolinyl, chromanyl, chromene, cinnolinyl decahydroquinolinyl, 2H,6H-1,5,2-dithiazinyl, dihydrofuro[2,3-b]tetrahydrofuranyl, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isoindolyl, isoindolinyl, isoquinolinyl, isothiazolyl, isoxazolyl, methylenedioxyphenyl, morpholinyl, naphthyridinyl, octahydro-isoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, hydroxindolyl, pyrimidinyl, phenanthridinyl, phenanthrolinyl, phenazine, phenothiazine, benzoxanthinyl, phenoloxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyrido-oxazolyl, pyrido-imidazolyl, pyrido-thiazolyl, pyridinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, isothiazolylthienyl, thieno-oxazolyl, thieno-thiazolyl, thieno-imidazolyl, thienyl, triazinyl, 1,2,3-triazolyl, 1,2,4-triazolyl, 1,2,5-triazolyl, 1,3,4-triazolyl and xanthenyl. Also included are fused-ring compounds and spiro compounds.

Unless otherwise specified, the term "hydrocarbyl" or its hyponyms (e.g. alkyl, alkenyl, alkynyl, and aryl, etc.), by itself or as part of another substituent, refers to a linear, branched chain or cyclic hydrocarbon radical or any combination thereof. They can be fully saturated (e.g. alkyl), mono- or polyunsaturated (e.g. alkenyl, alkynyl, and aryl), can be mono-, di- or poly-substituted, can be monovalent (e.g. methyl), divalent (e.g. methylene) or multivalent (e.g. methenyl), can also include a divalent or multivalent group, have a specified number of carbon atom (for example, $C_1$-$C_{12}$ indicates 1 to 12 carbon atoms, $C_{1-12}$ is selected from $C_1$, $C_2$, $C_3$, $C_4$, $C_5$, $C_6$, $C_7$, $C_8$, $C_9$, $C_{10}$, $C_{11}$ and $C_{12}$; $C_{3-12}$ is selected from $C_3$, $C_4$, $C_5$, $C_6$, $C_7$, $C_8$, $C_9$, $C_{10}$, $C_{11}$ and $C_{12}$). The term "hydrocarbyl" includes, but is not limited to aliphatic hydrocarbyl and aromatic hydrocarbyl. The aliphatic hydrocarbyl includes linear and cyclic hydrocarbyl, specifically includes but not limited to alkyl, alkenyl, and alkynyl. The aromatic hydrocarbyl includes but is not limited to 6-12 membered aromatic hydrocarbyl such as phenyl, naphthyl and the like. In some embodiments, the term "hydrocarbyl" refers to a linear or branched group or a combination thereof which can be fully saturated, mono- or polyunsaturated, and can include a divalent or multivalent group. Examples of the saturated hydrocarbyl group include, but are not limited to, methyl, ethyl, n-propyl, isopropyl, n-butyl, tert-butyl, isobutyl, sec-butyl, cyclohexyl, (cyclohexyl)methyl, cyclopropylmethyl, and the homolog or isomer of n-amyl, n-hexyl, n-heptyl, n-octyl and other atom groups. The unsaturated hydrocarbyl has one or more than one double or triple bonds. Examples of the unsaturated alkyl include but are not limited to, vinyl, 2-propenyl, butenyl, crotyl, 2-isopentenyl, 2-(butadienyl), 2,4-pentadienyl, 3-(1,4-pentadienyl), ethynyl, 1- and 3-propynyl, 3-butynyl, and more higher homologs and isomers.

Unless otherwise specified, the term "heterohydrocarbyl" or its hyponyms (such as heteroalkyl, heteroalkenyl, heteroalkynyl, and heteroaryl, etc.), by itself or as part of another substituent, refers to a stable linear, branched or cyclic hydrocarbon group or any combination thereof, which has a specified number of carbon atoms and at least one heteroatom. In some embodiments, the term "heteroalkyl" by itself or in combination with another term refers to a stable linear chain, branched hydrocarbon radical or a combination thereof which has a specified number of carbon atoms and at least one heteroatom. In a specific embodiment, a heteroatom is selected from B, O, N and S, wherein nitrogen and sulfur atoms are optionally oxidized and the nitrogen atom is optionally quaternized. The heteroatom or heteroatom group can be located at any interior position of a heterohydrocarbyl, including the position where the hydrocarbyl attaches to the rest part of the molecule. But the terms "alkoxy", "alkylamino" and "alkylthio" (or thioalkyl) are used by the conventional meaning and refer to an alkyl group connected to the rest part of the molecule via an oxygen atom, an amino or a sulfur atom respectively. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$—S(O)—CH$_3$, —CH$_2$—CH$_2$—S(O)$_2$—CH$_3$, —CH=CH—O—CH$_3$, —CH$_2$—CH=N—OCH$_3$ and —CH=CH—N(CH$_3$)—CH$_3$. Up to two consecutive heteroatoms can be present, such as, —CH$_2$—NH—OCH$_3$.

Unless otherwise specified, the term "cyclohydrocarbyl", "heterocyclohydrocarbyl" or its hyponyms (such as aryl, heteroaryl, cycloalkyl, heterocycloalkyl, cycloalkenyl, heterocycloalkenyl, cycloalkynyl, heterocycloalkynyl, etc.) by itself or in combination with another term refers to cyclized "hydrocarbyl" or "heterohydrocarbyl". Furthermore, for heterohydrocarbyl or heterocyclohydrocarbyl (e.g. heteroalkyl, and heterocycloalkyl), one heteroatom can occupy the position where the heterocycle attaches to the remainder position of the molecule. Examples of the cycloalkyl include, but are not limited to, cyclopentyl, cyclohexyl, 1-cyclohexenyl, 3-cyclohexenyl, cycloheptyl and the like. Non-limiting examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydro-thiophen-2-yl, tetrahydro-thiophen-3-yl, 1-piperazinyl and 2-piperazinyl.

Unless otherwise specified, the term "alkyl" refers to a linear chain or branched saturated hydrocarbon group, can be mono-substituted (e.g. —CH$_2$F) or poly-substituted (e.g. —CF$_3$), can be monovalent (e.g. methyl), divalent (e.g. methylene) or multivalent (e.g. methenyl). Examples of alkyl include methyl (Me), ethyl (Et), propyl (such as n-propyl and isopropyl), butyl (such as n-butyl, isobutyl, s-butyl, t-butyl), pentyl (such as n-pentyl, isopentyl, neopentyl) and the like.

Unless otherwise specified, the term "alkenyl" refers to an alkyl group having one or more than one carbon-carbon double bonds at any position on the chain, can be mono-substituted or poly-substituted, and can be monovalent, divalent or multivalent. Examples of alkenyl include ethenyl, propenyl, butenyl, pentenyl, hexenyl, butadienyl, pentadienyl, hexadienyl, and the like.

Unless otherwise specified, the term "alkynyl" refers to an alkyl group having one or more than one carbon-carbon triple bonds at any position on the chain, can be mono-substituted or poly-substituted, and can be monovalent, divalent or multivalent. Examples of alkynyl include ethynyl, propynyl, butynyl, pentynyl, hexynyl, and the like.

Unless otherwise specified, cycloalkyl includes any stable cyclic or polycyclic hydrocarbyl, and any carbon atom is saturated, can be mono-substituted or poly-substituted, and can be monovalent, divalent or multivalent. Examples of cycloalkyl include, but are not limited to, cyclopropyl, norbornanyl, [2.2.2]bicyclooctane, [4.4.0]bicyclodecanyl and the like.

Unless otherwise specified, cycloalkenyl includes any stable cyclic or polycyclic hydrocarbyl having one or more than one unsaturated carbon-carbon single bonds at any position on the ring, can be mono-substituted or poly-substituted, and can be monovalent, divalent or multivalent. Examples of the cycloalkenyl include, but are not limited to, cyclopentenyl, cyclohexenyl and the like.

Unless otherwise specified, cycloalkynyl includes any stable cyclic or polycyclic hydrocarbyl having one or more carbon-carbon triple bonds at any position on the ring, can be mono-substituted or poly-substituted, and can be monovalent, divalent or multivalent.

Unless otherwise specified, the term "halo" or "halogen" by itself or as part of another substituent refers to fluorine, chlorine, bromine or iodine atom. Furthermore, the term "haloalkyl" is meant to include monohaloalkyl and polyhaloalkyl. For example, the term "halo(C$_1$-C$_4$)alkyl" is meant to include, but not limited to, trifluoromethyl, 2,2,2-trifluoroethyl, 4-chlorobutyl, 3-bromopropyl and the like. Examples of haloalkyl include, but not limited to trifluoromethyl, trichloromethyl, pentafluoroethyl and pentachloroethyl.

The term "alkoxy" represents any alkyl defined above having a specified number of carbon atoms attached by an oxygen bridge. Unless otherwise specified, C$_{1-6}$ alkoxy includes C$_1$, C$_2$, C$_3$, C$_4$, C$_5$ and C$_6$ alkoxy. Examples of alkoxy include, but not limited to methoxy, ethoxy, n-propoxy, isopropoxy, n-butoxy, sec-butoxy, tert-butoxy, n-pentyloxy and S-pentoxy. Unless otherwise specified, the term "aryl" refers to a polyunsaturated aromatic substituent, can be mono-, di- or poly-substituted, can be a monovalent, divalent or multivalent, can be a single ring or a multiple ring (e.g. one to three rings; wherein at least one ring is aromatic), which are fused together or connected covalently. The term "heteroaryl" refers to an aryl (or ring) containing one to four heteroatoms. In an illustrative example, the heteroatom is selected from B, O, N and S, wherein nitrogen and sulfur atoms are optionally oxidized and nitrogen atom is optionally quaternized. A heteroaryl may attach to the rest part of a molecule via a heteroatom. Non-limiting examples of aryl or heteroaryl include phenyl, naphthyl, biphenyl, pyrrolyl, pyrazolyl, imidazolyl, pyrazinyl, oxazolyl, phenyl-oxazolyl, isoxazolyl, thiazolyl, furanyl, thienyl, pyridyl, pyrimidinyl benzothiazolyl, purinyl, benzimidazolyl, indolyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl and 6-quinolyl. The substituent of any of the above aryl and heteroaryl ring system is selected from the acceptable substituent described below.

Unless otherwise specified, when aryl combines with other terms (such as aryloxy, arylthio, arylalkyl), the aryl includes the aryl and heteroaryl ring as defined above. Thus, the term "aralkyl" is meant to include the group (e.g. benzyl, phenethyl, pyridylmethyl, etc.) where an aryl is attached to an alkyl, including an alkyl where the carbon atom (e.g. methylene) has been replaced by an atom such as oxygen, for example, phenoxymethyl, 2-pyridyloxy, 3-(1-naphthyloxy)propyl, and the like.

The term "leaving group" refers to a functional group or atom which can be replaced by another functional group or atom through a substitution reaction (such as affinity substitution reaction). For example, representative leaving groups include triflate; chlorine, bromine and iodine; sulfonate group, such as mesylate, tosylate, p-bromobenzenesulfonate, p-toluenesulfonates and the like; acyloxy, such as acetoxy, trifluoroacetoxy and the like.

The term "protecting group" includes, but is not limited to "amino protecting group", "hydroxy protecting group" or "thio protecting group". The term "amino protecting group" refers to a protecting group suitable for blocking the side reaction on the nitrogen of an amino. Representative amino protecting groups include, but are not limited to: formyl; acyl, such as alkanoyl (e.g. acetyl, trichloroacetyl or trifluoroacetyl); alkoxycarbonyl, such as tert-butoxycarbonyl (Boc); arylmethoxycarbonyl such as benzyloxycarbonyl (Cbz) and 9-fluorenylmethoxycarbonyl (Fmoc); arylmethyl such as benzyl (Bn), trityl (Tr), 1,1-bis-(4'-methoxyphenyl) methyl; silyl such as trimethylsilyl (TMS) and tert-butyldimethylsilyl (TBS) and the like. The term "hydroxy protecting group" refers to a protecting group suitable for blocking the side reaction on hydroxy. Representative hydroxy protecting groups include, but are not limited to: alkyl such as methyl, ethyl and tert-butyl; acyl such as alkanoyl (e.g. acetyl); arylmethyl such as benzyl (Bn), p-methoxybenzyl (PMB), 9-fluorenylmethyl (Fm), and diphenylmethyl (benzhydryl, DPM); silyl such as trimethylsilyl (TMS) and tert-butyl dimethyl silyl (TBS) and the like.

The compound of the present invention can be prepared by a variety of synthetic methods well known to the skilled in the art, including the following enumerative embodiment, the embodiment formed by the following enumerative embodiment in combination with other chemical synthesis methods and the equivalent replacement well known to the skilled in the art. The preferred embodiment includes, but is not limited to the embodiment of the present invention.

All of the solvents used in the present invention are commercially available. This present invention adopts the abbreviating words as followed: aq refers to aqueous; "HATU" refers to 2-(7-Azabenzotriazol-1-yl)-N,N,N',N'-tetramethyluroniumhexafluorophosphate; "EDC" refers to N-(3-Dimethylaminopropyl)-N'-ethylcarbodiimide hydrochloride; "m-CPBA" refers to 3-chloroperoxybenzoic acid; "eq" refers to equal; "CDI" refers to carbonyldiimidazole; "DCM" refers to dichloromethane; "PE" refers to petroleum ether; "DIAD" refers to diisopropyl azodiformate; "DMF" refers to N,N-dimethylformamide; "DMSO" refers to dimethyl sulfoxide; "EtOAc" refers to ethyl acetate; "EtOH" refers to ethanol; "MeOH" refers to methanol; "CBz" refers to carbobenzyloxy, a kind of protecting group for amine; "BOC" refers to t-butyloxy carbonyl; "HOAc" refers to acetic acid; "NaCNBH$_3$" refers to sodium cyanoborohydride; r.t. refers to room temperature; O/N refers to overnight; "THF" refers to tetrahydrofuran; "Boc$_2$O" refers to di-tert-butyl dicarbonate; "TFA" refers to trifluoroacetic acid; "DIPEA" refers to ethyldiisopropylamine; "SOCl$_2$" refers to thionyl chloride; "CS$_2$" refers to carbon disulfide; TsOH refers to p-toluenesulfonic acid; "NFSI" refers to N-Fluorobenzenesulfonimide; "NCS" refers to 1-chloropyrrolidine-2,5-diketone; "n-Bu4NF" refers to tetrabutylammonium fluoride; "iPrOH" refers to 2-propanol; "mp" refers to melting point. "LDA" refers to lithium diisopropylamide.

Compounds are named manually or by ChemDraw® software, the commercially available compounds use their vendor directory names.

DETAILED DESCRIPTION OF THE PREFERRED EMBODIMENT

The following examples further illustrate the present invention, but the present invention is not limited thereto. The present invention has been described in detail in the text, and its specific embodiments have also been disclosed, for one skilled in the art, it is obvious to modify and improve the embodiments of the present invention within the spirit and scope of the present invention.

Embodiment 1: WX001

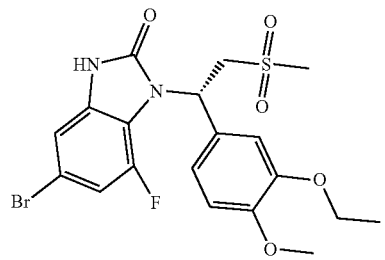 [SMILES: CCOc1cc([C@@H](CS(C)(=O)=O)n2c(=O)[nH]c3cc(Br)cc(F)c32)ccc1OC]

Synthesis Route:

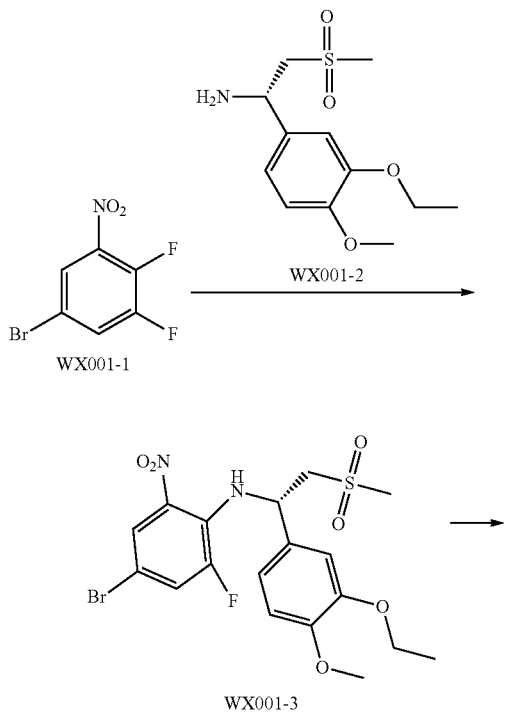

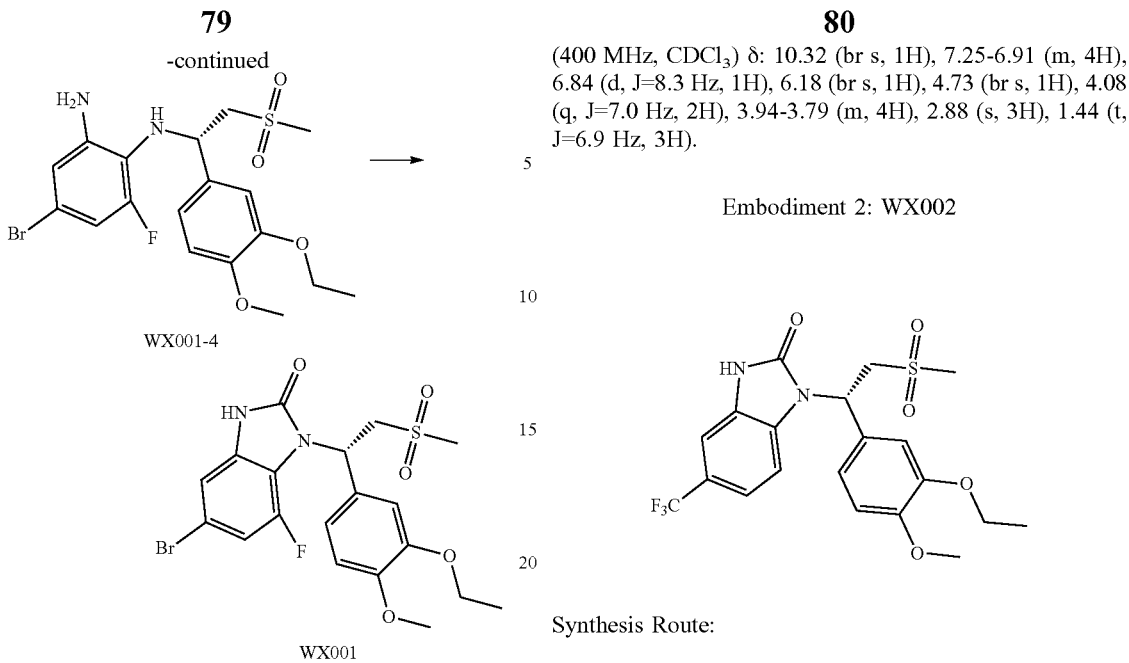

Step 1: Preparation of Compound WX001-3

Compound WX001-2 (285.00 mg, 1.04 mmol) and compound WX001-1 (250.00 mg, 1.05 mmol) were dissolved in acetonitrile (15 mL) at room temperature, followed by the addition of potassium carbonate (199.80 mg, 1.45 mmol). The reaction mixture was heated to 50° C. and stirred for 6 hours. After the reaction, the mixture was cooled to room temperature. Insolubles was removed by filtration and the filter cake was washed with dichloromethane (10 mL×2). The filtrate was combined and concentrated under reduced pressure. The obtained residue was purified by column chromatography (eluent:ethyl acetate/petroleum ether=1/1-2/1, volume ratio) to obtain the target product WX001-3. $^1$H NMR (400 MHz, CDCl$_3$) δ: 8.21-8.01 (m, 2H), 7.39-7.23 (m, 1H), 6.83 (d, J=12.5 Hz, 3H), 5.61-5.50 (m, 1H), 4.16-3.98 (m, 2H), 3.85 (s, 3H), 3.70-3.57 (m, 1H), 3.55-3.43 (m, 1H), 2.76 (s, 3H), 1.46 (t, J=6.9 Hz, 3H).

Step 2: Preparation of Compound WX001-4

Compound WX001-3 (270.00 mg, 549.53 μmol) was dissolved in methanol (20 mL) at room temperature, followed by the addition of zinc powder (359.34 mg, 5.50 mmol) and ammonium chloride (293.94 mg, 5.50 mmol). The reaction mixture was stirred at room temperature for 1.5 hours. After the reaction, insolubles was removed by filtration, and the filter cake was washed with methanol (10 mL×2). The filtrate was combined and concentrated under reduced pressure to obtain the crude product WX001-4.

Step 3: Preparation of Compound WX001

Compound WX001-4 (250.00 mg, 541.90 μmol) and triethylamine (329.01 mg, 3.25 mmol) were dissolved in tetrahydrofuran (50 mL) at 0° C., followed by the addition of triphosgene (192.97 mg, 650.28 μmol). The reaction mixture was stirred at 0° C. for 2 hours. After the reaction, the mixture was quenched with the aqueous solution of triethylamine (1 mL in 20 mL), diluted with saturated brine (20 mL), and extracted with ethyl acetate (20 mL×3). The organic phases were combined, washed with saturated brine (30 mL×2) and dried over anhydrous sodium sulfate, followed by filtration. The filtrate was concentrated under reduced pressure. The obtained residue was purified by preparative HPLC to obtain the target product WX001. MS-ESI m/z: 487.0 [M+H]$^+$, 489.0 [M+H+2]$^+$. $^1$H NMR (400 MHz, CDCl$_3$) δ: 10.32 (br s, 1H), 7.25-6.91 (m, 4H), 6.84 (d, J=8.3 Hz, 1H), 6.18 (br s, 1H), 4.73 (br s, 1H), 4.08 (q, J=7.0 Hz, 2H), 3.94-3.79 (m, 4H), 2.88 (s, 3H), 1.44 (t, J=6.9 Hz, 3H).

Embodiment 2: WX002

Synthesis Route:

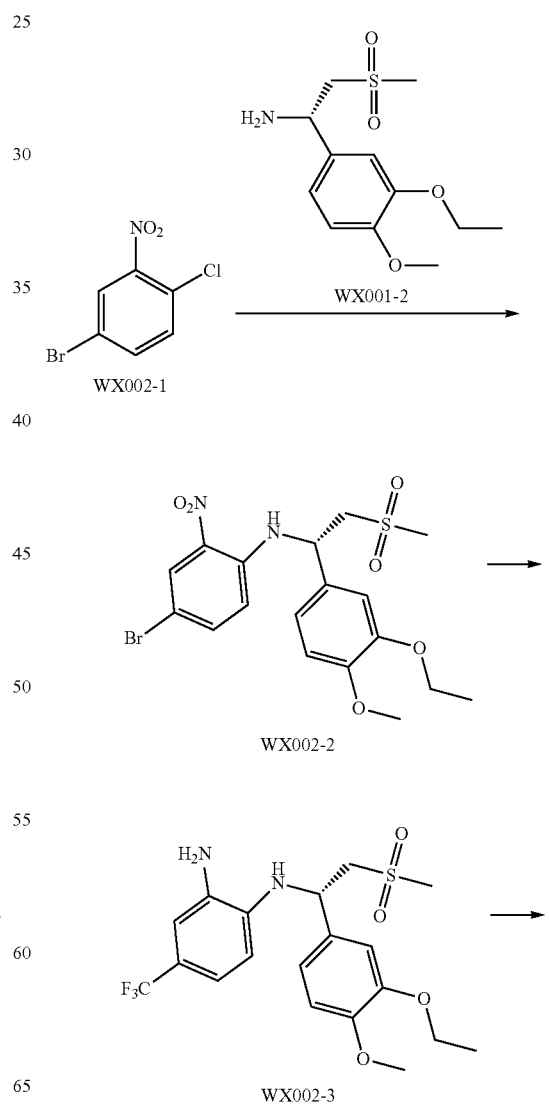

-continued

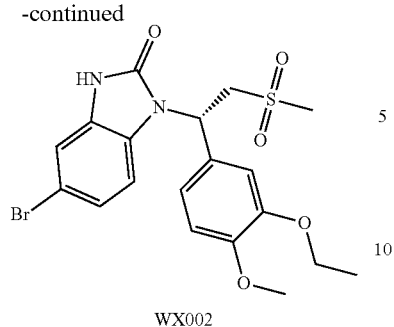

WX002

Step 1: Preparation of Compound WX002-2

Compound WX002-1 (151.52 mg, 671.80 μmol) and the N-acetyl-L-leucinate salt of compound WX001-2 (183.00 mg, 671.80 μmol) and potassium carbonate (185.70 mg, 1.34 mmol) were added to N,N-dimethylformamide (3.00 mL) at room temperature. The reaction mixture was heated to 70° C. and stirred for 3 hours. After the reaction, the mixture was cooled to room temperature, quenched with water (8 mL) and extracted with ethyl acetate (5 mL×2). The organic phases were combined and dried over anhydrous sodium sulfate, followed by filtration. The filtrate was concentrated under reduced pressure. The obtained residue was purified by flash silica gel column chromatography (4 g silica gel column, eluent: petroleum ether/ethyl acetate=9/1-1/1, volume ratio) to obtain the target product WX002-2. MS-ESI m/z: 526.0 [M+CH$_3$CN+Na]$^+$.

Step 2: Preparation of Compound WX002-3

Compound WX002-2 (70.00 mg, 151.37 μmol), zinc powder (79.18 mg, 1.21 mmol) and ammonium chloride (80.97 mg, 1.51 mmol) were added to methanol (3.00 mL) at room temperature. The reaction mixture was stirred at room temperature for 16 hours. After the reaction, ethyl acetate (8 mL) was added, and the insolubles was removed by filtration. The filtrate was concentrated under reduced pressure. The water (10 mL) was added to the residue and extracted with ethyl acetate (8 mL×2). The organic phases were combined and dried over anhydrous sodium sulfate, followed by filtration. The filtrate was concentrated under reduced pressure to obtain the crude product WX002-3. MS-ESI m/z: 455.0 [M+Na]$^+$.

Step 3: Preparation of Compound WX002

Compound WX002-3 (30.00 mg, 69.37 μmol) and triethylamine (42.12 mg, 416.22 μmol) were dissolved in tetrahydrofuran (3.00 mL) at 0° C., followed by the addition of triphosgene (10.29 mg, 34.69 μmol). The reaction mixture was stirred at 0° C. for 0.5 hour. After the reaction, the mixture was quenched with water (10 mL) and extracted with ethyl acetate (8 mL×2). The organic phases were combined and dried over anhydrous sodium sulfate, followed by filtration. The filtrate was concentrated under reduced pressure. The obtained residue was isolated by preparative HPLC to obtain the target product WX002. MS-ESI m/z: 459.0 [M+H]$^+$. $^1$H NMR (400 MHz, CDCl$_3$) δ: 9.47 (br s, 1H), 7.44-7.31 (m, 2H), 7.26-7.00 (m, 3H), 6.85 (d, J=7.3 Hz, 1H), 5.90 (br s, 1H), 4.74 (br s, 1H), 4.09 (m, 2H), 3.95-3.82 (m, 4H), 2.85 (br s, 3H), 1.45 (t, J=6.0 Hz, 3H).

Embodiment 3: WX003

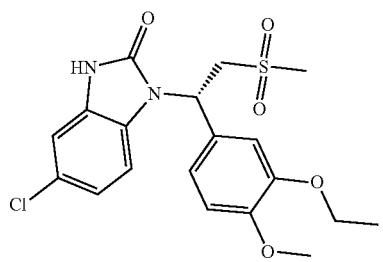 [SMILES: CCOc1cc([C@@H](CS(C)(=O)=O)n2c(=O)[nH]c3cc(Cl)ccc32)ccc1OC]

Synthesis Route:

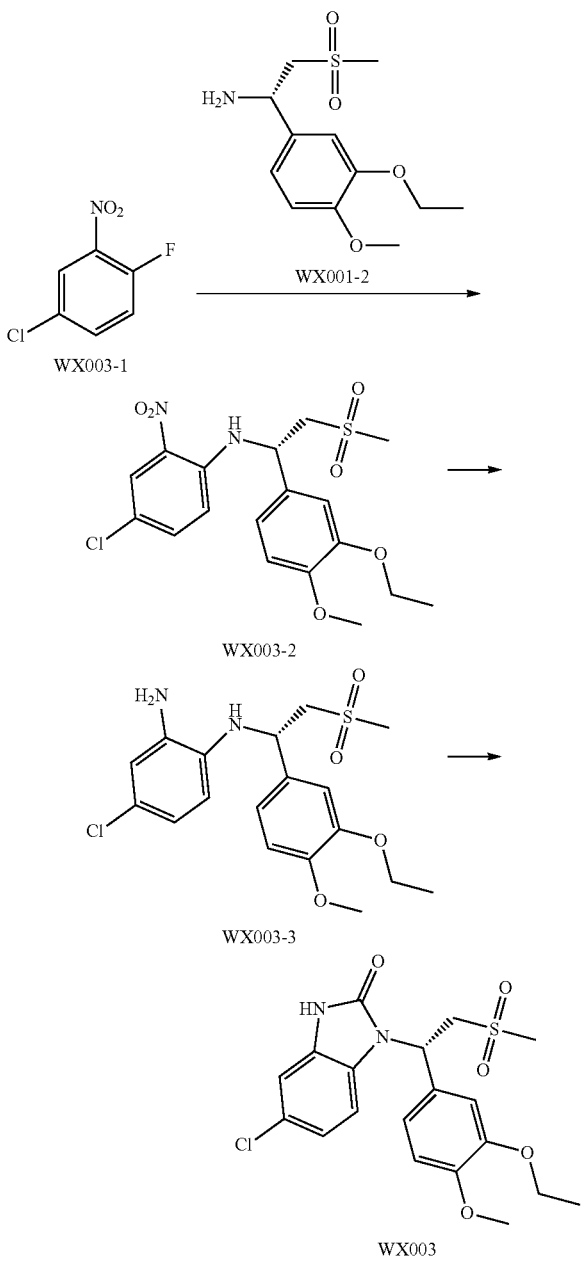

Step 1: Preparation of Compound WX003-2

Compound WX003-1 (5.00 g, 28.48 mmol), compound WX001-2 (7.79 g, 28.48 mmol) and diisopropylethylamine (11.04 g, 85.44 mmol, 14.92 mL) were dissolved in N,N-dimethylformamide (100.00 mL) at room temperature. The reaction mixture was heated to 100° C. and stirred for 3 hours. After the reaction, the mixture was cooled to room temperature and concentrated under reduced pressure. Methanol (150 mL) was added to the residue and stirred for 30 minutes, followed by filtration. The filter cake was washed with methanol (50 mL) and dried at 40° C. in vacuum to obtain the target product WX003-2. MS-ESI m/z: 451.0 [M+Na]$^+$.

Step 2: Preparation of Compound WX003-3

Compound WX003-2 (5.00 g, 11.66 mmol), zinc powder (6.10 g, 93.28 mmol) and ammonium chloride (6.24 g, 116.60 mmol) were added to methanol (100.00 mL) at room temperature. The reaction mixture was stirred at room temperature for 2 hours. After the reaction, insolubles was removed by filtration, and the filtrate was concentrated under reduced pressure. Dichloromethane (100 mL) was added to the obtained residue and stirred for 15 minutes, followed by filtration. The filtrate was concentrated under reduced pressure to obtain the target product WX003-3. MS-ESI m/z: 421.0 [M+Na]$^+$.

Step 3: Preparation of Compound WX003

Compound WX003-3 (4.00 g, 10.03 mmol) and triethylamine (3.04 g, 30.08 mmol, 4.17 mL) were dissolved in tetrahydrofuran (50 mL) at 0° C., followed by the portion-wise addition of triphosgene (1.19 g, 4.01 mmol). The reaction mixture was stirred at 0-5° C. for 1 hour. After the reaction, water (20 mL) and ethyl acetate (100 mL) were added. The organic phases were separated, washed with saturated brine (30 mL) and dried over anhydrous sodium sulfate, followed by filtration. The filtrate was concentrated under reduced pressure. The obtained residue was isolated by column chromatography (eluent: petroleum ether/ethyl acetate=5/1-1/1, volume ratio) to obtain the target product WX003. MS-ESI m/z: 425.1 [M+H]$^+$. $^1$H NMR (400 MHz, CD$_3$OD) δ: 7.32-7.10 (m, 2H), 7.10-6.98 (m, 3H), 6.94 (d, J=8.3 Hz, 1H), 6.03 (dd, J=3.8, 10.3 Hz, 1H), 4.59 (dd, J=10.7, 14.4 Hz, 1H), 4.13-3.96 (m, 3H), 3.81 (s, 3H), 2.97 (s, 3H), 1.37 (t, J=6.9 Hz, 3H).

Embodiment 4: WX004

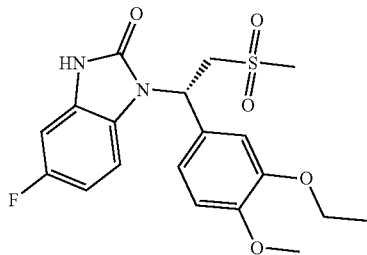 [SMILES: CCOc1cc([C@@H](CS(C)(=O)=O)n2c(=O)[nH]c3cc(F)ccc32)ccc1OC]

Synthesis Route:

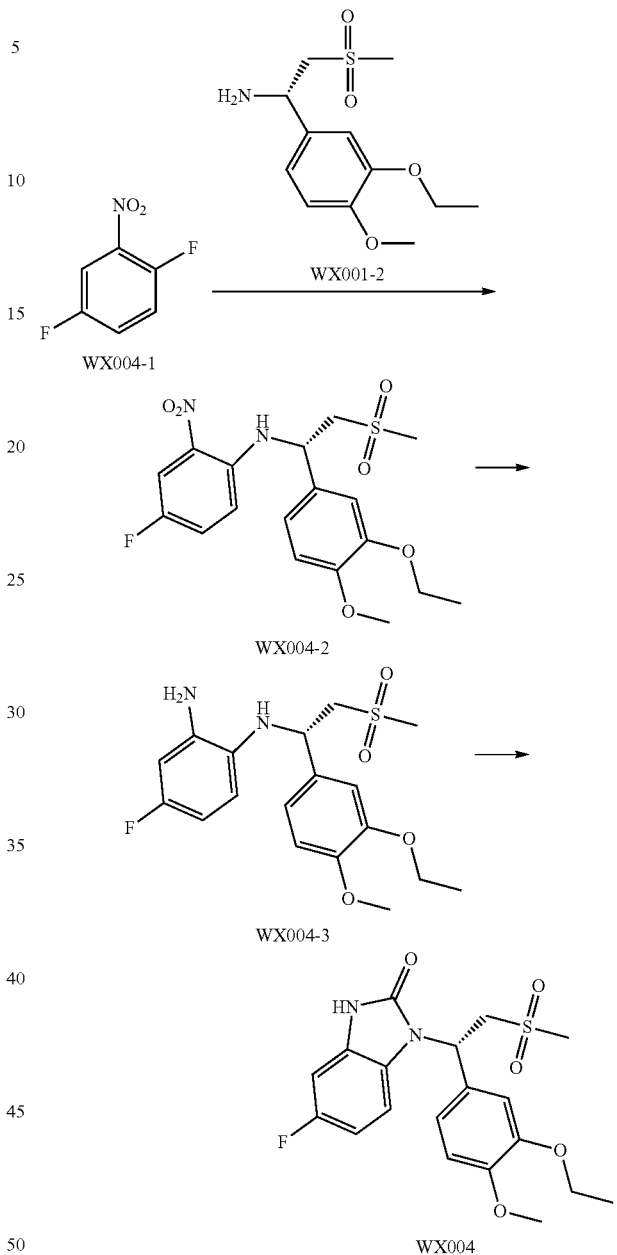

Step 1: Preparation of Compound WX004-2

Compound WX004-1 (142.50 mg, 895.74 μmol), the N-acetyl-L-leucinate salt of compound WX004-1 (200.00 mg, 447.87 μmol) and potassium carbonate (185.70 mg, 1.34 mmol) were added to N,N-dimethylformamide (4.00 mL) at room temperature. The reaction mixture was heated to 70° C. and stirred for 3 hours. After the reaction, the mixture was cooled to room temperature. Water (8 mL) was added and extracted with ethyl acetate (10 mL×2). The organic phases were combined and dried over anhydrous sodium sulfate, followed by filtration. The filtrate was concentrated under reduced pressure. The obtained residue was purified by preparative TLC (eluent: ethyl acetate/petroleum ether=1/1, volume ratio) to obtain the target product WX004-2. MS-ESI m/z: 413.1 [M+H]$^+$. $^1$H NMR (400

MHz, CDCl₃) δ: 8.51 (d, J=6.5 Hz, 1H), 7.91 (dd, J=2.8, 8.8 Hz, 1H), 7.21-7.15 (m, 1H), 6.97-6.92 (m, 1H), 6.89-6.84 (m, 2H), 6.80 (dd, J=4.3, 9.3 Hz, 1H), 5.21-5.14 (m, 1H), 4.12-4.06 (m, 2H), 3.86 (s, 3H), 3.63 (dd, J=8.3, 14.8 Hz, 1H), 3.51-3.44 (m, 1H), 2.80 (s, 3H), 1.46 (t, J=6.8 Hz, 3H).

Step 2: Preparation of Compound WX004-3

Compound WX004-2 (70.00 mg, 169.73 μmol), ammonium chloride (72.63 mg, 1.36 mmol) and iron powder (47.40 mg, 848.63 μmol) were added to methanol (3.00 mL) at room temperature. The reaction mixture was heated to 50° C. and stirred for 1 hour. After the reaction, the mixture was cooled to room temperature. Ethyl acetate (5 mL) was added, and the insolubles was removed by filtration. The filtrate was concentrated under reduced pressure. Water (8 mL) was added to the residue and extracted with ethyl acetate (5 mL×2). The organic phases were combined and dried over anhydrous sodium sulfate, followed by filtration. The filtrate was concentrated under reduced pressure to obtain the target product WX004-3. MS-ESI m/z: 423.0 [M+H2O+Na]⁺.

Step 3: Preparation of Compound WX004

Compound WX004-3 (25.00 mg, 65.37 μmol) and triethylamine (39.69 mg, 392.21 μmol) were dissolved in tetrahydrofuran (3.00 mL) at 0° C., followed by the addition of triphosgene (9.70 mg, 32.68 μmol). The reaction mixture was stirred at 0° C. for 0.5 hour. After the reaction, water (8 mL) was added to the mixture and extracted with ethyl acetate (5 mL×2). The organic phases were combined and dried over anhydrous sodium sulfate, followed by filtration. The filtrate was concentrated under reduced pressure. The obtained residue was purified by preparative HPLC to obtain the target product WX004. MS-ESI m/z: 409.1 [M+H]⁺. ¹H NMR (400 MHz, CD₃OD) δ: 7.20-7.06 (m, 3H), 6.98-6.73 (m, 3H), 6.03 (d, J=7.5 Hz, 1H), 4.68-4.59 (m, 2H), 4.11-4.04 (m, 2H), 3.82 (br s, 3H), 2.97 (br s, 3H), 1.38 (br s, 3H).

Embodiment 5: WX005

Synthesis Route:

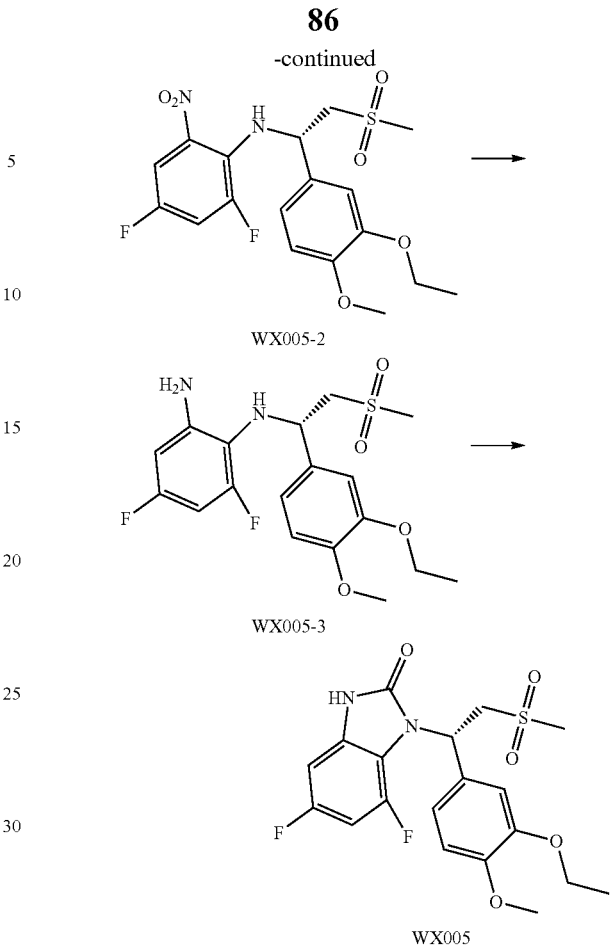

Step 1: Preparation of Compound WX005-2

The N-acetyl-L-leucinate (735.00 mg, 2.69 mmol) of compound WX001-2, compound WX005-1 (952.69 mg, 5.38 mmol) and potassium carbonate (1.12 g, 8.07 mmol) were added to N,N-dimethylformamide (6.00 mL) at room temperature. The reaction mixture was heated to 70° C. and stirred for 1.5 hours. After the reaction, the mixture was cooled to room temperature and ethyl acetate (5 mL) was added thereto, followed by filtration. The filtrate was concentrated under reduced pressure. Water (8 mL) was added into the obtained residue and extracted with ethyl acetate (5 mL×2). The organic phases were combined and dried over anhydrous sodium sulfate, followed by filtration. The filtrate was concentrated under reduced pressure. The obtained residue was purified by column chromatography (eluent: petroleum ether/ethyl acetate=1/0-1/1, volume ratio) to obtain the target product WX005-2. ¹H NMR (400 MHz, CDCl₃) δ: 7.85 (d, J=9.0 Hz, 1H), 7.68 (td, J=2.4, 8.5 Hz, 1H), 7.06 (ddd, J=3.0, 7.5, 12.8 Hz, 1H), 6.85-6.75 (m, 3H), 5.49 (dt, J=5.5, 8.5 Hz, 1H), 4.11-4.01 (m, 2H), 3.85 (s, 3H), 3.63 (dd, J=8.0, 14.8 Hz, 1H), 3.47 (dd, J=5.4, 14.7 Hz, 1H), 2.79 (s, 3H), 1.45 (t, J=7.0 Hz, 3H).

Step 2: Preparation of Compound WX005-3

Compound WX005-2 (800.00 mg, 1.86 mmol), ammonium chloride (994.19 mg, 18.60 mmol) and zinc powder (972.30 mg, 14.88 mmol) were added to methanol (10.00 mL) at room temperature. The reaction mixture was stirred at room temperature for 15 hours. After the reaction, ethyl acetate (10 mL) was added, followed by filtration, and the filtrate was concentrated under reduced pressure. Water (8 mL) was added to the obtained residue and extracted with ethyl acetate (10 mL×2). The organic phases were combined and dried over anhydrous sodium sulfate, followed by filtration. The filtrate was concentrated under reduced pressure to obtain the target product WX005-3. MS-ESI m/z: 422.9 [M+Na]⁺.

Step 3: Preparation of Compound WX005

Compound WX005-3 (580.00 mg, 1.45 mmol) and triethylamine (586.90 mg, 5.80 mmol) were dissolved in tetrahydrofuran (6.00 mL) at 0° C., followed by the addition of triphosgene (172.11 mg, 580.00 µmol). The reaction mixture was stirred at 0° C. for 0.5 hour. After the reaction, water (10 mL) was added to the mixture and extracted with ethyl acetate (8 mL×2). The organic phases were combined and dried over anhydrous sodium sulfate, followed by filtration. The filtrate was concentrated under reduced pressure. The obtained residue was purified by column chromatography (eluent: petroleum ether/ethyl acetate=1/0-1/2, volume ratio) to obtain the target product WX005. MS-ESI m/z: 427.0 [M+H]⁺. ¹H NMR (400 MHz, MeOD) δ: 7.08 (br s, 1H), 7.02-6.87 (m, 2H), 6.79-6.61 (m, 2H), 6.21 (d, J=8.0 Hz, 1H), 4.49 (br s, 1H), 4.14-3.93 (m, 3H), 3.81 (s, 3H), 3.00 (s, 3H), 1.36 (t, J=6.9 Hz, 3H).

Embodiment 6: WX006

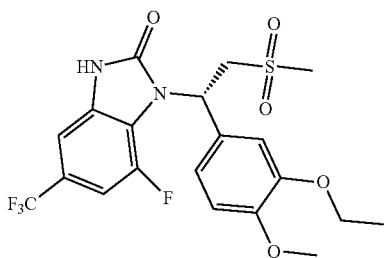 [SMILES: CCOc1cc([C@@H](CS(C)(=O)=O)n2c(=O)[nH]c3cc(C(F)(F)F)cc(F)c32)ccc1OC]

Synthesis Route:

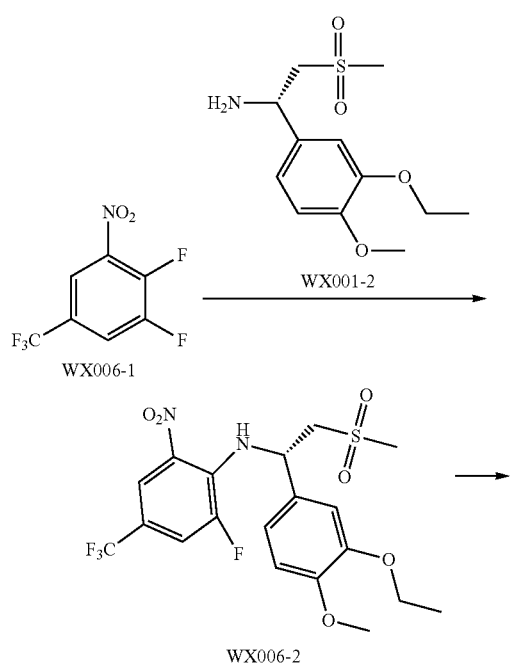

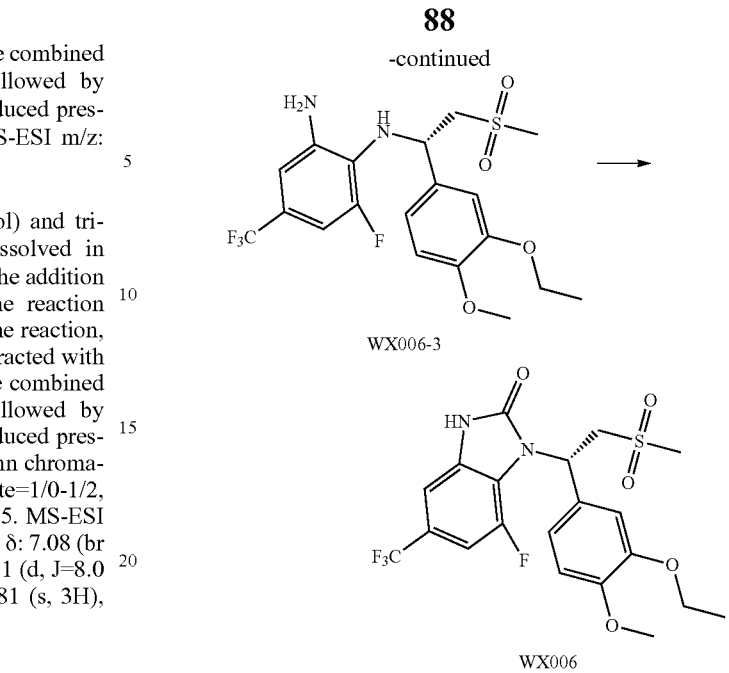

Step 1: Preparation of Compound WX006-2

Compound WX006-1 (500.00 mg, 2.20 mmol) was dissolved in N,N-dimethylformamide (10.00 mL) at room temperature, followed by the addition of diisopropylethylamine (853.67 mg, 6.60 mmol, 1.15 mL) and compound WX001-2 (601.85 mg, 2.20 mmol). The reaction mixture was heated to 120° C. and stirred for 12 hours under nitrogen atmosphere. After the reaction, the mixture was cooled to room temperature and concentrated under reduced pressure. Methanol (30 mL) was added to the obtained residue, stirred for 10 minutes and filtered to obtain crude product WX006-2.

Step 2: Preparation of Compound WX006-3

Compound WX006-2 (1.20 g, 2.50 mmol) and ammonium chloride (1.18 g, 22.11 mmol) were added to methanol (30.00 mL) at 0° C., followed by the addition of zinc powder (828.08 mg, 12.66 mmol). The reaction mixture was stirred at 0° C. for 1 hour under nitrogen atmosphere. After the reaction, insolubles was removed by filtration, and the filtrate was concentrated under reduced pressure. Dichloromethane (50 mL) was added to the obtained residue and stirred for 10 min, followed by filtration. The filtrate was concentrated under reduced pressure to obtain the crude product WX006-3. MS-ESI m/z: 472.9 [M+Na]⁺.

Step 3: Preparation of Compound WX006

Compound WX006-3 (200.00 mg, 444.00 µmol) and triethylamine (247.11 mg, 2.44 mmol, 338.50 µL) were dissolved in tetrahydrofuran (2.00 mL) at 0° C., followed by the addition of triphosgene (158.11 mg, 532.80 µmol). The reaction mixture was stirred at 0° C. for 1 hour under nitrogen atmosphere. After the reaction, the mixture was concentrated under reduced pressure. The obtained residue was purified by preparative HPLC to obtain the target product WX006. MS-ESI m/z: 499.0 [M+Na]⁺. ¹H NMR (400 MHz, CDCl₃) δ: 10.15 (br, s, 1H), 7.19-7.02 (m, 4H), 6.81 (d, J=8.3 Hz, 1H), 6.23 (br s, 1H), 4.17-4.09 (m, 1H), 4.06 (q, J=6.9 Hz, 2H), 3.91-3.78 (m, 4H), 2.88 (s, 3H), 1.41 (t, J=6.9 Hz, 3H).

Embodiment 7: WX007

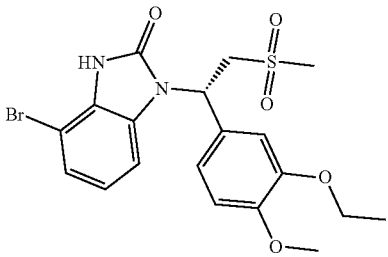 [SMILES: CCOc1cc([C@@H](CS(C)(=O)=O)n2c(=O)[nH]c3c(Cl)cccc32)ccc1OC]

Synthesis Route:

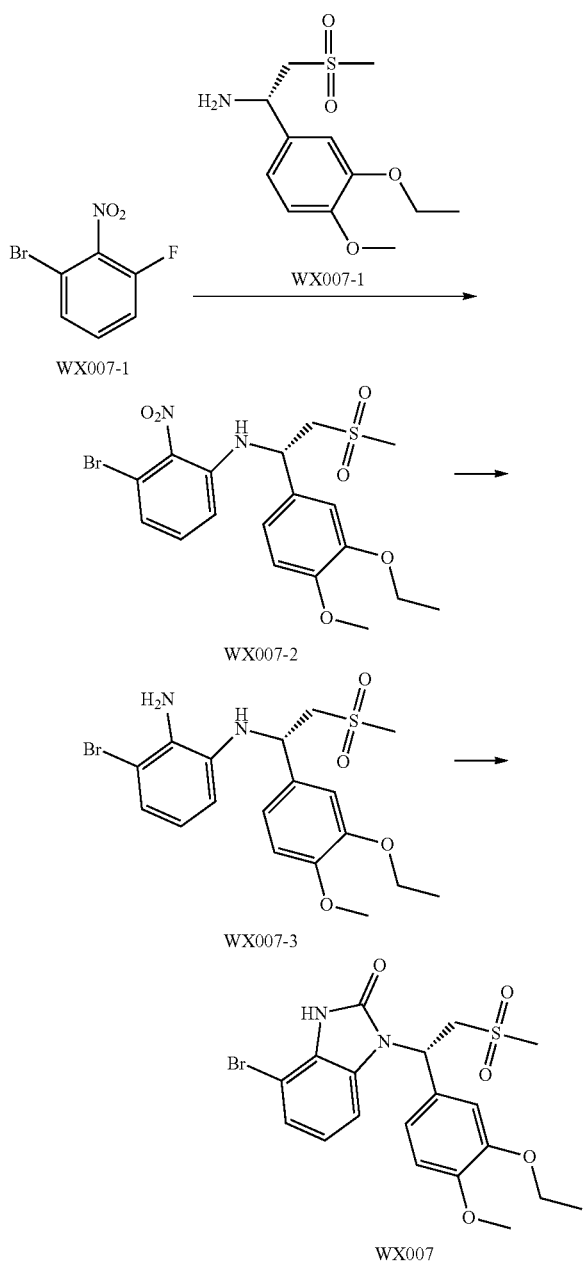

Step 1: Preparation of Compound WX007-2

Compound WX007-1 (5.03 g, 22.86 mmol) and compound WX001-2 (5.00 g, 18.29 mmol) were dissolved in N,N-dimethylformamide (100.00 mL) at room temperature, followed by the dropwise addition of diisopropylethylamine (7.99 g, 54.87 mmol). The reaction mixture was heated to 90° C. and stirred for 30 hours under nitrogen atmosphere. After the reaction, the mixture was cooled to room temperature, diluted with water (20 mL), and extracted with ethyl acetate (50 mL×4). The organic phases were combined, washed with saturated brine (50 mL) and dried over anhydrous sodium sulfate, followed by filtration. The filtrate was concentrated under reduced pressure. The obtained residue was purified by silica gel column chromatography (eluent: ethyl acetate/petroleum ether=0/1-1/1, volume ratio) to obtain the target product WX007-2. $^1$H NMR (400 MHz, CDCl$_3$) δ: 7.08-7.03 (m, 1H), 7.02-6.98 (m, 1H), 6.93-6.89 (m, 1H), 6.87-6.83 (m, 2H), 6.68 (d, J=7.5 Hz, 1H), 6.23 (d, J=6.0 Hz, 1H), 5.07 (td, J=5.2, 8.4 Hz, 1H), 4.10-4.03 (m, 2H), 3.85 (s, 3H), 3.57-3.49 (m, 1H), 3.44-3.36 (m, 1H), 2.78 (s, 3H), 1.44 (t, J=7.0 Hz, 3H).

Step 2: Preparation of Compound WX007-3

Compound WX007-2 (1.35 g, 2.85 mmol) and ammonium chloride (1.52 g, 28.50 mmol) were added to water (3.00 mL) and ethanol (30.00 mL) at room temperature, followed by the addition of iron powder (796.44 mg, 14.25 mmol). The reaction mixture was heated to 80° C. and stirred for 1 hour under nitrogen atmosphere. After the reaction, insolubles was removed by filtration, and the filtrate was concentrated under reduced pressure. Dichloromethane (100 mL) was added to the obtained residue, followed by filtration and the filtrate was concentrated under reduced pressure. The obtained residue was purified by chromatography column (eluent:ethyl acetate/petroleum ether=1/4-4/1, volume ratio) to obtain the target product WX007-3. $^1$H NMR (400 MHz, CDCl$_3$) δ: 6.93 (dd, J=8.0, 14.6 Hz, 2H), 6.89-6.82 (m, 2H), 6.52-6.44 (m, 1H), 6.44-6.35 (m, 1H), 4.92 (br s, 1H), 4.47 (br s, 1H), 4.06 (q, J=6.7 Hz, 2H), 3.85 (s, 3H), 3.60-3.49 (m, 1H), 3.47-3.37 (m, 1H), 2.81 (s, 3H), 1.43 (t, J=6.8 Hz, 3H).

Step 3: Preparation of Compound WX007

Compound WX007-3 (50.00 mg, 112.78 μmol) and triethylamine (57.06 mg, 563.89 μmol, 78.16 uL) were dissolved in tetrahydrofuran (5.00 mL) at room temperature, then the reaction mixture was cooled to 0° C., followed by the addition of triphosgene (16.73 mg, 56.39 μmol). The reaction mixture was stirred at 0° C. for 30 minutes under nitrogen atmosphere. After the reaction, the mixture was quenched with water (20 mL), the organic phase was separated and extracted with ethyl acetate (50 mL×3). The organic phases were combined, washed with saturated brine (20 mL) and dried over anhydrous sodium sulfate, followed by filtration. The filtrate was concentrated under reduced pressure. The obtained residue was purified by column chromatography (eluent:ethyl acetate/petroleum ether=0/1-4/1, volume ratio) to obtain the target product WX007. MS-ESI m/z: 469.0 [M+H]$^+$, 471.0 [M+H+2]$^+$. $^1$H NMR (400 MHz, CDCl$_3$) δ: 8.40 (s, 1H), 7.21 (d, J=7.5 Hz, 1H), 7.14 (d, J=2.0 Hz, 1H), 7.07-7.02 (m, 2H), 7.02-6.96 (m, 1H), 6.82 (d, J=8.5 Hz, 1H), 5.75 (dd, J=4.5, 9.5 Hz, 1H), 4.75 (dd, J=9.5, 14.8 Hz, 1H), 4.07 (q, J=7.0 Hz, 2H), 3.88-3.82 (m, 4H), 2.79 (s, 3H), 1.44 (t, J=6.9 Hz, 3H).

Embodiment 8: WX008

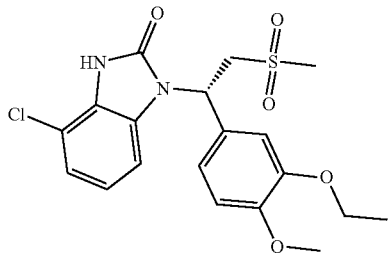

Synthesis Route:

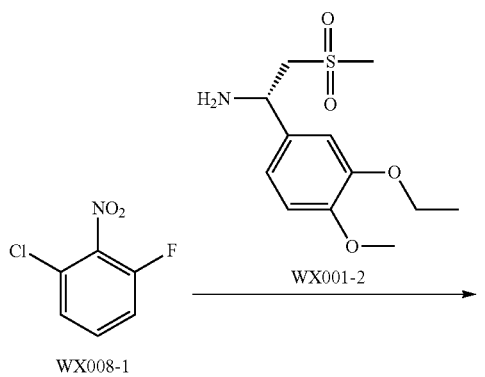

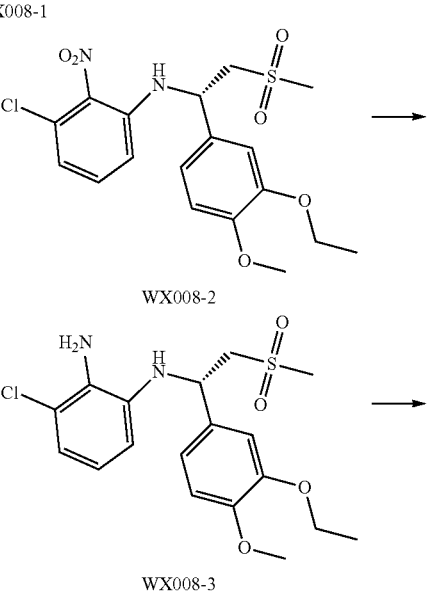

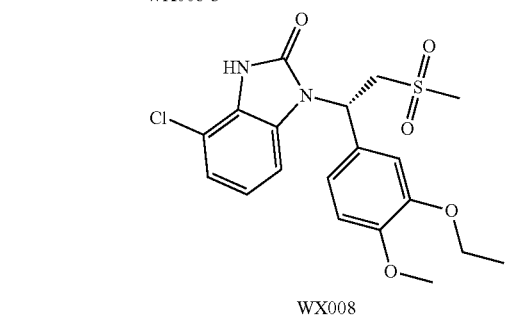

Step 1: Preparation of Compound WX008-2

Compound WX008-1 (963.27 mg, 5.49 mmol) was dissolved in N,N-dimethylformamide (15.00 mL) at room temperature, followed by the addition of diisopropylethylamine (2.13 g, 16.47 mmol, 2.88 mL)) and compound WX001-2 (1.50 g, 5.49 mmol). The reaction mixture was heated to 130° C. and stirred for 12 hours under nitrogen atmosphere. After the reaction, the mixture was cooled to room temperature and concentrated under reduced pressure. Water (20 mL) was added to the obtained residue, extracted with ethyl acetate (15 mL×3) and dried over anhydrous sodium sulfate, followed by filtration. The filtrate was concentrated under reduced pressure to obtain the crude product WX008-2. MS-ESI m/z: 451.1 [M+Na]$^+$.

Step 2: Preparation of Compound WX008-3

Compound WX008-2 (2.00 g, 4.66 mmol) and ammonium chloride (2.49 g, 46.60 mmol, 1.63 mL) were added to methanol (20.00 mL) at room temperature, followed by the portionwise addition of zinc powder (1.52 g, 23.30 mmol). The reaction mixture was stirred at room temperature for 10 minutes under nitrogen atmosphere. After the reaction, insolubles was removed by filtration, and the filtrate was concentrated under reduced pressure. Water (50 mL) and ethyl acetate (50 mL) were added to the obtained residue, and the organic phase was separated. The aqueous phases were extracted with ethyl acetate (30 mL×3). The organic phases were combined, washed with saturated brine (50 mL) and dried over anhydrous sodium sulfate, followed by filtration. The filtrate was concentrated under reduced pressure to obtain the crude product WX008-3. MS-ESI m/z: 421.1 [M+Na]$^+$.

Step 3: Preparation of Compound WX008

Compound WX008-3 (100.00 mg, 250.69 μmol) and triethylamine (139.52 mg, 1.38 mmol, 191.12 μL) were dissolved in tetrahydrofuran (1.00 mL) at 0° C., followed by the addition of triphosgene (40.92 mg, 137.88 μmol). The reaction mixture was warmed to room temperature and stirred for 12 hours. After the reaction, the mixture was concentrated under reduced pressure. The obtained residue was purified by preparative HPLC to obtain the target product WX008. MS-ESI m/z: 425.0 [M+H]$^+$. $^1$H NMR (400 MHz, CDCl$_3$) δ: 9.30 (br s, 1H), 7.12 (d, J=2.0 Hz, 1H), 7.11-7.01 (m, 4H), 6.82 (d, J=8.3 Hz, 1H), 5.79 (dd, J=4.5, 9.5 Hz, 1H), 4.73 (dd, J=9.7, 14.9 Hz, 1H), 4.06 (q, J=6.9 Hz, 2H), 3.91-3.79 (m, 4H), 2.80 (s, 3H), 1.42 (t, J=7.0 Hz, 3H).

Embodiment 9: WX009

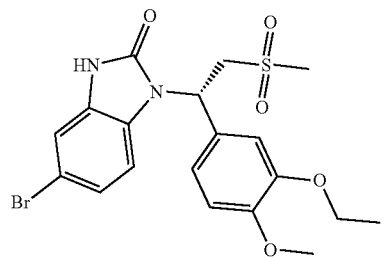

Synthesis Route:

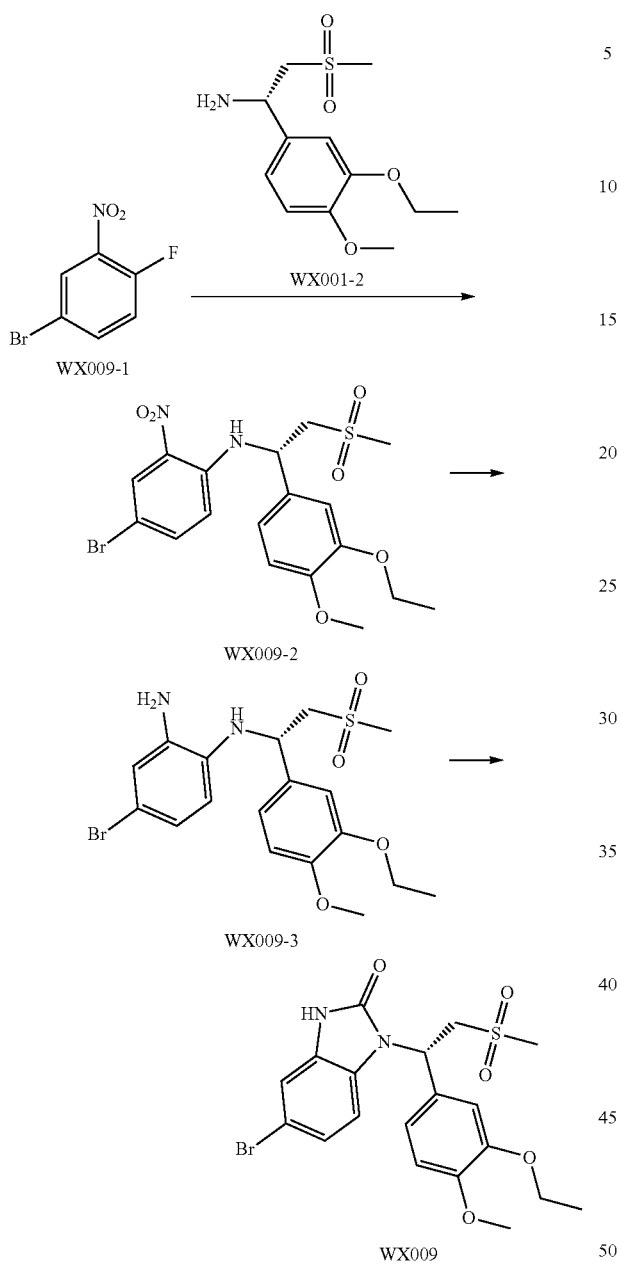

Step 1: Preparation of Compound WX009-2

The N-acetyl-L-leucinate salt (500.00 mg, 1.12 mmol) of compound WX001-2 and compound WX009-1 (248.86 mg, 1.13 mmol) were dissolved in N,N-dimethylformamide (5.00 mL) at room temperature, followed by the addition of potassium carbonate (300.21 mg, 2.17 mmol). The reaction mixture was heated to 80° C. and stirred for 4 hours. After the reaction, the mixture was cooled to room temperature, quenched with saturated brine (10 mL), diluted with water (30 mL) and extracted with dichloromethane (20 mL×3). The organic phases were combined, washed with water (100 mL×2) and dried over anhydrous sodium sulfate, followed by filtration. The filtrate was concentrated under reduced pressure. The obtained residue was purified by column chromatography (eluent: dichloromethane/petroleum ether=3/1-5/1, volume ratio) to obtain the target product WX009-2. $^1$H NMR (400 MHz, DMSO_d$_6$) δ: 8.67 (d, J=6.0 Hz, 1H), 8.18 (br s, 1H), 7.59 (d, J=8.3 Hz, 1H), 7.16 (br s, 1H), 7.08-6.77 (m, 3H), 5.24 (br s, 1H), 4.26-4.12 (m, 1H), 4.08-3.94 (m, 2H), 3.71 (br s, 4H), 2.96 (br s, 3H), 1.31 (d, J=6.0 Hz, 3H).

Step 2: Preparation of Compound WX009-3

Compound WX009-2 (200.00 mg, 422.53 μmol) was dissolved in methanol (5.00 mL) at room temperature, followed by the addition of zinc powder (276.29 mg, 4.23 mmol) and ammonium chloride (226.01 mg, 4.23 mmol). The reaction mixture was stirred at room temperature for 1 hour. After the reaction, the insolubles was removed by filtration, and the filter cake was washed with methanol (10 mL×2). The filtrate was combined and concentrated under reduced pressure to obtain the crude product WX009-3. $^1$H NMR (400 MHz, DMSO_d$_6$) δ: 7.15-6.95 (m, 1H), 6.87 (br s, 2H), 6.69 (br s, 1H), 6.46 (d, J=7.5 Hz, 1H), 6.28 (d, J=8.0 Hz, 1H), 5.24 (d, J=8.3 Hz, 1H), 4.93 (br s, 2H), 4.81 (br s, 1H), 4.19-3.86 (m, 2H), 3.70 (br s, 4H), 3.09-2.88 (m, 3H), 1.31 (d, J=6.5 Hz, 3H).

Step 3: Preparation of Compound WX009

Compound WX009-3 (150.00 mg, 338.33 μmol) and triethylamine (188.30 mg, 1.86 mmol) were dissolved in tetrahydrofuran (20.00 mL) at 0° C., followed by the addition of triphosgene (120.48 mg, 406.00 μmol). The reaction mixture was stirred at 0° C. for 2 hours. After the reaction, the mixture was quenched with saturated brine (15 mL), diluted with water (15 mL) and extracted with ethyl acetate (10 mL×3). The organic phases were combined, washed with water (25 mL×2) and dried over anhydrous sodium sulfate, followed by filtration. The filtrate was concentrated under reduced pressure. The obtained residue was purified by preparative HPLC to obtain the target product WX009. MS-ESI m/z: 469.0 [M+H]$^+$, 471.0 [M+H+2]$^+$. $^1$H NMR (400 MHz, DMSO_d$_6$) δ: 11.16 (s, 1H), 7.24-7.06 (m, 4H), 7.02-6.86 (m, 2H), 5.91 (d, J=6.8 Hz, 1H), 4.56-4.39 (m, 1H), 4.23-4.11 (m, 1H), 4.05-3.90 (m, 2H), 3.71 (s, 3H), 3.01 (s, 3H), 1.30 (t, J=6.8 Hz, 3H).

Embodiment 10: WX010

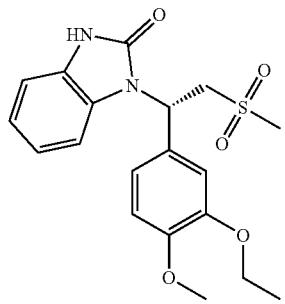 [SMILES: CCOc1cc([C@@H](CS(C)(=O)=O)n2c(=O)[nH]c3ccccc32)ccc1OC]

Synthesis Route:

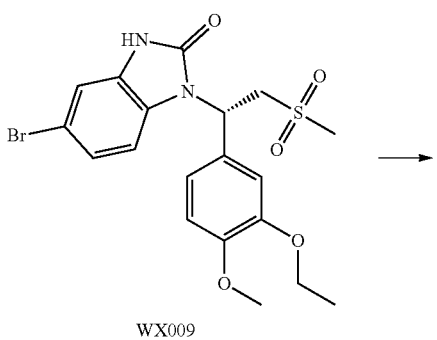

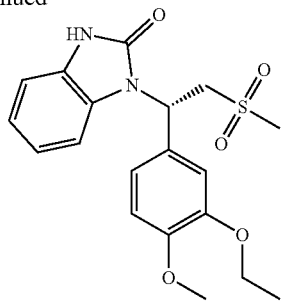

WX010

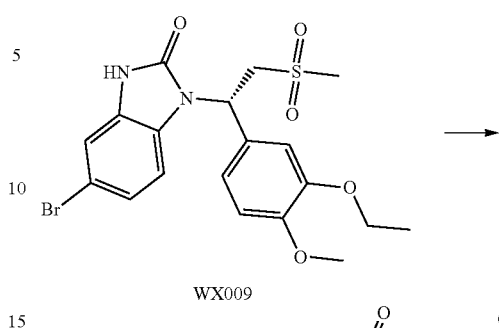

WX009

Compound WX009 (2.00 g, 4.26 mmol) was dissolved in methanol (40.00 mL) at room temperature, followed by the addition of palladium charcoal (0.50 g, 10% purity) under argon atmosphere. The reaction system was depressurized to vacuum and filled with hydrogen. The above procedure was repeated three times. The reaction mixture was stirred at room temperature under hydrogen atmosphere (30 psi) for 10 hours. After the reaction, insolubles was removed by filtration, and the filtrate was concentrated under reduced pressure. The obtained residue was purified by preparative HPLC to obtain the target product WX010. MS-ESI m/z: 391.1 [M+H]$^+$. $^1$H NMR (400 MHz, CDCl$_3$) δ: 9.71 (br s, 1H), 7.22-6.95 (m, 6H), 6.81 (d, J=7.0 Hz, 1H), 5.86 (br s, 1H), 4.76 (br s, 1H), 4.06 (d, J=6.5 Hz, 2H), 3.91 (d, J=13.3 Hz, 1H), 3.83 (br s, 3H), 2.76 (br s, 3H), 1.41 (t, J=5.9 Hz, 3H).

Embodiment 11: WX011

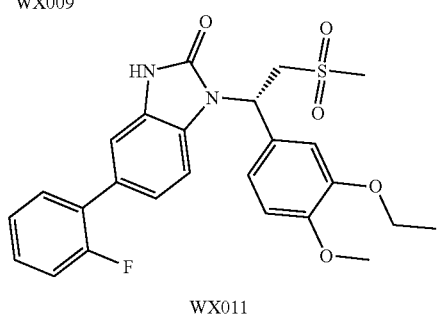

WX011

Compound WX009 (280 mg, 596.57 μmol) and o-fluorophenylboronic acid (125.21 mg, 894.86 μmol) were dissolved in dioxane (5.00 mL) and water (2.00 mL) at room temperature, followed by the addition of tetrakistriphenylphosphine palladium (68.94 mg, 59.66 μmol) and potassium carbonate (90.70 mg, 656.23 μmol). The reaction mixture was heated to 80° C. and stirred for 12 hours under nitrogen atmosphere. After the reaction, the mixture was cooled to room temperature, quenched with saturated brine (20 mL), diluted with water (20 mL) and extracted with ethyl acetate (10 mL×3). The organic phases were combined, washed with water (30 mL×2) and dried over anhydrous sodium sulfate, followed by filtration. The filtrate was concentrated under reduced pressure. The obtained residue was purified by preparative HPLC to obtain the target product WX011. MS-ESI m/z: 485.2 [M+H]$^+$. $^1$H NMR (400 MHz, CDCl$_3$) δ: 9.20 (br s, 1H), 7.39 (t, J=7.7 Hz, 1H), 7.44-7.28 (m, 1H), 7.35-7.24 (m, 4H), 7.24-7.03 (m, 5H), 7.24-7.00 (m, 1H), 6.82 (d, J=8.3 Hz, 1H), 5.87 (d, J=4.8 Hz, 1H), 4.78 (dd, J=9.7, 14.2 Hz, 1H), 4.07 (q, J=6.8 Hz, 2H), 3.96-3.74 (m, 4H), 2.81 (s, 3H), 1.42 (t, J=6.9 Hz, 3H).

The compounds of each embodiment in the following table were prepared according to the method of embodiment 11.

TABLE 1

| Embodiment | Fragment 1 | Fragment 2 | Structure | Compound |
|---|---|---|---|---|
| 12 | 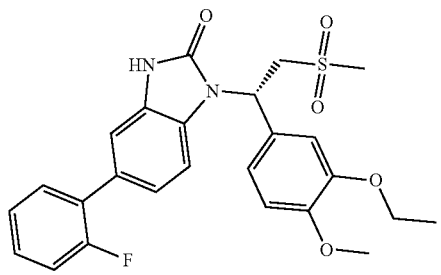 [SMILES: CCOc1cc([C@@H](CS(C)(=O)=O)n2c(=O)[nH]c3cc(-c4ccccc4F)ccc32)ccc1OC]<br>WX009 | F-C6H4-B(OH)2 (3-fluorophenylboronic acid) | (structure shown) | WX012 |

TABLE 1-continued

| Embodiment | Fragment 1 | Fragment 2 | Structure | Compound |
|---|---|---|---|---|
| 13 | WX009 | 4-fluorophenylboronic acid | 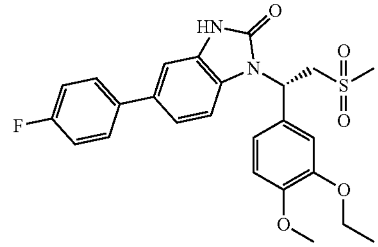 [SMILES: CCOc1cc([C@@H](CS(C)(=O)=O)n2c(=O)[nH]c3cc(-c4ccc(F)cc4)ccc32)ccc1OC] | WX013 |
| 14 | WX009 | 2-methylphenylboronic acid | 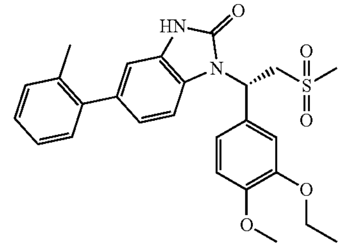 [SMILES: CCOc1cc([C@@H](CS(C)(=O)=O)n2c(=O)[nH]c3cc(-c4ccccc4C)ccc32)ccc1OC] | WX014 |
| 15 | WX009 | 2-chlorophenylboronic acid | 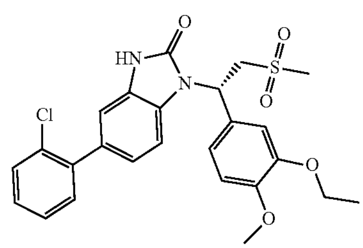 [SMILES: CCOc1cc([C@@H](CS(C)(=O)=O)n2c(=O)[nH]c3cc(-c4ccccc4Cl)ccc32)ccc1OC] | WX015 |
| 16 | WX009 | 2-methoxyphenylboronic acid | 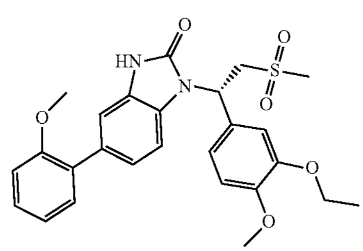 [SMILES: CCOc1cc([C@@H](CS(C)(=O)=O)n2c(=O)[nH]c3cc(-c4ccccc4OC)ccc32)ccc1OC] | WX016 |
| 17 | WX009 | 2-(trifluoromethyl)phenylboronic acid | 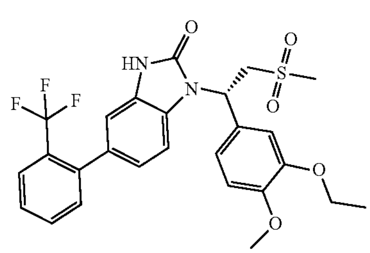 [SMILES: CCOc1cc([C@@H](CS(C)(=O)=O)n2c(=O)[nH]c3cc(-c4ccccc4C(F)(F)F)ccc32)ccc1OC] | WX017 |

TABLE 1-continued

| Embodiment | Fragment 1 | Fragment 2 | Structure | Compound |
|---|---|---|---|---|
| 18 | WX009 | | 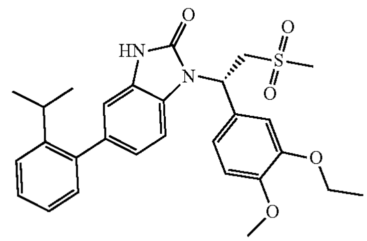 [SMILES: CCOc1cc([C@@H](CS(C)(=O)=O)n2c(=O)[nH]c3cc(-c4ccccc4C(C)C)ccc32)ccc1OC] | WX018 |
| 19 | WX009 | | 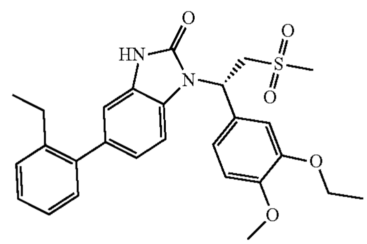 [SMILES: CCOc1cc([C@@H](CS(C)(=O)=O)n2c(=O)[nH]c3cc(-c4ccccc4CC)ccc32)ccc1OC] | WX019 |

LCMS and ¹H NMR data of each embodiment

TABLE 2

| Embodiment | Compound | HNMR | LCMS |
|---|---|---|---|
| 12 | WX012 | ¹H NMR (400 MHz, CDCl$_3$) δ: 8.74 (br s, 1H), 7.44-7.35 (m, 1H), 7.30 (d, J = 8.0 Hz, 2H), 7.26-7.13 (m, 4H), 7.12-6.97 (m, 2H), 6.83 (d, J = 8.0 Hz, 1H), 5.86 (dd, J = 4.0, 9.3 Hz, 1H), 4.78 (dd, J = 9.3, 14.6 Hz, 1H), 4.08 (q, J = 6.9 Hz, 2H), 3.98-3.78 (m, 4H), 2.81 (s, 3H), 1.43 (t, J = 6.9 Hz, 3H). | MS-ESI m/z: 485.2 [M + H]$^+$. |
| 13 | WX013 | ¹H NMR (400 MHz, CDCl$_3$) δ: 8.98 (br s, 1H), 7.47 (dd, J = 5.3, 8.5 Hz, 2H), 7.23 (d, J = 11.3 Hz, 2H), 7.19-7.03 (m, 5H), 6.83 (d, J = 8.0 Hz, 1H), 5.87 (d, J = 5.5 Hz, 1H), 4.84-4.70 (m, 1H), 4.08 (q, J = 6.9 Hz, 2H), 3.96-3.77 (m, 4H), 2.81 (s, 3H), 1.42 (t, J = 6.9 Hz, 3H). | MS-ESI m/z: 485.2 [M + H]$^+$. |
| 14 | WX014 | ¹H NMR (400 MHz, CDCl$_3$) δ: 9.08 (br s, 1H), 7.25-7.13 (m, 6H), 7.11-7.01 (m, 3H), 6.83 (d, J = 8.5 Hz, 1H), 5.85 (dd, J = 4.6, 9.2 Hz, 1H), 4.75 (dd, J = 9.4, 14.7 Hz, 1H), 4.07 (q, J = 6.9 Hz, 2H), 3.90 (dd, J = 4.6, 14.7 Hz, 1H), 3.83 (s, 3H), 2.79 (s, 3H), 2.24 (s, 3H), 1.42 (t, J = 7.0 Hz, 3H). | MS-ESI m/z: 481.0 [M + H]$^+$. |
| 15 | WX015 | ¹H NMR (400 MHz, CDCl$_3$) δ: 10.11 (s, 1H), 7.49-7.45 (m, 1H), 7.34-7.26 (m, 3H), 7.22-7.16 (m, 4H), 7.16-7.09 (m, 1H), 6.84 (d, J = 8.3 Hz, 1H), 5.89 (dd, J = 4.5, 9.0 Hz, 1H), 4.78 (dd, J = 9.0, 14.8 Hz, 1H), 4.17-4.03 (m, 2H), 3.95 (dd, J = 4.5, 14.8 Hz, 1H), 3.84 (s, 3H), 2.80 (s, 3H), 1.40 (t, J = 7.0 Hz, 3H). | MS-ESI m/z: 501.0 [M + H]$^+$. |
| 16 | WX016 | ¹H NMR (400 MHz, CDCl$_3$) δ: 8.70 (br s, 1H), 7.36-7.24 (m, 4H), 7.20-7.13 (m, 2H), 7.09 (dd, J = 1.8, 8.3 Hz, 1H), 7.06-6.98 (m, 2H), 6.84 (d, J = 8.3 Hz, 1H), 5.85 (dd, J = 4.5, 9.3 Hz, 1H), 4.80 (dd, J = 9.3, 14.8 Hz, 1H), 4.09 (q, J = 7.0 Hz, 2H), 3.93-3.87 (m, 1H), 3.85 (s, 3H), 3.82 (s, 3H), 2.79 (s, 3H), 1.44 (t, J = 6.9 Hz, 3H). | MS-ESI m/z: 497.0 [M + H]$^+$. |

TABLE 2-continued

| Embodiment | Compound | HNMR | LCMS |
|---|---|---|---|
| 17 | WX017 | ¹H NMR (400 MHz, CDCl₃) δ: 9.96 (br s, 1H), 7.73 (d, J = 7.8 Hz, 1H), 7.58-7.51 (m, 1H), 7.50-7.40 (m, 1H), 7.30 (d, J = 7.3 Hz, 1H), 7.17 (br s, 1H), 7.13 (d, J = 8.0 Hz, 1H), 7.09 (d, J = 8.5 Hz, 1H), 7.07-7.02 (m, 2H), 6.83 (d, J = 8.3 Hz, 1H), 5.85 (dd, J = 4.6, 8.4 Hz, 1H), 4.72 (dd, J = 9.3, 14.6 Hz, 1H), 4.05 (q, J = 6.7 Hz, 2H), 3.93 (dd, J = 4.0, 14.8 Hz, 1H), 3.83 (s, 3H), 2.75 (s, 3H), 1.37 (t, J = 6.8 Hz, 3H). | MS-ESI m/z: 535.1 [M + H]⁺. |
| 18 | WX018 | ¹H NMR (400 MHz, CDCl₃) δ: 7.42-7.31 (m, 2H), 7.24-7.16 (m, 2H), 7.12 (d, J = 7.8 Hz, 3H), 7.04-6.94 (m, 2H), 6.85 (d, J = 8.3 Hz, 1H), 5.88-5.78 (m, 1H), 4.78 (dd, J = 9.4, 14.9 Hz, 1H), 4.09 (q, J = 6.8 Hz, 2H), 3.95-3.81 (m, 4H), 3.07-2.97 (m, 1H), 2.86-2.73 (m, 3H), 1.47-1.39 (m, 3H), 1.14 (d, J = 6.8 Hz, 6H). | MS-ESI m/z: 509.1 [M + H]⁺. |
| 19 | WX019 | ¹H NMR (400 MHz, CDCl₃) δ: 9.62 (br s, 1H), 7.34-7.27 (m, 2H), 7.23-7.15 (m, 3H), 7.13 (d, J = 7.5 Hz, 1H), 7.11-7.03 (m, 3H), 6.84 (d, J = 8.3 Hz, 1H), 5.89 (dd, J = 4.5, 9.0 Hz, 1H), 4.70 (dd, J = 9.4, 14.7 Hz, 1H), 4.08 (q, J = 6.9 Hz, 2H), 3.92 (dd, J = 4.5, 14.8 Hz, 1H), 3.84 (s, 3H), 2.80 (s, 3H), 2.56 (q, J = 7.5 Hz, 2H), 1.42 (t, J = 6.9 Hz, 3H), 1.08 (t, J = 7.5 Hz, 3H). | MS-ESI m/z: 495.1 [M + H]⁺. |

Embodiment 20: WX020

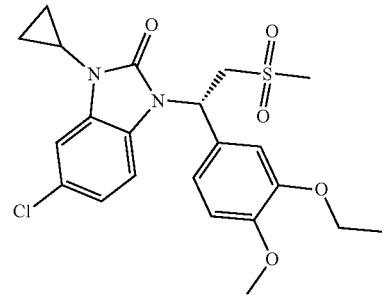 [SMILES: CCOc1cc([C@@H](CS(C)(=O)=O)n2c(=O)n(C3CC3)c3cc(Cl)ccc32)ccc1OC]

Synthesis Route:

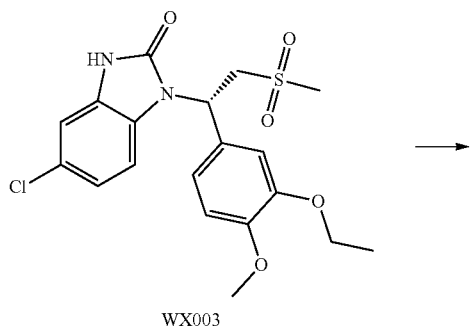

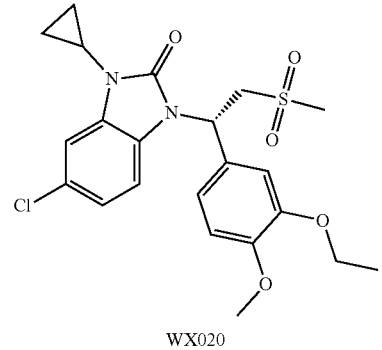

WX020

Compound WX003 (50.00 mg, 117.67 μmol) and cyclopropylboronic acid (20.22 mg, 235.34 μmol) were dissolved in dichloromethane (2.00 mL) at room temperature, followed by the addition of 2,2'-bipyridine (18.38 mg, 117.67 μmol) and copper acetate (42.74 mg, 235.34 μmol). The reaction mixture was stirred at room temperature for 24 hours. After the reaction, water (10 mL) was added and extracted with ethyl acetate (10 mL×3). The organic phases were combined, washed with saturated brine (10 mL×2) and dried over anhydrous sodium sulfate, followed by filtration. The filtrate was concentrated under reduced pressure. The obtained residue was purified by preparative HPLC to obtain the target product WX020. MS-ESI m/z: 465.1 [M+H]⁺. ¹H NMR (400 MHz, MeOD) δ: 7.30 (d, J=1.5 Hz, 1H), 7.17-7.10 (m, 2H), 7.07 (d, J=8.5 Hz, 2H), 6.95 (d, J=8.5 Hz, 1H), 6.02 (dd, J=3.8, 10.8 Hz, 1H), 4.56 (dd, J=10.8, 14.3 Hz, 1H), 4.16-3.97 (m, 3H), 3.82 (s, 3H), 3.04-2.87 (m, 4H), 1.39 (t, J=6.8 Hz, 3H), 1.20-1.06 (m, 2H), 1.01-0.93 (m, 2H).

The compounds of each embodiment in the following table were prepared according to the method of embodiment 20.

TABLE 3

| Embodiment | Fragment 1 | Fragment 2 | Structure | Compound |
|---|---|---|---|---|
| 21 | WX004 | (cyclopropyl boronic acid) | 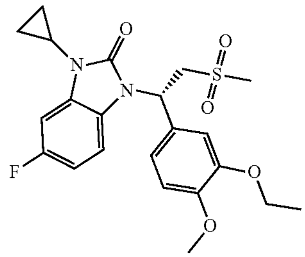 [SMILES: CCOc1cc([C@@H](CS(C)(=O)=O)n2c(=O)n(C3CC3)c3cc(F)ccc32)ccc1OC] | WX021 |
| 22 | WX002 | (cyclopropyl boronic acid) | 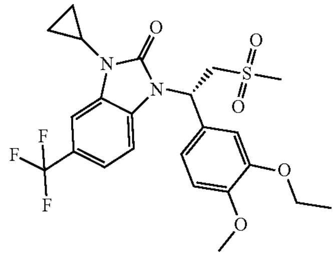 [SMILES: CCOc1cc([C@@H](CS(C)(=O)=O)n2c(=O)n(C3CC3)c3cc(C(F)(F)F)ccc32)ccc1OC] | WX022 |
| 23 | WX011 | (cyclopropyl boronic acid) | 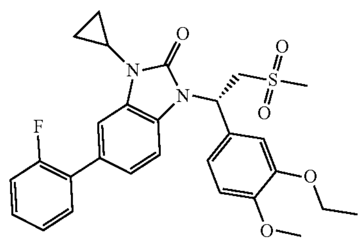 [SMILES: CCOc1cc([C@@H](CS(C)(=O)=O)n2c(=O)n(C3CC3)c3cc(-c4ccccc4F)ccc32)ccc1OC] | WX023 |

LCMS and ¹H NMR data of each embodiment

TABLE 4

| Embodiment | Compound | HNMR | LCMS |
|---|---|---|---|
| 21 | WX021 | ¹H NMR (400 MHz, MeOD) δ: 7.30 (d, J = 1.5 Hz, 1H), 7.17-7.10 (m, 2H), 7.07 (d, J = 8.5 Hz, 2H), 6.95 (d, J = 8.5 Hz, 1H), 6.02 (dd, J = 3.8, 10.8 Hz, 1H), 4.56 (dd, J = 10.8, 14.3 Hz, 1H), 4.16-3.97 (m, 3H), 3.82 (s, 3H), 3.04-2.87 (m, 4H), 1.39 (t, J = 6.8 Hz, 3H), 1.20-1.06 (m, 2H), 1.01-0.93 (m, 2H). | MS-ESI m/z: 449.1 [M + H]⁺. |
| 22 | WX022 | ¹H NMR (400 MHz, MeOD) δ: 7.52 (s, 1H), 7.44-7.31 (m, 2H), 7.15 (d, J = 1.5 Hz, 1H), 7.11-7.05 (m, 1H), 6.96 (d, J = 8.5 Hz, 1H), 6.09 (dd, J = 3.8, 10.8 Hz, 1H), 4.60 (dd, J = 11.0, 14.6 Hz, 1H), 4.17-3.97 (m, 3H), 3.83 (s, 3H), 3.05-2.94 (m, 4H), 1.39 (t, J = 6.8 Hz, 3H), 1.23-1.13 (m, 2H), 1.05-0.93 (m, 2H). | MS-ESI m/z: 499.1 [M + H]⁺. |

TABLE 4-continued

| Embodiment | Compound | HNMR | LCMS |
|---|---|---|---|
| 23 | WX023 | $^1$H NMR (400 MHz, CDCl$_3$) δ: 7.48-7.37 (m, 2H), 7.36-7.29 (m, 1H), 7.26-7.12 (m, 5H), 7.09 (d, J = 8.0 Hz, 1H), 6.83 (d, J = 8.3 Hz, 1H), 5.80 (dd, J = 4.4, 8.9 Hz, 1H), 4.75 (dd, J = 9.3, 14.6 Hz, 1H), 4.10 (q, J = 6.8 Hz, 2H), 3.95-3.79 (m, 4H), 2.92 (d, J = 3.3 Hz, 1H), 2.76 (s, 3H), 1.46 (t, J = 6.9 Hz, 3H), 1.14 (d, J = 4.8 Hz, 2H), 1.02 (d, J = 2.8 Hz, 2H). | MS-ESI m/z: 525.2 [M + H]$^+$. |

Embodiment 24: WX024

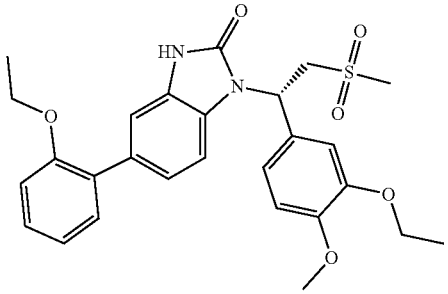 [SMILES: CCOc1cc([C@@H](CS(C)(=O)=O)n2c(=O)[nH]c3cc(-c4ccccc4OCC)ccc32)ccc1OC]

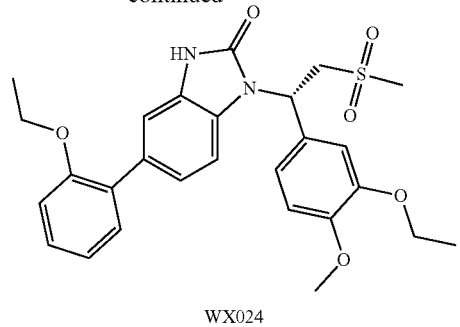

WX024

Synthesis Route:

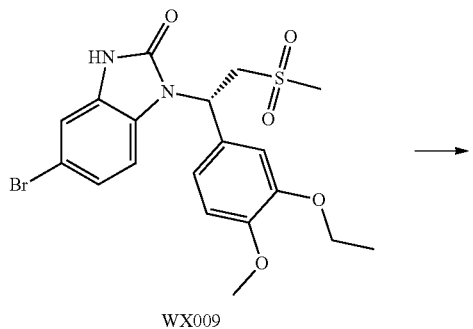

WX009

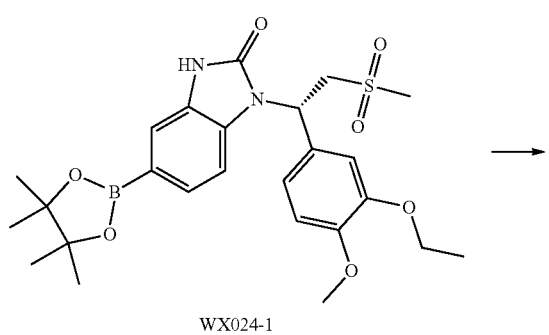

WX024-1

Step 1: Preparation of WX024-1

Compound WX009 (3.00 g, 6.39 mmol) and bis(pinacolato)diboron (1.78 g, 7.03 mmol) were dissolved in dioxane (60.00 mL) at room temperature, followed by the addition of (1,1'-bis(diphenylphosphine)ferrocene) palladium dichloride dichloromethane complex (521.83 mg, 639.00 µmol) and potassium acetate (1.88 g, 19.17 mmol). The reaction mixture was heated to 80° C. and stirred for 4 hours under nitrogen atmosphere. After the reaction, the mixture was cooled to room temperature, and the insolubles was removed by filtration. The filtrate was concentrated under reduced pressure. The residue was purified by flash silica gel column chromatography (eluent:ethyl acetate/petroleum ether=0/1-17/1, volume ratio) to obtain the target product WX024-1. $^1$H NMR (400 MHz, CDCl$_3$) δ: 8.67 (br s, 1H), 7.60 (dd, J=0.9, 7.9 Hz, 1H), 7.50 (s, 1H), 7.21-7.10 (m, 2H), 7.06 (dd, J=2.0, 8.3 Hz, 1H), 6.87-6.74 (m, 1H), 5.82 (dd, J=4.8, 9.3 Hz, 1H), 4.74 (dd, J=9.4, 14.9 Hz, 1H), 4.07 (q, J=7.0 Hz, 2H), 3.90 (dd, J=4.8, 14.8 Hz, 1H), 3.84 (s, 3H), 2.73 (s, 3H), 1.34 (s, 12H), 1.31-1.23 (m, 3H).

Step 2: Preparation of WX024

Compound WX024-1 (50.00 mg, 96.82 µmol) and 1-bromo-2-ethoxybenzene (38.93 mg, 193.64 µmol) were dissolved in dioxane (3.00 mL) and water (1.00 mL) at room temperature, followed by the addition of potassium carbonate (26.76 mg, 193.64 µmol) and (1,1'-bis(diphenylphosphino)ferrocene) palladium chloride dichloromethane complex (3.54 mg, 4.84 µmol). The reaction mixture was heated to 80° C. and stirred for 12 hours under nitrogen atmosphere. After the reaction, the mixture was cooled to room temperature, added with water (5.00 mL), stirred for 5 minutes, and extracted with ethyl acetate (10 mL×3). The organic phases were combined, washed with saturated brine (8 mL×2) and dried over anhydrous sodium sulfate, followed by filtration. The filtrate was concentrated under reduced pressure. The obtained residue was purified by preparative TLC (eluent: ethyl acetate/petroleum ether=2/1, volume ratio), and further purified by preparative HPLC to obtain the target product WX024. MS-ESI m/z: 511.1 [M+H]⁺. ¹H NMR (400 MHz, CDCl₃) δ: 9.50 (br s, 1H), 7.35-7.26 (m, 4H), 7.19-7.12 (m, 2H), 7.07 (d, J=8.3 Hz, 1H), 7.04-6.93 (m, 2H), 6.81 (d, J=8.3 Hz, 1H), 5.99-5.79 (m, 1H), 4.71 (dd, J=9.5, 14.1 Hz, 1H), 4.10-4.00 (m, 4H), 3.92 (d, J=14.6 Hz, 1H), 3.82 (br s, 3H), 2.77 (br s, 3H), 1.44-1.39 (m, 3H), 1.36-1.30 (m, 3H).

The compounds of each embodiment in the following table were prepared according to the method of embodiment 24.

TABLE 5

| Embodiment | Fragment 1 | Fragment 2 | Structure | Compound |
|---|---|---|---|---|
| 25 | WX024-1 | | 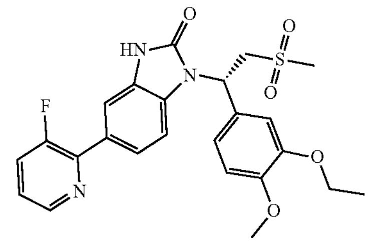 [SMILES: CCOc1cc([C@@H](CS(C)(=O)=O)n2c(=O)[nH]c3cc(-c4ncccc4F)ccc32)ccc1OC] | WX025 |
| 26 | WX024-1 | | 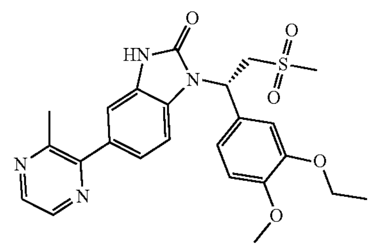 [SMILES: CCOc1cc([C@@H](CS(C)(=O)=O)n2c(=O)[nH]c3cc(-c4nccnc4C)ccc32)ccc1OC] | WX026 |
| 27 | WX024-1 | | 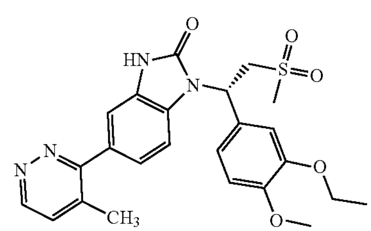 [SMILES: CCOc1cc([C@@H](CS(C)(=O)=O)n2c(=O)[nH]c3cc(-c4nnccc4C)ccc32)ccc1OC] | WX027 |
| 28 | WX024-1 | | 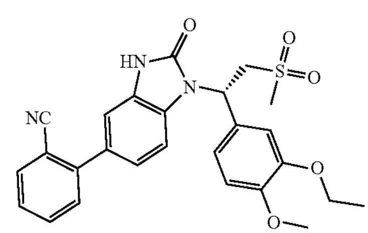 [SMILES: CCOc1cc([C@@H](CS(C)(=O)=O)n2c(=O)[nH]c3cc(-c4ccccc4C#N)ccc32)ccc1OC] | WX028 |
| 29 | WX024-1 | | 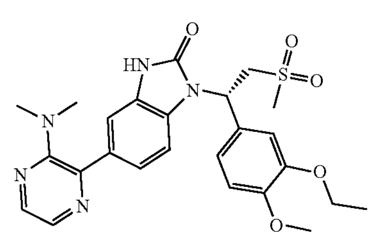 [SMILES: CCOc1cc([C@@H](CS(C)(=O)=O)n2c(=O)[nH]c3cc(-c4nccnc4N(C)C)ccc32)ccc1OC] | WX029 |

TABLE 5-continued

| Embodiment | Fragment 1 | Fragment 2 | Structure | Compound |
|---|---|---|---|---|
| 30 | 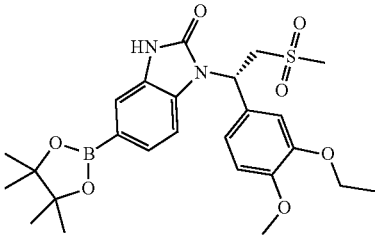 [SMILES: CCOc1cc([C@@H](CS(C)(=O)=O)n2c(=O)[nH]c3cc(B4OC(C)(C)C(C)(C)O4)ccc32)ccc1OC] WX024-1 | 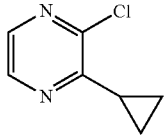 | 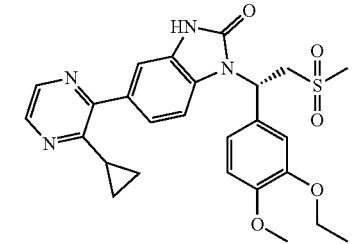 [SMILES: CCOc1cc([C@@H](CS(C)(=O)=O)n2c(=O)[nH]c3cc(-c4nccnc4C4CC4)ccc32)ccc1OC] | WX030 |

LCMS and ¹H NMR data of each embodiment

TABLE 6

| Embodiment | Compound | HNMR | LCMS |
|---|---|---|---|
| 25 | WX025 | ¹H NMR (400 MHz, CDCl$_3$) δ: 9.38 (s, 1H), 8.50 (d, J = 4.5 Hz, 1H), 7.80-7.72 (m, 2H), 7.48 (ddd, J = 1.1, 8.3, 11.2 Hz, 1H), 7.27-7.22 (m, 1H), 7.20 (d, J = 8.3 Hz, 1H), 7.15 (d, J = 2.0 Hz, 1H), 7.07 (dd, J = 2.0, 8.5 Hz, 1H), 6.83 (d, J = 8.3 Hz, 1H), 5.87 (dd, J = 4.5, 9.3 Hz, 1H), 4.75 (dd, J = 9.4, 14.9 Hz, 1H), 4.07 (q, J = 6.9 Hz, 2H), 3.91 (dd, J = 4.5, 14.8 Hz, 1H), 3.83 (s, 3H), 2.77 (s, 3H), 1.41 (t, J = 7.0 Hz, 3H). | MS-ESI m/z: 486.1 [M + H]⁺. |
| 26 | WX026 | ¹H NMR (400 MHz, CDCl$_3$) δ: 9.30 (s, 1H), 8.48-8.41 (m, 2H), 7.35-7.29 (m, 2H), 7.18 (d, J = 8.0 Hz, 1H), 7.14 (d, J = 2.0 Hz, 1H), 7.07 (dd, J = 1.9, 8.4 Hz, 1H), 6.83 (d, J = 8.5 Hz, 1H), 5.87 (dd, J = 4.5, 9.3 Hz, 1H), 4.75 (dd, J = 9.5, 14.8 Hz, 1H), 4.07 (q, J = 7.0 Hz, 2H), 3.89 (dd, J = 4.5, 14.8 Hz, 1H), 3.84 (s, 3H), 2.79 (s, 3H), 2.65 (s, 3H), 1.42 (t, J = 7.0 Hz, 3H). | MS-ESI m/z: 483.1 [M + H]⁺. |
| 27 | WX027 | ¹H NMR (400 MHz, CDCl$_3$) δ: 9.50 (s, 1H), 9.05 (d, J = 5.0 Hz, 1H), 7.53 (s, 1H), 7.41 (d, J = 5.3 Hz, 1H), 7.27 (d, J = 1.3 Hz, 1H), 7.24-7.14 (m, 2H), 7.09 (dd, J = 2.0, 8.3 Hz, 1H), 6.86 (d, J = 8.3 Hz, 1H), 5.88 (dd, J = 4.4, 9.4 Hz, 1H), 4.83 (dd, J = 9.5, 15.1 Hz, 1H), 4.10 (q, J = 6.9 Hz, 2H), 3.92-3.82 (m, 4H), 2.82 (s, 3H), 2.44 (s, 3H), 1.46 (t, J = 7.0 Hz, 3H). | MS-ESI m/z: 484.1 [M + H]⁺. |
| 28 | WX028 | ¹H NMR (400 MHz, CDCl$_3$) δ: 9.55 (br s, 1H), 7.77 (d, J = 7.5 Hz, 1H), 7.70-7.61 (m, 1H), 7.54-7.42 (m, 2H), 7.34-7.23 (m, 3H), 7.16 (d, J = 1.5 Hz, 1H), 7.10 (dd, J = 1.8, 8.3 Hz, 1H), 6.86 (d, J = 8.3 Hz, 1H), 5.91 (dd, J = 4.8, 9.3 Hz, 1H), 4.74 (dd, J = 9.4, 14.7 Hz, 1H), 4.10 (q, J = 7.0 Hz, 2H), 3.94 (dd, J = 4.4, 14.7 Hz, 1H), 3.86 (s, 3H), 2.84 (s, 3H), 1.44 (t, J = 7.0 Hz, 3H). | MS-ESI m/z: 492.1 [M + H]⁺. |
| 29 | WX029 | ¹H NMR (400 MHz, CDCl$_3$) δ: 9.20 (br, s, 1H), 8.17-7.96 (m, 2H), 7.61-7.43 (m, 2H), 7.20-7.00 (m, 3H), 6.81 (d, J = 8.0 Hz, 1H), 5.85 (d, J = 4.5 Hz, 1H), 4.77-4.61 (m, 1H), 4.06 (q, J = 6.9 Hz, 2H), 3.93-3.73 (m, 4H), 2.82-2.77 (m, 9H), 1.42 (t, J = 6.9 Hz, 3H). | MS-ESI m/z: 512.2 [M + H]⁺. |
| 30 | WX030 | ¹H NMR (400 MHz, CDCl$_3$) δ: 9.73 (br s, 1H), 8.60 (br s, 1H), 8.47 (br s, 1H), 7.62 (br s, 1H), 7.48 (d, J = 6.0 Hz, 1H), 7.22-7.05 (m, 3H), 6.84 (d, J = 8.0 Hz, 1H), 5.88 (d, J = 5.5 Hz, 1H), 4.82-4.66 (m, 1H), 4.08 (q, J = 6.5 Hz, 2H), 3.85 (s, 4H), 2.82 (s, 3H), 2.34 (br s, 1H), 1.45-1.36 (m, 3H), 1.30 (br s, 2H), 1.13 (d, J = 5.5 Hz, 2H). | MS-ESI m/z: 509.1 [M + H]⁺. |

Embodiment 31: WX031

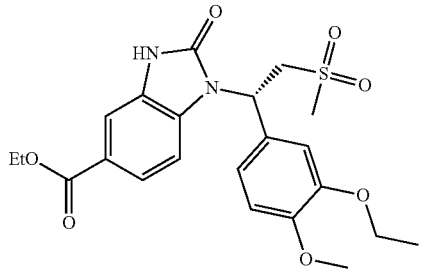 [SMILES: CCOC(=O)c1ccc2c(c1)[nH]c(=O)n2[C@H](CS(C)(=O)=O)c1ccc(OC)c(OCC)c1]

Synthesis Route:

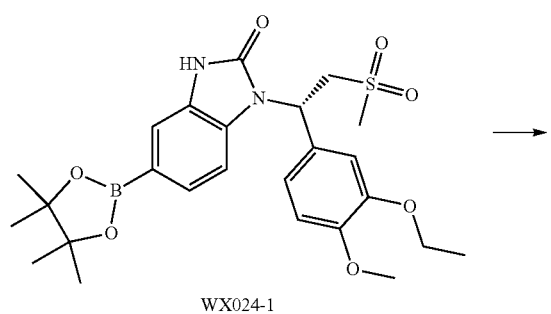

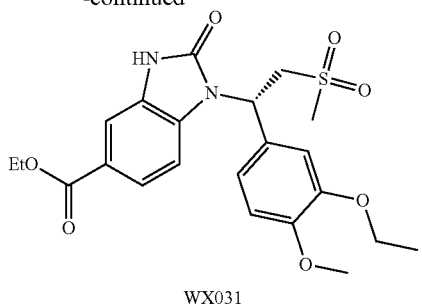

Compound WX024-1 (150.00 mg, 290.47 µmol), triphenylphosphine (7.62 mg, 29.05 µmol) and benzophenone (52.93 mg, 290.47 µmol) were dissolved in ethanol (1.00 mL) at room temperature, followed by the addition of palladium acetate (3.26 mg, 14.52 µmol). The reaction mixture was stirred at room temperature for 16 hours under carbon monoxide (15 psi) atmosphere. The insolubles was removed by filtration, and the filtrate was directly purified by preparative HPLC to obtain the target product WX031. MS-ESI m/z: 463.1 [M+H]$^+$. $^1$H NMR (400 MHz, CDCl$_3$) δ: 9.96 (br s, 1H), 7.84 (dd, J=1.4, 8.4 Hz, 1H), 7.75 (d, J=1.0 Hz, 1H), 7.18-7.09 (m, 2H), 7.05 (dd, J=1.6, 8.4 Hz, 1H), 6.82 (d, J=8.3 Hz, 1H), 5.88 (dd, J=4.5, 9.3 Hz, 1H), 4.71 (dd, J=9.5, 14.6 Hz, 1H), 4.35 (q, J=7.2 Hz, 2H), 4.04 (q, J=6.9 Hz, 2H), 3.92 (dd, 14.6 Hz, 1H), 3.82 (s, 3H), 2.80 (s, 3H), 1.39 (td, J=6.9, 10.5 Hz, 6H).

The compounds of each embodiment in the following table were prepared according to the method of embodiment 31.

TABLE 7

| Embodiment | Fragment 1 | Fragment 2 | Structure | Compound |
|---|---|---|---|---|
| 32 | ![WX024-1] | isopropanol (OH) | structure | WX032 |
| 33 | ![WX024-1] | F₃C-CH₂-OH | structure | WX033 |

LCMS and ¹H NMR data of each embodiment

TABLE 8

| Embodiment | Compound | HNMR | LCMS |
|---|---|---|---|
| 32 | WX032 | ¹H NMR (400 MHz, CDCl₃) δ: 8.70 (br s, 1H), 7.85 (dd, J = 1.3, 8.3 Hz, 1H), 7.74 (s, 1H), 7.16-7.09 (m, 2H), 7.05 (d, J = 8.3 Hz, 1H), 6.82 (d, J = 8.3 Hz, 1H), 5.85 (dd, J = 4.4, 9.4 Hz, 1H), 5.23 (quin, J = 6.2 Hz, 1H), 4.70 (dd, J = 9.8, 14.6 Hz, 1H), 4.06 (q, J = 7.0 Hz, 2H), 3.92-3.79 (m, 4H), 2.78 (s, 3H), 1.43 (t, J = 7.0 Hz, 3H), 1.35 (d, J = 6.3 Hz, 6H). | MS-ESI m/z: 477.2 [M + H]⁺. |
| 33 | WX033 | ¹H NMR (400 MHz, CDCl₃) δ: 9.61 (br s, 1H), 7.86 (dd, J = 1.0, 8.5 Hz, 1H), 7.73 (s, 1H), 7.20-6.99 (m, 3H), 6.82 (d, J = 8.3 Hz, 1H), 5.89 (dd, J = 4.1, 9.7 Hz, 1H), 4.80-4.62 (m, 3H), 4.05 (q, J = 6.9 Hz, 2H), 3.89 (dd, J = 4.3, 14.6 Hz, 1H), 3.83 (s, 3H), 2.84 (s, 3H), 1.41 (t, J = 6.9 Hz, 3H). | MS-ESI m/z: 539.1 [M + H]⁺. |

Embodiment 34: WX034

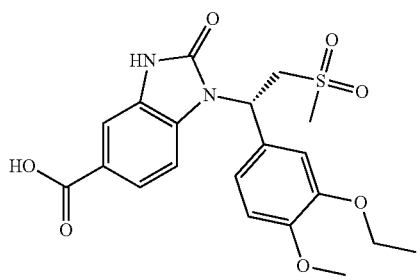 [SMILES: CCOc1cc([C@@H](CS(C)(=O)=O)n2c(=O)[nH]c3cc(C(=O)O)ccc32)ccc1OC]

Synthesis Route:

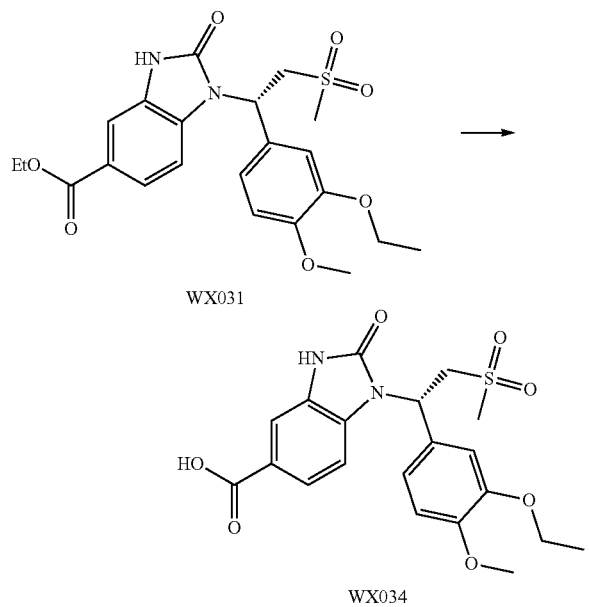

Compound WX031 (255.00 mg, 551.33 μmol) was dissolved in methanol (15.00 mL) and water (15.00 mL) at room temperature, followed by the addition of lithium hydroxide monohydrate (69.40 mg, 1.65 mmol). The reaction mixture was heated to 60° C. and stirred for 0.5 hours. After the reaction, the mixture was cooled to room temperature and extracted with dichloromethane (15 mL×3). The organic phases were discarded and the aqueous phases were acidified with dilute aqueous hydrochloric acid (3 M) to pH=4 and extracted with ethyl acetate (15 mL×3). The organic phases were combined, washed with saturated brine (45 mL×2) and dried over anhydrous sodium sulfate, followed by filtration. The filtrate was concentrated under reduced pressure. The obtained residue was purified by preparative HPLC to obtain the target product WX034. MS-ESI m/z: 435.0 [M+H]⁺. ¹H NMR (400 MHz, CDCl₃) δ: 11.23 (s, 1H), 7.61 (dd, J=1.1, 8.4 Hz, 1H), 7.50 (s, 1H), 7.35 (d, J=8.3 Hz, 1H), 7.15 (d, J=1.5 Hz, 1H), 7.06-6.97 (m, 1H), 6.96-6.89 (m, 1H), 5.97 (dd, J=4.0, 10.0 Hz, 1H), 4.53 (br dd, J=10.4, 14.4 Hz, 1H), 4.20 (br dd, J=4.0, 14.6 Hz, 1H), 4.00 (br t, J=6.8 Hz, 2H), 3.72 (s, 3H), 3.02 (s, 3H), 1.31 (t, J=7.0 Hz, 3H).

Embodiment 35: WX035

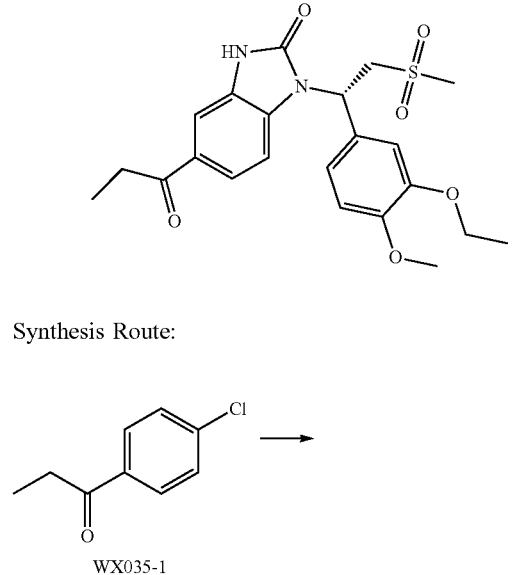

Synthesis Route:

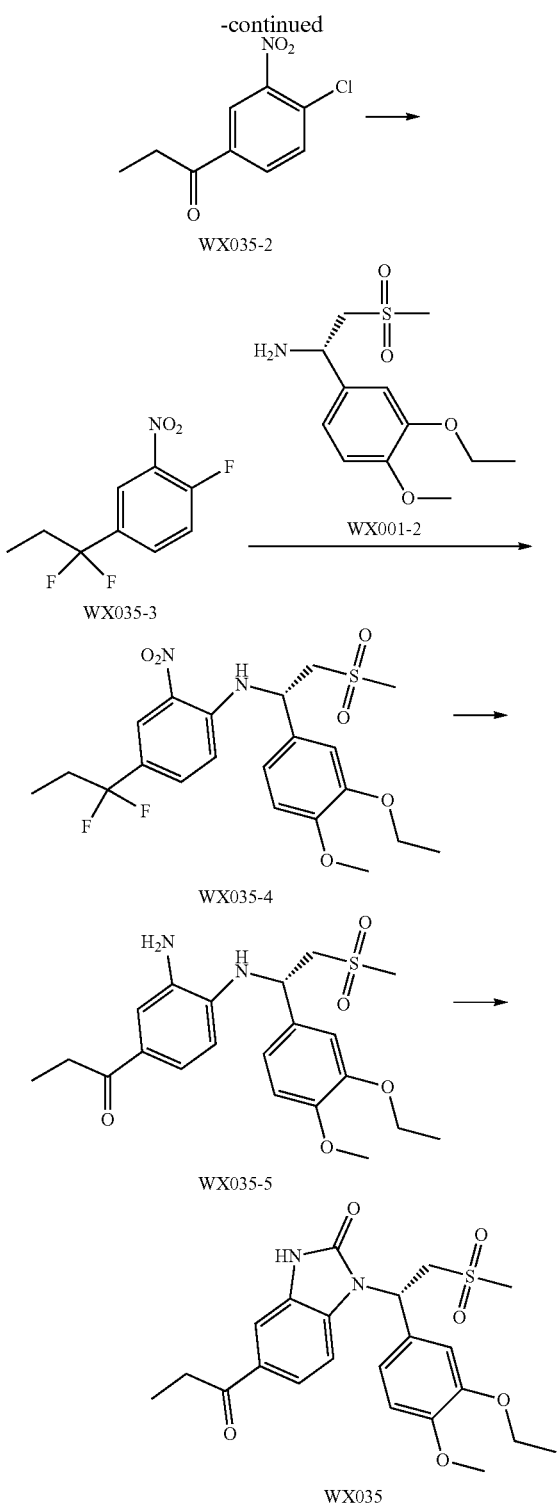

Step 1: Preparation of WX035-2

Compound WX035-1 (2.16 g, 12.81 mmol) was added to concentrated sulfuric acid (17 mL, 98%) at room temperature. The reaction mixture was cooled to −15° C., followed by the dropwise addition of the mixture of concentrated nitric acid (0.915 mL, 63%) and concentrated sulfuric acid (3 mL, 98%). The reaction was carried out for 30 minutes with stirring. After the reaction, the reaction mixture was poured into ice water (50 mL), followed by the addition of ethyl acetate (100 mL). The organic phases were washed with saturated brine (30 mL×2) and dried over anhydrous sodium sulfate, followed by filtration. The filtrate was concentrated under reduced pressure. The obtained residue was purified by column chromatography (eluent:ethyl acetate/petroleum ether=1/5, volume ratio) to obtain the target product WX035-2. $^1$H NMR (400 MHz, CDCl$_3$) δ: 8.43 (d, J=1.6 Hz, 1H), 8.09 (dd, J=2.0, 8.4 Hz, 1H)), 7.67 (d, J=8.0 Hz, 1H), 3.02 (q, J=7.6 Hz, 2H), 1.26 (t, J=7.2 Hz, 3H).

Step 2: Preparation of WX035-3

Compound WX035-2 (2.00 g, 9.36 mmol) and diethylaminosulfur trifluoride (7.55 g, 46.81 mmol) were dissolved in dichloromethane (50.00 mL) at room temperature. The reaction mixture was heated to 60° C. and stirred for 16 hours under nitrogen atmosphere. After the reaction, the mixture was cooled to room temperature, poured into ice water (30 mL), followed by the addition of dichloromethane (100 mL) with stirring for 10 minutes. The organic phases were washed with saturated brine (30 mL×2) and dried over anhydrous sodium sulfate, followed by filtration. The filtrate was concentrated under reduced pressure. The obtained residue was purified by column chromatography (eluent: ethyl acetate/petroleum ether=1/20, volume ratio) to obtain the target product WX035-3. $^1$H NMR (400 MHz, CDCl$_3$) δ: 7.98 (s, 1H), 7.65-7.60 (m, 2H), 2.23-2.09 (m, 2H), 1.02 (t, J=7.6 Hz, 3H).

Step 3: Preparation of WX035-4

Compound WX035-3 (950.00 mg, 4.03 mmol), compound WX001-2 (1.65 g, 6.05 mmol) and diisopropylethylamine (1.56 g, 12.10 mmol, 2.11 mL) were dissolved in N,N-dimethylformamide (20.00 mL) at room temperature. The reaction mixture was heated to 100° C. and stirred for 12 hours under nitrogen atmosphere. After the reaction, the mixture was cooled to room temperature and concentrated under reduced pressure. Ethyl acetate (100 mL) and water (30 mL) was added and washed with saturated brine (30 mL×2) and dried over anhydrous sodium sulfate, followed by filtration. The filtrate was concentrated under reduced pressure. The obtained residue was purified by preparative TLC (eluent:ethyl acetate/petroleum ether=1/1, volume ratio) to obtain the target product WX035-4. MS-ESI m/z: 495.2 [M+Na]$^+$.

Step 4: Preparation of WX035-5

Compound WX035-4 (280.00 mg, 592.59 μmol), zinc powder (310.00 mg, 4.74 mmol) and ammonium chloride (253.58 mg, 4.74 mmol) were added to methanol (10.00 mL) at room temperature. The reaction mixture was stirred at room temperature for 2 hours under nitrogen atmosphere. The insolubles was removed by filtration and the filtrate was concentrated under reduced pressure. Dichloromethane (50 mL) was added to the residue and stirred for 15 minutes. The insolubles was removed by filtration again and the filtrate was concentrated under reduced pressure. The obtained residue was purified by preparative HPLC to obtain the target product WX035-5. MS-ESI m/z: 443.1 [M+Na]$^+$.

Step 5: Preparation of WX035

Compound WX035-5 (30.00 mg, 71.34 μmol), triphosgene (10.59 mg, 35.67 μmol) and triethylamine (21.66 mg, 214.02 μmol, 29.67 μL) were dissolved in tetrahydrofuran (2.00 mL) at 0-5° C. The reaction mixture was stirred at 0-5° C. for 2 hours under nitrogen atmosphere. The reaction mixture was then poured into ice water (10 mL) with stirring at room temperature for 10 minutes and then extracted with ethyl acetate (30 mL×2). The organic phases were separated and the aqueous phase was extracted with ethyl acetate (30 mL×2). The organic phases were combined, washed with saturated brine (30 mL) and dried over anhydrous sodium sulfate, followed by filtration. The filtrate was concentrated under reduced pressure. The obtained residue was purified by preparative HPLC to obtain the target product WX035. MS-ESI m/z: 447.0 [M+H]+. $^1$H NMR (400 MHz, CDCl$_3$) δ: 8.54 (s, 1H), 7.77 (d, J=8.4 Hz, 1H), 7.70 (s, 1H), 7.15-7.05 (m, 3H), 6.84 (d, J=8.4 Hz 1H), 5.85 (dd, J=4.0, 9.2 Hz, 1H), 4.73 (dd, J=9.6, 14.8 Hz, 1H), 2.98 (q, J=7.2 Hz, 2H), 3.91-3.85 (m, 4H), 2.98 (q, J=7.2 Hz, 2H), 2.81 (s, 3H), 1.44 (t, J=6.8 Hz, 3H), 1.23 (t, J=7.2 Hz, 3H).

Embodiment 36: WX036

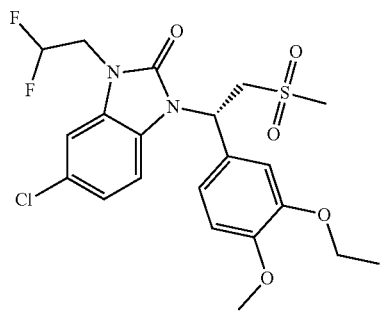 [SMILES: CCOc1cc([C@@H](CS(C)(=O)=O)n2c(=O)n(CC(F)F)c3cc(Cl)ccc32)ccc1OC]

Synthesis Route:

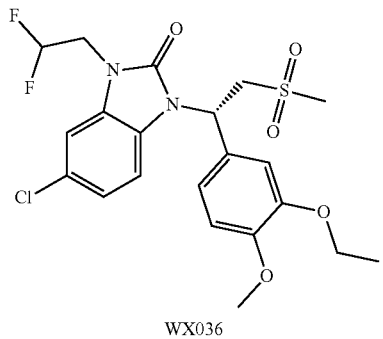
WX036

Compound WX003 (300.00 mg, 706.05 μmol), 2,2-difluoroethyl-4-methylbenzenesulfonate (498.25 mg, 2.12 mmol) and potassium carbonate (292.75 mg, 2.12 mmol) were dissolved in N,N-dimethylformamide (10.00 mL) at room temperature. The reaction mixture was stirred at room temperature for 12 hours under nitrogen atmosphere. After the reaction, ethyl acetate (100 mL) and water (30 mL) were added to the mixture, and the organic phases were separated. The aqueous phases were washed with saturated brine (30 mL) and dried over anhydrous sodium sulfate, followed by filtration. The filtrate was concentrated under reduced pressure. The obtained residue was purified by column chromatography (eluent:ethyl acetate/petroleum ether=1/5-1/1) to obtain the target product WX036. MS-ESI m/z: 511.0 [M+Na]+. $^1$H NMR (400 MHz, CDCl$_3$) δ: 7.09-6.82 (m, 6H), 6.03-6.02 (m, 1H), 5.80-5.76 (m, 1H), 4.71-4.66 (m, 1H), 4.22-4.03 (m, 4H), 3.85-3.81 (m, 4H), 2.77 (s, 3H), 1.45 (t, J=6.4 Hz, 3H).

The compounds of each embodiment in the following table were prepared according to the method of embodiment 36.

TABLE 9

| Embodiment | Fragment 1 | Fragment 2 | Structure | Compound |
|---|---|---|---|---|
| 37 | WX003 | F₃C-CH₂-OTf | 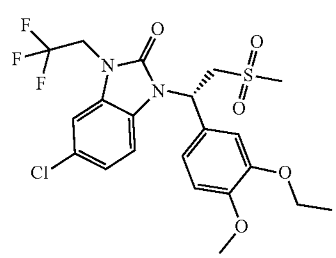 [SMILES: CCOc1cc([C@@H](CS(C)(=O)=O)n2c(=O)n(CC(F)(F)F)c3cc(Cl)ccc32)ccc1OC] | WX037 |

TABLE 9-continued

| Embodiment | Fragment 1 | Fragment 2 | Structure | Compound |
|---|---|---|---|---|
| 38 | WX003 | Me—I | 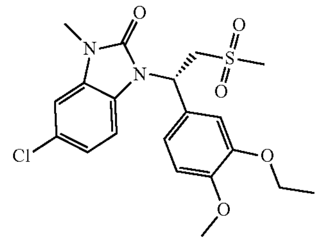 [SMILES: CCOc1cc([C@@H](CS(C)(=O)=O)n2c(=O)n(C)c3cc(Cl)ccc32)ccc1OC] | WX038 |
| 39 | WX003 | Et—Br | 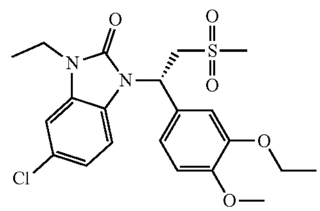 [SMILES: CCOc1cc([C@@H](CS(C)(=O)=O)n2c(=O)n(CC)c3cc(Cl)ccc32)ccc1OC] | WX039 |
| 40 | WX003 | cyclopropyl-CH2Br | 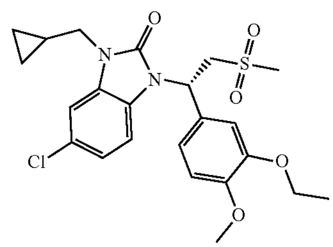 [SMILES: CCOc1cc([C@@H](CS(C)(=O)=O)n2c(=O)n(CC3CC3)c3cc(Cl)ccc32)ccc1OC] | WX040 |
| 41 | WX003 | cyclobutyl-CH2Br | 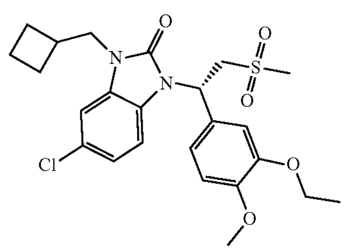 [SMILES: CCOc1cc([C@@H](CS(C)(=O)=O)n2c(=O)n(CC3CCC3)c3cc(Cl)ccc32)ccc1OC] | WX041 |
| 42 | WX003 | MeOCH2CH2Br | 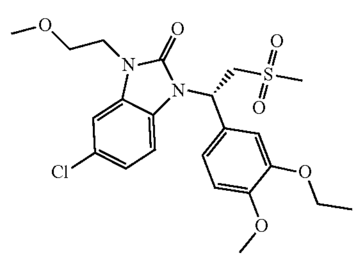 [SMILES: CCOc1cc([C@@H](CS(C)(=O)=O)n2c(=O)n(CCOC)c3cc(Cl)ccc32)ccc1OC] | WX042 |

TABLE 9-continued

| Embodiment | Fragment 1 | Fragment 2 | Structure | Compound |
|---|---|---|---|---|
| 43 | WX003 | HO-CH2CH2-Br | 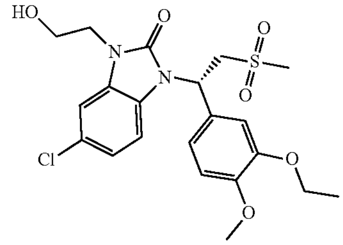 [SMILES: CCOc1cc([C@@H](CS(C)(=O)=O)n2c(=O)n(CCO)c3cc(Cl)ccc32)ccc1OC] | WX043 |
| 44 | WX003 | isopropyl iodide | 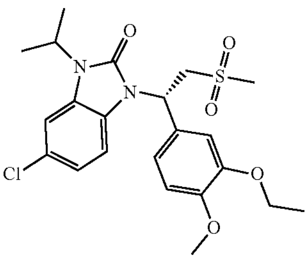 [SMILES: CCOc1cc([C@@H](CS(C)(=O)=O)n2c(=O)n(C(C)C)c3cc(Cl)ccc32)ccc1OC] | WX044 |
| 45 | WX003 | NC-CH2-Br | 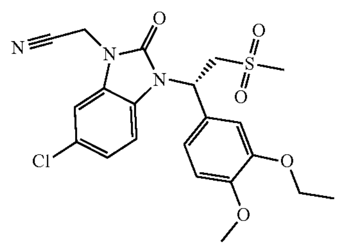 [SMILES: CCOc1cc([C@@H](CS(C)(=O)=O)n2c(=O)n(CC#N)c3cc(Cl)ccc32)ccc1OC] | WX045 |
| 46 | WX004 | CHF2CH2-OTs | 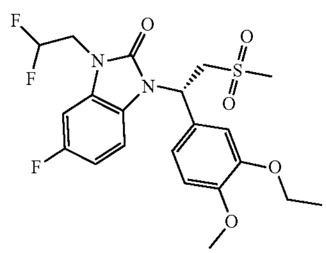 [SMILES: CCOc1cc([C@@H](CS(C)(=O)=O)n2c(=O)n(CC(F)F)c3cc(F)ccc32)ccc1OC] | WX046 |
| 47 | WX004 | CF3CH2-OTf | 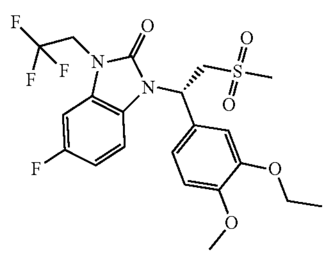 [SMILES: CCOc1cc([C@@H](CS(C)(=O)=O)n2c(=O)n(CC(F)(F)F)c3cc(F)ccc32)ccc1OC] | WX047 |

TABLE 9-continued

| Embodiment | Fragment 1 | Fragment 2 | Structure | Compound |
|---|---|---|---|---|
| 48 | WX004 | Me—I | 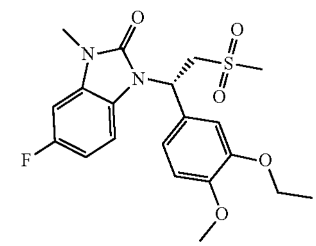 [SMILES: CCOc1cc([C@@H](CS(C)(=O)=O)n2c(=O)n(C)c3cc(F)ccc32)ccc1OC] | WX048 |
| 49 | WX004 | NC—CH2—Br | 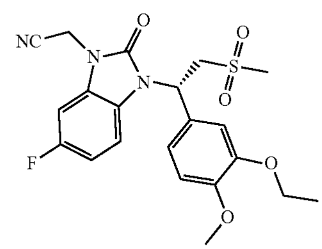 [SMILES: CCOc1cc([C@@H](CS(C)(=O)=O)n2c(=O)n(CC#N)c3cc(F)ccc32)ccc1OC] | WX049 |
| 50 | WX004 | HO—CH2CH2—Br | 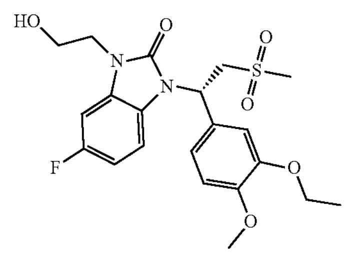 [SMILES: CCOc1cc([C@@H](CS(C)(=O)=O)n2c(=O)n(CCO)c3cc(F)ccc32)ccc1OC] | WX050 |
| 51 | WX002 | CHF2CH2—OTs | 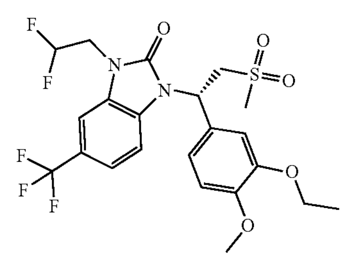 [SMILES: CCOc1cc([C@@H](CS(C)(=O)=O)n2c(=O)n(CC(F)F)c3cc(C(F)(F)F)ccc32)ccc1OC] | WX051 |
| 52 | WX002 | CF3CH2—OTf | 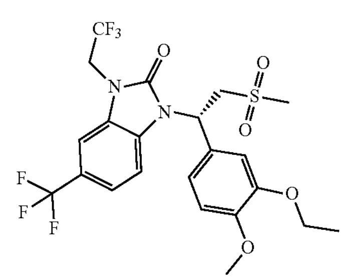 [SMILES: CCOc1cc([C@@H](CS(C)(=O)=O)n2c(=O)n(CC(F)(F)F)c3cc(C(F)(F)F)ccc32)ccc1OC] | WX052 |

TABLE 9-continued

| Embodiment | Fragment 1 | Fragment 2 | Structure | Compound |
|---|---|---|---|---|
| 53 | WX002 | Me—I | 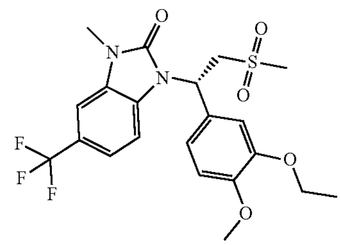 [SMILES: CCOc1cc([C@@H](CS(C)(=O)=O)n2c(=O)n(C)c3cc(C(F)(F)F)ccc32)ccc1OC] | WX053 |
| 54 | WX002 | CH₃CH₂—Br | 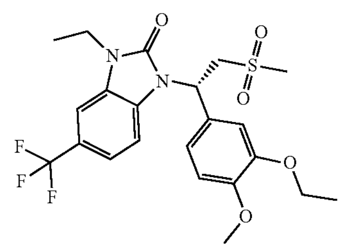 [SMILES: CCOc1cc([C@@H](CS(C)(=O)=O)n2c(=O)n(CC)c3cc(C(F)(F)F)ccc32)ccc1OC] | WX054 |
| 55 | WX002 | NC—CH₂—Br | 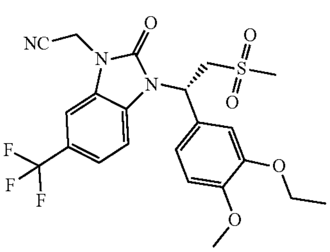 [SMILES: CCOc1cc([C@@H](CS(C)(=O)=O)n2c(=O)n(CC#N)c3cc(C(F)(F)F)ccc32)ccc1OC] | WX055 |
| 56 | WX002 | HO—CH₂CH₂—Br | 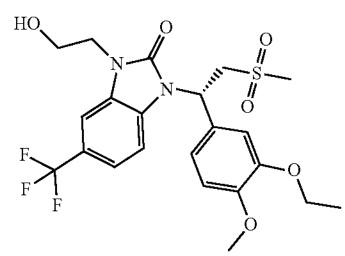 [SMILES: CCOc1cc([C@@H](CS(C)(=O)=O)n2c(=O)n(CCO)c3cc(C(F)(F)F)ccc32)ccc1OC] | WX056 |
| 57 | WX005 | Me—I | 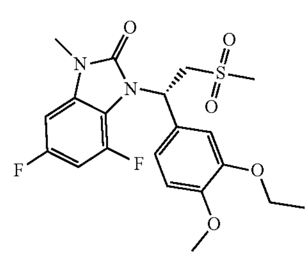 [SMILES: CCOc1cc([C@@H](CS(C)(=O)=O)n2c(=O)n(C)c3cc(F)cc(F)c32)ccc1OC] | WX057 |

TABLE 9-continued

| Embodiment | Fragment 1 | Fragment 2 | Structure | Compound |
|---|---|---|---|---|
| 58 | WX005 | NC–CH₂–Br | 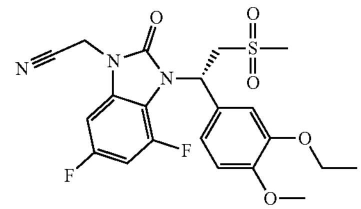 [SMILES: CCOc1cc([C@@H](CS(C)(=O)=O)n2c(=O)n(CC#N)c3cc(F)cc(F)c32)ccc1OC] | WX058 |
| 59 | WX005 | HO–CH₂CH₂–Br | 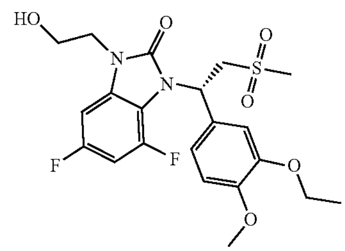 [SMILES: CCOc1cc([C@@H](CS(C)(=O)=O)n2c(=O)n(CCO)c3cc(F)cc(F)c32)ccc1OC] | WX059 |
| 60 | WX006 | 2-fluorobenzyl bromide | 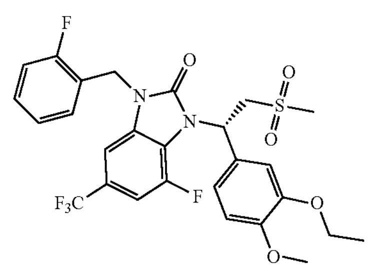 [SMILES: CCOc1cc([C@@H](CS(C)(=O)=O)n2c(=O)n(Cc3ccccc3F)c3cc(C(F)(F)F)cc(F)c32)ccc1OC] | WX060 |
| 61 | WX008 | CHF₂CH₂–OTs | 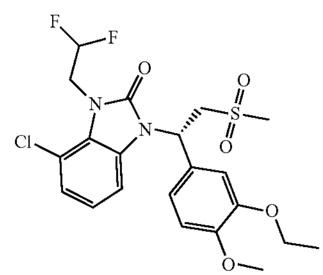 [SMILES: CCOc1cc([C@@H](CS(C)(=O)=O)n2c(=O)n(CC(F)F)c3c(Cl)cccc32)ccc1OC] | WX061 |
| 62 | WX008 | CF₃CH₂–OTf | 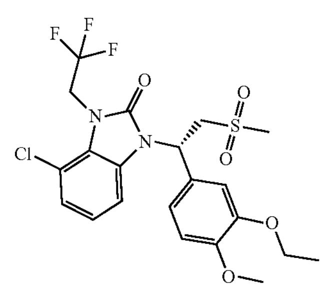 [SMILES: CCOc1cc([C@@H](CS(C)(=O)=O)n2c(=O)n(CC(F)(F)F)c3c(Cl)cccc32)ccc1OC] | WX062 |

TABLE 9-continued

| Embodi-ment | Fragment 1 | Fragment 2 | Structure | Compound |
|---|---|---|---|---|
| 63 | WX009 | | 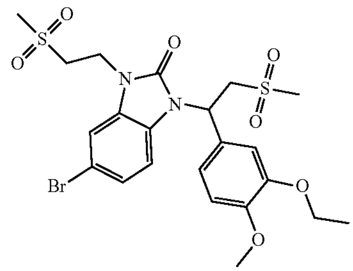 [SMILES: CCOc1cc(C(CS(C)(=O)=O)n2c(=O)n(CCS(C)(=O)=O)c3cc(Br)ccc32)ccc1OC] | WX063 |
| 64 | WX009 | | 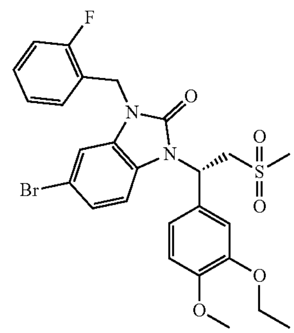 [SMILES: CCOc1cc([C@@H](CS(C)(=O)=O)n2c(=O)n(Cc3ccccc3F)c3cc(Br)ccc32)ccc1OC] | WX064 |
| 65 | WX009 | | 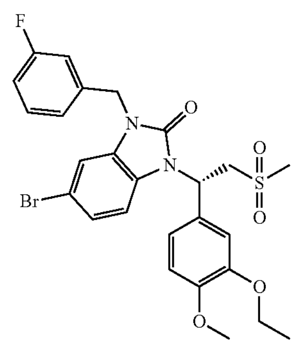 [SMILES: CCOc1cc([C@@H](CS(C)(=O)=O)n2c(=O)n(Cc3cccc(F)c3)c3cc(Br)ccc32)ccc1OC] | WX065 |
| 66 | WX009 | | 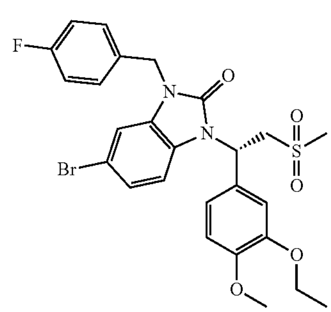 [SMILES: CCOc1cc([C@@H](CS(C)(=O)=O)n2c(=O)n(Cc3ccc(F)cc3)c3cc(Br)ccc32)ccc1OC] | WX066 |

TABLE 9-continued

| Embodiment | Fragment 1 | Fragment 2 | Structure | Compound |
|---|---|---|---|---|
| 67 | WX010 | 2-F-benzyl bromide | 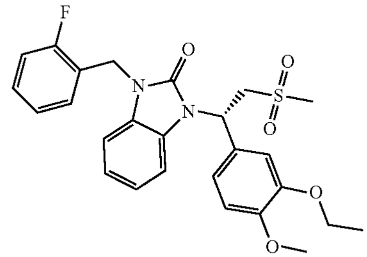 [SMILES: CCOc1cc([C@@H](CS(C)(=O)=O)n2c(=O)n(Cc3ccccc3F)c3ccccc32)ccc1OC] | WX067 |
| 68 | WX011 | Me—I | 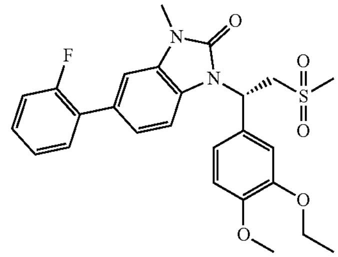 [SMILES: CCOc1cc([C@@H](CS(C)(=O)=O)n2c(=O)n(C)c3cc(-c4ccccc4F)ccc32)ccc1OC] | WX068 |
| 69 | WX011 | Et—Br | 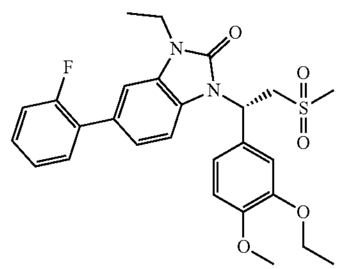 [SMILES: CCOc1cc([C@@H](CS(C)(=O)=O)n2c(=O)n(CC)c3cc(-c4ccccc4F)ccc32)ccc1OC] | WX069 |
| 70 | WX011 | iPr—I | 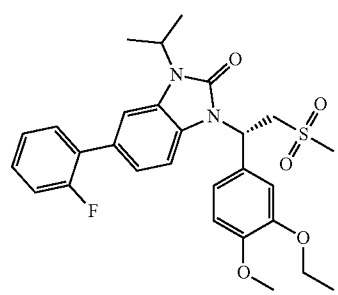 [SMILES: CCOc1cc([C@@H](CS(C)(=O)=O)n2c(=O)n(C(C)C)c3cc(-c4ccccc4F)ccc32)ccc1OC] | WX070 |
| 71 | WX011 | NC—CH2—Br | 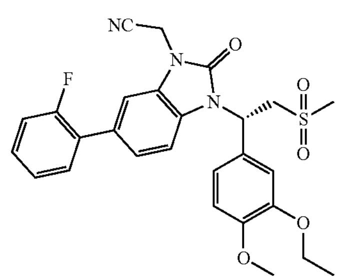 [SMILES: CCOc1cc([C@@H](CS(C)(=O)=O)n2c(=O)n(CC#N)c3cc(-c4ccccc4F)ccc32)ccc1OC] | WX071 |

TABLE 9-continued

| Embodiment | Fragment 1 | Fragment 2 | Structure | Compound |
|---|---|---|---|---|
| 72 | WX031 | F-CHF-CH2-OTs | 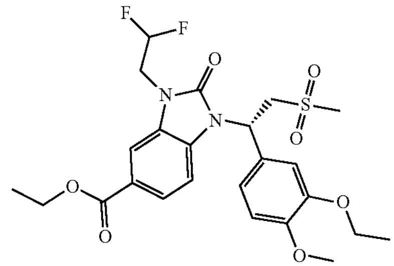 [SMILES: CCOC(=O)c1ccc2c(c1)n(CC(F)F)c(=O)n2[C@H](CS(C)(=O)=O)c1ccc(OC)c(OCC)c1] | WX072 |
| 73 | WX031 | CF3-CH2-OTf | 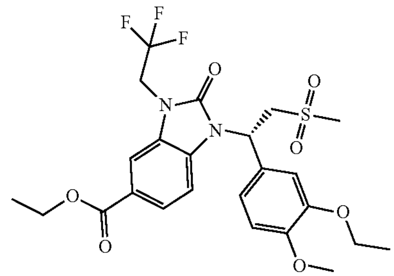 [SMILES: CCOC(=O)c1ccc2c(c1)n(CC(F)(F)F)c(=O)n2[C@H](CS(C)(=O)=O)c1ccc(OC)c(OCC)c1] | WX073 |
| 74 | WX031 | Me—I | 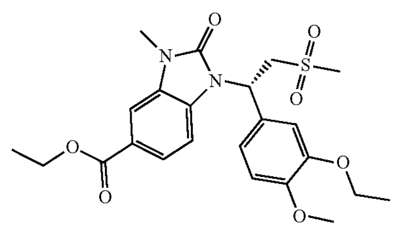 [SMILES: CCOC(=O)c1ccc2c(c1)n(C)c(=O)n2[C@H](CS(C)(=O)=O)c1ccc(OC)c(OCC)c1] | WX074 |

LCMS and ¹H NMR data of each embodiment

TABLE 10

| Embodiment | Compound | HNMR | LCMS |
|---|---|---|---|
| 37 | WX037 | ¹H NMR (400 MHz, CDCl₃) δ: 7.12-6.82 (m, 6H), 5.75 (dd, J = 4.4, 10.0 Hz, 1H), 4.78-4.72 (m, 1H), 4.49-4.38 (m, 2H), 4.08-4.03 (m, 2H), 3.85-3.80 (m, 4H), 2.75 (s, 3H), 1.45 (t, J = 7.2 Hz, 3H). | MS-ESI m/z: 529.0 [M + Na]⁺. |
| 38 | WX038 | ¹H NMR (400 MHz, MeOD) δ: 7.22-7.13 (m, 2H), 7.10 (d, J = 1.8 Hz, 1H), 7.06-7.01 (m, 2H), 6.92 (d, J = 8.5 Hz, 1H), 6.02 (dd, J = 3.8, 10.5 Hz, 1H), 4.57 (dd, J = 10.5, 14.6 Hz, 1H), 4.11-3.97 (m, 3H), 3.79 (s, 3H), 3.39 (s, 3H), 2.95 (s, 3H), 1.35 (t, J = 7.0 Hz, 3H). | MS-ESI m/z: 439.1 [M + H]⁺. |
| 39 | WX039 | ¹H NMR (400 MHz, MeOD) δ: 7.25 (s, 1H), 7.20-7.02 (m, 4H), 6.95 (d, J = 8.3 Hz, 1H), 6.05 (dd, J = 3.5, 10.5 Hz, 1H), 4.61 (dd, J = 10.9, 14.4 Hz, 1H), 4.18-3.90 (m, 5H), 3.82 (s, 3H), 2.97 (s, 3H), 1.41-1.28 (m, 6H). | MS-ESI m/z: 453.1 [M + H]⁺. |
| 40 | WX040 | ¹H NMR (400 MHz, CDCl₃) δ: 7.15 (d, J = 1.8 Hz, 1H), 7.11-7.00 (m, 4H), 6.84 (d, J = 8.3 Hz, 1H), 5.76 (dd, J = 4.5, 9.5 Hz, 1H), 4.81 (dd, J = 9.8, 14.8 Hz, 1H), 4.09 (q, J = 6.9 Hz, 2H), 3.91-3.73 (m, | MS-ESI m/z: 479.1 [M + H]⁺. |

TABLE 10-continued

| Embodiment | Compound | HNMR | LCMS |
|---|---|---|---|
| | | 6H), 2.75 (s, 3H), 1.46 (t, J = 6.9 Hz, 3H), 1.26-1.18 (m, 1H), 0.61-0.52 (m, 2H), 0.44 (br d, J = 4.3 Hz, 2H). | |
| 41 | WX041 | $^1$H NMR (400 MHz, CDCl$_3$) δ: 7.1 (s, 1H), 7.07-7.00 (m, 4H), 6.83 (d, J = 8.0 Hz, 1H), 5.78-5.75 (m, 1H), 4.83-4.77 (m, 1H), 4.07 (q, J = 6.0 Hz, 2H), 3.92-3.83 (m, 6H), 2.82-2.80 (m, 1H), 2.75 (s, 3H), 2.04-1.85 (m, 6H), 1.46 (t, J = 10.8 Hz, 3H). | MS-ESI m/z: 493.1 [M + H]$^+$. |
| 42 | WX042 | $^1$H NMR (400 MHz, CDCl$_3$) δ: 7.21-6.90 (m, 5H), 6.83 (br s, 1H), 5.76 (br s, 1H), 4.78 (br s, 1H), 4.24-3.98 (m, 4H), 3.87-3.63 (m, 6H), 3.31 (br s, 3H), 2.73 (br s, 3H), 1.45 (br s, 3H). | MS-ESI m/z: 483.0 [M + H]$^+$. |
| 43 | WX043 | $^1$H NMR (400 MHz, CDCl$_3$) δ: 7.14-7.02 (m, 4H), 6.94 (d, J = 8.3 Hz, 1H), 6.86 (d, J = 8.3 Hz, 1H), 5.89 (dd, J = 3.4, 10.4 Hz, 1H), 4.66 (dd, J = 10.8, 14.3 Hz, 1H), 4.10-4.02 (m, 4H), 3.98-3.92 (m, 2H), 3.88 (s, 3H), 3.78 (dd, J = 3.4, 14.7 Hz, 1H), 2.89 (s, 3H), 1.46 (t, J = 6.9 Hz, 3H). | MS-ESI m/z: 469.1 [M + H]$^+$. |
| 44 | WX044 | $^1$H NMR (400 MHz, CDCl$_3$) δ: 7.17-7.02 (m, 5H), 6.85 (d, J = 8.0 Hz, 1H), 5.80 (d, J = 5.3 Hz, 1H), 4.72 (d, J = 9.5 Hz, 1H), 4.09 (q, J = 7.0 Hz, 2H), 3.96-3.82 (m, 4H), 2.77 (s, 3H), 2.19-2.16 (m, 1H), 1.54 (br d, J = 6.3 Hz, 6H), 1.46 (t, J = 6.9 Hz, 3H). | MS-ESI m/z: 467.2 [M + H]$^+$. |
| 45 | WX045 | $^1$H NMR (400 MHz, CDCl$_3$) δ: 7.28 (s, 1H), 7.19-7.00 (m, 4H), 6.86 (d, J = 7.5 Hz, 1H), 5.80 (br s, 1H), 4.80 (br s, 2H), 4.63 (d, J = 11.3 Hz, 1H), 4.09 (d, J = 6.5 Hz, 2H), 3.87 (br s, 4H), 2.82 (br s, 3H), 1.47 (br s, 3H). | MS-ESI m/z: 486.1 [M + Na]$^+$. |
| 46 | WX046 | $^1$H NMR (400 MHz, CDCl$_3$) δ: 7.10-7.03 (m, 1H), 7.02 (d, J = 5.6 Hz, 2H), 6.83-6.82 (m, 3H), 6.03 (t, J = 65 Hz, 1H), 5.80-5.77 (m, 1H), 4.73-4.69 (m, 1H), 4.23-4.18 (m, 2H), 4.09-4.04 (m, 2H), 3.81 (s, 3H), 3.93-3.80 (m, 1H), 2.77 (br. s., 3H), 1.44 (t, J = 7.2 Hz, 3H). | MS-ESI m/z: 495.0 [M + Na]$^+$. |
| 47 | WX047 | $^1$H NMR (400 MHz, CDCl$_3$) δ: 7.12 (d, J = 2.0 Hz, 1H), 7.08-6.96 (m, 2H), 6.91-6.79 (m, 3H), 5.75 (dd, J = 4.3, 9.8 Hz, 1H), 4.76 (dd, J = 9.8, 14.8 Hz, 1H), 4.60-4.30 (m, 2H), 4.06 (q, J = 7.0 Hz, 2H), 3.90-3.76 (m, 4H), 2.75 (s, 3H), 1.44 (t, J = 7.0 Hz, 3H). | MS-ESI m/z: 491.0 [M + H]$^+$. |
| 48 | WX048 | $^1$H NMR (400 MHz, MeOD) δ: 7.21-7.11 (m, 2H), 7.07 (dd, J = 1.5, 8.3 Hz, 1H), 7.03-6.91 (m, 2H), 6.87-6.76 (m, 1H), 6.05 (dd, J = 3.8, 10.5 Hz, 1H), 4.61 (dd, J = 10.5, 14.6 Hz, 1H), 4.13-3.98 (m, 3H), 3.82 (s, 3H), 3.42 (s, 3H), 2.97 (s, 3H), 1.38 (t, J = 6.9 Hz, 3H). | MS-ESI m/z: 423.1 [M + H]$^+$. |
| 49 | WX049 | $^1$H NMR (400 MHz, CD$_3$OD) δ: 7.34-7.05 (m, 4H), 7.00-6.83 (m, 2H), 6.05 (dd, J = 3.8, 10.5 Hz, 1H), 5.04 (s, 2H), 4.62 (dd, J = 10.8, 14.6 Hz, 1H), 4.21-4.00 (m, 3H), 3.83 (s, 3H), 2.99 (s, 3H), 1.38 (t, J = 6.9 Hz, 3H). | MS-ESI m/z: 448.1 [M + H]$^+$. |
| 50 | WX050 | $^1$H NMR (400 MHz, CD$_3$OD) δ: 7.22-7.04 (m, 4H), 6.95 (d, J = 8.0 Hz, 1H), 6.86-6.75 (m, 1H), 6.04 (dd, J = 3.8, 10.3 Hz, 1H), 4.64 (dd, J = 10.3, 14.8 Hz, 1H), 4.15-3.96 (m, 5H), 3.89-3.75 (m, 5H), 2.95 (s, 3H), 1.38 (t, J = 7.0 Hz, 3H). | MS-ESI m/z: 453.1 [M + H]$^+$. |
| 51 | WX051 | $^1$H NMR (400 MHz, MeOD) δ: 7.54 (s, 1H), 7.47-7.33 (m, 2H), 7.23-7.06 (m, 2H), 6.96 (d, J = 8.0 Hz, 1H), 6.41-6.01 (m, 2H), 4.66 (dd, J = 11.0, 14.6 Hz, 1H), 4.41 (dt, J = 3.3, 14.9 Hz, 2H), 4.16-3.95 (m, 3H), 3.82 (s, 3H), 2.99 (s, 3H), 1.37 (t, J = 7.0 Hz, 3H). | MS-ESI m/z: 545.0 [M + Na]$^+$. |

TABLE 10-continued

| Embodiment | Compound | HNMR | LCMS |
|---|---|---|---|
| 52 | WX052 | $^1$H NMR (400 MHz, CD$_3$OD) δ: 7.58 (s, 1H), 7.51-7.37 (m, 2H), 7.24-7.05 (m, 2H), 6.97 (d, J = 8.5 Hz, 1H), 6.12 (dd, J = 3.6, 10.7 Hz, 1H), 4.85-4.65 (m, 3H), 4.21-3.94 (m, 3H), 3.83 (s, 3H), 2.99 (s, 3H), 1.38 (t, J = 7.0 Hz, 3H). | MS-ESI m/z: 541.1 [M + H]$^+$. |
| 53 | WX053 | $^1$H NMR (400 MHz, MeOD) δ: 7.51-7.34 (m, 3H), 7.16 (d, J = 1.5 Hz, 1H), 7.13-7.04 (m, 1H), 6.96 (d, J = 8.5 Hz, 1H), 6.12 (dd, J = 4.0, 10.5 Hz, 1H), 4.64 (dd, J = 10.8, 14.3 Hz, 1H), 4.20-3.99 (m, 3H), 3.83 (s, 3H), 3.48 (s, 3H), 2.99 (s, 3H), 1.38 (t, J = 7.0 Hz, 3H). | MS-ESI m/z: 473.1 [M + H]$^+$. |
| 54 | WX054 | $^1$H NMR (400 MHz, MeOD) δ: 7.54-7.32 (m, 3H), 7.23-7.04 (m, 2H), 6.97 (d, J = 8.0 Hz, 1H), 6.12 (dd, J = 3.8, 10.8 Hz, 1H), 4.65 (dd, J = 10.8, 14.3 Hz, 1H), 4.19-3.99 (m, 5H), 3.83 (s, 3H), 3.00 (s, 3H), 1.40-1.30 (m, 6H). | MS-ESI m/z: 487.1 [M + H]$^+$. |
| 55 | WX055 | $^1$H NMR (400 MHz, MeOD) δ: 7.65 (s, 1H), 7.56-7.36 (m, 2H), 7.22-7.06 (m, 2H), 6.97 (d, J = 8.0 Hz, 1H), 6.12 (dd, J = 3.8, 10.8 Hz, 1H), 5.11 (s, 2H), 4.65 (dd, J = 10.5, 14.6 Hz, 1H), 4.23-3.98 (m, 3H), 3.83 (s, 3H), 3.01 (s, 3H), 1.38 (t, J = 7.0 Hz, 3H). | MS-ESI m/z: 520.1 [M + Na]$^+$. |
| 56 | WX056 | $^1$H NMR (400 MHz, CD$_3$OD) δ: 7.56 (s, 1H), 7.39 (s, 2H), 7.18 (d, J = 2.0 Hz, 1H), 7.11 (dd, J = 2.0, 8.3 Hz, 1H), 6.96 (d, J = 8.3 Hz, 1H), 6.11 (dd, J = 4.0, 10.5 Hz, 1H), 4.67 (dd, J = 10.5, 14.6 Hz, 1H), 4.19-3.98 (m, 5H), 3.88-3.82 (m, 5H), 2.98 (s, 3H), 1.39 (t, J = 7.0 Hz, 3H). | MS-ESI m/z: 503.1 [M + H]$^+$. |
| 57 | WX057 | $^1$H NMR (400 MHz, MeOD) δ: 7.11 (br s, 1H), 7.05-6.84 (m, 3H), 6.83-6.72 (m, 1H), 6.23 (d, J = 7.3 Hz, 1H), 4.88-4.77 (m, 1H), 4.15-3.99 (m, 3H), 3.82 (s, 3H), 3.42 (s, 3H), 3.00 (s, 3H), 1.39 (t, J = 7.0 Hz, 3H). | MS-ESI m/z: 441.0 [M + H]$^+$. |
| 58 | WX058 | $^1$H NMR (400 MHz, MeOD) δ: 7.26-6.99 (m, 3H), 6.99-6.78 (m, 2H), 6.23 (d, J = 7.0 Hz, 1H), 5.04 (s, 2H), 4.85-4.77 (m, 1H), 4.21-3.94 (m, 3H), 3.83 (s, 3H), 3.01 (s, 3H), 1.38 (t, J = 6.9 Hz, 3H). | MS-ESI m/z: 488.1 [M + Na]$^+$. |
| 59 | WX059 | $^1$H NMR (400 MHz, CD$_3$OD) δ: 7.13 (br s, 1H), 7.06-6.90 (m, 3H), 6.83-6.70 (m, 1H), 6.24 (d, J = 7.5 Hz, 1H), 4.88-4.87 (m, 1H), 4.15-3.96 (m, 5H), 3.90-3.76 (m, 5H), 2.99 (s, 3H), 1.38 (t, J = 6.9 Hz, 3H). | MS-ESI m/z: 471.1 [M + H]$^+$. |
| 60 | WX060 | $^1$H NMR (400 MHz, CDCl$_3$) δ: 7.26 (br s, 2H), 7.21-7.04 (m, 5H), 7.01 (s, 1H), 6.83 (d, J = 8.3 Hz, 1H), 6.22 (br s, 1H), 5.24-5.03 (m, 2H), 4.8 (br, s, 1H), 4.06 (q, J = 6.8 Hz, 2H), 3.85 (s, 4H), 2.82 (br s, 3H), 1.44 (t, J = 6.8 Hz, 3H). | MS-ESI m/z: 607.0 [M + Na]$^+$. |
| 61 | WX061 | $^1$H NMR (400 MHz, CDCl$_3$) δ: 7.11 (d, J = 2.3 Hz, 1H), 7.10-7.03 (m, 3H), 7.01 (dd, J = 2.0, 8.3 Hz, 1H), 6.82 (d, J = 8.3 Hz, 1H), 6.30-5.92 (m, 1H), 5.77 (dd, J = 4.5, 9.8 Hz, 1H), 4.81 (dd, J = 9.8, 14.8 Hz, 1H), 4.73-4.58 (m, 2H), 4.06 (q, J = 7.0 Hz, 2H), 3.88-3.73 (m, 4H), 2.76 (s, 3H), 1.44 (t, J = 7.0 Hz, 3H). | MS-ESI m/z: 511.0 [M + Na]$^+$. |
| 62 | WX062 | $^1$H NMR (400 MHz, CDCl$_3$) δ: 7.12 (d, J = 2.3 Hz, 1H), 7.10-7.06 (m, 3H), 7.00 (dd, J = 2.0, 8.3 Hz, 1H), 6.81 (d, J = 8.3 Hz, 1H), 5.76 (dd, J = 4.4, 9.7 Hz, 1H), 5.03-4.77 (m, 3H), 4.09-4.01 (m, 2H), 3.86-3.76 (m, 4H), 2.74 (s, 3H), 1.44 (t, J = 7.0 Hz, 3H). | MS-ESI m/z: 529.0 [M + Na]$^+$. |
| 63 | WX063 | $^1$H NMR (400 MHz, CDCl$_3$) δ: 7.25 (s, 1H), 7.21 (d, J = 8.3 Hz, 1H), 7.02 (s, 1H), 6.98 (d, J = 8.5 Hz, 1H), 6.91 (d, J = 8.5 Hz, 1H), 6.82 (d, J = 8.3 Hz, 1H), 5.84 (dd, J = 3.6, 10.4 Hz, 1H), 4.62 (dd, | MS-ESI m/z: 574.9 [M + H]$^+$, 577.0 [M + H + 2]$^+$. |

TABLE 10-continued

| Embodiment | Compound | HNMR | LCMS |
|---|---|---|---|
| | | J = 10.5, 14.3 Hz, 1H), 4.44-4.23 (m, 2H), 4.08-4.00 (m, 2H), 3.84 (s, 3H), 3.75 (dd, J = 3.6, 14.4 Hz, 1H), 3.55-3.34 (m, 2H), 2.90 (s, 3H), 2.86 (s, 3H), 1.43 (t, J = 6.9 Hz, 3H). | |
| 64 | WX064 | $^1$H NMR (400 MHz, CDCl$_3$) δ: 7.33-7.27 (m, 1H), 7.26-7.16 (m, 2H), 7.14-6.93 (m, 6H), 6.83 (d, J = 8.3 Hz, 1H), 5.79 (dd, J = 4.3, 9.8 Hz, 1H), 5.17-5.02 (m, 2H), 4.78 (dd, J = 9.8, 14.6 Hz, 1H), 4.04 (q, J = 7.0 Hz, 2H), 3.90-3.78 (m, 4H), 2.74 (s, 3H), 1.44 (t, J = 6.9 Hz, 3H). | MS-ESI m/z: 577.1 [M + H]$^+$, 579.0 [M + H + 2]$^+$. |
| 65 | WX065 | $^1$H NMR (400 MHz, CDCl$_3$) δ: 7.30 (d, J = 6.0 Hz, 1H), 7.19 (d, J = 7.8 Hz, 1H), 7.14-6.91 (m, 7H), 6.84 (d, J = 8.0 Hz, 1H), 5.82 (d, J = 7.8 Hz, 1H), 5.03 (s, 2H), 4.75 (t, J = 11.0 Hz, 1H), 4.05 (q, J = 6.5 Hz, 2H), 3.86 (s, 4H), 2.79 (s, 3H), 1.44 (t, J = 6.5 Hz, 3H). | MS-ESI m/z: 577.0 [M + H]$^+$, 579.1 [M + H + 2]$^+$. |
| 66 | WX066 | $^1$H NMR (400 MHz, CDCl$_3$) δ: 7.31-7.22 (m, 2H), 7.18 (dd, J = 1.6, 8.4 Hz, 1H), 7.10 (s, 1H), 7.07-6.91 (m, 5H), 6.83 (d, J = 8.3 Hz, 1H), 5.82 (dd, J = 3.6, 9.7 Hz, 1H), 5.00 (d, J = 2.0 Hz, 2H), 4.74 (dd, J = 10.0, 14.3 Hz, 1H), 4.04 (q, J = 7.0 Hz, 2H), 3.90-3.78 (m, 4H), 2.77 (s, 3H), 1.44 (t, J = 6.9 Hz, 3H). | MS-ESI m/z: 577.0 [M + H]$^+$, 579.0 [M + H + 2]$^+$. |
| 67 | WX067 | $^1$H NMR (400 MHz, CDCl$_3$) δ: 7.31-7.21 (m, 2H), 7.16 (d, J = 2.0 Hz, 1H), 7.14-7.09 (m, 1H), 7.09-7.01 (m, 5H), 6.96 (d, J = 7.3 Hz, 1H), 6.82 (d, J = 8.5 Hz, 1H), 5.84 (dd, J = 4.5, 9.5 Hz, 1H), 5.24-5.04 (m, 2H), 4.83 (dd, J = 9.7, 14.9 Hz, 1H), 4.05 (q, J = 7.0 Hz, 2H), 3.93-3.78 (m, 4H), 2.71 (s, 3H), 1.43 (t, J = 6.9 Hz, 3H). | MS-ESI m/z: 499.1 [M + H]$^+$. |
| 68 | WX068 | $^1$H NMR (400 MHz, CDCl$_3$) δ: 7.42 (dt, J = 1.8, 7.8 Hz, 1H), 7.37-7.28 (m, 2H), 7.25-7.12 (m, 5H), 7.09 (dd, J = 2.0, 8.3 Hz, 1H), 6.84 (d, J = 8.3 Hz, 1H), 5.84 (dd, J = 4.8, 9.3 Hz, 1H), 4.78 (dd, J = 9.3, 14.8 Hz, 1H), 4.10 (q, J = 7.0 Hz, 2H), 3.90 (dd, J = 4.6, 14.9 Hz, 1H), 3.85 (s, 3H), 3.45 (s, 3H), 2.76 (s, 3H), 1.46 (t, J = 7.0 Hz, 3H). | MS-ESI m/z: 499.1 [M + H]$^+$. |
| 69 | WX069 | $^1$H NMR (400 MHz, CDCl$_3$) δ: 7.42 (dt, J = 1.8, 7.8 Hz, 1H), 7.31 (ddd, J = 1.9, 5.4, 7.8 Hz, 1H), 7.26-7.12 (m, 6H), 7.08 (dd, J = 2.0, 8.3 Hz, 1H), 6.84 (d, J = 8.3 Hz, 1H), 5.83 (dd, J = 4.5, 9.3 Hz, 1H), 4.82 (dd, J = 9.5, 14.8 Hz, 1H), 4.10 (q, J = 7.0 Hz, 2H), 3.98 (dq, J = 2.9, 7.2 Hz, 2H), 3.85 (s, 4H), 2.75 (s, 3H), 1.46 (t, J = 6.9 Hz, 3H), 1.35 (t, J = 7.2 Hz, 3H). | MS-ESI m/z: 513.1 [M + H]$^+$. |
| 70 | WX070 | $^1$H NMR (400 MHz, CDCl$_3$) δ: 7.42 (dt, J = 1.8, 7.8 Hz, 1H), 7.37-7.29 (m, 2H), 7.26-7.12 (m, 5H), 7.08 (dd, J = 2.0, 8.3 Hz, 1H), 6.84 (d, J = 8.5 Hz, 1H), 5.83 (dd, J = 4.5, 9.5 Hz, 1H), 4.91-4.65 (m, 2H), 4.10 (q, J = 7.0 Hz, 2H), 3.90-3.82 (m, 4H), 2.75 (s, 3H), 1.56 (d, J = 6.8 Hz, 6H), 1.45 (t, J = 7.0 Hz, 3H). | MS-ESI m/z: 527.2 [M + H]$^+$. |
| 71 | WX071 | $^1$H NMR (400 MHz, CDCl$_3$) δ: 7.47-7.28 (m, 4H), 7.26-7.11 (m, 4H), 7.08 (d, J = 7.8 Hz, 1H), 6.86 (d, J = 8.3 Hz, 1H), 5.86 (dd, J = 4.4, 9.2 Hz, 1H), 4.93-4.77 (m, 2H), 4.68 (dd, J = 9.4, 14.7 Hz, 1H), 4.10 (q, J = 6.8 Hz, 2H), 3.96-3.82 (m, 4H), 2.80 (s, 3H), 1.47 (t, J = 6.9 Hz, 3H). | MS-ESI m/z: 524.0 [M + H]$^+$. |
| 72 | WX072 | $^1$H NMR (400 MHz, CDCl$_3$) δ: 7.88 (d, J = 8.3 Hz, 1H), 7.74 (s, 1H), 7.18-7.08 (m, 2H), 7.03 (d, J = 8.3 Hz, 1H), 6.33-5.61 (m, 2H), 4.70 (dd, J = 9.8, 14.6 Hz, 1H), 4.42-4.17 (m, 4H), 4.05 (q, J = 6.9 Hz, 2H), 3.89-3.80 (m, 4H), 2.76 (s, | MS-ESI m/z: 527.1 [M + H]$^+$. |

TABLE 10-continued
| Embodiment | Compound | HNMR | LCMS |
|---|---|---|---|
| | | 3H), 1.80 (br s, 1H), 1.41 (td, J = 7.0, 18.8 Hz, 6H). | |
| 73 | WX073 | $^1$H NMR (400 MHz, CDCl$_3$) δ: 7.90 (d, J = 8.0 Hz, 1H), 7.74 (s, 1H), 7.19 (d, J = 8.5 Hz, 1H), 7.11 (s, 1H), 7.03 (d, J = 8.0 Hz, 1H), 6.82 (d, J = 8.3 Hz, 1H), 5.83 (dd, J = 4.4, 9.4 Hz, 1H), 4.73 (dd, J = 9.8, 14.6 Hz, 1H), 4.62-4.31 (m, 4H), 4.04 (q, J = 6.9 Hz, 2H), 3.90-3.78 (m, 4H), 2.74 (s, 3H), 1.40 (td, J = 7.1, 17.0 Hz, 6H). | MS-ESI m/z: 545.2 [M + H]$^+$. |
| 74 | WX074 | $^1$H NMR (400 MHz, CDCl$_3$) δ: 7.86 (dd, J = 1.5, 8.3 Hz, 1H), 7.67 (d, J = 1.3 Hz, 1H), 7.16-7.10 (m, 2H), 7.05 (dd, J = 2.0, 8.3 Hz, 1H), 6.82 (d, J = 8.3 Hz, 1H), 5.84 (dd, J = 4.6, 9.4 Hz, 1H), 4.69 (dd, J = 9.3, 14.6 Hz, 1H), 4.38 (q, J = 7.1 Hz, 2H), 4.06 (dq, J = 2.1, 7.0 Hz, 2H), 3.95-3.80 (m, 4H), 3.45 (s, 3H), 2.75 (s, 3H), 1.41 (td, J = 7.1, 18.4 Hz, 6H). | MS-ESI m/z: 477.1 [M + H]$^+$. |
Embodiment 75: WX075
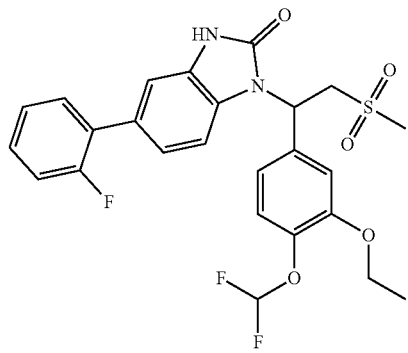 [SMILES: CCOc1cc(C(CS(C)(=O)=O)n2c(=O)[nH]c3cc(-c4ccccc4F)ccc32)ccc1OC(F)F]
Synthesis Route:
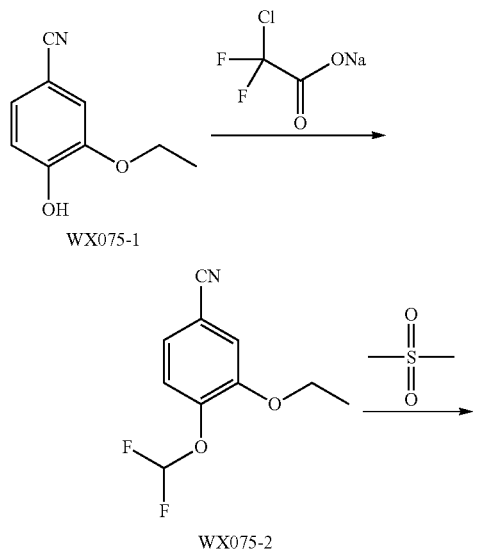
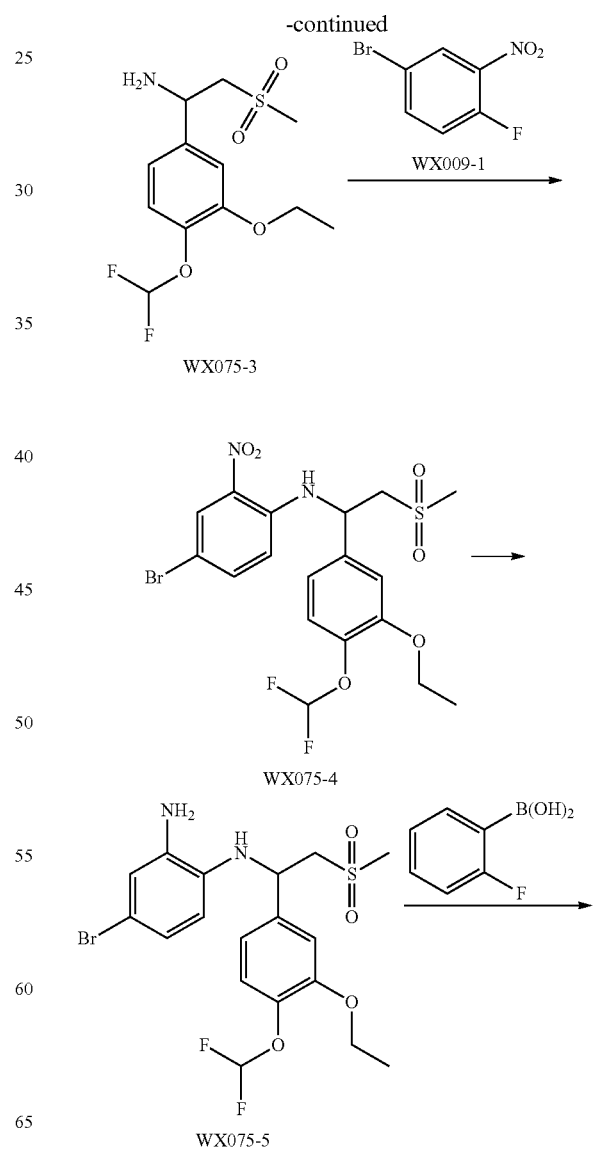

-continued

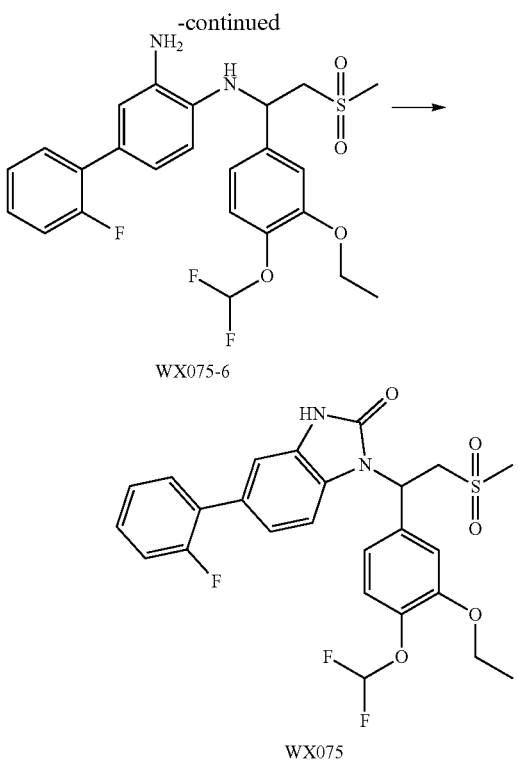

Step 1: Preparation of WX075-2

Compound WX075-1 (29.00 g, 177.73 mmol), sodium difluorochloroacetate (62.32 g, 408.78 mmol) and cesium carbonate (86.86 g, 266.60 mmol) were added to N,N-dimethylformamide (600 mL) and water (150 mL). The reaction mixture was heated to 100° C. and stirred for 3 hours under nitrogen atmosphere. After the reaction, the mixture was cooled to room temperature, ethyl acetate (1000 mL) and water (200 mL) were added. The organic phases were separated, washed with saturated brine (200 mL×2) and dried over anhydrous sodium sulfate, followed by filtration. The filtrate was concentrated under reduced pressure. The obtained residue was purified by column chromatography (eluent:ethyl acetate/petroleum ether=1/10-1/3, volume ratio) to obtain the target product WX075-2. $^1$H NMR (400 MHz, CDCl$_3$) δ: 7.20-7.13 (m, 3H), 6.58 (t, J=74.4 Hz, 1H), 4.05 (q, J=6.8 Hz, 2H), 1.41 (t, J=6.8 Hz, 3H).

Step 2: Preparation of WX075-3

Dimethyl sulfone (9.71 g, 103.20 mmol, 8.37 mL) was dissolved in tetrahydrofuran (300 mL) at room temperature, after cooling to 0° C., n-butyllithium (2.5 M, 41.28 mL) was added dropwise. The reaction mixture was stirred at 0-5° C. for 1 hour under nitrogen atmosphere. The compound WX075-2 (20.00 g, 93.82 mmol) in tetrahydrofuran (200 mL) was added dropwise to the above reaction mixture. Subsequently, the reaction mixture was stirred at 0-5° C. for 30 minutes, and then warmed to room temperature and stirred for 1.5 hours. Sodium borohydride (4.61 g, 121.97 mmol) was added to the above reaction mixture at room temperature. After stirring for 30 minutes, the mixture was cooled to 0° C., and acetic acid (25.92 g, 431.57 mmol, 24.69 mL) was added. The reaction mixture was stirred at 0-5° C. for 2 hours. Finally, an aqueous sodium hydroxide solution (2.5 M, 123.84 mL) was added to the reaction system. The reaction mixture was stirred at 0-5° C. for 30 minutes, and then heated to 60° C. and stirred for further 12 hours. After the reaction and the mixture was cooled to room temperature, ethyl acetate (1000 mL) and water (200 mL) were added. The organic phases were separated, washed with saturated brine (200 mL×2) and dried over anhydrous sodium sulfate, followed by filtration. The filtrate was concentrated under reduced pressure. The obtained residue was purified by column chromatography (eluent:ethyl acetate/petroleum ether=1/100-1/10, volume ratio) to obtain the target product WX075-3. $^1$H NMR (400 MHz, CDCl$_3$) δ: 7.08-6.84 (m, 3H), 6.50 (t, J=75.2 Hz, 1H), 4.58 (dd, J=2.8, 9.6 Hz, 1H), 4.04 (dd, J6.8, 13.2 Hz, 2H), 3.27-3.12 (m, 2H), 2.90 (s, 3H), 1.38 (t, J=7.2 Hz, 3H).

Step 3: Preparation of WX075-4

Compound WX075-3 (400.00 mg, 1.29 mmol) and compound WX009-1 (426.73 mg, 1.94 mmol) were dissolved in N,N-dimethylformamide (15.00 mL) at room temperature, followed by the addition of diisopropylethylamine (501.37 mg, 3.88 mmol). The reaction mixture was heated to 90° C. and stirred for 15 hours under nitrogen atmosphere. After the reaction, the reaction mixture was cooled to room temperature, diluted with water (30 mL) and extracted with ethyl acetate (40 mL×3). The organic phases were combined, washed with saturated brine (20 mL) and dried over anhydrous sodium sulfate, followed by filtration. The filtrate was concentrated under reduced pressure. The obtained residue was purified by column chromatography (eluent:ethyl acetate/petroleum ether=1/9-1/1, volume ratio) to obtain the target product WX075-4. $^1$H NMR (400 MHz, CDCl$_3$) δ: 8.65 (d, J=6.3 Hz, 1H), 8.34 (d, J=2.3 Hz, 1H), 7.45 (dd, J=2.3, 9.0 Hz, 1H), 7.18 (d, J=8.5 Hz, 1H), 6.97-6.92 (m, 2H), 6.75 (s, 0.25H), 6.66 (d, J=9.3 Hz, 1H), 6.57 (s, 0.5H), 6.38 (s, 0.25H), 5.27-5.19 (m, 1H), 4.10-4.00 (m, 2H), 3.63 (dd, J=8.8, 14.6 Hz, 1H), 3.46 (dd, J=4.0, 14.6 Hz, 1H), 2.88 (s, 3H), 1.44 (t, J=6.9 Hz, 3H).

Step 4: Preparation of WX075-5

Compound WX075-4 (200.00 mg, 392.68 μmol) and ammonium chloride (210.04 mg, 3.93 mmol) were dissolved in ethanol (10.00 mL) and water (1.00 mL) at room temperature, followed by the addition of iron powder (109.66 mg, 1.96 mmol). The reaction mixture was heated to 80° C. and stirred for 1 hour under nitrogen atmosphere. After the reaction, the mixture was cooled to room temperature, concentrated under reduced pressure. Dichloromethane (50 mL) was added to the residue and the insolubles was removed by filtration. The filtrate was concentrated under reduced pressure. The obtained residue was purified by column chromatography (eluent:ethyl acetate/petroleum ether=1/4-4/1, volume ratio) to obtain the target product WX075-5. $^1$H NMR (400 MHz, CDCl$_3$) δ: 7.15 (d, J=7.8 Hz, 1H), 6.96-6.90 (m, 2H), 6.84 (d, J=2.0 Hz, 1H), 6.75 (s, 0.25H), 6.70 (dd, J=2.1, 8.4 Hz, 1H), 6.56 (s, 0.5H), 6.37 (s, 0.25H), 6.22 (d, J=8.5 Hz, 1H), 4.92 (td, J=4.4, 9.5 Hz, 1H), 4.43 (d, J=5.0 Hz, 1H), 4.04 (dq, J=2.1, 7.0 Hz, 2H), 3.65 (s, 2H), 3.54-3.45 (m, 1H), 3.43-3.37 (m, 1H), 2.90 (s, 3H), 1.41 (t, J=7.0 Hz, 3H).

Step 5: Preparation of WX075-6

Compound WX075-5 (190.00 mg, 396.38 o-fluorophenylboronic acid (72.10 mg, 515.29 μmol), (1,1'-bis(diphenylphosphino)ferrocene) palladium dichloride dichloromethane complex (16.18 mg, 19.82 μmol) and potassium carbonate (136.96 mg, 990.95 μmol) were added to dioxane (4.50 mL) and water (1.50 mL) at room temperature. The reaction mixture was heated to 70° C. and stirred for 15 hours under nitrogen atmosphere. After the reaction, the mixture was cooled to room temperature, diluted with water (20 mL) and ethyl acetate (30 mL), and filtered to remove insolubles. The organic phases were separated and the aqueous phases were extracted with ethyl acetate (20 mL×3). The organic phases were combined and washed with saturated brine (20 mL), and dried over anhydrous sodium sulfate, followed by filtration. The filtrate was concentrated under reduced pressure. The obtained residue was purified by column chromatography (eluent:ethyl acetate/petroleum ether=0/1-3/2, volume ratio) to obtain the target product WX075-6. $^1$H NMR (400 MHz, CDCl$_3$) δ: 7.34 (dt, J=1.6, 7.7 Hz, 1H), 7.25-7.19 (m, 1H), 7.19-7.12 (m, 2H), 7.12-7.06 (m, 1H), 7.03-6.95 (m, 3H), 6.85 (d, J=8.0 Hz, 1H), 6.75 (s, 0.25H), 6.57 (s, 0.5H), 6.47 (d, J=8.0 Hz, 1H), 6.38 (s, 0.25H), 5.02 (dd, J=3.6, 9.4 Hz, 1H), 4.07 (q, J=6.9 Hz, 2H), 3.58-3.51 (m, 1H), 3.46-3.41 (m, 1H), 2.91 (s, 3H), 1.42 (t, J=6.9 Hz, 3H).

Step 6: Preparation of WX075

Compound WX075-6 (100.00 mg, 202.21 μmol) and triethylamine (122.77 mg, 1.21 mmol, 168.18 μL) were dissolved in tetrahydrofuran (10.00 mL). The reaction mixture was cooled to 0° C., followed by the addition of triphosgene (36.00 mg, 121.33 μmol). The reaction mixture was stirred at 0° C. for 30 minutes under nitrogen atmosphere. After the reaction, the mixture was quenched with water (3 mL) and concentrated under reduced pressure. The obtained residue was purified by preparative HPLC to obtain the target product WX075. MS-ESI m/z: 521.0 [M+H]$^+$. $^1$H NMR (400 MHz, CD$_3$OD) δ: 7.45 (dt, J=1.6, 7.8 Hz, 1H), 7.36-7.30 (m, 1H), 7.29-7.27 (m, 1H), 7.27-7.23 (m, 3H), 7.22 (d, J=1.0 Hz, 1H), 7.18 (d, J=1.0 Hz, 1H), 7.14 (s, 1H), 7.13-7.09 (m, 1H), 6.90 (s, 0.25H), 6.71 (s, 0.5H), 6.52 (s, 0.25H), 6.13 (dd, J=3.8, 10.5 Hz, 1H), 4.68 (dd, J=10.5, 14.8 Hz, 1H), 4.16-4.05 (m, 3H), 2.99 (s, 3H), 1.39 (t, J=7.0 Hz, 3H).

Embodiment 76: WX076

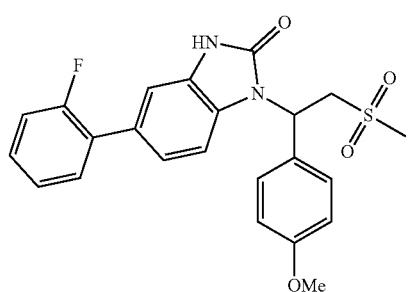 [SMILES: COc1ccc(C(CS(C)(=O)=O)n2c(=O)[nH]c3cc(-c4ccccc4F)ccc32)cc1]

Synthesis Route:

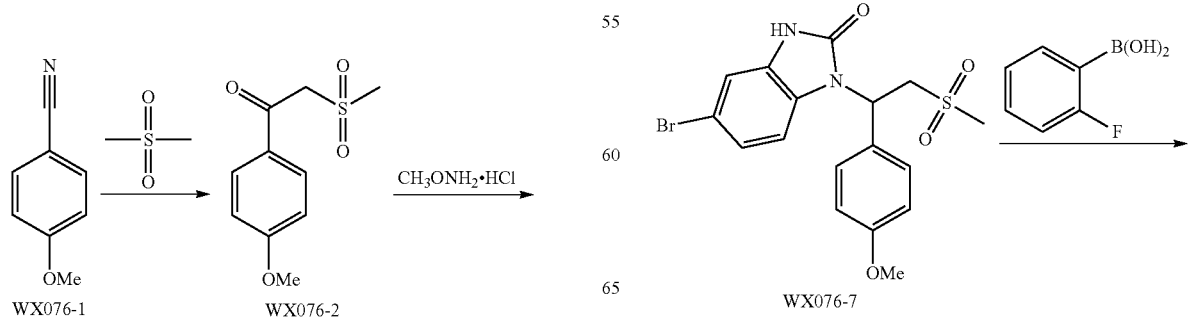

-continued

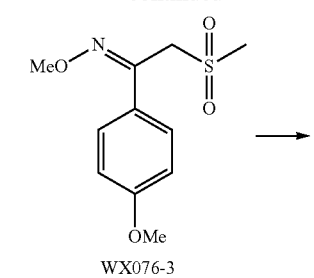

WX076-3

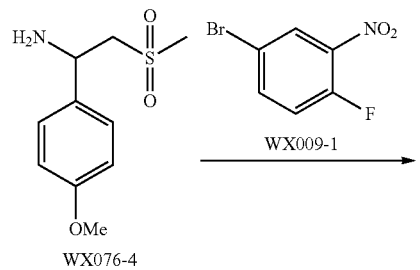

WX076-4

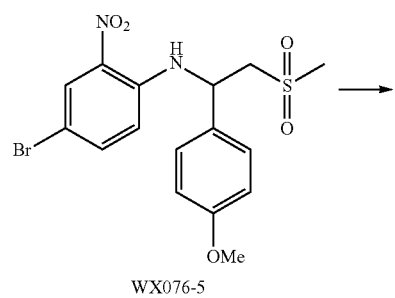

WX076-5

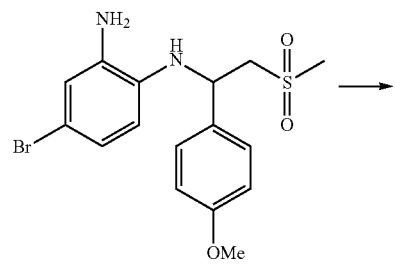

WX076-6

WX076-7

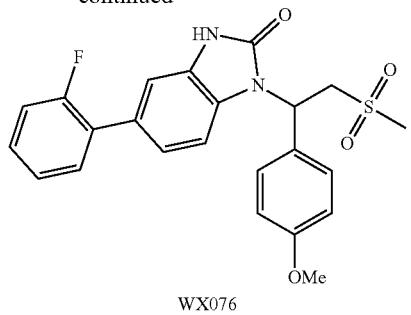

WX076

Step 1: Preparation of WX076-2

Dimethyl sulfone (848.34 mg, 9.01 mmol, 731.33 µL) was dissolved in tetrahydrofuran (10.00 mL), cooled to 0° C., followed by the dropwise addition of n-butyllithium (2.5 M, 3.30 mL) under nitrogen atmosphere. The reaction mixture was stirred at 0° C. for 1 hour. To the above reaction system, a solution of compound WX076-1 (1.00 g, 7.51 mmol) in tetrahydrofuran (10.00 mL) was added dropwise, and the reaction mixture was stirred at 0° C. for 15 minutes, then warmed to room temperature and stirred for another 1.5 hours. The reaction mixture was again cooled to 0° C. and sodium borohydride (369.35 mg, 9.76 mmol) was added thereto with stirring for 10 minutes. Then, acetic acid (2.03 g, 33.80 mmol, 1.93 mL) was added thereto at 0° C. with stirring for 2 hours. Finally, an aqueous sodium hydroxide solution (2.5 M, 9.91 mL) was added thereto at 0° C. with stirring for 15 minutes, and then heated to 60° C. with stirring for further 12 hours. After the reaction, the mixture was cooled to room temperature, quenched with saturated ammonium chloride solution (5 mL), extracted with ethyl acetate (10 mL×3) and dried over anhydrous sodium sulfate, followed by filtration. The filtrate was concentrated under reduced pressure to obtain the crude product WX076-2.

Step 2: Preparation of WX076-3

Compound WX076-2 (1.00 g, 4.38 mmol) and pyridine (5.20 g, 65.70 mmol, 5.31 mL) were dissolved in ethanol (10.00 mL) at room temperature, followed by the addition of O-methylhydroxylamine hydrochloride (1.10 g, 13.14 mmol). The reaction mixture was heated to 80° C. and stirred for 4 hours. After the reaction, the mixture was cooled to room temperature, diluted with saturated brine (40 mL), and extracted with dichloromethane (10 mL×3). The organic phases were combined, washed with 10% dilute hydrochloric acid (30 mL) and water (30 mL) respectively and dried over anhydrous sodium sulfate, followed by filtration. The filtrate was concentrated under reduced pressure to obtain the crude product WX076-3.

Step 3: Preparation of WX076-4

Compound WX076-3 (2.00 g, 7.77 mmol) was dissolved in tetrahydrofuran (40.00 mL) at room temperature and cooled to 0° C., followed by the dropwise addition of borane dimethyl sulfide solution (10 M, 3.89 mL). The reaction mixture was warmed to room temperature and stirred for 2.5 hours under nitrogen atmosphere. After the reaction, methanol was slowly added to the mixture to quench the reaction until no gas was produced. Then, the mixture was concentrated under reduced pressure and aqueous sodium hydroxide solution (2 M, 10 mL) was added thereto and extracted with ethyl acetate (15 mL×3). The organic phases were combined, washed with saturated brine (50 mL×2) and dried over anhydrous sodium sulfate, followed by filtration. The filtrate was concentrated under reduced pressure to obtain the crude product WX076-4.

Step 4: Preparation of WX076-5

Compound WX076-4 (1.10 g, 3.84 mmol) and 4-bromo-1-fluoro-2-nitrobenzene (1.69 g, 7.68 mmol) were dissolved in N,N-dimethylformamide (30.00 mL) at room temperature, followed by the addition of diisopropylethylamine (1.49 g, 11.52 mmol, 2.01 mL). The reaction mixture was heated to 80° C. and stirred for 4 hours. After the reaction, the mixture was cooled to room temperature, quenched with saturated brine (20 mL), diluted with water (40 mL) and extracted with ethyl acetate (20 mL×3). The organic phases were combined, washed with saturated brine (40 mL×2) and dried over anhydrous sodium sulfate, followed by filtration. The filtrate was concentrated under reduced pressure. The obtained residue was purified by column chromatography (eluent:ethyl acetate/petroleum ether=1/8-1/2, volume ratio) to obtain the target product WX076-5. $^1$H NMR (400 MHz, CDCl$_3$) δ: 8.64 (d, J=6.8 Hz, 1H), 8.34 (d, J=2.3 Hz, 1H), 7.44 (dd, J=2.4, 9.2 Hz, 1H), 7.36-7.29 (m, 2H), 7.00-6.85 (m, 2H), 6.72 (d, J=9.0 Hz, 1H), 5.29-5.16 (m, 1H), 3.81 (s, 3H), 3.68-3.58 (m, 1H), 3.54-3.44 (m, 1H), 2.77 (s, 3H).

Step 5: Preparation of WX076-6

Compound WX076-5 (1.35 g, 3.14 mmol) was dissolved in methanol (25.00 mL) at room temperature, followed by the addition of zinc powder (1.03 g, 15.70 mmol) and ammonium chloride (1.68 g, 31.40 mmol, 1.10 mL). The reaction mixture was stirred at room temperature for 1 hour. After the reaction, insolubles was removed by filtration. The filtrate was concentrated under reduced pressure. Dichloromethane (20 mL) was added to the residue with stirring for 10 minutes, followed by filtration. The filtrate was concentrated under reduced pressure to obtain the crude product WX076-6. $^1$H NMR (400 MHz, CDCl$_3$) δ: 7.28 (d, J=7.8 Hz, 2H), 6.90 (d, J=8.5 Hz, 2H), 6.83 (d, J=2.3 Hz, 1H), 6.70 (dd, J=2.1, 8.4 Hz, 1H), 6.28 (d, J=8.5 Hz, 1H), 5.01-4.84 (m, 1H), 4.34 (br. s., 1H), 3.80 (s, 3H), 3.74-3.58 (m, 2H), 3.58-3.36 (m, 2H), 2.81 (s, 3H).

Step 6: Preparation of WX076-7

Compound WX076-6 (1.25 g, 3.13 mmol) and triethylamine (1.27 g, 12.52 mmol, 1.74 mL) were dissolved in tetrahydrofuran (40.00 mL) at room temperature and cooled to 0° C., followed by the portionwise addition of triphosgene (371.59 mg, 1.25 mmol). The reaction mixture was warmed to room temperature and stirred for 6 hours. After the reaction, the mixture was quenched with saturated brine (10 mL), diluted with water (50 mL) and extracted with ethyl acetate (15 mL×3). The organic phases were combined, washed with saturated brine (50 mL×2) and dried over anhydrous sodium sulfate, followed by filtration. The filtrate was concentrated under reduced pressure. The obtained residue was purified by column chromatography (eluent: ethyl acetate/petroleum ether=1/3-1/1, volume ratio) to obtain the target product WX076-7.

Step 7: Preparation of WX076

Compound WX076-7 (250.00 mg, 587.82 µmol) and o-fluorophenylboronic acid (99.52 mg, 711.26 µmol) were dissolved in dioxane (10.00 mL) at room temperature, followed by the addition of (1,1'-bis(diphenylphosphino)ferrocene) palladium dichloride dichloromethane complex (48.00 mg, 58.78 µmol), potassium carbonate (121.86 mg, 881.73 µmol) and water (3.00 mL). The reaction mixture was heated to 80° C. and stirred for 3 hours under nitrogen atmosphere. After the reaction, the mixture was cooled to room temperature, quenched with saturated brine (5 mL), diluted with water (25 mL) and extracted with ethyl acetate (5 mL×3). The organic phases were combined, washed with water (20 mL×2) and dried over anhydrous sodium sulfate, followed by filtration. The filtrate was concentrated under reduced pressure. The obtained residue was purified by preparative HPLC to obtain the target product WX076. MS-ESI m/z: 441.1 [M+H]$^+$. $^1$H NMR (400 MHz, CDCl$_3$) δ: 8.61 (br s, 1H), 7.49 (d, J=8.5 Hz, 2H), 7.44-7.37 (m, 1H), 7.31 (d, J=7.0 Hz, 2H), 7.26 (br s, 1H), 7.24-7.09 (m, 3H), 6.90 (d, J=8.5 Hz, 2H), 5.90 (dd, J=4.3, 9.5 Hz, 1H), 4.79 (dd, J=9.8, 14.8 Hz, 1H), 3.87 (dd, J=3.5, 14.3 Hz, 1H), 3.79 (s, 3H), 2.80 (s, 3H).

Embodiment 77: WX077

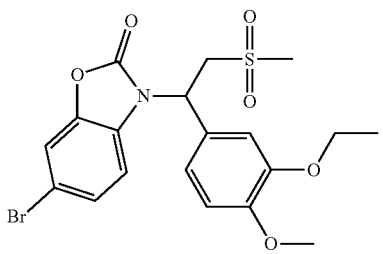 [SMILES: CCOc1cc(C(CS(C)(=O)=O)n2c(=O)oc3cc(Br)ccc32)ccc1OC]

Synthesis Route:

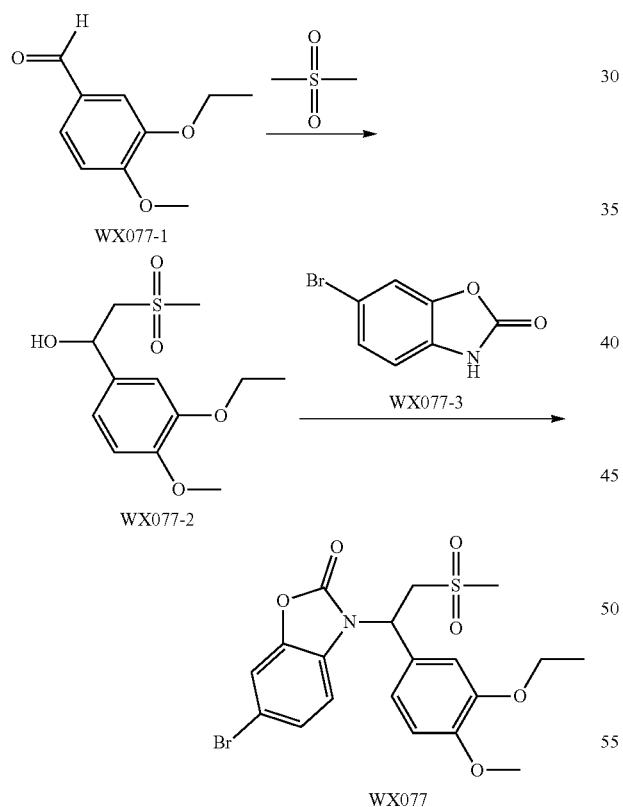

Step 1: Preparation of WX077-2

Dimethyl sulfone (5.22 g, 55.50 mmol) was dissolved in tetrahydrofuran (50.00 mL) under nitrogen atmosphere and cooled to 0° C., followed by the dropwise addition of n-butyllithium (2.5 M, 22.20 mL) with stirring at 0° C. for 1 hour. Then, a solution of the compound WX077-1 (5.00 g, 27.75 mmol) in tetrahydrofuran (20.00 mL) was added dropwise to the above system, and the mixture was stirred at 0° C. for 1.5 hours. After the reaction, the mixture was warmed to room temperature and quenched with saturated ammonium chloride solution (50 mL), diluted with water (150 mL) and extracted with ethyl acetate (50 mL×3). The organic phases were combined, washed with water (100 mL×2) and dried over anhydrous sodium sulfate, followed by filtration. The filtrate was concentrated under reduced pressure. The obtained residue was recrystallized with ethyl acetate (20 mL) to obtain the target product WX077-2. $^1$H NMR (400 MHz, DMSO_d$_6$) δ: 6.99 (s, 1H), 6.91 (s, 2H), 5.83 (d, J=4.0 Hz, 1H), 4.96 (ddd, J=2.8, 4.3, 10.0 Hz, 1H), 4.02 (q, J=7.0 Hz, 2H), 3.73 (s, 3H), 3.57 (dd, J=10.0, 14.6 Hz, 1H), 3.15 (d, J=14.6 Hz, 1H), 3.01 (s, 3H), 1.33 (t, J=7.0 Hz, 3H).

Step 2: Preparation of WX077

Compound WX077-2 (300.00 mg, 1.09 mmol), compound WX077-3 (233.28 mg, 1.09 mmol) and triphenylphosphine (343.08 mg, 1.31 mmol) were dissolved in tetrahydrofuran (5.00 mL) under nitrogen atmosphere and cooled to 0° C., followed by the dropwise addition of diisopropyl azodicarboxylate (264.49 mg, 1.31 mmol). The reaction mixture was warmed to room temperature and stirred for 24 hours. After the reaction, the mixture was quenched with saturated brine (10 mL), diluted with water (20 mL) and extracted with ethyl acetate (15 mL×3). The organic phases were combined, washed with water (25 mL×2) and dried over anhydrous sodium sulfate, followed by filtration. The filtrate was concentrated under reduced pressure. The obtained residue was purified by column chromatography (eluent: methanol/dichloromethane=0/1-1/30, volume ratio), followed by preparative HPLC to obtained the target product WX077. MS-ESI m/z: 492.0 [M+Na]$^+$, 494.0 [M+Na+2]$^+$. $^1$H NMR (400 MHz, DMSO_d$_6$) δ: 7.67 (s, 1H), 7.38 (s, 2H), 7.14 (d, J=1.5 Hz, 1H), 7.07 (d, J=8.3 Hz, 1H), 6.95 (d, J=8.3 Hz, 1H), 5.89 (dd, J=4.0, 10.5 Hz, 1H), 4.43 (dd, J=10.8, 14.6 Hz, 1H), 4.24 (dd, J=4.0, 14.6 Hz, 1H), 4.06-3.96 (m, 2H), 3.73 (s, 3H), 3.06 (s, 3H), 1.31 (t, J=6.9 Hz, 3H).

Embodiment 78: WX078

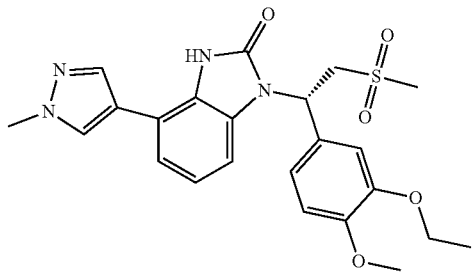 [SMILES: CCOc1cc([C@@H](CS(C)(=O)=O)n2c(=O)[nH]c3c(-c4cnn(C)c4)cccc32)ccc1OC]

Synthesis Route:

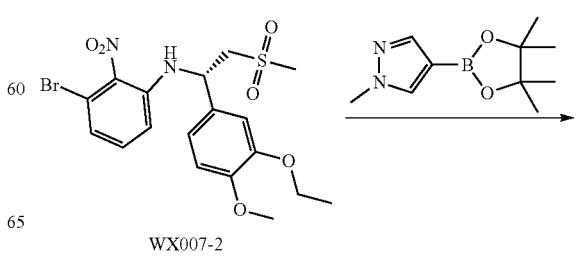

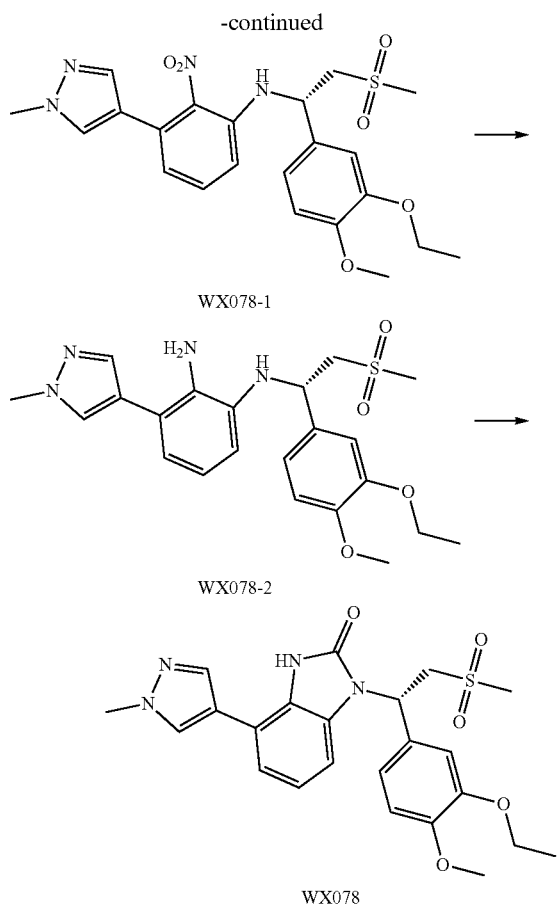

Step 1: Preparation of WX078-1

Compound WX007-2 (450.00 mg, 950.69 μmol), 1-methyl-4-(4,4,5,5-tetramethyl-1,3,2-dioxaborolane-2-yl)pyrazole (296.70 mg, 1.43 mmol) and potassium carbonate (394.18 mg, 2.85 mmol) were dissolved in dioxane (14.00 mL) and water (4.30 mL) at room temperature, followed by the addition of (1,1'-bis(diphenylphosphino)ferrocene) palladium dichloride dichloromethane complex (116.46 mg, 142.60 μmol). The reaction mixture was heated to 75° C. and stirred for 13 hours under nitrogen atmosphere. After the reaction, the mixture was cooled to room temperature, and water (30 mL) and ethyl acetate (40 mL) was added thereto with stirring for 5 minutes. Insolubles was removed by filtration, and the filter cake was washed with ethyl acetate (30 mL). The filtrate was combined and the organic phase was separated, washed with water (50 mL×3) and dried over anhydrous sodium sulfate, followed by filtration. The filtrate was concentrated under reduced pressure. The obtained residue was purified by column chromatography (eluent: ethyl acetate/petroleum ether=1/2-2/1, volume ratio) to obtain the target product WX078-1. $^1$H NMR (400 MHz, CDCl$_3$) δ: 7.40-7.51 (m, 2H), 7.18 (t, J=8.0 Hz, 1H), 6.92 (br d, J=1.8 Hz, 1H), 6.83-6.89 (m, 2H), 6.74 (d, J=7.3 Hz, 1H), 6.65 (d, J=8.3 Hz, 1H), 5.95 (d, J=6.0 Hz, 1H), 5.06-5.12 (m, 1H), 4.02-4.09 (m, 2H), 3.90 (s, 3H), 3.84 (s, 3H), 3.36-3.60 (m, 2H), 2.80 (s, 3H), 1.42 (t, J=7.0 Hz, 3H).

Step 2: Preparation of WX078-2

Compound WX078-1 (415.00 mg, 874.55 μmol) and ammonium chloride (467.80 mg, 8.75 mmol) were dissolved in methanol (10.00 mL) at room temperature, followed by the addition of zinc powder (285.93 mg, 4.37 mmol). The reaction mixture was stirred at room temperature for 1 hour under nitrogen atmosphere. The insolubles was removed by filtration, and the filter cake was added to a mixed solvent of ethyl acetate (50 mL) and dichloromethane (5 mL) with stirring at room temperature for 15 minutes, followed by filtration. The insolubles was removed by filtration. The filtrate was combined, washed with saturated brine (50 mL×2) and dried over anhydrous sodium sulfate, followed by filtration. The filtrate was concentrated under reduced pressure to obtain the crude product WX078-2. MS-ESI m/z: 467.1 [M+Na]$^+$.

Step 3: Preparation of WX078

Compound WX078-2 (450.00 mg, 1.01 mmol) and triethylamine (563.37 mg, 5.57 mmol, 771.74 μL) were dissolved in tetrahydrofuran (15.00 mL) at room temperature, followed by the addition of triphosgene (240.31 mg, 809.81 μmol). The reaction mixture was stirred at room temperature for 15 hours under nitrogen atmosphere. After the reaction, the solvent was removed by concentration under reduced pressure. Water (40 mL) was added to the obtained residue and extracted with ethyl acetate (30 mL×3). The organic phases were combined, washed with saturated brine (60 mL) and dried over anhydrous sodium sulfate, followed by filtration. The filtrate was concentrated under reduced pressure. The obtained residue was purified by preparative HPLC to obtain the target product WX078. MS-ESI m/z: 471.1 [M+H]$^+$. $^1$H NMR (400 MHz, CDCl$_3$) δ: 9.95 (br s, 1H), 7.86 (s, 1H), 7.70 (s, 1H), 7.02-7.17 (m, 5H), 6.82 (d, J=8.3 Hz, 1H), 5.85 (dd, J=9.0, 4.8 Hz, 1H), 4.71 (dd, J=14.7, 9.4 Hz, 1H), 4.04 (q, J=6.9 Hz, 2H), 3.97 (s, 3H), 3.90-3.96 (m, 1H), 3.83 (s, 3H), 2.74 (s, 3H), 1.41 (t, J=6.9 Hz, 3H).

Embodiment 79: WX079

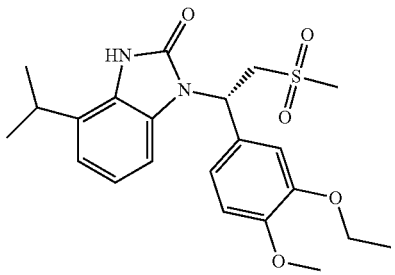 [SMILES: CCOc1cc([C@@H](CS(C)(=O)=O)n2c(=O)[nH]c3c(C(C)C)cccc32)ccc1OC]

Synthesis Route:

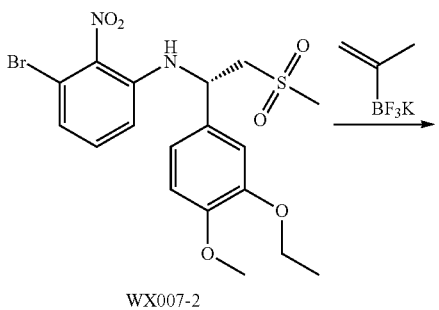

WX007-2

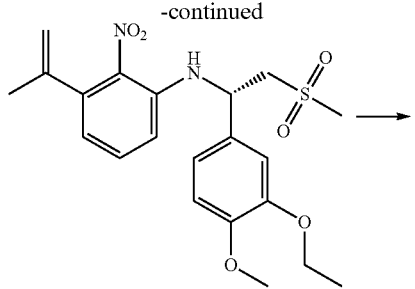

WX079-1

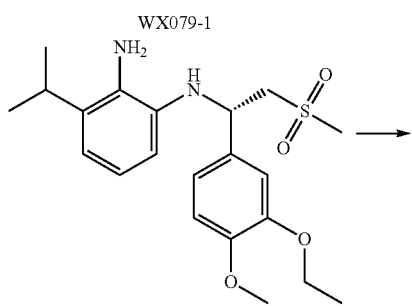

WX079-2

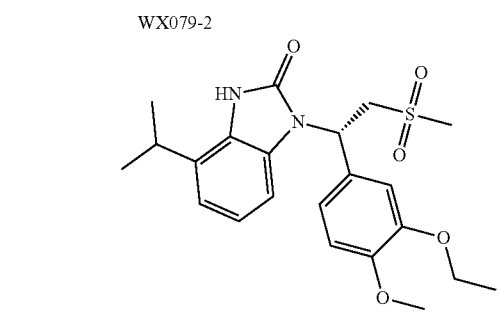

WX079

Step 1: Preparation of WX079-1

Compound WX007-2 (150.00 mg, 316.90 μmol), potassium isopropenyl trifluoroborate (70.34 mg, 475.35 μmol), (1,1'-bis(diphenylphosphino)ferrocene) palladium dichloride dichloromethane complex (25.88 mg, 31.69 μmol) and potassium carbonate (87.60 mg, 633.80 μmol) were dissolved in dioxane (1.00 mL) and water (300.00 μL) at room temperature. The reaction mixture was heated to 80° C. and stirred for 10 hours under nitrogen atmosphere. After the reaction, the mixture was cooled to room temperature and water (20 mL) was added and extracted with ethyl acetate (20 mL×2). The organic phases were combined, washed with saturated brine (20 mL×3) and dried over anhydrous sodium sulfate, followed by filtration. The filtrate was concentrated under reduced pressure. The obtained residue was purified by preparative TLC (eluent:ethyl acetate/petroleum ether=1/1, volume ratio) to obtain the target product WX079-1. MS-ESI m/z: 457.2 [M+Na]⁺.

Step 2: Preparation of WX079-2

Compound WX079-1 (110.00 mg, 253.16 μmol) and palladium hydroxide (40.89 mg, 58.23 μmol, 20% purity) were dissolved in ethanol (1.50 mL) at room temperature. The reaction mixture was stirred at room temperature for 12 hours under hydrogen (30 psi) atmosphere. After the reaction, the insolubles was removed by filtration, and the filtrate was concentrated under reduced pressure to obtain the target product WX079-2. MS-ESI m/z: 429.1 [M+Na]⁺.

Step 3: Preparation of WX079

Compound WX079-2 (100.00 mg, 245.98 μmol), triethylamine (124.45 mg, 1.23 mmol, 170.48 μL) and triphosgene (29.20 mg, 98.39 μmol) were dissolved in tetrahydrofuran (1.00 mL) at room temperature. The reaction mixture was cooled to 0-5° C. and stirred for 10 hours under nitrogen atmosphere. After the reaction, water (10 mL) was added and extracted with ethyl acetate (10 mL×2). The organic phases were combined, washed with saturated brine (10 mL×3) and dried over anhydrous sodium sulfate, followed by filtration. The filtrate was concentrated under reduced pressure. The obtained residue was purified by preparative HPLC to obtain the target product WX079. MS-ESI m/z: 433.1 [M+H]⁺. ¹H NMR (400 MHz, CDCl₃) δ: 8.55 (br s, 1H), 7.16 (s, 1H), 7.07 (t, J=7.8 Hz, 2H), 7.00-6.95 (m, 2H), 6.80 (d, J=8.3 Hz, 1H), 5.78 (dd, J=4.6, 8.9 Hz, 1H), 4.76 (dd, J=9.2, 14.9 Hz, 1H), 4.07 (q, J=6.9 Hz, 2H), 3.89 (dd, J=4.6, 14.9 Hz, 1H), 3.82 (s, 3H), 2.73 (s, 3H), 1.42 (t, J=6.9 Hz, 3H), 1.30 (t, J=6.8 Hz, 7H).

Embodiment 80: WX080

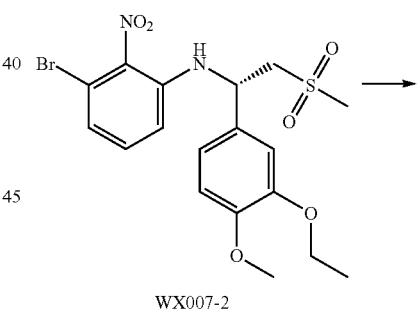

Synthesis Route:

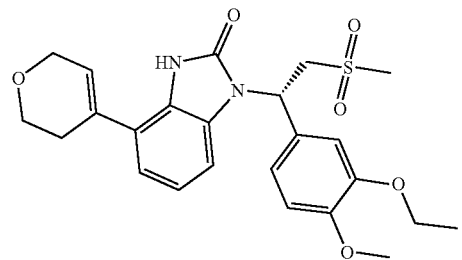 [SMILES: CCOc1cc([C@@H](CS(C)(=O)=O)n2c(=O)[nH]c3c(C4=CCOCC4)cccc32)ccc1OC]

WX007-2

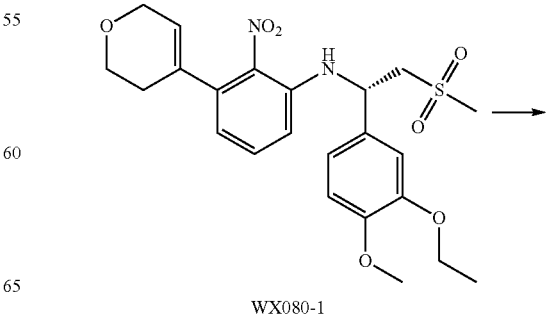

WX080-1

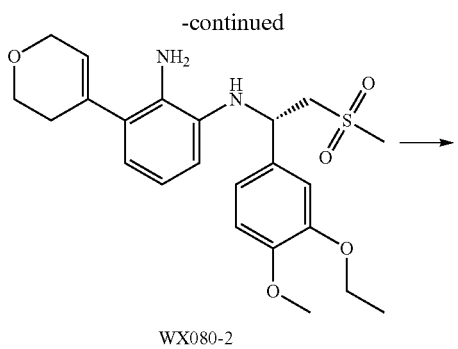

WX080-2

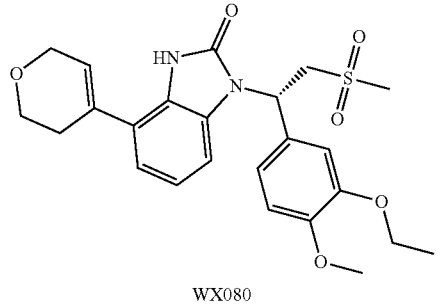

WX080

Step 1: Preparation of WX080-1

Compound WX007-2 (500.00 mg, 1.06 mmol), 2-(3,6-dihydro-2H-pyran-4-yl)-4,4,5,5-tetramethyl-1,3,2-dioxolpentane (334.03 mg, 1.59 mmol), (1,1'-bis(diphenylphosphino)ferrocene) palladium dichloride dichloromethane complex (86.56 mg, 106.00 µmol) and potassium carbonate (293.01 mg, 2.12 mmol) were dissolved in 1,4-dioxane (1.00 mL) and water (300.00 µL) at room temperature. The reaction mixture was heated to 80° C. and stirred for 4 hours under nitrogen atmosphere. After the reaction, the mixture was cooled to room temperature and water (20 mL) was added thereto and extracted with ethyl acetate (20×2). The organic phases were combined, washed with saturated brine (25 mL×3) and dried over anhydrous sodium sulfate, followed by filtration. The filtrate was concentrated under reduced pressure. The obtained residue was isolated by column chromatography (eluent: petroleum ether/ethyl acetate=1/0-3/1-1/1, volume ratio) to obtain the target product WX080-1. MS-ESI m/z: 499.1 [M+Na]⁺. ¹H NMR (400 MHz, CDCl₃) δ: 7.22 (t, J=8.0 Hz, 1H), 6.96-6.85 (m, 4H), 6.71 (d, J=8.5 Hz, 1H), 6.58 (d, J=7.5 Hz, 1H), 5.61 (br s, 1H), 5.14-5.08 (m, 1H), 4.24 (d, J=2.5 Hz, 2H), 4.13-4.05 (m, 2H), 3.89 (t, J=5.3 Hz, 2H), 3.86 (s, 3H), 3.58-3.51 (m, 1H), 3.45-3.38 (m, 1H), 2.78 (s, 3H), 2.31 (br s, 2H), 1.45 (t, J=7.0 Hz, 3H).

Step 2: Preparation of WX080-2

Zinc powder (315.60 mg, 4.83 mmol) and ammonium chloride (258.17 mg, 4.83 mmol) were added to a solution of compound WX080-1 (230.00 mg, 482.65 µmol) in methanol (10.00 mL) at room temperature. The reaction mixture was stirred at room temperature for 12 hours. After the reaction, insolubles was removed by filtration, and the filtrate was concentrated under reduced pressure to remove solvent. The obtained residue was added to dichloromethane (30 mL) with stirring for 30 min, followed by filtration. The filtrate was concentrated under reduced pressure to obtain the target product WX080-2. MS-ESI m/z: 469.1 [M+Na]⁺.

Step 3: Preparation of WX080

A solution of compound WX080-2 (180.00 mg, 403.08 µmol), triethylamine (203.94 mg, 2.02 mmol) and triphosgene (47.85 mg, 161.23 µmol) in tetrahydrofuran (10.00 mL) were stirred at 0-5° C. for 12 hours under nitrogen atmosphere. After the reaction, the mixture was poured into water (50 mL) and extracted with ethyl acetate (50 mL×2). The organic phases were combined, washed with saturated brine (50 mL×3) and dried over anhydrous sodium sulfate, followed by filtration. The filtrate was concentrated under reduced pressure. The obtained residue was purified by preparative HPLC to obtain the target product WX080. MS-ESI m/z: 473.1 [M+H]⁺. ¹H NMR (400 MHz, CDCl₃) δ: 9.57 (s, 1H), 7.17 (d, J=1.8 Hz, 1H), 7.12-7.06 (m, 2H), 7.05-7.01 (m, 1H), 6.96 (d, J=7.5 Hz, 1H), 6.82 (d, J=8.3 Hz, 1H), 5.99 (br s, 1H), 5.78 (dd, J=5.3, 8.8 Hz, 1H), 4.67 (dd, J=8.8, 14.8 Hz, 1H), 4.34 (d, J=2.5 Hz, 2H), 4.06 (q, J=6.9 Hz, 3H), 3.95 (q, J=5.5 Hz, 2H), 3.83 (s, 3H), 2.73 (s, 3H), 2.50 (d, J=1.8 Hz, 2H), 1.41 (t, J=7.0 Hz, 3H).

Embodiment 81: WX081

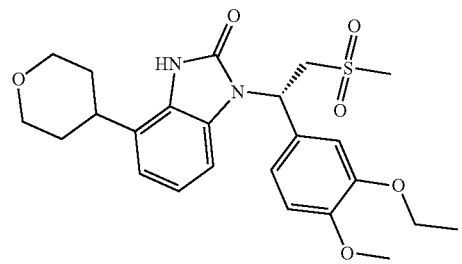 [SMILES: CCOc1cc([C@@H](CS(C)(=O)=O)n2c(=O)[nH]c3c(C4CCOCC4)cccc32)ccc1OC]

Synthesis Route:

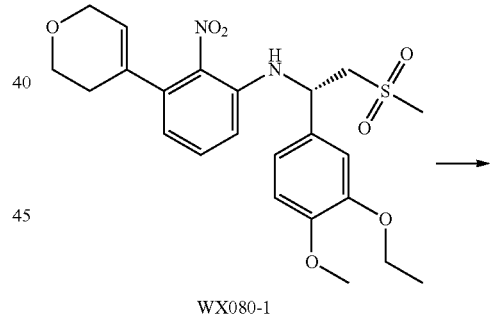

WX080-1

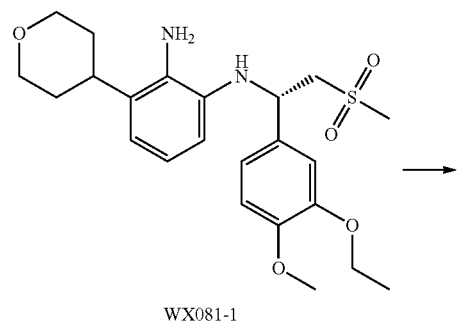

WX081-1

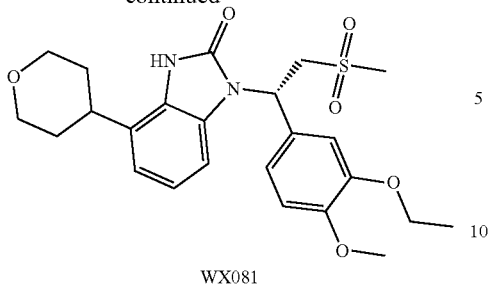

WX081

Step 1: Preparation of WX081-1

A solution of compound WX080-1 (200.00 mg, 419.69 μmol) and palladium hydroxide (67.78 mg, 96.53 μmol, 20% purity) in ethanol (10.00 mL) was stirred at room temperature for 12 hours under a hydrogen (30 psi) atmosphere. After the reaction, insolubles was removed by filtration, and then the filtrate was concentrated under reduced pressure to remove the solvent to obtain the crude product WX081-1.

MS-ESI m/z: 449.2 [M+H]$^+$.

Step 2: Preparation of WX081

A solution of compound WX081-1 (188.00 mg, 419.10 μmol), triethylamine (212.04 mg, 2.10 mmol) and triphosgene (49.75 mg, 167.64 μmol) in tetrahydrofuran (10.00 mL) at was stirred at 0-5° C. for 12 hours under a nitrogen atmosphere. After the reaction, the mixture was poured into water (50 mL) and extracted with ethyl acetate (50 mL×2). The organic phases were combined, washed with brine (50 mL×3) and dried over anhydrous sodium sulfate, followed by filtration. The filtrate was concentrated under reduced pressure. The obtained residue was purified by preparative HPLC to obtain the target product WX081. MS-ESI m/z: 475.1 [M+H]$^+$. $^1$H NMR (400 MHz, CDCl$_3$) δ: 10.96 (br s, 1H), 7.22-7.13 (m, 2H), 7.12-7.02 (m, 2H), 6.97 (d, J=7.0 Hz, 1H), 6.82 (d, J=8.3 Hz, 1H), 5.80 (br s, 1H), 4.62 (dd, J=8.9, 13.7 Hz, 1H), 4.27-4.18 (m, 1H), 4.17-3.98 (m, 4H), 3.82 (s, 3H), 3.67-3.49 (m, 2H), 3.01-2.86 (m, 1H), 2.70 (s, 3H), 2.02 (t, J=12.2 Hz, 2H), 1.74 (d, J=12.0 Hz, 2H), 1.40 (t, J=6.7 Hz, 3H).

Embodiment 82: WX082

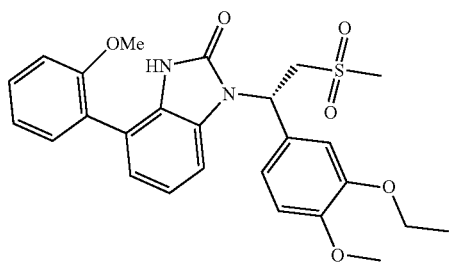 [SMILES: CCOc1cc([C@@H](CS(C)(=O)=O)n2c(=O)[nH]c3c(-c4ccccc4OC)cccc32)ccc1OC]

Synthesis Route:

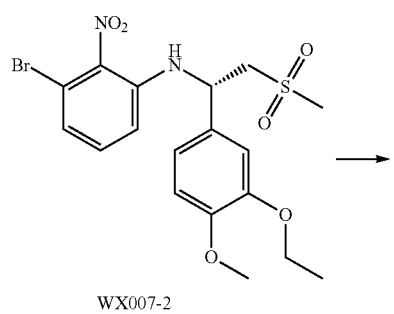

WX007-2

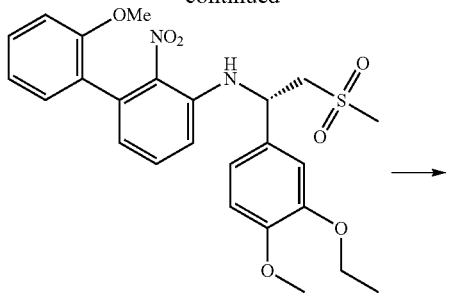

WX082-1

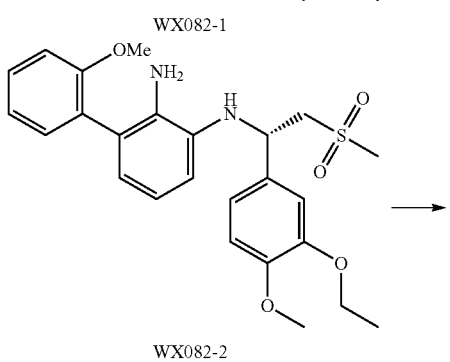

WX082-2

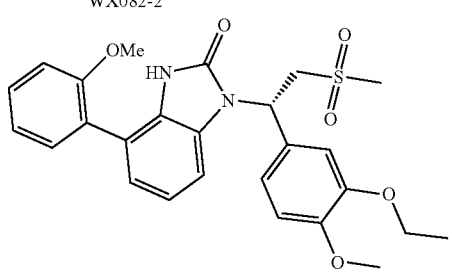

WX082

Step 1: Preparation of WX082-1

Oxybenzene boronic acid (77.05 mg, 507.04 μmol) and (1,1'-bis(diphenylphosphino)ferrocene) palladium dichloride (15.46 mg, 21.13 μmol) were added to a solution of the compound WX007-2 (200.00 mg, 422.53 μmol) and potassium carbonate (175.19 mg, 1.27 mmol) in 1,4-dioxane (6.00 mL) and water (2.00 mL) at room temperature. The reaction mixture was heated to 80° C. and stirred for 16 hours under a nitrogen atmosphere. After the reaction, the reaction mixture was poured into water (10 mL) and extracted with ethyl acetate (10 mL×3). The organic phases were combined, washed with brine (10 mL×2) and dried over anhydrous sodium sulfate, followed by filtration. The filtrate was concentrated under reduced pressure. The obtained residue was isolated by preparative TLC (eluent: petroleum ether/ethyl acetate=2/1, volume ratio) to obtain the target product WX082-1. MS-ESI m/z: 523.1 [M+Na]$^-$, $^1$H NMR (400 MHz, CDCl$_3$) δ: 7.41-7.29 (m, 2H), 7.12-6.77 (m, 7H), 6.69 (d, J=7.5 Hz, 1H), 5.16 (s, 1H), 4.19-4.03 (m, 1H), 3.87 (s, 3H), 3.71 (s, 3H), 3.63-3.54 (m, 1H), 3.52-3.38 (m, 2H), 2.90-2.59 (m, 3H), 1.46 (s, 3H).

Step 2: Preparation of WX082-2

Zinc powder (248.20 mg, 3.80 mmol) and ammonium chloride (203.03 mg, 3.80 mmol) were added to a solution of compound WX082-1 (190.00 mg, 379.57 μmol) in methanol (10.00 mL) at room temperature. The reaction was stirred at room temperature for 0.1 hour. After the reaction, insolubles was removed by filtration and the filter cake was washed with dichloromethane (20 mL×2). The filtrate was combined and concentrated under reduced pressure to obtain the target product WX082-2. MS-ESI m/z: 471.1 [M+H]+.

Step 3: Preparation of WX082

Triphosgene (42.88 mg, 144.50 μmol) was added in one time to a solution of compound WX082-2 (170.00 mg, 361.26 μmol) and triethylamine (182.78 mg, 1.81 mmol) in tetrahydrofuran (25.00 mL) at 0° C. The reaction mixture was stirred at 0° C. for 2.5 hours. After the reaction, the mixture was poured into water (10 mL) and extracted with ethyl acetate (10 mL×3). The organic phases were combined, washed with brine (10 mL×2) and dried over anhydrous sodium sulfate, followed by filtration. The filtrate was concentrated under reduced pressure. The obtained residue was purified by preparative HPLC to obtain the target product WX082. MS-ESI m/z: 497.1 [M+H]+. 1H NMR (400 MHz, CDCl3) δ: 8.13 (s., 1H), 7.40-7.46 (m, 1H), 7.36 (dd, J=7.53, 1.8 Hz, 1H), 7.24-7.16 (m, 2H), 7.15-7.02 (m, 5H), 6.85 (d, J=8.28 Hz, 1H), 5.80 (s., 1H), 4.76 (d, J=4.8 Hz, 1H), 4.22-4.04 (m, 2H), 3.96-3.67 (m, 7H), 2.70 (s, 3H), 1.46 (t, J=6.9 Hz, 3H).

Embodiment 83: WX083

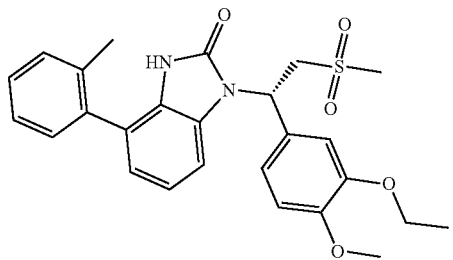 [SMILES: CCOc1cc([C@@H](CS(C)(=O)=O)n2c(=O)[nH]c3c(-c4ccccc4C)cccc32)ccc1OC]

Synthesis Route:

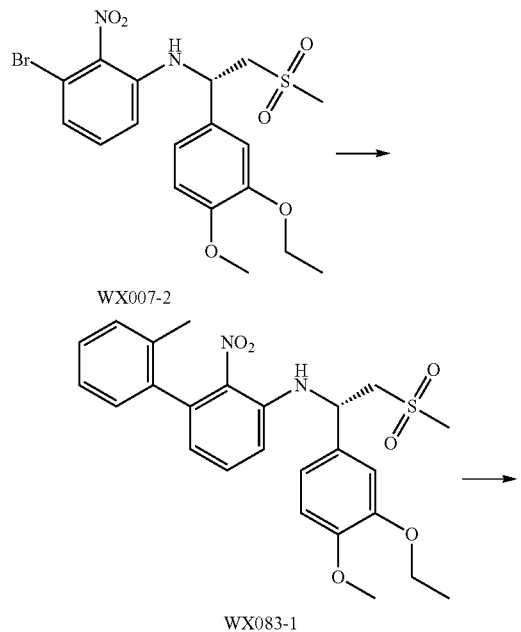

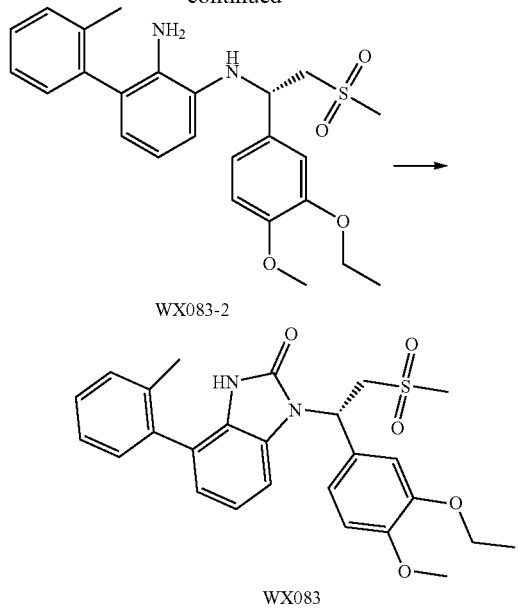

Step 1: Preparation of WX083-1

Benzoboronic acid (68.94 mg, 507.04 μmol) and (1,1'-bis(diphenylphosphino)ferrocene) palladium dichloride (15.46 mg, 21.13 μmol) were added to a solution of the compound WX007-2 (200.00 mg, 422.53 μmol) and potassium carbonate (175.19 mg, 1.27 mmol) in 1,4-dioxane (6.00 mL) and water (2.00 mL) at room temperature. The reaction mixture was heated to 80° C. and stirred for 16 hours under nitrogen atmosphere. After the reaction, the mixture was cooled to room temperature, poured into water (10 mL) and extracted with ethyl acetate (10 mL×3). The organic phases were combined and concentrated under reduced pressure. The obtained residue was isolated by preparative TLC (eluent: petroleum ether/ethyl acetate=2/1, volume ratio) to obtain the target product WX083-1. MS-ESI m/z: 507.2 [M+Na]+. 1H NMR (400 MHz, CDCl3) δ: 7.34-7.28 (m, 1H), 7.25-7.14 (m, 2H), 7.07 (m, 1H), 7.01-6.95 (m, 1H), 6.94-6.87 (m, 2H), 6.81 (dd, J=8.0, 4.3 Hz, 1H), 6.75 (t, J=6.7 Hz, 2H), 6.62-6.56 (m, 1H), 5.22-5.10 (m, 1H), 4.13-4.02 (m, 2H), 3.88 (s, 3H), 3.63-3.53 (m, 1H), 3.51-3.38 (m, 1H), 2.78 (d, J=10.6 Hz, 3H), 2.23-2.09 (m, 3H), 1.46 (q, J=7.2 Hz, 3H).

Step 2: Preparation of WX083-2

Zinc powder (242.90 mg, 3.71 mmol) and ammonium chloride (198.70 mg, 3.71 mmol) were added to a solution of compound WX083-1 (180.00 mg, 371.46 μmol) in methanol (10.00 mL) at room temperature. The reaction was stirred at room temperature for 0.1 hour. After the reaction, insolubles was removed by filtration, and the filter cake was washed with dichloromethane (20 mL×2). The filtrate was combined and concentrated under reduced pressure to obtain the target product WX083-2. (20 mL, EtOAc). MS-ESI m/z: 477.2 [M+Na]+.

Step 3: Preparation of WX083

Triphosgene (37.86 mg, 127.59 μmol) was added in one time to a solution of compound WX083-2 (145.00 mg, 318.98 μmol.) and triethylamine (161.39 mg, 1.59 mmol) in tetrahydrofuran (25.00 mL) at 0° C. The reaction mixture was stirred at 0° C. for 2.5 hours. After the reaction, the solution was poured into water (10 mL) and extracted with ethyl acetate (10 mL×3). The organic phases were combined, washed with brine (10 mL×2) and dried over anhydrous sodium sulfate, followed by filtration. The filtrate was concentrated under reduced pressure to remove the solvent. The obtained residue was beating with methanol (10 mL), followed by filtration, and the filter cake was wash with methanol (10 mL×3). The filter cake was concentrated under reduced pressure to obtain the target product WX083. MS-ESI m/z: 481.1 [M+H]$^+$. $^1$H NMR (400 MHz, CDCl$_3$) δ: 7.37-7.27 (m, 3H), 7.25-7.20 (m, 1H), 7.18-7.05 (m, 4H), 6.98 (dd, J=7.3, 1.0 Hz, 1H), 6.84 (d, J=8.3 Hz, 1H), 5.97-5.58 (m, 1H), 4.65 (dd, J=14.2, 9.2 Hz, 1H), 4.06 (q, J=6.8 Hz, 2H), 3.92-3.77 (m, 4H), 2.66 (s, 3H), 2.18 (s, 3H), 1.43 (t, J=6.90 Hz, 3H).

Embodiment 84: WX084

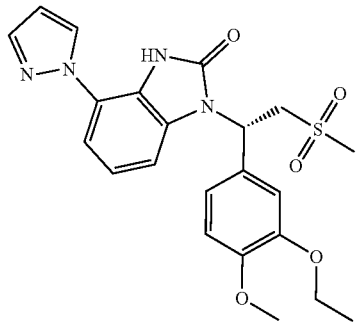 [SMILES: CCOc1cc([C@@H](CS(C)(=O)=O)n2c(=O)[nH]c3c(-n4cccn4)cccc32)ccc1OC]

Synthesis Route:

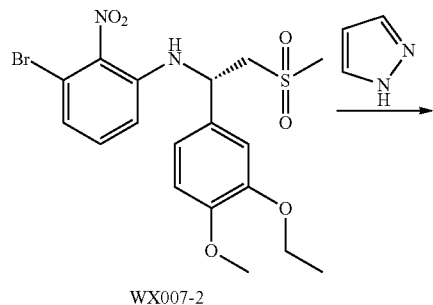

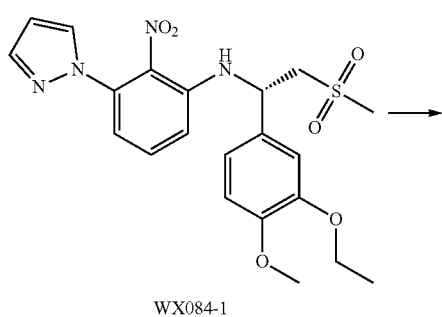

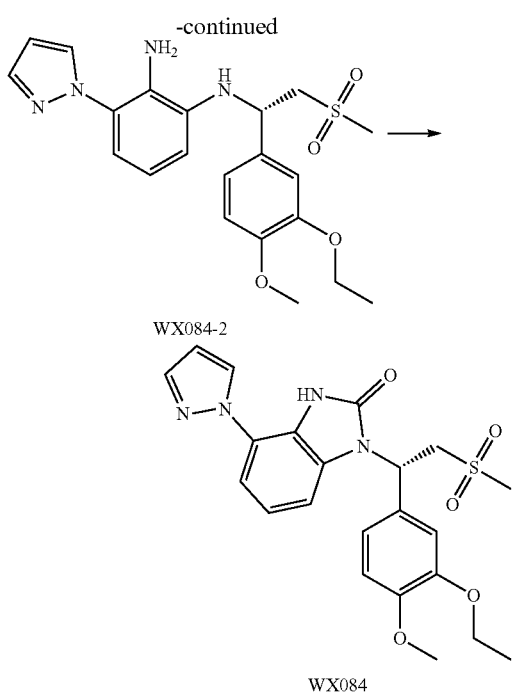

Step 1: Preparation of WX084-1

Cuprous iodide (40.24 mg, 211.26 μmol), (1S, 2S)-cyclohexane-1,2-diamine (48.25 mg, 422.53 μmol) and potassium carbonate (218.99 mg, 1.58 mmol) were added to a solution of compound WX007-2 (500.00 mg, 1.06 mmol) and pyrazole (107.87 mg, 1.58 mmol) in 1,4-dioxane (5.00 mL) at room temperature. The reaction was heated to 80° C. and stirred for 4 hours under a nitrogen atmosphere. After the reaction, the mixture was cooled to room temperature, and brine (10 mL) and water (30 mL) were added thereto and extracted with ethyl acetate (10 mL×3). The organic phases were combined, washed with water (50 mL×2) and dried over anhydrous sodium sulfate, followed by filtration. The filtrate was concentrated under reduced pressure. The obtained residue was isolated by column chromatography (eluent: petroleum ether/ethyl acetate=2/1-1/1, volume ratio) to obtain the target product WX084-1. $^1$H NMR (400 MHz, CDCl$_3$) δ: 7.70 (dd, J=2.0, 5.8 Hz, 2H), 7.33 (t, J=8.2 Hz, 1H), 6.98-6.91 (m, 1H), 6.90-6.84 (m, 2H), 6.81 (d, J=8.0 Hz, 2H), 6.60 (d, J=6.5 Hz, 1H), 6.46 (t, J=2.1 Hz, 1H), 5.21-5.10 (m, 1H), 4.13-4.03 (m, 2H), 3.87 (s, 3H), 3.66-3.51 (m, 1H), 3.50-3.38 (m, 1H), 2.80 (s, 3H), 1.46 (t, J=6.9 Hz, 3H).

Step 2: Preparation of WX084-2

Zinc powder (567.99 mg, 8.69 mmol) and ammonium chloride (464.62 mg, 8.69 mmol) were added to a solution of compound WX084-1 (400.00 mg, 868.62 μmol) in methanol (10.00 mL) at room temperature. The reaction was stirred at room temperature for 1 hour. After the reaction, insolubles was removed by filtration, and the filtrate was concentrated under reduced pressure. Dichloromethane (15 mL) was added to the residue with stirring at room temperature for 5 minutes, followed by filtration to remove insolubles. The filtrate was concentrated under reduced pressure to obtain the target product WX084-2.

Step 3: Preparation of WX084

Triphosgene (110.29 mg, 371.64 μmol) was slowly added to a solution of compound WX084-2 (400.00 mg, 929.11 μmol) and triethylamine (470.08 mg, 4.65 mmol) in tetrahydrofuran (30.00 mL) at 0° C. The reaction mixture was warmed to room temperature and stirred for 6 hours. After the reaction, the mixture was filtered, and the filtrate was concentrated. The obtained residue was purified by preparative HPLC to obtain the target product WX084. MS-ESI m/z: 457.1 [M+H]⁺. ¹H NMR (400 MHz, CDCl₃) δ: 9.87 (s, 1H), 8.03 (d, J=2.3 Hz, 1H), 7.76 (d, J=1.8 Hz, 1H), 7.24-7.11 (m, 3H), 7.09-6.98 (m, 2H), 6.83 (d, J=8.3 Hz, 1H), 6.50 (t, J=2.1 Hz, 1H), 5.83 (dd, J=4.4, 9.7 Hz, 1H), 4.83 (dd, J=9.7, 14.9 Hz, 1H), 4.08 (q, J=6.9 Hz, 2H), 3.90-3.80 (m, 4H), 2.78 (s, 3H), 1.45 (t, J=7.0 Hz, 3H).

Embodiment 85: WX085

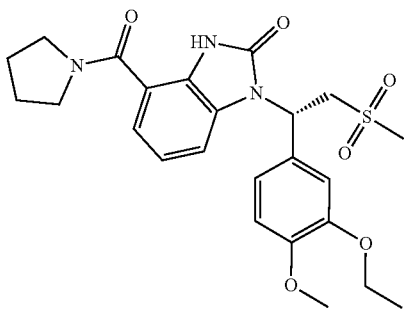 [SMILES: CCOc1cc([C@@H](CS(C)(=O)=O)n2c(=O)[nH]c3c(C(=O)N4CCCC4)cccc32)ccc1OC]

Synthesis Route:

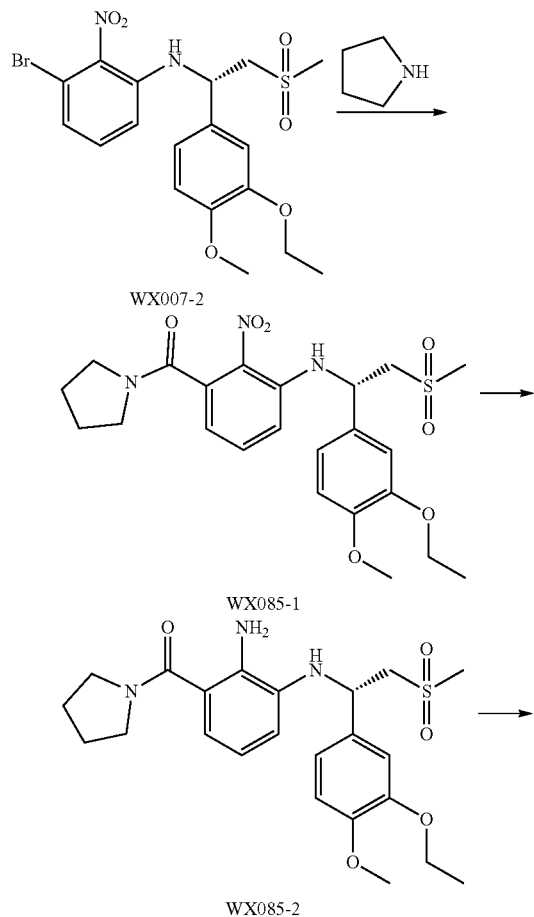

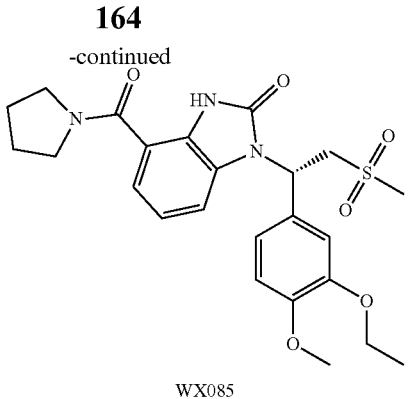

WX085

Step 1: Preparation of WX085-1

Triethylamine (292.00 mg, 2.89 mmol) and (1,1'-bis(diphenylphosphino)ferrocene) palladium dichloride dichloromethane complex (224.58 mg, 275.00 μmol) were added to a solution of compound WX007-2 (1.30 g, 2.75 mmol) and pyrrolidine (254.25 mg, 3.58 mmol) in N,N-dimethylformamide (30.00 mL). The reaction mixture was heated to 80° C. and stirred for 24 hours under a carbon monoxide (50 psi) atmosphere. After the reaction, the mixture was cooled to room temperature, and the insolubles was removed by filtration. The filtrate was concentrated under reduced pressure, and the obtained residue was separated by column chromatography (eluent: petroleum ether/ethyl acetate=10/1-1/1, volume ratio) to obtain the target product WX085-1. ¹H NMR (400 MHz, CDCl₃) δ: 8.36 (d, J=6.8 Hz, 1H), 7.41-7.30 (m, 1H), 6.99-6.76 (m, 4H), 6.64 (dd, J=1.0, 7.3 Hz, 1H), 5.26-5.11 (m, 1H), 4.10 (q, J=7.0 Hz, 2H), 3.88 (s, 3H), 3.73-3.57 (m, 3H), 3.51-3.42 (m, 1H), 3.26-3.15 (m, 2H), 2.79 (s, 3H), 2.03-1.86 (m, 4H), 1.48 (t, J=6.9 Hz, 3H).

Step 2: Preparation of WX085-2

Zinc powder (186.24 mg, 2.85 mmol) was slowly added to a solution of compound WX085-1 (280.00 mg, 569.62 μmol) and ammonium chloride (304.69 mg, 5.70 mmol) in methanol (10.00 mL) at room temperature. The reaction mixture was stirred at room temperature for 2 hours under a nitrogen atmosphere. After the reaction, the insolubles was removed by filtration and the filtrate was concentrated under reduced pressure. Dichloromethane (15 mL) was added to the obtained residue with stirring at room temperature for 5 minutes, followed by filtration. The filtrate was concentrated under reduced pressure to obtain the target product WX085-2.

Step 3: Preparation of WX085

Triphosgene (72.01 mg, 242.65 μmol) was slowly added to a solution of compound WX085-2 (280.00 mg, 606.63 μmol) and triethylamine (306.92 mg, 3.03 mmol) in tetrahydrofuran (20.00 mL) at 0° C. The reaction mixture was warmed to room temperature and stirred for 12 hours. After the reaction, insolubles was removed by filtration, and the filtrate was concentrated under reduced pressure to remove solvent. The obtained residue was purified by preparative HPLC to obtain the target product WX085. MS-ESI m/z: 488.1 [M+H]⁺. ¹H NMR (400 MHz, CDCl₃) δ: 9.50 (br s, 1H), 7.27 (t, J=3.9 Hz, 1H), 7.23-7.16 (m, 1H), 7.15-7.00 (m, 3H), 6.82 (d, J=8.3 Hz, 1H), 5.81 (dd, J=4.3, 9.5 Hz, 1H), 4.79 (dd, J=9.8, 14.8 Hz, 1H), 4.15-3.97 (m, 2H), 3.93-3.76 (m, 4H), 3.68 (t, J=6.4 Hz, 4H), 2.80 (s, 3H), 1.96 (d, J=11.8 Hz, 4H), 1.44 (t, J=7.0 Hz, 3H).

Embodiment 86: WX086

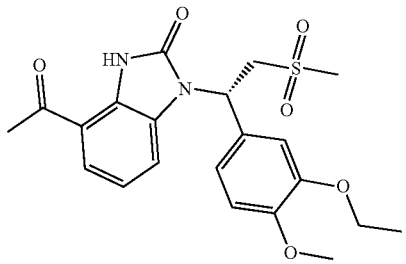 [SMILES: CCOc1cc([C@@H](CS(C)(=O)=O)n2c(=O)[nH]c3c(C(C)=O)cccc32)ccc1OC]

Synthesis Route:

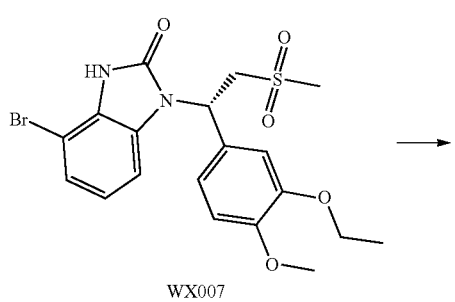

A solution of compound WX007 (300.00 mg, 639.18 μmol), tributyl(1-ethoxyvinyl)tin (1.32 g, 3.65 mmol) and tetrakistriphenylphosphine palladium (147.72 mg, 127.84 μmol) in toluene (50.00 mL) was heated to 100-110° C. and stirred for 12 hours under a nitrogen atmosphere. After the reaction, the mixture was cooled to room temperature, and the insolubles was removed by filtration. The filtrate was concentrated under reduced pressure to remove the solvent. The obtained residue was poured into ethyl acetate (50 mL) and hydrochloric acid/ethyl acetate (4 M, 1.60 mL) with stirring at room temperature for 1.5 hours. Then, the mixture was concentrated under reduced pressure. The obtained residue was purified by preparative HPLC to obtain the target product WX086. MS-ESI m/z: 433.1 [M+H]$^+$. $^1$H NMR (400 MHz, CDCl$_3$) δ: 9.62 (s, 1H), 7.57 (d, J=8.0 Hz, 1H), 7.31-7.29 (m, 1H), 7.18-7.16 (m, 3H), 6.84 (d, J=8.0 Hz, 1H), 5.80 (dd, J=4.0, 9.2 Hz, 1H), 4.82 (dd, J=10.0, 14.8 Hz, 1H), 4.12-4.07 (m, 2H), 3.88-3.84 (m, 4H), 2.79 (s, 3H), 2.64 (s, 3H), 1.46 (t, J=6.8 Hz, 3H).

Embodiment 87: WX087

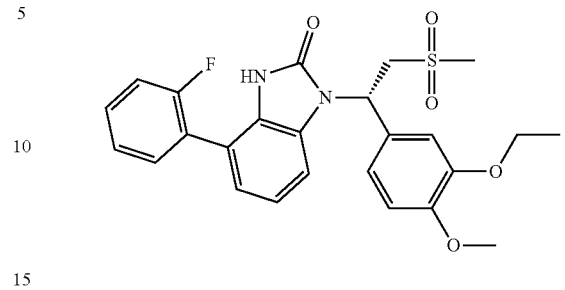

Synthesis Route:

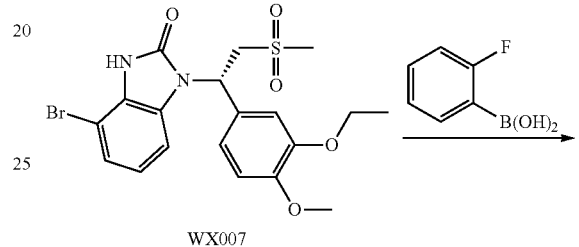

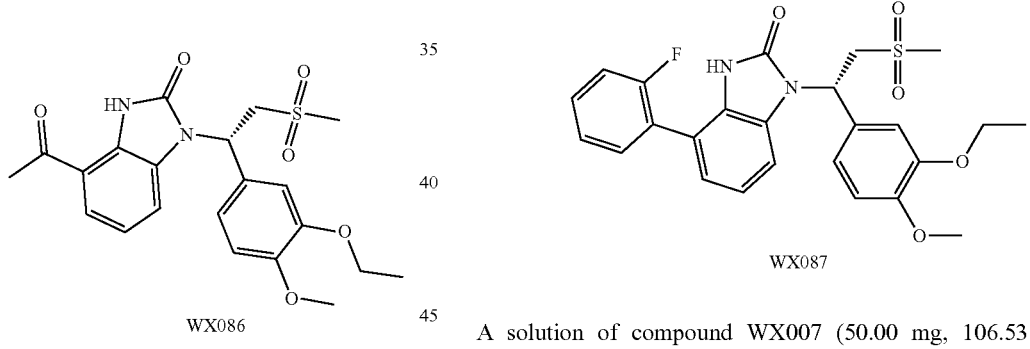

A solution of compound WX007 (50.00 mg, 106.53 μmol), o-fluorophenylboronic acid (19.38 mg, 138.49 μmol.), potassium carbonate (36.81 mg, 266.33 μmol) and (1,1'-bis(diphenylphosphino)ferrocene) palladium dichloride dichloromethane complex (4.35 mg, 5.33 μmol) in 1,4-dioxane (3.00 mL) and water (1.00 mL) was heated to 70° C. and stirred for 10 hours under a nitrogen atmosphere. After the reaction, the mixture was cooled to room temperature. Water (5 mL) and ethyl acetate (5 mL) were added thereto and insolubles was removed by filtration. The filtrate was concentrated under reduced pressure. The obtained residue was purified by preparative HPLC to obtain the target product WX087. MS-ESI m/z: 485.1 [M+H]$^+$. $^1$H NMR (400 MHz, CD$_3$OD) δ: 7.49-7.39 (m, 2H), 7.31-7.25 (m, 1H), 7.25-7.18 (m, 2H), 7.16-7.07 (m, 3H), 7.06-7.02 (m, 1H), 6.95 (d, J=8.5 Hz, 1H), 6.06 (dd, J=4.1, 10.2 Hz, 1H), 4.65 (dd, J=10.4, 14.7 Hz, 1H), 4.12-3.99 (m, 3H), 3.81 (s, 3H), 2.94 (s, 3H), 1.36 (t, J=7.0 Hz, 3H).

The compounds of each embodiment in the following table were prepared according to the method of embodiment 87.

TABLE 11

| Embodiment | Fragment 1 | Fragment 2 | Structure | Compound |
|---|---|---|---|---|
| 88 | WX007 | 3-fluorophenylboronic acid | 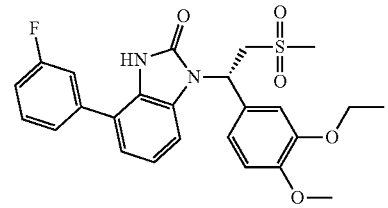 [SMILES: CCOc1cc([C@@H](CS(C)(=O)=O)n2c(=O)[nH]c3c(-c4cccc(F)c4)cccc32)ccc1OC] | WX088 |
| 89 | WX007 | 4-fluorophenylboronic acid | 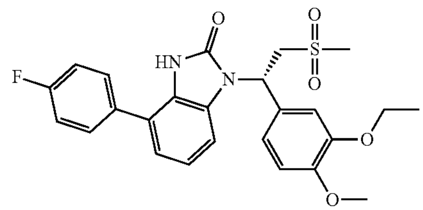 [SMILES: CCOc1cc([C@@H](CS(C)(=O)=O)n2c(=O)[nH]c3c(-c4ccc(F)cc4)cccc32)ccc1OC] | WX089 |
| 90 | WX007 | phenylboronic acid | 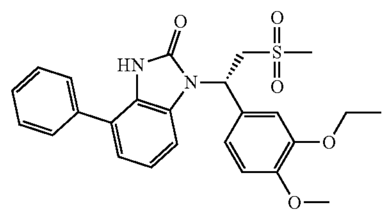 [SMILES: CCOc1cc([C@@H](CS(C)(=O)=O)n2c(=O)[nH]c3c(-c4ccccc4)cccc32)ccc1OC] | WX090 |
| 91 | WX007 | cyclopropylboronic acid | 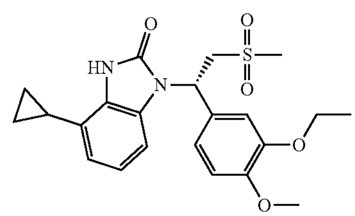 [SMILES: CCOc1cc([C@@H](CS(C)(=O)=O)n2c(=O)[nH]c3c(C4CC4)cccc32)ccc1OC] | WX091 |
| 92 | WX007 | isopropenyl BF₃K | 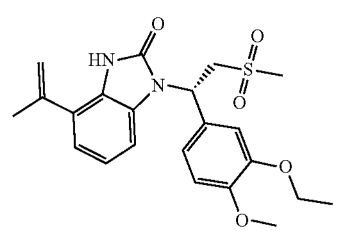 [SMILES: C=C(C)c1cccc2c1[nH]c(=O)n2[C@H](CS(C)(=O)=O)c1ccc(OC)c(OCC)c1] | WX092 |
| 93 | WX007 | thiophene-2-boronic acid | 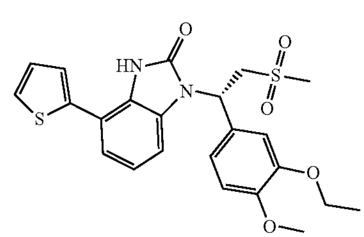 [SMILES: CCOc1cc([C@@H](CS(C)(=O)=O)n2c(=O)[nH]c3c(-c4cccs4)cccc32)ccc1OC] | WX093 |

LCMS and ¹H NMR data of each embodiment

TABLE 12

| Embodiment | Compound | HNMR | LCMS |
|---|---|---|---|
| 88 | WX088 | ¹H NMR (400 MHz, CD$_3$OD) δ: 7.49 (dt, J = 6.0, 8.0 Hz, 1H), 7.34 (d, J = 7.8 Hz, 1H), 7.27 (td, J = 2.0, 9.9 Hz, 1H), 7.21-7.17 (m, 1H), 7.16-7.06 (m, 5H), 6.95 (d, J = 8.3 Hz, 1H), 6.07 (dd, J = 3.9, 10.4 Hz, 1H), 4.66 (dd, J = 10.5, 14.6 Hz, 1H), 4.12-4.00 (m, 3H), 3.81 (s, 3H), 2.96 (s, 3H), 1.36 (t, J = 6.9 Hz, 3H). | MS-ESI m/z: 485.1 [M + H]$^+$. |
| 89 | WX089 | ¹H NMR (400 MHz, CD$_3$OD) δ: 7.55-7.50 (m, 2H), 7.24-7.14 (m, 4H), 7.13-7.07 (m, 2H), 7.06-7.03 (m, 1H), 6.94 (d, J = 8.3 Hz, 1H), 6.06 (dd, J = 3.9, 10.4 Hz, 1H), 4.65 (dd, J = 10.4, 14.7 Hz, 1H), 4.12-3.98 (m, 3H), 3.81 (s, 3H), 2.96 (s, 3H), 1.36 (t, J = 6.9 Hz, 3H). | MS-ESI m/z: 485.0 [M + H]$^+$. |
| 90 | WX090 | ¹H NMR (400 MHz, CDCl$_3$) δ: 8.67 (br s, 1H), 7.52-7.48 (m, 4H), 7.43-7.36 (m, 1H), 7.20-7.05 (m, 5H), 6.82 (d, J = 8.3 Hz, 1H), 5.77 (dd, J = 4.8, 9.3 Hz, 1H), 4.76 (dd, J = 9.2, 14.9 Hz, 1H), 4.04 (q, J = 7.0 Hz, 2H), 3.92-3.77 (m, 4H), 2.71 (s, 3H), 1.42 (t, J = 7.0 Hz, 3H). | MS-ESI m/z: 467.1 [M + H]$^+$. |
| 91 | WX091 | ¹H NMR (400 MHz, CD$_3$OD) δ: 7.11 (d, J = 2.0 Hz, 1H), 7.05 (dd, J = 1.8, 8.3 Hz, 1H), 6.98-6.88 (m, 3H), 6.64 (dd, J = 1.4, 6.9 Hz, 1H), 6.02 (dd, J = 3.8, 10.3 Hz, 1H), 4.61 (dd, J = 10.3, 14.6 Hz, 1H), 4.09-3.96 (m, 3H), 3.79 (s, 3H), 2.92 (s, 3H), 2.02-1.93 (m, 1H), 1.35 (t, J = 6.9 Hz, 3H), 1.02-0.93 (m, 2H), 0.73-0.64 (m, 2H). | MS-ESI m/z: 431.1 [M + H]$^+$. |
| 92 | WX092 | ¹H NMR (400 MHz, CDCl$_3$) δ: 8.07 (s., 1 H), 7.18 (s, 1 H), 7.11-6.97 (m, 4 H), 6.82 (d, J = 8.3 Hz, 1 H), 5.8 (d, J = 4.3 Hz, 1 H), 5.34 (s, 1 H), 5.18 (s, 1 H), 4.87-4.67 (m, 1 H), 4.08 (q, J = 7.0 Hz, 2 H), 3.93-3.68 (m, 4 H), 2.75 (s, 3 H), 2.15 (s, 3 H), 1.44 (t, J = 6.9 Hz, 3 H). | MS-ESI m/z: 431.1 [M + H]$^+$. |
| 93 | WX093 | ¹H NMR (400 MHz, CDCl$_3$) δ: 8.45 (s, 1H), 7.40 (d, J = 5.2 Hz, 1H), 7.25-7.09 (m, 7H), 6.84 (d, J = 4.0 Hz, 1H), 5.79 (d, J = 4.0 Hz, 1H), 4.78 (dd, J = 14.0, 9.6 Hz, 1H), 4.08 (q, J = 14.4 Hz, 2H), 3.89-3.84 (m, 4H), 2.76 (s, 3H), 1.44 (t, J = 6.8 Hz, 3H). | MS-ESI m/z: 473.0 [M + H]$^+$. |

Embodiment 94: WX094

Synthesis Route:

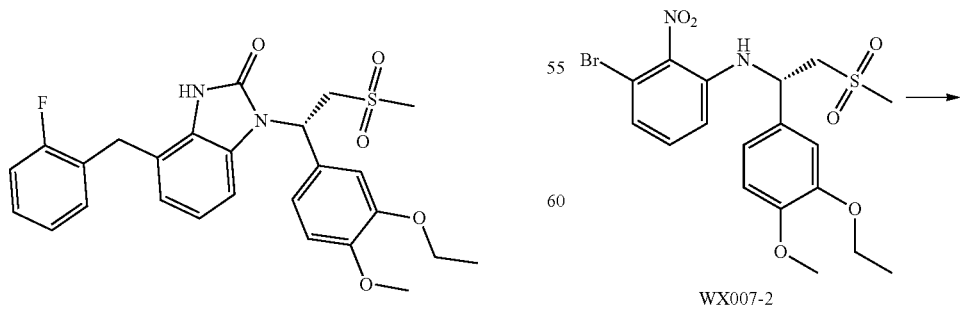

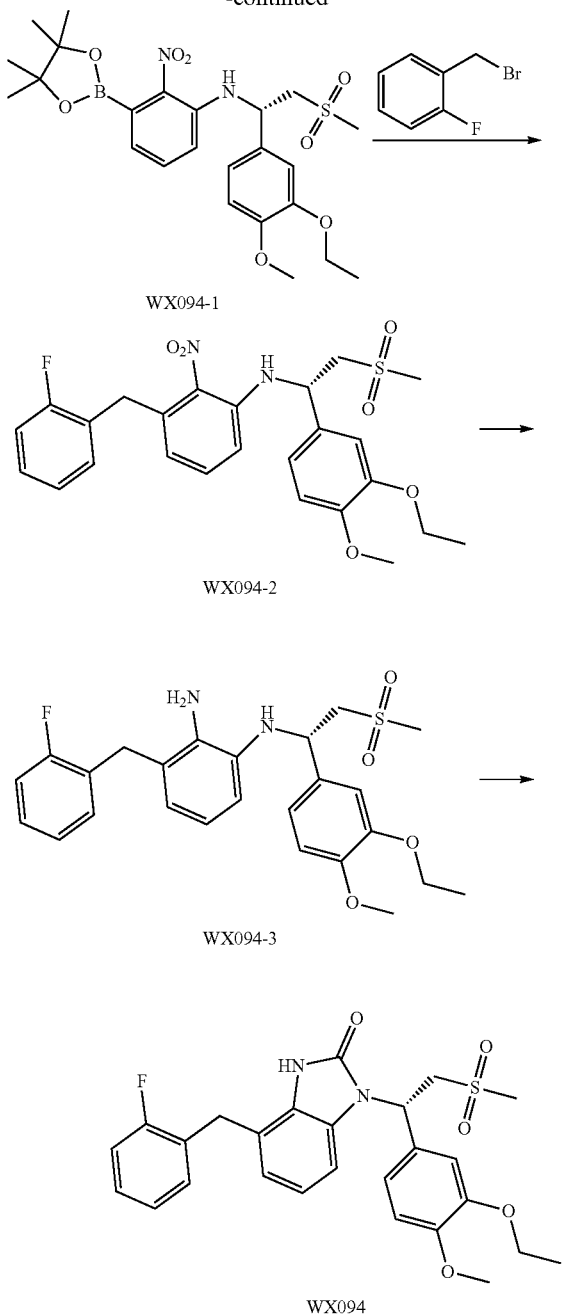

Step 1: Preparation of WX094-1

A solution of compound WX007-2 (2.62 g, 5.54 mmol), bis(pinacolato)diboron (2.81 g, 11.08 mmol), potassium acetate (1.63 g, 16.62 mmol) and (1,1'-bis(diphenylphosphino)ferrocene) palladium dichloride dichloromethane complex (452.02 mg, 554.00 μmol) in 1,4-dioxane (30.00 mL) was heated to 80° C. and stirred for 12 hours under nitrogen atmosphere. After the reaction, the mixture was cooled to room temperature. Water (100 mL) was added thereto, and extracted with ethyl acetate (100 mL×3). The organic phases were combined, washed with saturated brine (150 mL×3) and dried over anhydrous sodium sulfate, followed by filtration. The filtrate was concentrated under reduced pressure. The obtained residue was isolated by preparative column chromatography (eluent: petroleum ether/ethyl acetate=1/0-4/1-2/1-1/1, volume ratio) to obtain the target product WX094-1. MS-ESI m/z: 543.0 [M+Na]$^+$. $^1$H NMR (400 MHz, CDCl$_3$) δ: 8.63 (d, J=7.0 Hz, 1H), 7.41-7.33 (m, 1H), 6.92-6.88 (m, 1H), 6.87-6.79 (m, 3H), 6.75 (d, J=6.8 Hz, 1H), 5.26-5.19 (m, 1H), 4.09-4.04 (m, 2H), 3.86 (s, 3H), 3.66-3.57 (m, 1H), 3.50-3.42 (m, 1H), 2.77 (s, 3H), 1.46 (t, J=6.9 Hz, 3H), 1.40 (s, 12H).

Step 2: Preparation of WX094-2

Compound WX094-1 (500.00 mg, 960.80 μmol), o-fluorobenzyl bromide (363.24 mg, 1.92 mmol, 231.36 μL), potassium phosphate (407.90 mg, 1.92 mmol) and tetratriphenylphosphine palladium (1.11 g, 960.80 μmol) were dissolved in ethylene glycol dimethyl ether (4.00 mL), ethanol (1.00 mL) and water (1.00 mL) at room temperature. The reaction mixture was heated to 90° C. and stirred for 12 hours under nitrogen atmosphere. After the reaction, the mixture was cooled to room temperature. Then water (30 mL) was added thereto and extract with ethyl acetate (40 mL×2). The organic phases were combined, washed with saturated brine (30 mL×3) and dried over anhydrous sodium sulfate, followed by filtration. The filtrate was concentrated under reduced pressure. The obtained residue was isolated by preparative column chromatography (eluent: petroleum ether/ethyl acetate=9/1-4/1-2/1, volume ratio) to obtain the target product WX094-2. MS-ESI m/z: 525.1 [M+Na]$^+$. $^1$H NMR (400 MHz, CDCl$_3$) δ: 7.16 (t, J=8.2 Hz, 1H), 7.07-7.03 (m, 2H), 7.03-6.99 (m, 1H), 6.95-6.91 (m, 1H), 6.88-6.84 (m, 2H), 6.70-6.64 (m, 2H), 6.51 (d, J=7.5 Hz, 1H), 5.13-5.07 (m, 1H), 4.16-4.12 (m, 2H), 4.07 (dquin, J=2.6, 7.1 Hz, 2H), 3.86 (s, 3H), 3.58-3.49 (m, 1H), 3.43 (d, J=5.0 Hz, 1H), 2.76 (s, 3H), 1.48-1.41 (m, 3H).

Step 3: Preparation of WX094-3

Zinc powder (299.26 mg, 4.58 mmol) and ammonium chloride (244.80 mg, 4.58 mmol) were added to a solution of compound WX094-2 (230.00 mg, 457.66 μmol) in methanol (10.00 mL) at room temperature. The reaction mixture was stirred at room temperature for 12 hours. After the reaction, insolubles was removed by filtration, and the filtrate was concentrated under reduced pressure. Dichloromethane (30 mL) was added to the obtained residue with stirring for 30 minutes, followed by filtration to remove the insolubles. The filtrate was concentrated under reduced pressure to remove the solvent to obtain the target product WX094-3. MS-ESI m/z: 473.1 [M+H]$^+$.

Step 4: Preparation of WX094

Compound WX094-3 (210.00 mg, 444.38 μmol), triethylamine (224.83 mg, 2.22 mmol) and triphosgene (52.75 mg, 177.75 μmol) were dissolved in tetrahydrofuran (10.00 mL) under nitrogen atmosphere. The reaction mixture was stirred at −5° C. for 2.5 hours. After the reaction, water (40 mL) was added thereto and extracted with ethyl acetate (40 mL×2). The organic phases were washed with saturated brine (45 mL×3) and dried over anhydrous sodium sulfate, followed by filtration. The obtained residue was purified by preparative HPLC to obtain the target product WX094. MS-ESI m/z: 499.1 [M+H]$^+$. $^1$H NMR (400 MHz, CDCl$_3$) δ: 10.44 (br s, 1H), 7.41-7.29 (m, 1H), 7.24-6.97 (m, 8H), 6.90 (d, J=7.0 Hz, 1H), 5.88 (br s, 1H), 4.78 (d, J=12.5 Hz, 1H), 4.29-4.12 (m, 4H), 4.04 (d, J=12.3 Hz, 1H), 3.93 (br s, 3H), 2.97-2.58 (m, 3H), 1.51 (br s, 3H).

Embodiment 95: WX095

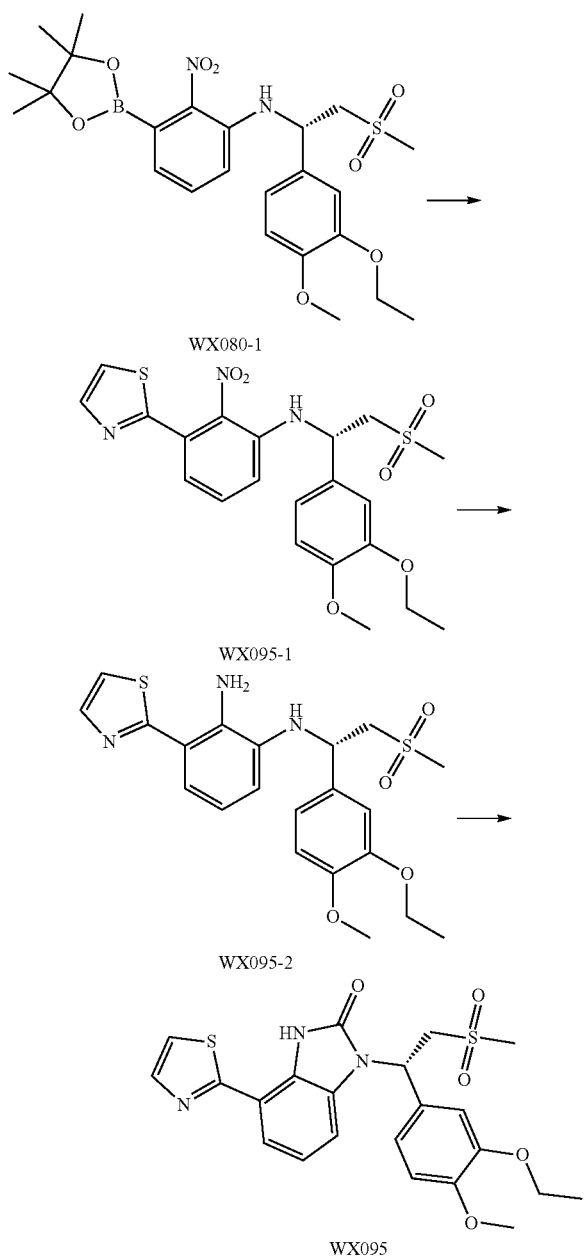

Synthesis Route:

WX080-1

WX095-1

WX095-2

WX095

Step 1: Preparation of WX095-1

2-Bromothiazole (75.64 mg, 461.18 μmol) and 1,1'-bis(diphenylphosphino)-ferrocene palladium dichloride (14.06 mg, 19.22 μmol) were added to a mixed solution of compound WX080-1 (200.00 mg, 384.32 μmol) and potassium carbonate (159.35 mg, 1.15 mmol) in 1,4-dioxane (3.00 mL) and water (1.00 mL) at room temperature. The reaction mixture was heated to 80° C. and stirred for 2 hours under nitrogen atmosphere. After the reaction, the mixture was cooled to room temperature, poured into water (10 mL) and extracted with ethyl acetate (10 mL×3). The organic phase was combined, washed with saturated brine (10 mL×2) and dried over anhydrous sodium sulfate, followed by filtration. The filtrate was concentrated under reduced pressure. The obtained residue was purified by preparative TLC (eluent: petroleum ether/ethyl acetate=2/1, volume ratio) to obtain the target product WX095-1. MS-ESI m/z: 500.1 [M+Na]$^+$.

Step 2: Preparation of WX095-2

Zinc powder (205.39 mg, 3.14 mmol) and ammonium chloride (168.01 mg, 3.14 mmol) were added to a solution of compound WX095-1 (150.00 mg, 314.10 μmol) in methanol (10.00 mL) at room temperature. The reaction mixture was stirred at room temperature for 0.1 hour. After the reaction, insolubles was removed by filtration, and the filter cake was washed with dichloromethane (20 mL×2). The filtrate was combined and concentrated under reduced pressure to obtain the crude product WX095-2. MS-ESI m/z: 448.1 [M+H]$^+$.

Step 3: Preparation of WX095

Triphosgene (31.83 mg, 107.25 μmol) was added in one time to a solution of compound WX095-2 (120.00 mg, 268.11 μmol) and triethylamine (135.65 mg, 1.34 mmol) in tetrahydrofuran (25.00 mL) at 0° C. The reaction mixture was warmed to room temperature and stirred for 16 hours under nitrogen atmosphere. After the reaction, the mixture was poured into water (10 mL) and extracted with ethyl acetate (10 mL×3). The organic phase was combined, washed with water (10 mL×2) and dried over anhydrous sodium sulfate, followed by filtration. The filtrate was concentrated under reduced pressure. The obtained residue was purified by preparative HPLC to obtain the target product WX095. MS-ESI m/z: 474.0 [M+H]$^+$. $^1$H NMR (400 MHz, CDCl$_3$) δ: 9.99 (s, 1H), 7.88 (d, J=3.0 Hz, 1H), 7.46 (t, J=4.4 Hz, 1H), 7.34 (d, J=3.0 Hz, 1H), 7.22-7.10 (m, 3H), 7.06 (d, J=7.8 Hz, 1H), 6.82 (d, J=8.3 Hz, 1H), 5.81 (d, J=5.3 Hz, 1H), 4.85 (dd, J=9.8 Hz, 1H), 4.08 (q, J=6.9 Hz, 2H), 3.92-3.75 (m, 4H), 2.77 (s, 3H), 1.44 (t, J=6.9 Hz, 3H).

Embodiment 96: WX096

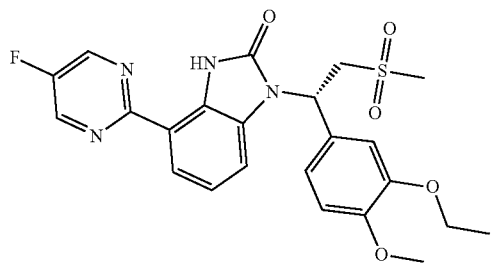 [SMILES: CCOc1cc([C@@H](CS(C)(=O)=O)n2c(=O)[nH]c3c(-c4ncc(F)cn4)cccc32)ccc1OC]

Synthesis Route:

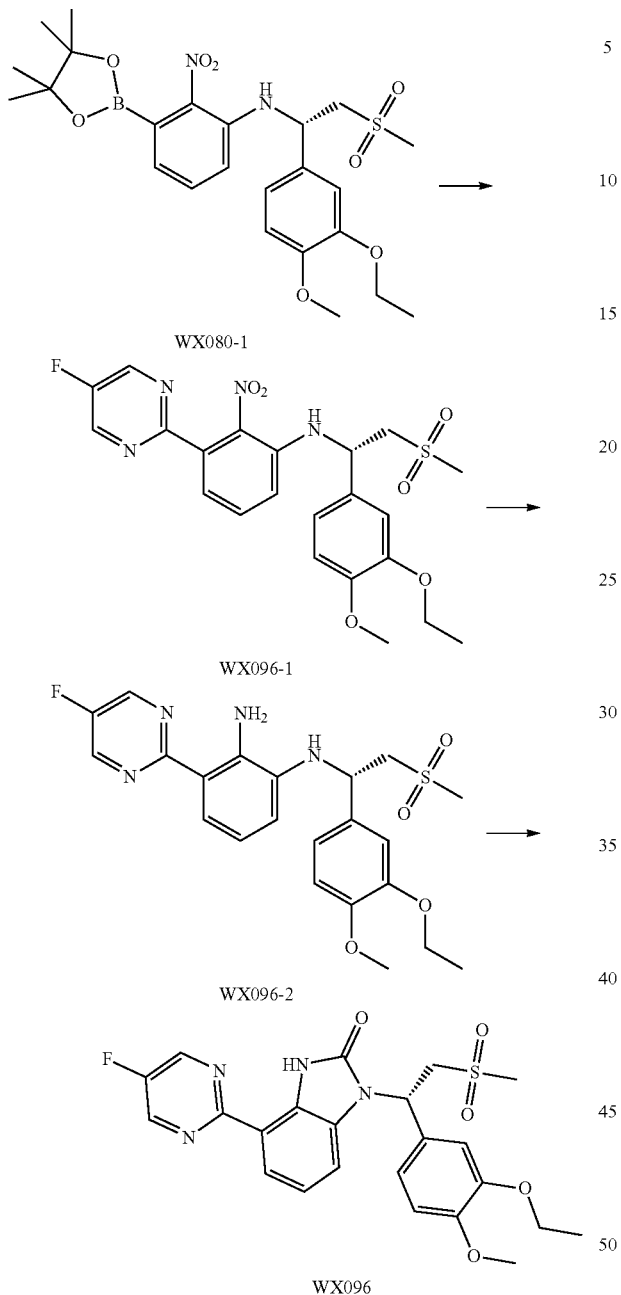

was concentrated under reduced pressure. The obtained residue was purified by preparative TLC (eluent: petroleum ether/ethyl acetate=2/1, volume ratio) to obtain the target product WX096-1. MS-ESI m/z: 513.0 [M+Na]$^+$.

Step 2: Preparation of WX096-1

Ammonium chloride (229.01 mg, 4.28 mmol) and zinc powder (279.96 mg, 4.28 mmol) were added in one time to a solution of compound WX096-1 (210.00 mg, 428.13 μmol) in methanol (10.00 mL) at room temperature. The reaction was stirred at room temperature for 0.1 hour. After the reaction, insolubles was removed by filtration, and the filter cake was washed with dichloromethane (20 mL×2). The filtrate was combined and concentrated under reduced pressure to obtain crude product WX096-2. MS-ESI m/z: 461.0 [M+H]$^+$.

Step 3: Preparation of WX096

Triphosgene (43.82 mg, 147.66 μmol) was added in one time to a solution of compound WX096-2 (170.00 mg, 369.15 μmol) and triethylamine (186.77 mg, 1.85 mmol) in tetrahydrofuran (25.00 mL) at 0° C. The reaction mixture was stirred at 0° C. for 2.5 hours. After the reaction, water (10 mL) was added and extracted with ethyl acetate (10 mL×3). The organic phases were combined, washed with saturated brine (10 mL×2) and dried over anhydrous sodium sulfate, followed by filtration. The filtrate was concentrated under reduced pressure. The obtained residue was purified by preparative HPLC to obtain the target product WX096. MS-ESI m/z: 487.0 [M+H]$^+$. $^1$H NMR (400 MHz, CDCl$_3$) δ: 9.97 (s, 1H), 8.68 (s, 2H), 8.18-8.04 (m, 1H), 7.25-7.14 (m, 3H), 7.07 (d, J=8.3 Hz, 1H), 6.83 (d, J=8.0 Hz, 1H), 5.84 (d, J=5.3 Hz, 1H), 4.85 (d, J=4.3 Hz, 1H), 4.08 (q, J=6.9 Hz, 2H), 3.84 (m, 4H), 2.78 (s, 3H), 1.45 (t, J=6.8 Hz, 3H).

Embodiment 97: WX097

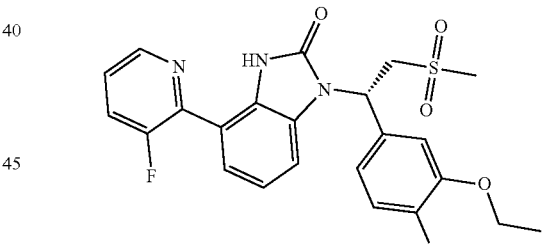

Synthesis Route:

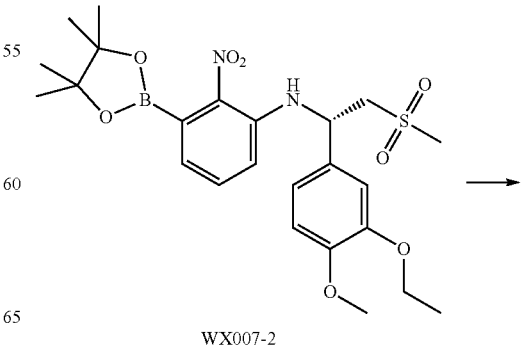

Step 1: Preparation of WX096-1

2-Chloro-5-fluoro-pyridine (61.12 mg, 461.18 μmol) and (1,1'-bis(diphenylphosphino)ferrocene)palladium dichloride dichloromethane complex (14.06 mg, 19.22 μmol) were added to a mixed solution of compound WX080-1 (200.00 mg, 384.32 μmol) and potassium carbonate (159.35 mg, 1.15 mmol) in water (2.00 mL) and 1,4-dioxane (6.00 mL) at room temperature. The reaction mixture was heated to 80° C. and stirred for 2 hours under nitrogen atmosphere. After the reaction, the mixture was cooled to room temperature. Water (10 mL) was added thereto and extracted with ethyl acetate (10 mL×3). The organic phases were combined, washed with saturated brine (10 mL×2) and dried over anhydrous sodium sulfate, followed by filtration. The filtrate -continued

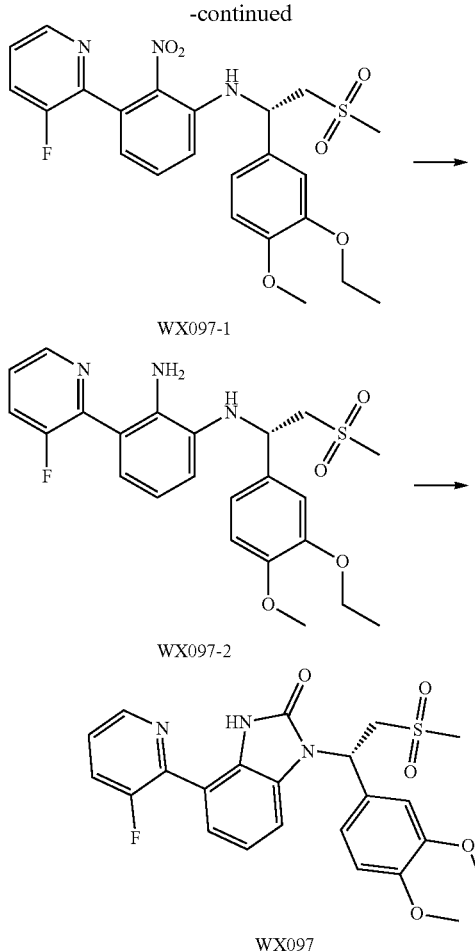

WX097-1

WX097-2

WX097

Step 1: Preparation of WX097-1

Compound WX007-2 (500.00 mg, 960.80 μmol), 2-chloro-3-3-fluoro-pyridine (189.58 mg, 1.44 mmol), (1,1'-bis(diphenylphosphino)ferrocene) palladium chloride dichloromethane complex (78.46 mg, 96.08 μmol) and potassium carbonate (265.58 mg, 1.92 mmol) were dissolved in 1,4-dioxane (5.00 mL) and water (1.50 mL) at room temperature. The reaction mixture was heated to 80° C. and stirred for 12 hours under nitrogen atmosphere. After the reaction, the reaction mixture was cooled to room temperature. Water (30 mL) was added thereto and extracted with ethyl acetate (30 mL×2). The organic phases were combined, washed with saturated brine (20 mL×3) and dried over anhydrous sodium sulfate, followed by filtration. The filtrate was concentrated under reduced pressure. The filtrate was concentrated under reduced pressure to obtain the crude product WX097-1. MS-ESI m/z: 512.1 [M+Na]⁺.

Step 2: Preparation of WX097-2

Compound WX097-1 (560.00 mg, 1.14 mmol), zinc powder (745.45 mg, 11.40 mmol) and ammonium chloride (609.79 mg, 11.40 mmol) were dissolved in methanol (5.00 mL) at room temperature. The reaction mixture was stirred at room temperature for 2 hours under nitrogen atmosphere. After the reaction, insolubles was removed by filtration, and the filtrate was concentrated under reduced pressure. Dichloromethane (20 mL) was added to the obtained residue with stirring at room temperature for 30 minutes, followed by filtration. The filtrate was concentrated under reduced pressure to obtain the crude product WX097-2. MS-ESI m/z: 482.2 [M+Na]⁺.

Step 3: Preparation of WX097

Compound WX097-2 (470.00 mg, 1.02 mmol), triethylamine (516.07 mg, 5.10 mmol) and triphosgene (121.07 mg, 408.00 μmol) were dissolved in tetrahydrofuran (5.00 mL) at 0-5° C. The reaction mixture was stirred at 0-5° C. for 1.5 hours under nitrogen atmosphere. After the reaction, water (30 mL) was added and extracted with ethyl acetate (30 mL×2). The organic phases were combined, washed with saturated brine (30 mL×3) and dried over anhydrous sodium sulfate, followed by filtration. The obtained residue was purified by preparative HPLC to obtain the target product WX097. MS-ESI m/z: 486.1 [M+H]⁺. ¹H NMR (400 MHz, CDCl₃) δ: 10.62 (br s, 1H), 8.52 (br s, 1H), 7.92 (br s, 1H), 7.59-7.50 (m, 1H), 7.33-7.28 (m, 1H), 7.20 (d, J=6.0 Hz, 3H), 7.06 (d, J=7.5 Hz, 1H), 6.82 (d, J=8.0 Hz, 1H), 5.85 (d, J=4.8 Hz, 1H), 4.84 (dd, J=9.4, 14.7 Hz, 1H), 4.08 (q, J=6.6 Hz, 2H), 3.89-3.82 (m, 4H), 2.76 (s, 3H), 1.44 (t, J=6.8 Hz, 3H).

Embodiment 98: WX098

Synthesis Route:

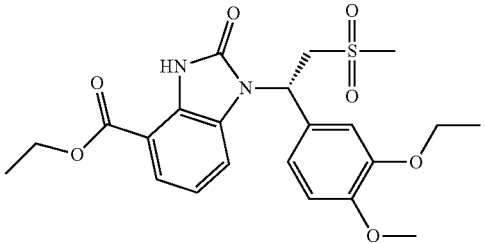 [SMILES: CCOC(=O)c1cccc2c1[nH]c(=O)n2[C@H](CS(C)(=O)=O)c1ccc(OC)c(OCC)c1]

WX007

WX098

(1,1'-Bis(diphenylphosphino)ferrocene) palladium dichloride dichloromethane complex (46.98 mg, 57.53 μmol) was added to a solution of compound WX007 (270.00 mg, 575.26 μmol) and triethylamine (174.63 mg, 1.73 mmol) in ethanol (15.00 mL) at room temperature. The reaction mixture was heated to 80° C. and stirred for 12 hours under carbon monoxide atmosphere. After the reaction, the mixture was cooled to room temperature, and the insolubles was removed by filtration. The obtained residue was isolated by column chromatography (eluent: petroleum ether/ethyl acetate=1/0-7/10, volume ratio) to obtain the target product WX098. MS-ESI m/z: 463.1 [M+H]$^+$. $^1$H NMR (400 MHz, CD$_3$OD) δ: 7.63 (dd, J=0.9, 8.2 Hz, 1H), 7.37 (dd, J=0.9, 7.9 Hz, 1H), 7.13-7.05 (m, 3H), 6.93 (d, J=8.5 Hz, 1H), 6.06 (dd, J=4.0, 10.5 Hz, 1H), 4.62 (d, J=3.8 Hz, 1H), 4.42 (q, J=7.2 Hz, 2H), 4.12-3.97 (m, 3H), 3.80 (s, 3H), 2.97 (s, 3H), 1.37 (td, J=7.0, 16.9 Hz, 6H).

Biological Assays

Inhibitory activity of the compounds against PDE 4B

The assay is based on the fluorescence polarization measuring AMP/GMP production as a result of the enzyme activity by displacement of Tracer binding to the AMP/GMP antibody.

Reagents:

Reaction Buffer:

10 mM Tris-HCl (pH 7.5), 5 mM MgCl$_2$, 0.01% Brij 35, 1 mM DTT and 1% DMSO.

Enzyme:

Recombinant human PDE4B (Gene accession number: NM_002600; amino acid 305-end) was expressed by baculovirus in Sf9 insect cells using an N-terminal GST tag. MW=78 kDa.

Enzyme Substrate:

1 μM cAMP

Detection:

Transcreener® AMP$^2$/GMP$^2$ antibody and AMP$^2$/GMP$^2$ AlexaFluor 633 tracer Reaction Procedure:

i) Recombinant human PDE4B and the enzyme substrate (1 μM cAMP) were dissolved in the newly-prepared buffer solution, respectively.

ii) The PDE4B buffer solution defined as above was transferred into the reaction wells.

iii) The compound which was dissolved in 100% DMSO was added to the reaction wells of the PDE4B buffer solution by Acoustic technology (Echo550; nanoliter range) and incubated at room temperature for 10 minutes.

iv) The enzymatic buffer solution was then added to the reaction wells defined as above to initiate the reaction.

v) The reaction was incubated at room temperature for 1 hour.

vi) The reaction was terminated by adding detecting mixture (Transcreener® AMP$^2$/GMP$^2$ antibody and AMP$^2$/GMP$^2$ AlexaFluor 633 tracer) and incubated for 90 minutes with gentle mixing. The measurement range of fluorescence polarization is Ex/Em=620/688.

Data Analysis:

The fluorescence polarization signal was converted into nM based on the AMP/GMP standard curve and the percent enzyme activity relative to DMSO calculated by Excel. GraphPad Prism was used to plot the curves (Drawing Medicine Icon)

TABLE 13

In vitro screening test results of the compounds of the present invention

| Compound | IC$_{50}$(nM) |
|---|---|
| WX001 | 3.68 |
| WX002 | 6.27 |
| WX003 | 2.22 |
| WX004 | 11.5 |
| WX005 | 92.4 |
| WX006 | 25.7 |
| WX007 | 9.20 |
| WX008 | 22.3 |
| WX009 | 6.29 |
| WX010 | 19.5 |
| WX011 | 0.526 |
| WX012 | 2.18 |
| WX013 | 6.11 |
| WX014 | 0.606 |
| WX015 | 0.676 |
| WX016 | <0.5 |
| WX017 | <0.5 |
| WX018 | <0.5 |
| WX019 | <0.5 |
| WX020 | 12.6 |
| WX021 | 64.4 |
| WX022 | 39.5 |
| WX023 | 1.89 |
| WX024 | <0.5 |
| WX025 | 1.42 |
| WX026 | 8.44 |
| WX027 | 17.8 |
| WX028 | <0.5 |
| WX029 | <0.5 |
| WX030 | 1.31 |
| WX031 | 3.30 |
| WX032 | 2.05 |
| WX033 | 1.10 |
| WX034 | 22.4 |
| WX035 | 8.30 |
| WX036 | 9.12 |
| WX037 | 10.8 |
| WX038 | 7.99 |
| WX039 | 9.96 |
| WX040 | 7.54 |
| WX041 | 11.9 |
| WX042 | 6.83 |
| WX043 | 4.50 |
| WX044 | 5.12 |
| WX045 | 3.56 |
| WX046 | 10.1 |
| WX047 | 44.9 |
| WX048 | 57.8 |
| WX049 | 11.4 |
| WX050 | 30.6 |
| WX051 | 26.9 |
| WX052 | 13.7 |
| WX053 | 26.4 |
| WX054 | 13.2 |
| WX055 | 21.2 |
| WX056 | 4.28 |
| WX057 | 99.6 |
| WX058 | 8.46 |
| WX059 | 68.3 |
| WX060 | 34.4 |
| WX061 | 39.0 |
| WX062 | 54.9 |
| WX063 | 20.8 |
| WX064 | 0.910 |
| WX065 | 1.43 |
| WX066 | 1.54 |
| WX067 | 10.1 |
| WX068 | 0.707 |
| WX069 | 0.477 |
| WX070 | 1.25 |
| WX071 | <0.5 |
| WX072 | 14.8 |
| WX073 | 31.8 |
| WX074 | 10.2 |
| WX075 | 0.680 |
| WX076 | 21.8 |
| WX077 | 46.8 |
| WX078 | 0.822 |
| WX079 | 2.53 |
| WX080 | 1.03 |
| WX081 | 1.38 |

TABLE 13-continued

In vitro screening test results of the compounds of the present invention

| Compound | IC$_{50}$(nM) |
|---|---|
| WX082 | <0.5 |
| WX083 | <0.5 |
| WX084 | 18.1 |
| WX085 | 5.64 |
| WX086 | 36.2 |
| WX087 | 1.29 |
| WX088 | 2.40 |
| WX089 | 2.52 |
| WX090 | 0.341 |
| WX091 | 3.98 |
| WX092 | 2.15 |
| WX093 | 1.25 |
| WX094 | <0.5 |
| WX095 | 6.58 |
| WX096 | 7.30 |
| WX097 | 5.04 |
| WX098 | 18.1 |
| / | / |

CONCLUSION

The compounds of the present invention all exhibit excellent in vitro inhibitory activity against PDE4B.

What is claimed is:

1. A compound as shown in formula (I) or a pharmaceutically acceptable salt thereof,

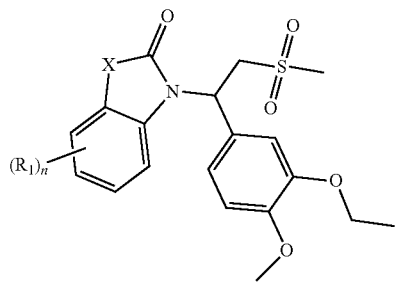

(I)

wherein,

X is O or N(R$_2$);

R$_2$ is H, F, Cl, Br, I, OH, NH$_2$ or R$_3$-L$_1$-, or selected from the group consisting of C$_{1-6}$ alkyl, C$_{1-6}$ heteroalkyl, C$_{3-6}$ cycloalkyl, 3-6 membered heterocycloalkyl, phenyl and 5-6 membered heteroaryl, each of which is optionally substituted by 1, 2 or 3 R;

R$_3$ is selected from the group consisting of C$_{3-6}$ cycloalkyl, 3-6 membered heterocycloalkyl, phenyl and 5-6 membered heteroaryl, each of which is optionally substituted by 1, 2 or 3 R;

L$_1$ is selected from the group consisting of —CH$_2$—, —CH$_2$CH$_2$—, O, S, NH and —C(=O)—;

n is selected from the group consisting of 1, 2 and 3;

R$_1$ is selected from H, F, Cl, Br, I, OH, NH$_2$, COOH, or R$_4$-L$_2$-, or selected from the group consisting of C$_{1-6}$ alkyl, C$_{1-6}$ heteroalkyl, C$_{2-6}$ alkenyl, C$_{3-6}$ cycloalkenyl, 3-6 membered heterocycloalkenyl, C$_{3-6}$ cycloalkyl, 3-6 membered heterocycloalkyl, phenyl and 5-6 membered heteroaryl, each of which is optionally substituted by 1, 2 or 3 R;

R$_4$ is selected from the group consisting of C$_{3-6}$ cycloalkyl, 3-6 membered heterocycloalkyl, 3-6 membered heterocycloalkenyl, phenyl and 5-6 membered heteroaryl, each of which is optionally substituted by 1, 2 or 3 R;

L$_2$ is selected from the group consisting of —CH$_2$—, —CH$_2$CH$_2$—, O, S, NH, —C(=O)NH—, —C(=O)O— and —C(=O)—;

R is selected from H, halogen, OH, NH$_2$, or CN, or selected from the group consisting of C$_{1-6}$ alkyl, C$_{1-6}$ heteroalkyl, C$_{3-6}$ cycloalkyl, N,N'-di(C$_{1-3}$ alkyl)amino, and 3-6 membered heterocycloalkyl, each of which is optionally substituted by 1, 2 or 3 R';

R' is selected from the group consisting of H, F, Cl, Br, I, OH, CN, NH$_2$, Me, Et, CF$_3$, CHF$_2$, CH$_2$F, NHCH$_3$ and N(CH$_3$)$_2$;

the "hetero" in the C$_{1-6}$ heteroalkyl, 3-6 membered heterocycloalkyl, 5-6 membered heteroaryl and 3-6 membered heterocycloalkenyl is selected from —C(=O)NH—, —NH—, —C(=NH)—, —S(=O)$_2$NH—, —S(=O)NH—, —O—, —S—, =O, =S, —O—N=, —C(=O)O—, —C(=O)—, —C(=S)—, —S(=O)—, —S(=O)$_2$— and —NHC(=O)NH—;

in any of the above cases, the number of the heteroatom or the heteroatom group is independently selected from 1, 2 or 3.

2. The compound or the pharmaceutically acceptable salt thereof according to claim 1, wherein R is H, F, Cl, Br, I, OH, CN or NH$_2$, or selected from the group consisting of C$_{1-3}$ alkyl, C$_{1-3}$ alkoxy, C$_{1-3}$ alkylthio, C$_{1-3}$ alkylamino, C$_{1-4}$-alkyl-OC(=O)—, N,N'-di(C$_{1-3}$ alkyl)amino and C$_{3-6}$ cycloalkyl, each of which is optionally substituted by 1, 2 or 3 R'.

3. The compound or the pharmaceutically acceptable salt thereof according to claim 2, wherein R is H, F, Cl, Br, I, OH, CN, NH$_2$, Me, CF$_3$, CHF$_2$, CH$_2$F, Et,

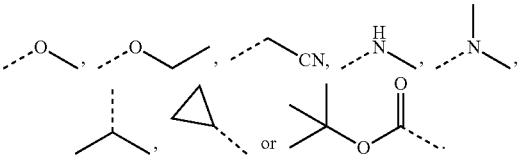

4. The compound or the pharmaceutically acceptable salt thereof according to claim 1, wherein R$_3$ is selected from the group consisting of cyclopropyl, cyclobutyl, phenyl, pyridyl, pyrimidinyl, pyrazinyl, thienyl, imidazolyl, pyrazolyl, oxazolyl, thiazolyl, isoxazolyl and isothiazolyl, each of which is optionally substituted by 1, 2 or 3 R.

5. The compound or the pharmaceutically acceptable salt thereof according to claim 4, wherein R$_3$ is

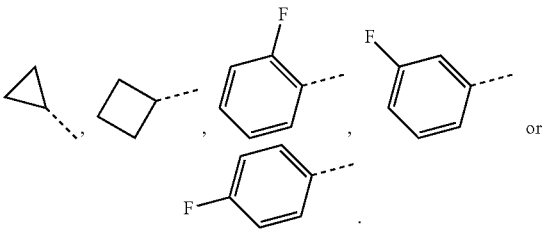

6. The compound or the pharmaceutically acceptable salt thereof according to claim 1, wherein $R_3$-$L_1$- is

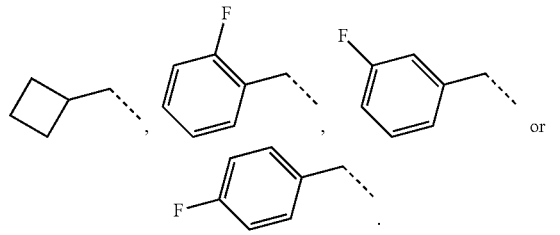

7. The compound or the pharmaceutically acceptable salt thereof according to claim 1, wherein $R_2$ is H, F, Cl, Br, I, OH, $NH_2$ or $R_3$-$L_1$-, or selected from the group consisting of $C_{1-3}$ alkyl, $C_{1-3}$-alkyl-S(=O)$_2$—$C_{1-3}$ alkyl-, cyclopropyl, cyclobutyl, phenyl and 5-6 membered heteroaryl, each of which is optionally substituted by 1, 2 or 3 R.

8. The compound or the pharmaceutically acceptable salt thereof according to claim 7, wherein $R_2$ is H, F, $C_1$, Br, I, OH, $NH_2$ or $R_3$-$L_1$-, or selected from the group consisting of Me, Et,

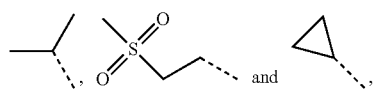

each of which is optionally substituted by 1, 2 or 3 R.

9. The compound or the pharmaceutically acceptable salt thereof according to claim 1, wherein $R_2$ is H, F, Cl, Br, I, OH, $NH_2$, Me, Et,

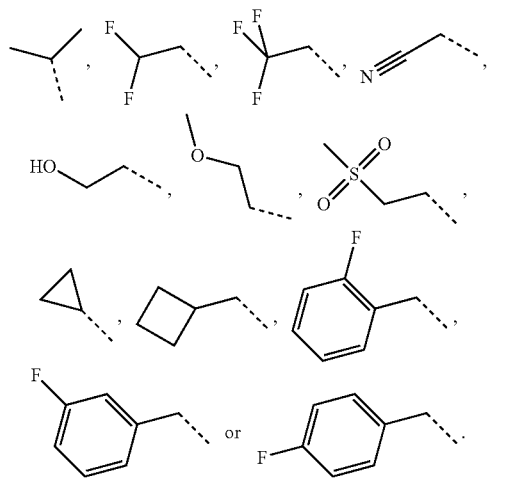

10. The compound or the pharmaceutically acceptable salt thereof according to claim 1, wherein X is

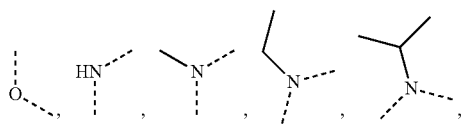

-continued

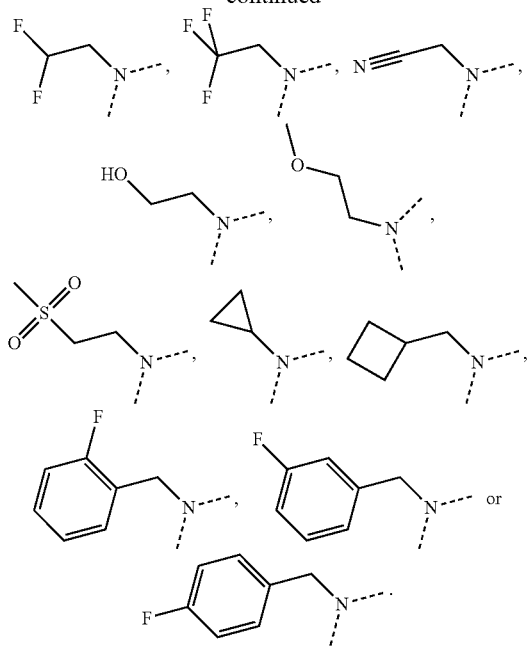

11. The compound or the pharmaceutically acceptable salt thereof according to claim 1, wherein $R_4$ is selected from the group consisting of phenyl, pyrrolidinyl, pyridyl, pyrimidinyl, pyrazinyl, and pyridazinyl, each of which is optionally substituted by 1, 2 or 3 R.

12. The compound or the pharmaceutically acceptable salt thereof according to claim 10, wherein $R_4$ is selected from the group consisting of

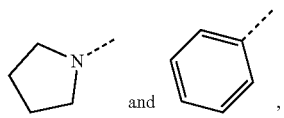

each of which is optionally substituted by 1, 2 or 3 R.

13. The compound or the pharmaceutically acceptable salt thereof according to claim 12, wherein $R_4$ is

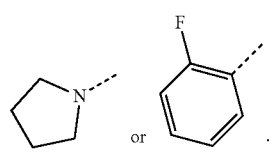

14. The compound or the pharmaceutically acceptable salt thereof according to claim 1, wherein $R_4$-$L_2$- is

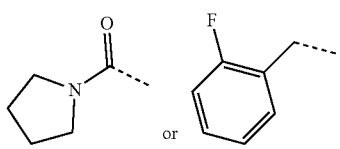

15. The compound or the pharmaceutically acceptable salt thereof according to claim 1, wherein $R_1$ is H, F, Cl, Br, I, OH, NH₂, COOH or R₄-L₂-, or selected from the group consisting of C$_{1-3}$ alkyl, C$_{1-3}$ alkyl-C(=O)—, C$_{1-3}$ alkyl-OC(=O)—, C$_{2-4}$ alkenyl, C$_{4-6}$ cycloalkenyl, 3,6-dihydro-2H-pyranyl, C$_{3-6}$ cycloalkyl, tetrahydropyranyl, phenyl, pyridyl, pyrimidinyl, pyrazinyl, pyridazinyl, pyrazolyl, imidazolyl, thienyl, thiazolyl, isothiazolyl, oxazolyl and isoxazolyl, each of which is optionally substituted by 1, 2 or 3 R.

16. The compound or the pharmaceutically acceptable salt thereof according to claim 13, wherein R₁ is H, F, Cl, Br, I, OH, NH₂, COOH or R₄-L₂-, or selected from the group consisting of Me, Et,

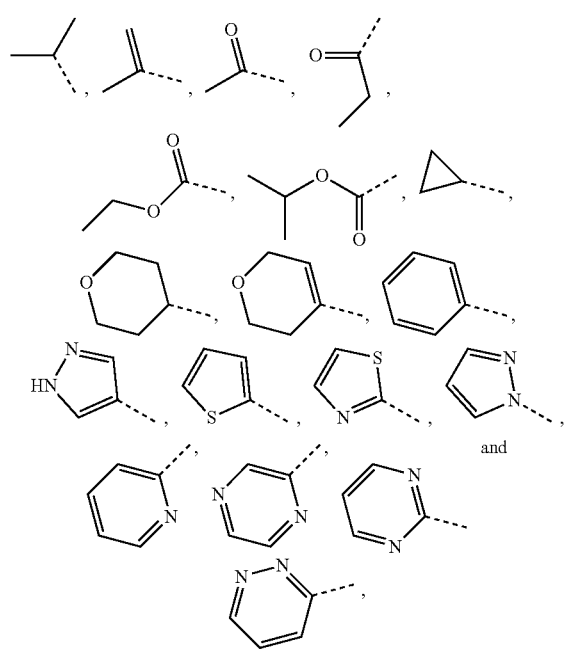

each of which is optionally substituted by 1, 2 or 3 R.

17. The compound or the pharmaceutically acceptable salt thereof according to claim 1, wherein R₁ is H, F, Cl, Br, I, OH, NH₂, COOH,

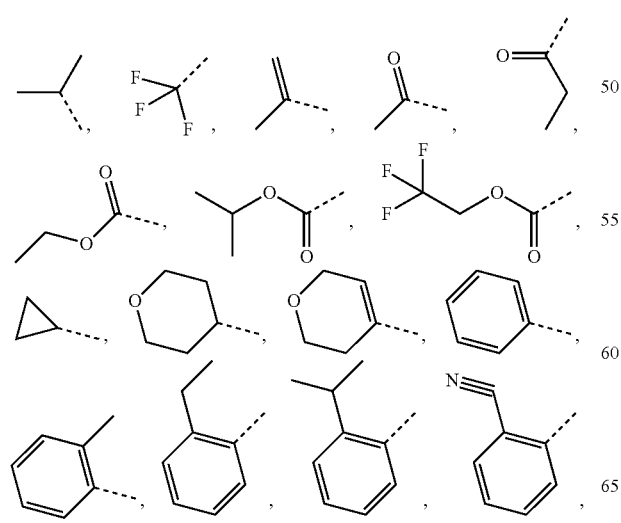

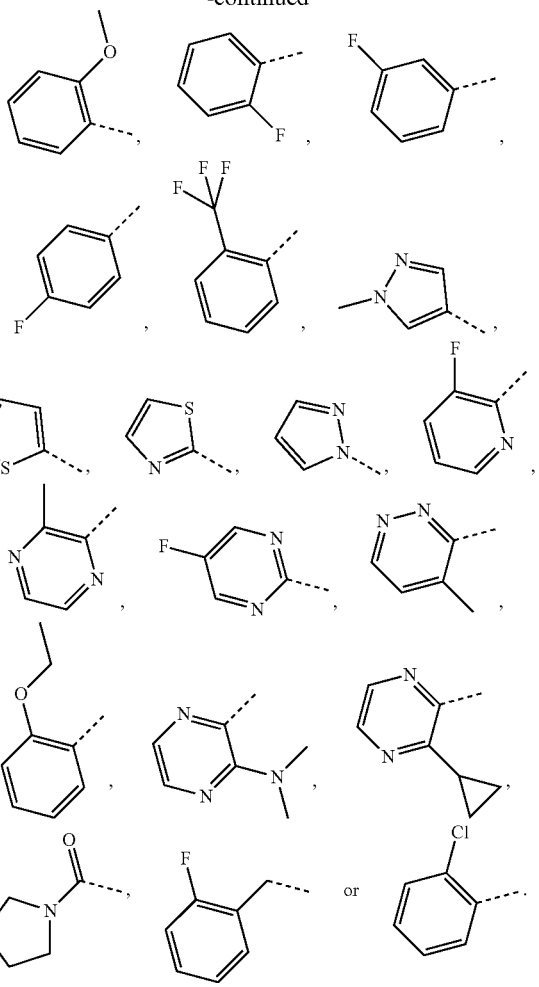

18. The compound or the pharmaceutically acceptable salt thereof according to claim 1, which is

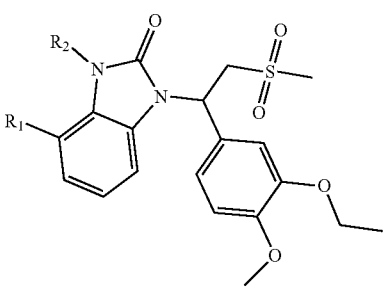

(I-1)

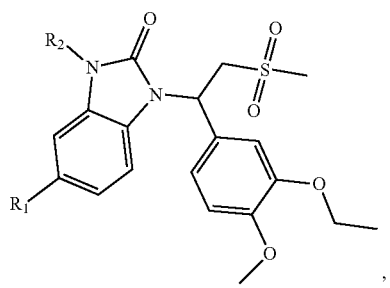

(I-2)

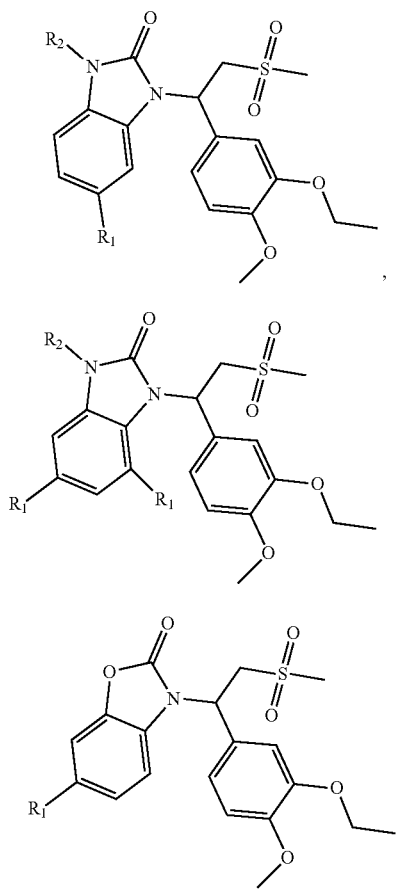
(I-3)
(I-4)
or
(I-5)
wherein, $R_1$ and $R_2$ are defined as claim 1.
19. The compound or the pharmaceutically acceptable salt thereof according to claim 1, which is selected from
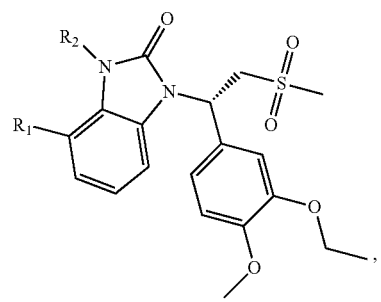
(I-1A)
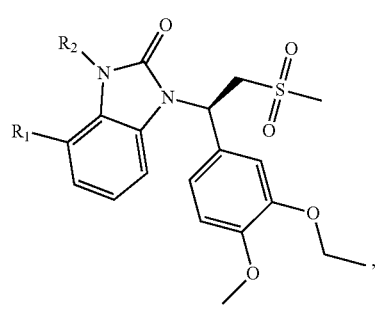
(I-1B)
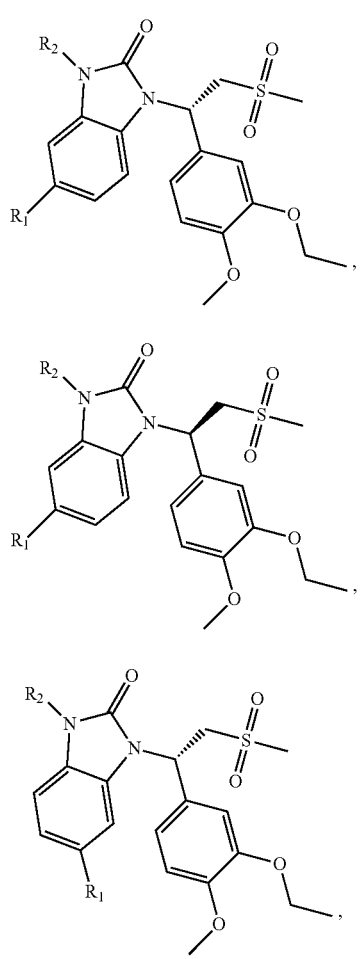
(I-2A)
(I-2B)
(I-3A)
(I-3B)
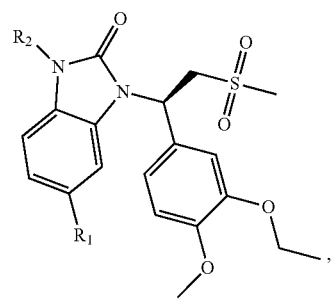
(I-4A)

-continued
(I-4B)
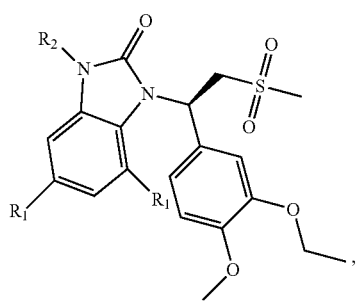
(I-5A)
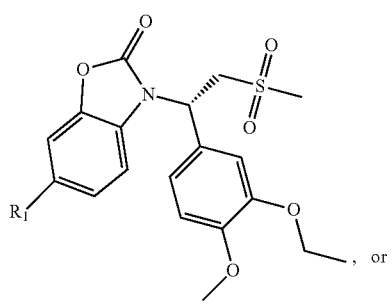, or
(I-5B)
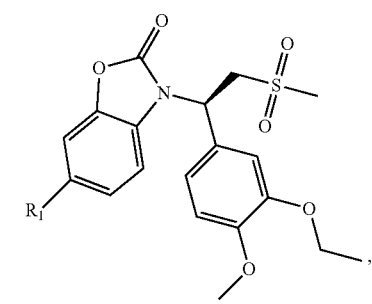,
wherein, $R_1$ and $R_2$ are defined as claim 1.
20. A compound or a pharmaceutically acceptable salt thereof, which is selected from the group consisting of
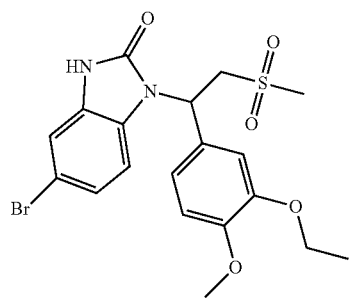
-continued
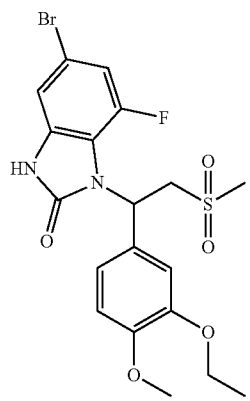
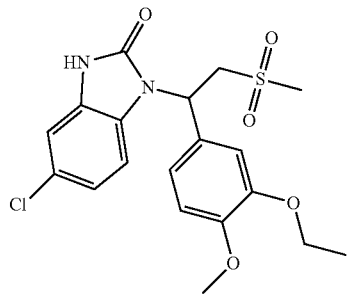
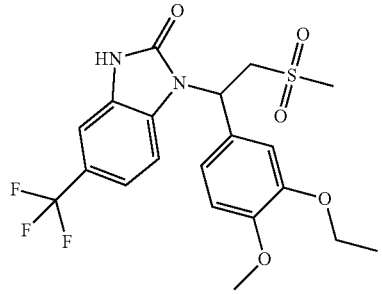
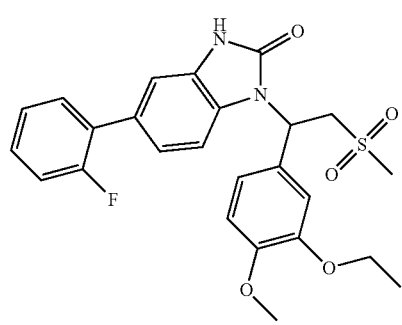
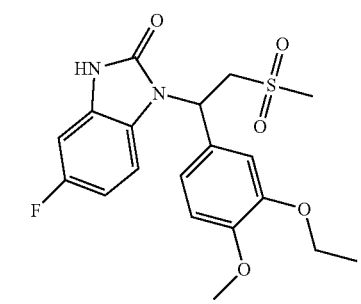

191
-continued
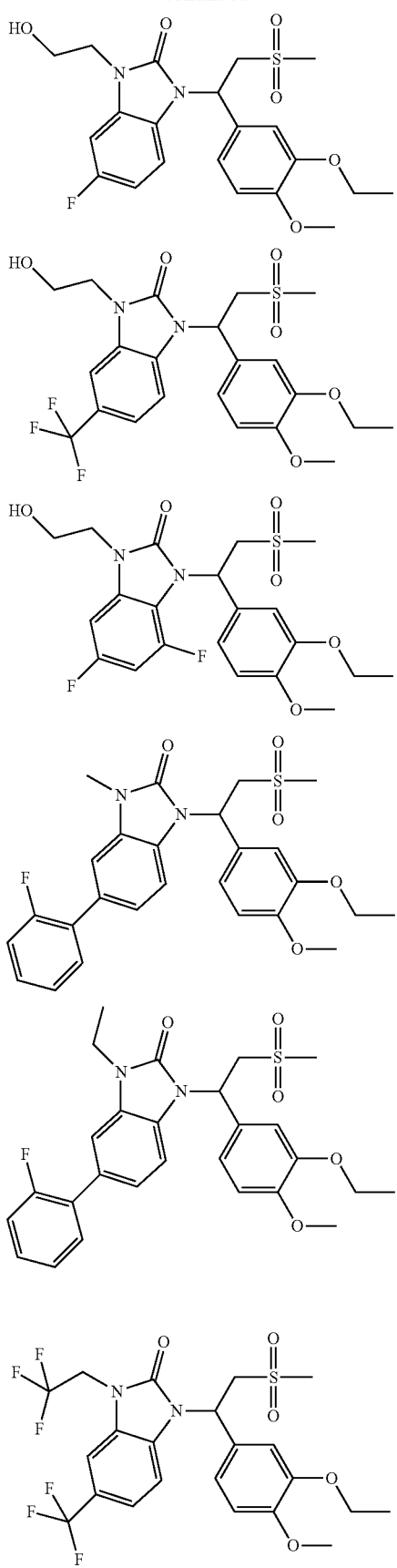
192
-continued
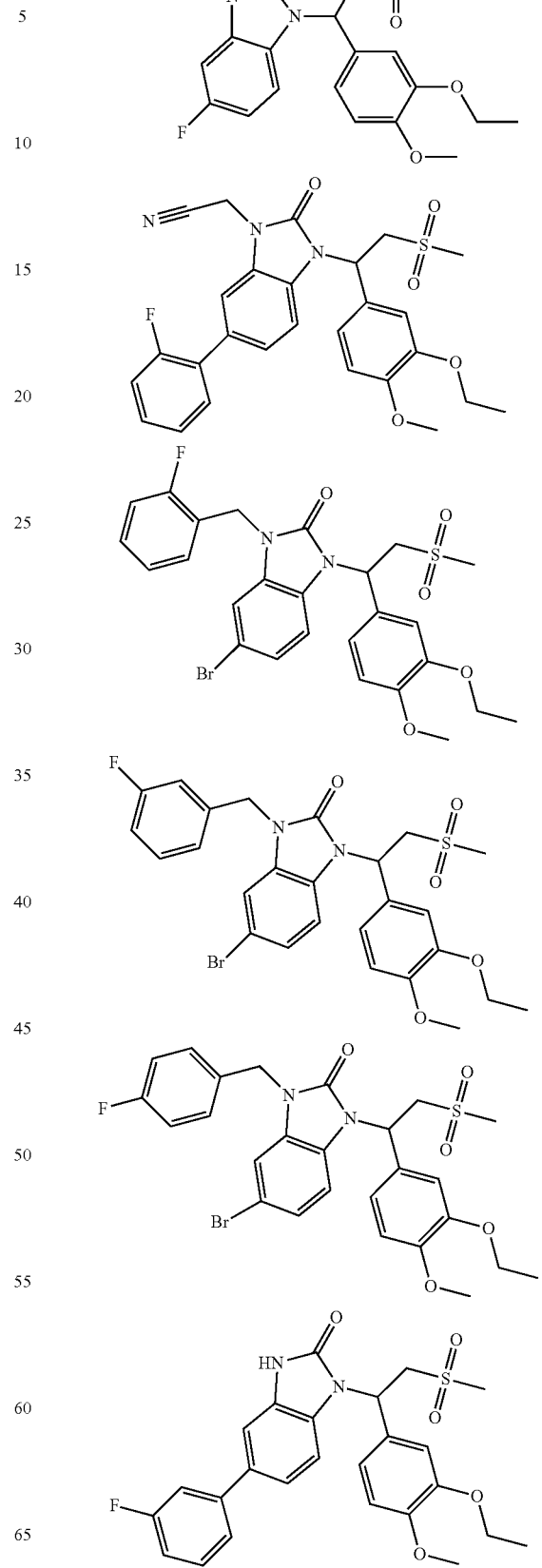

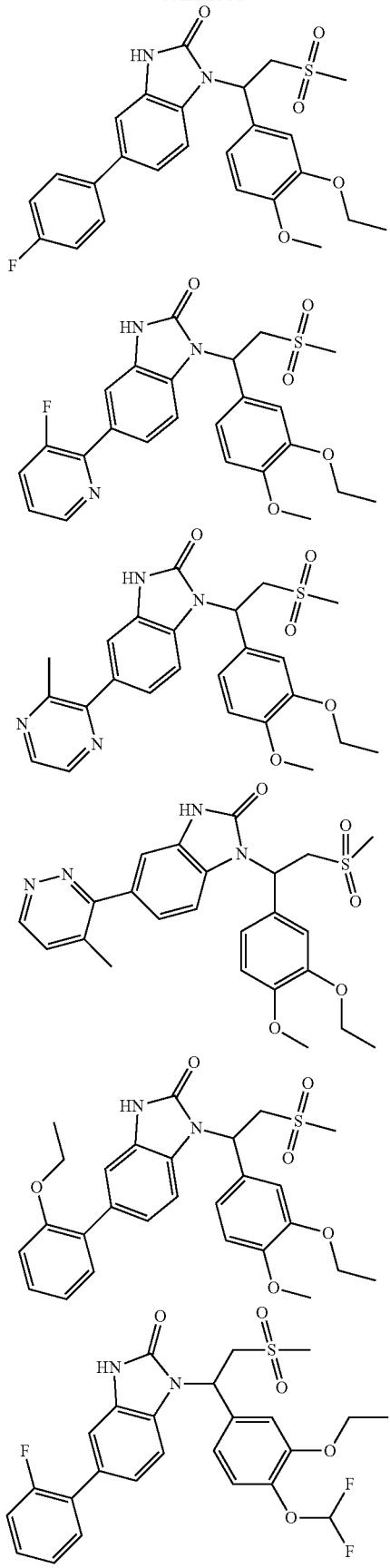
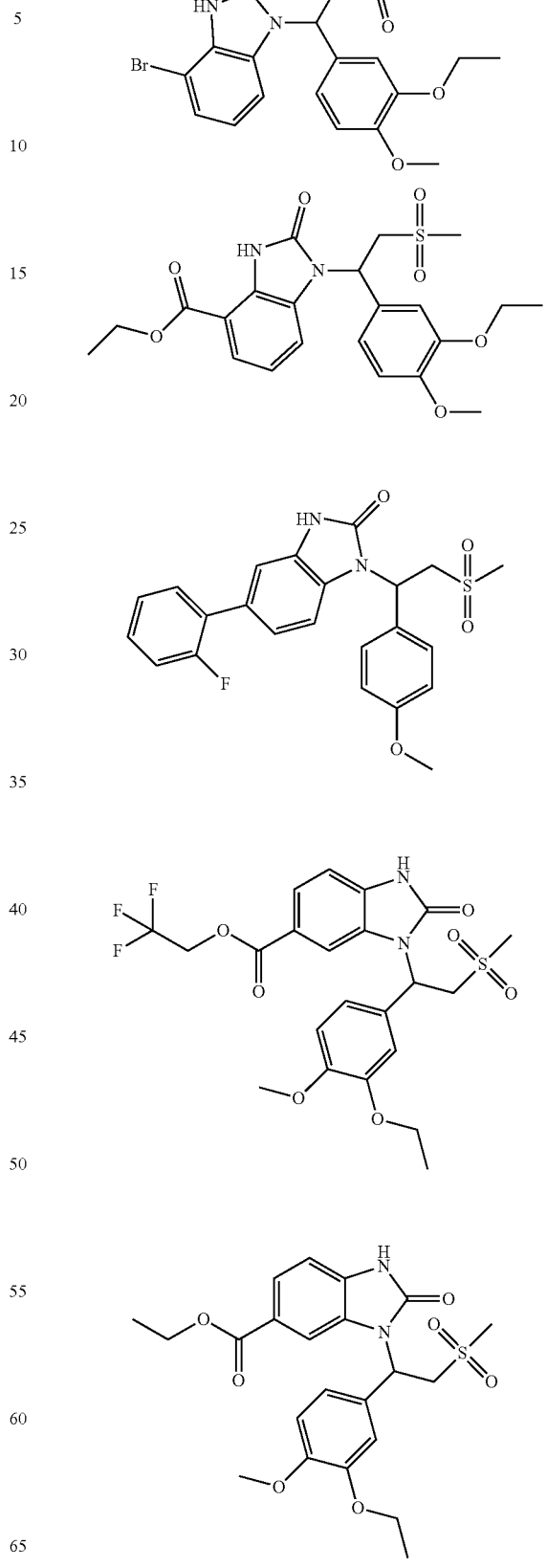

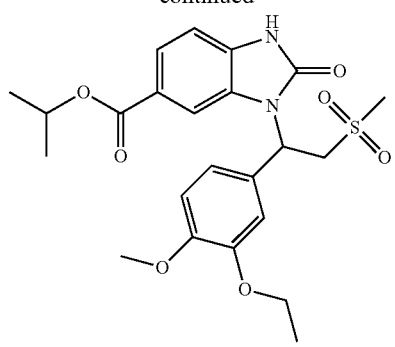
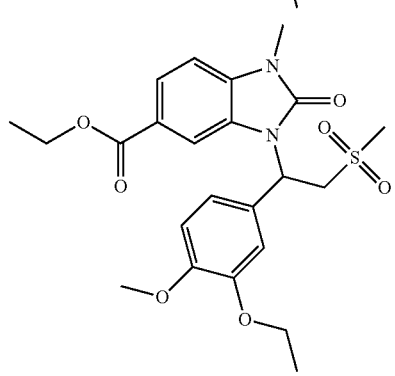
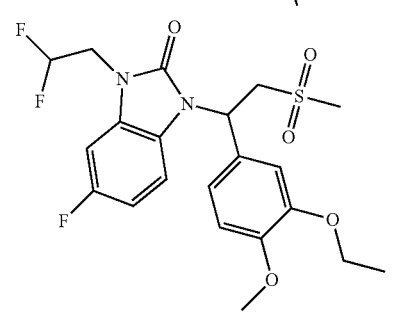
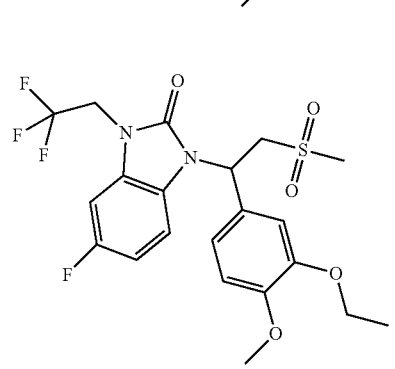
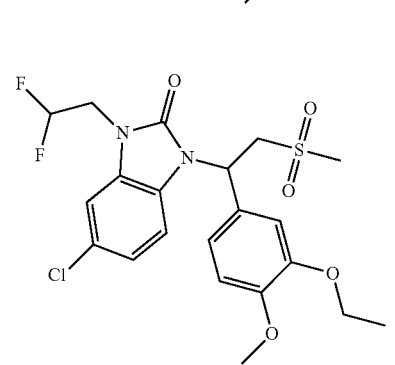
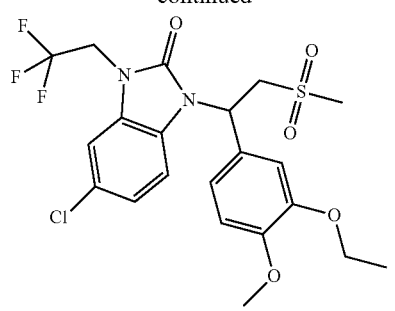
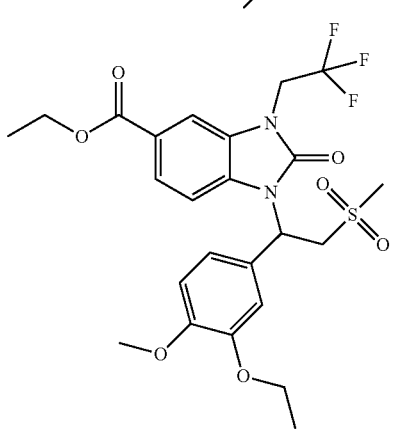
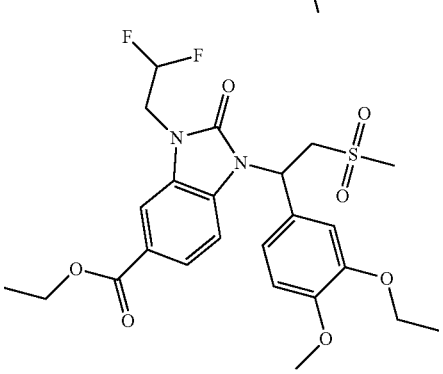
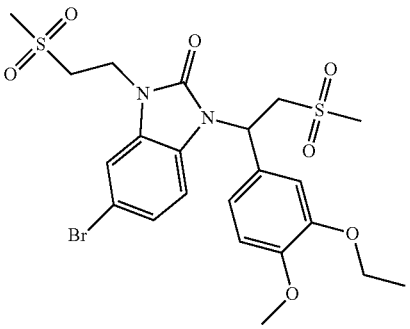
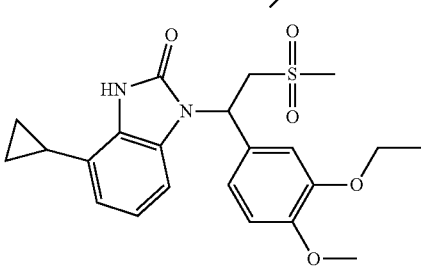

197
-continued
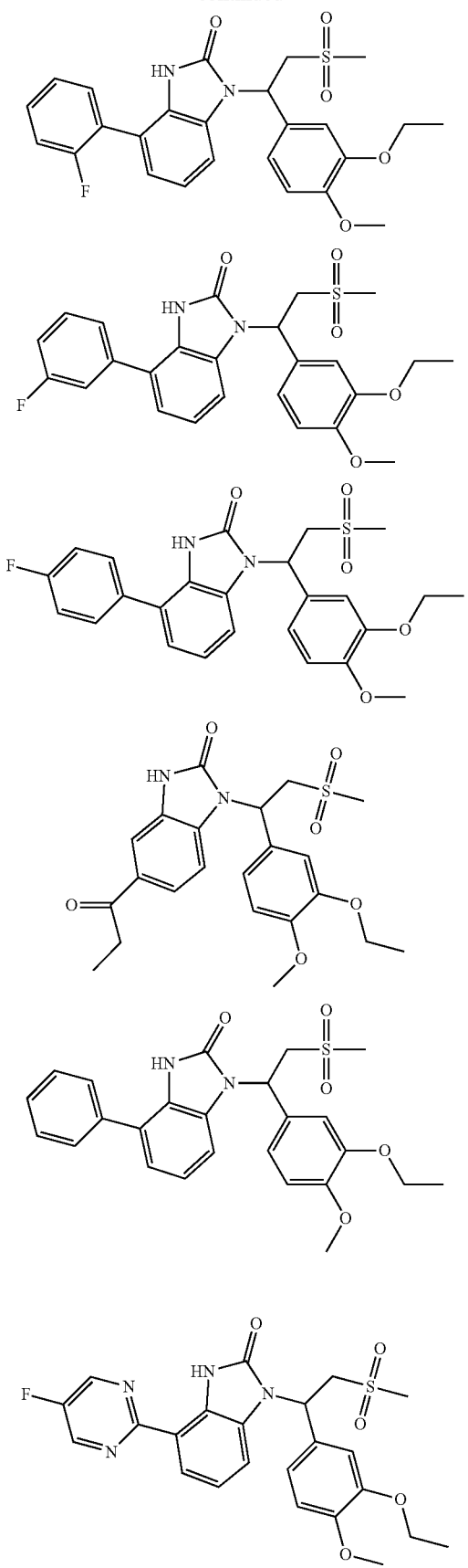
198
-continued
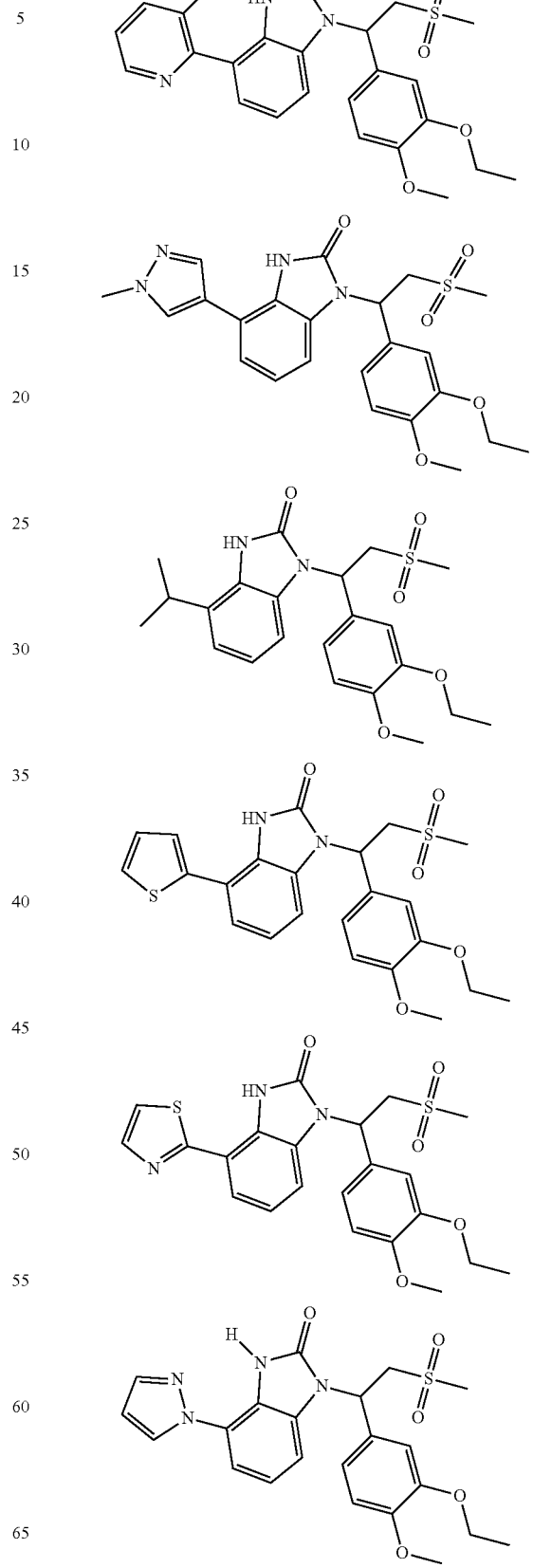

199
-continued
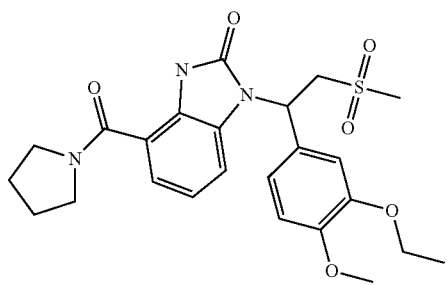
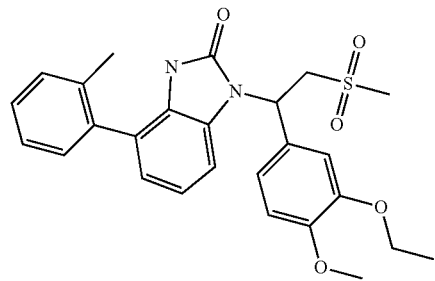
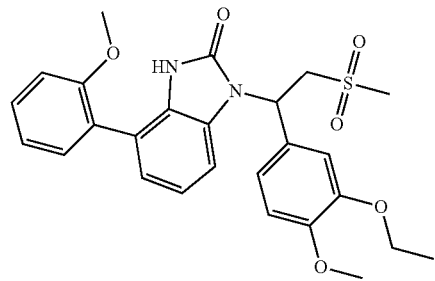
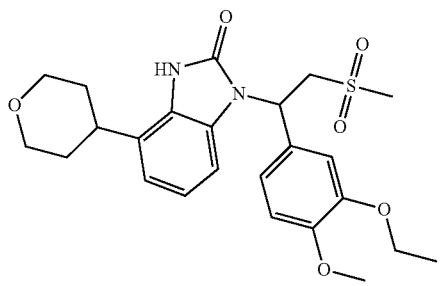
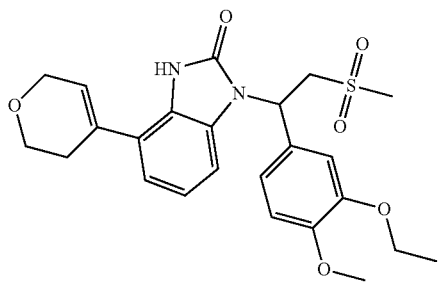
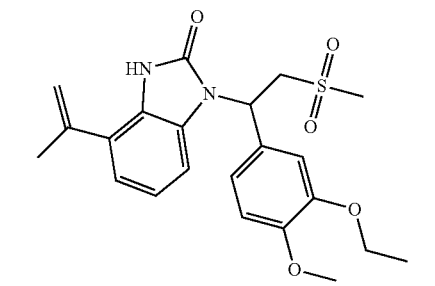
200
-continued
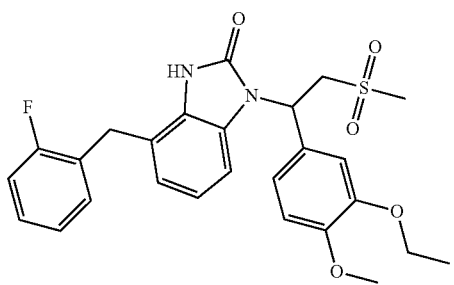
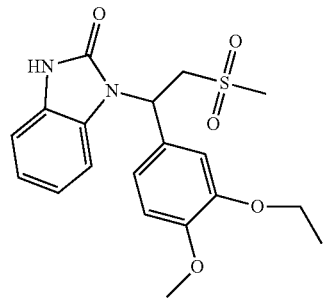
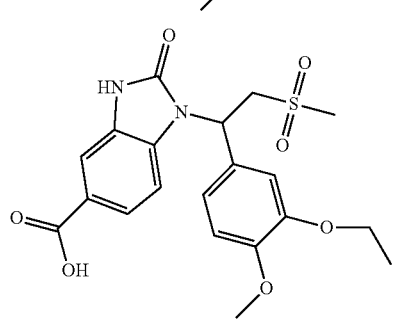
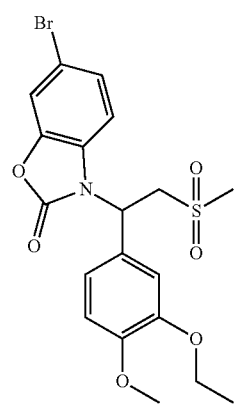
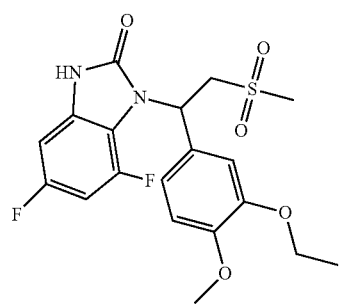

-continued
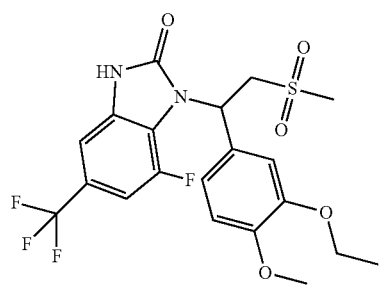
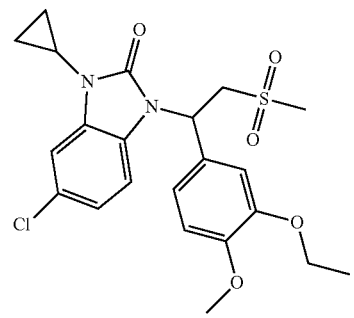
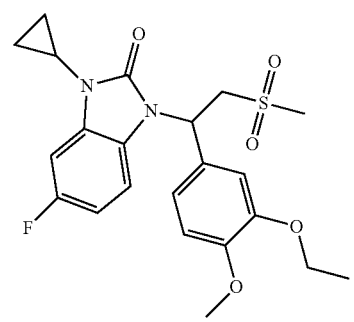
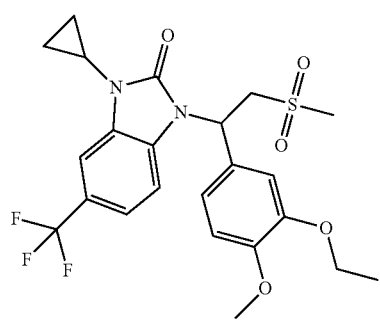
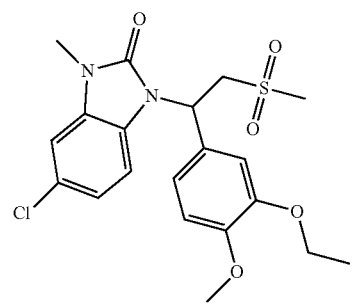
-continued
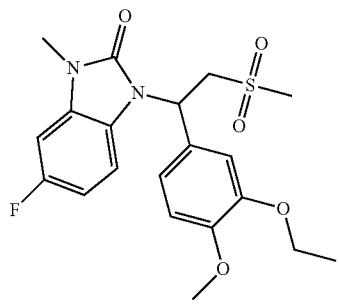
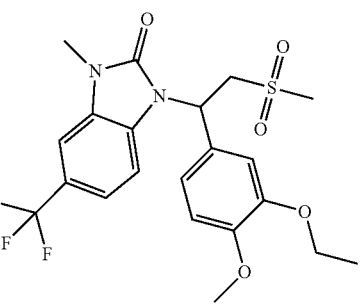
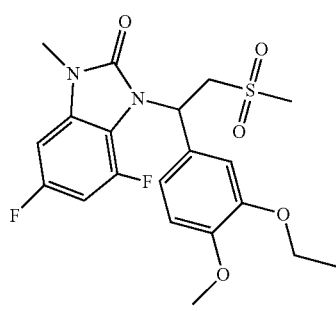
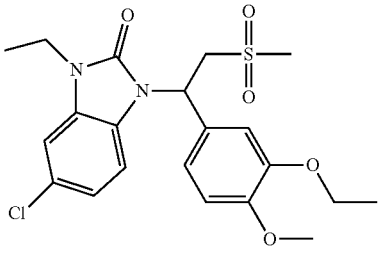
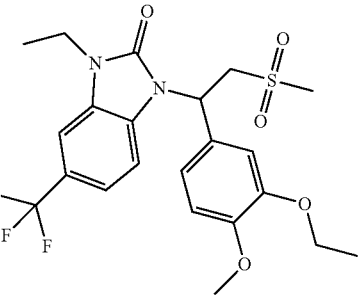

203
-continued
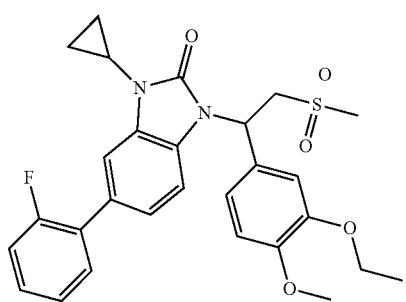
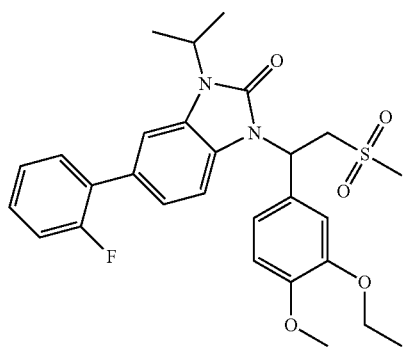
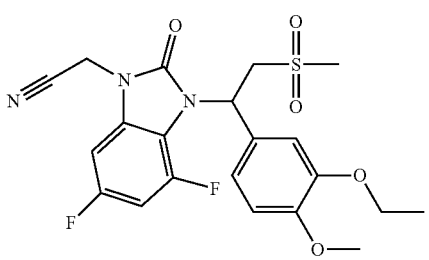
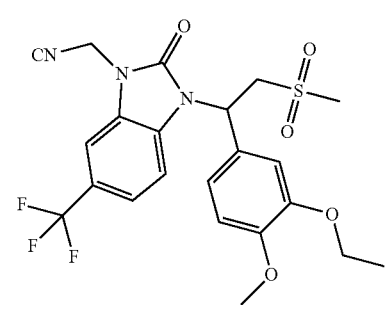
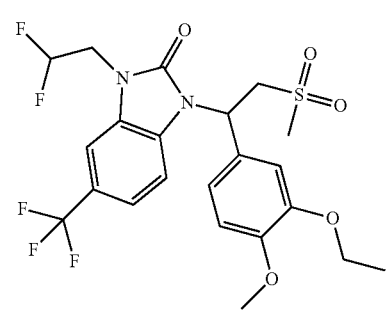
204
-continued
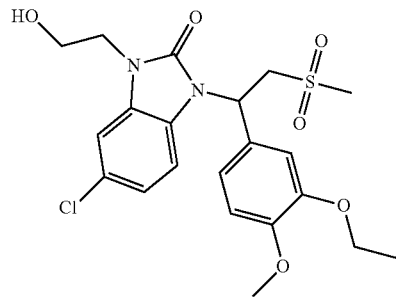
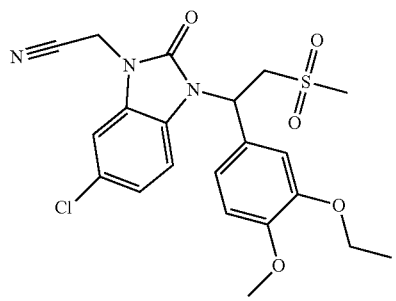
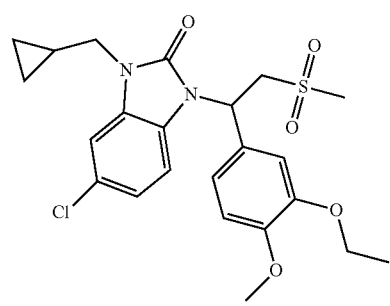
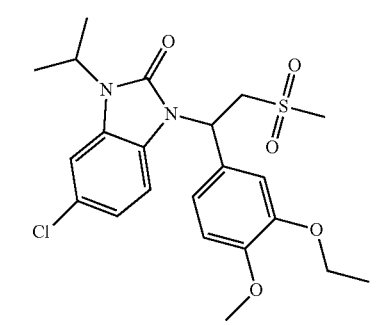
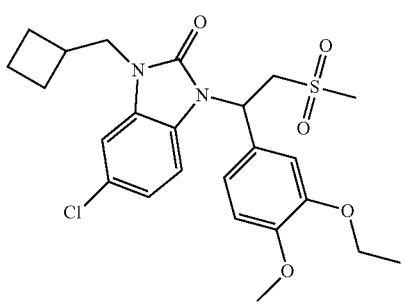

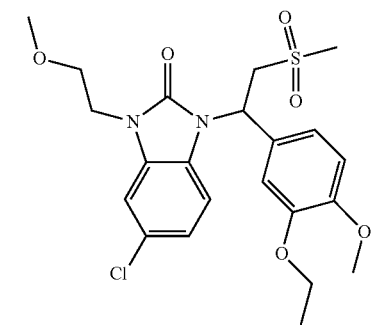
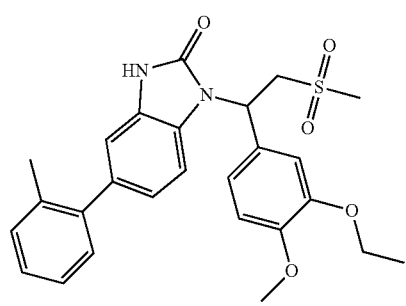
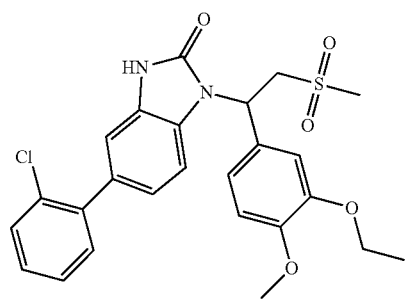
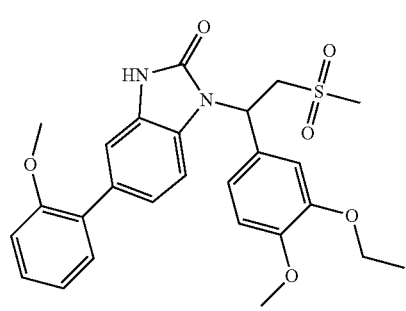
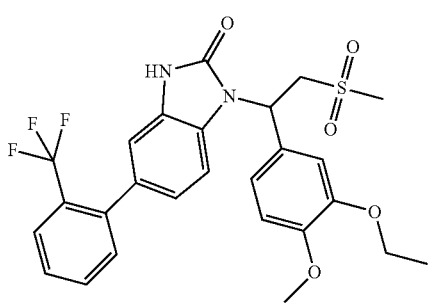
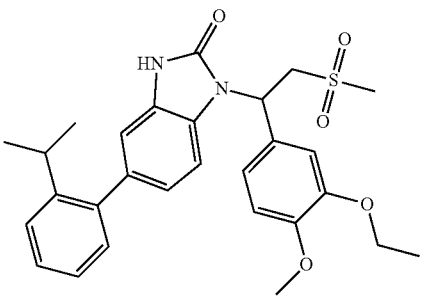
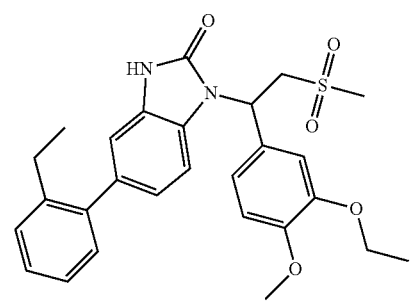
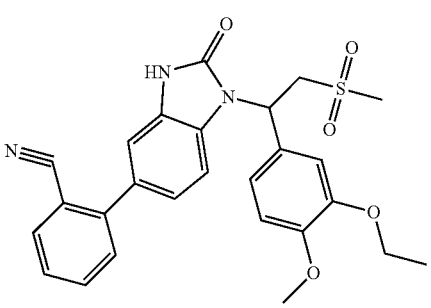
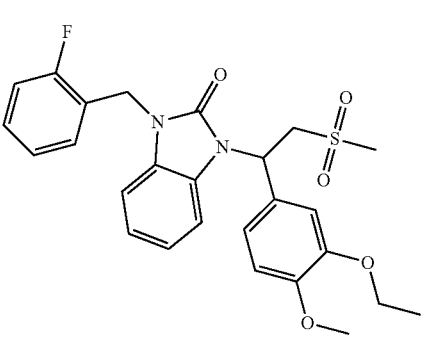
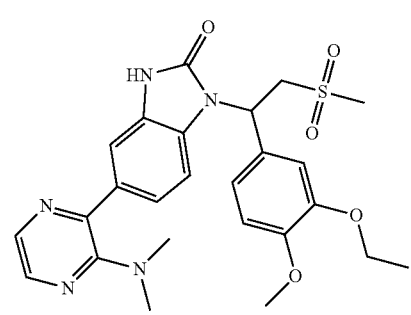

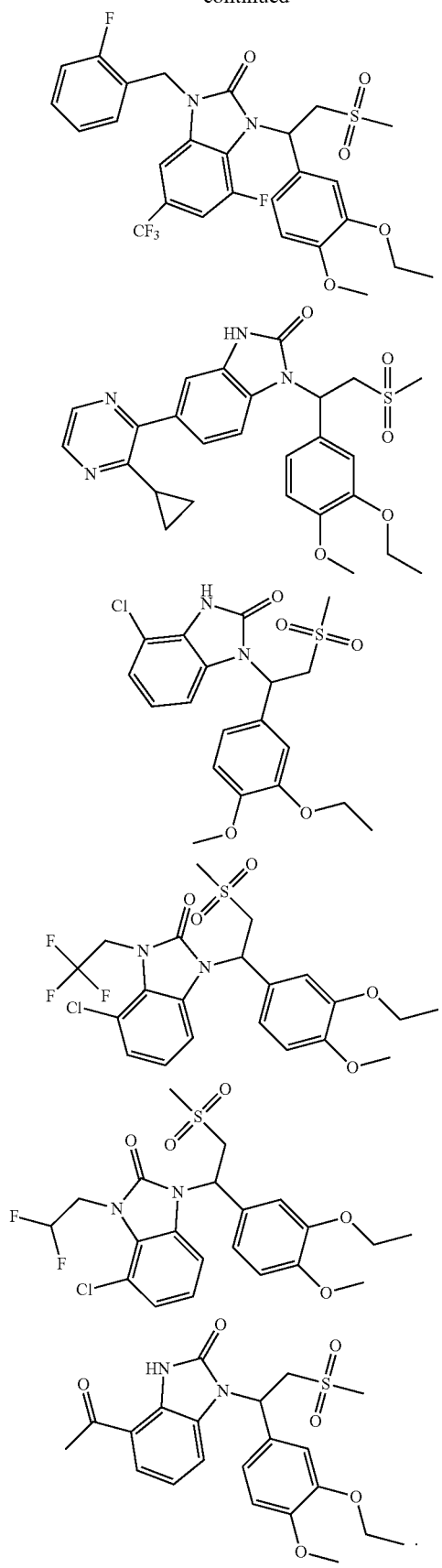
21. The compound or the pharmaceutically acceptable salt thereof according to claim 20, which is selected from the group consisting of
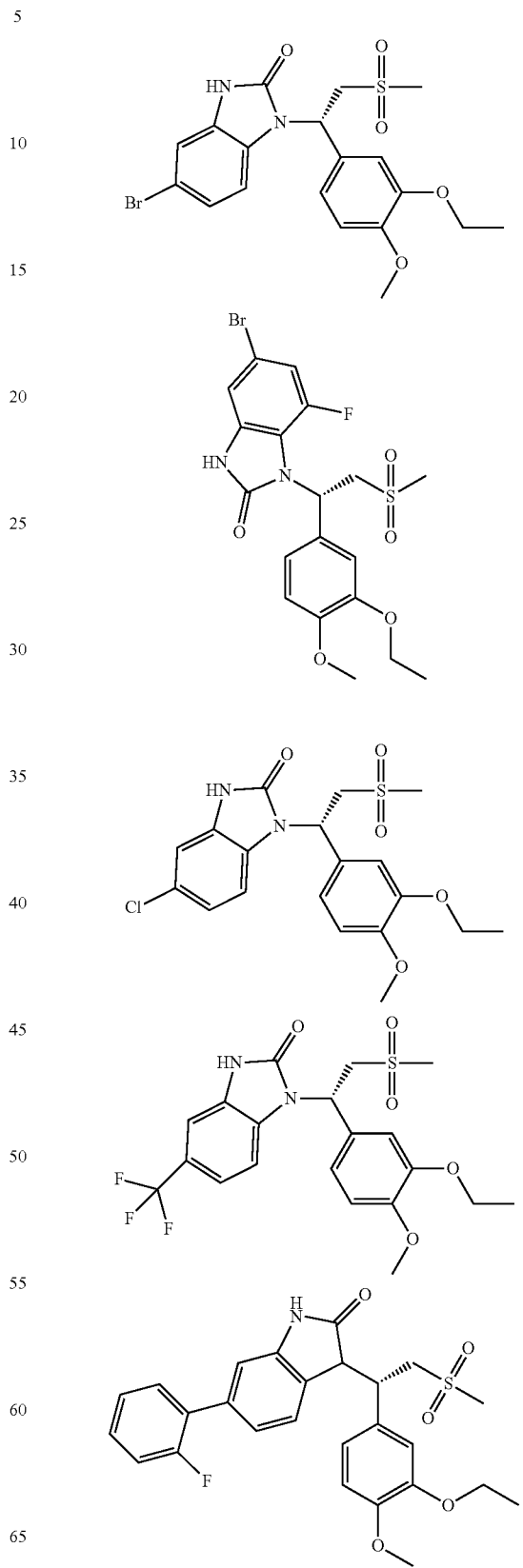
and 209
-continued
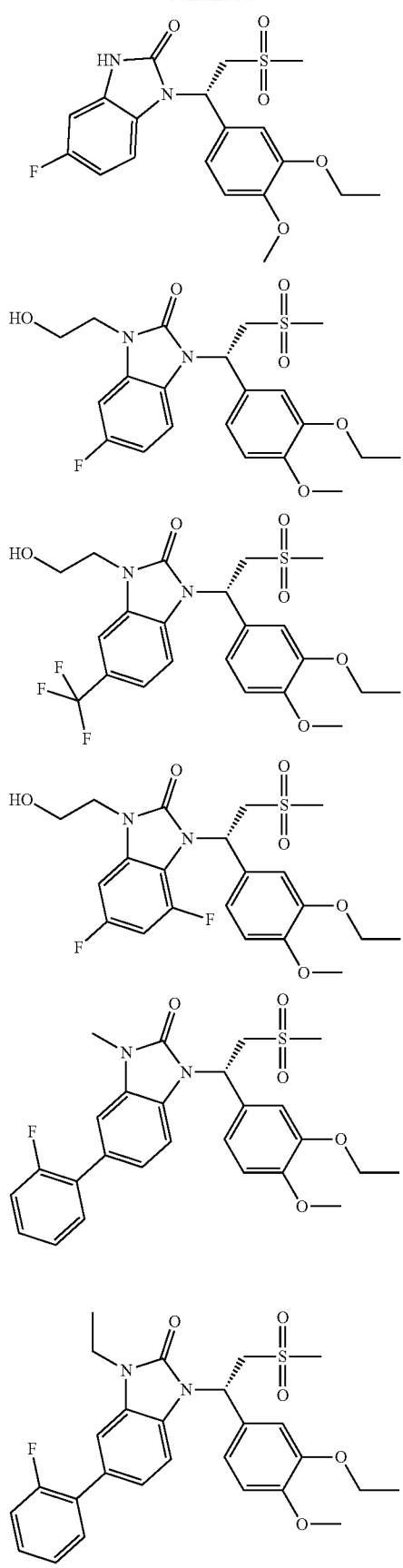
210
-continued
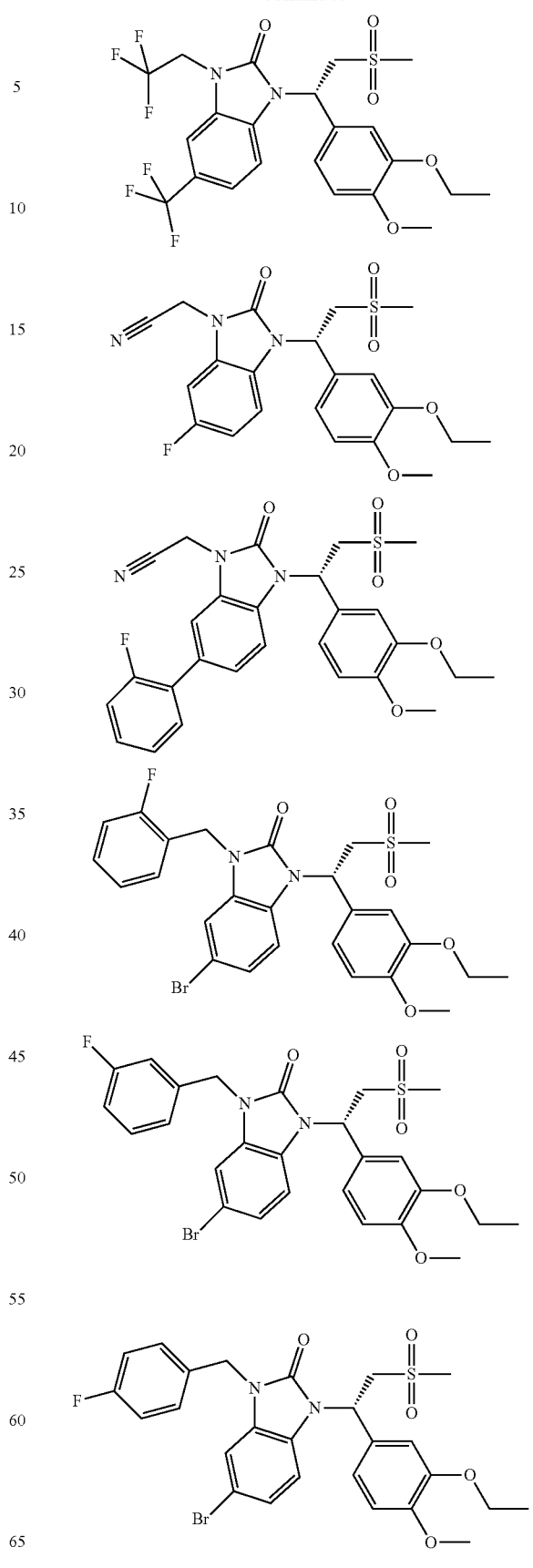

211
-continued
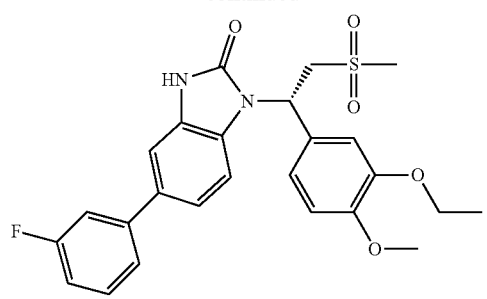
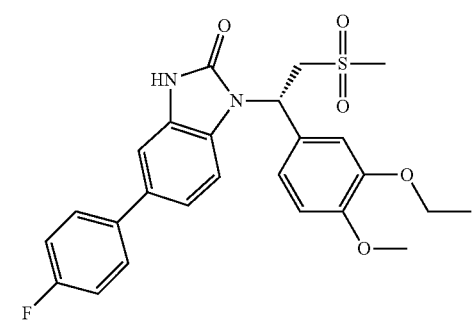
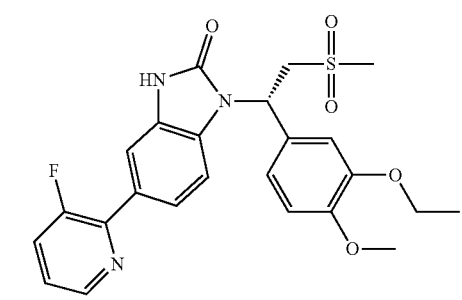
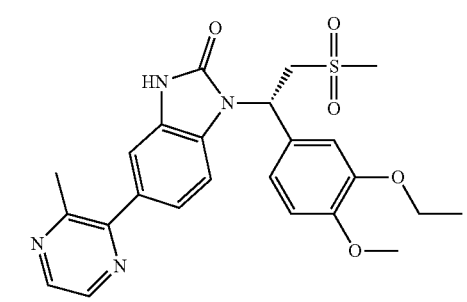
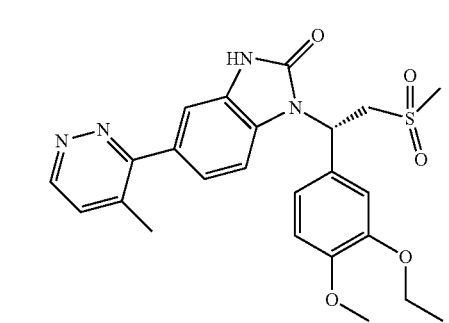
212
-continued
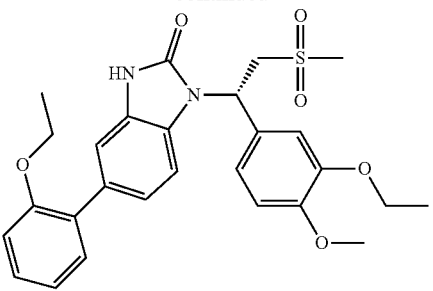
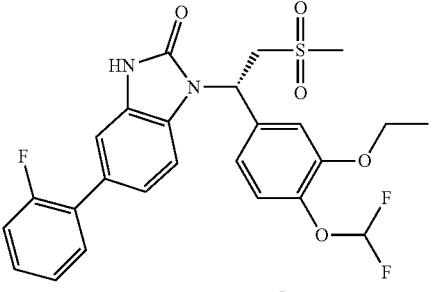
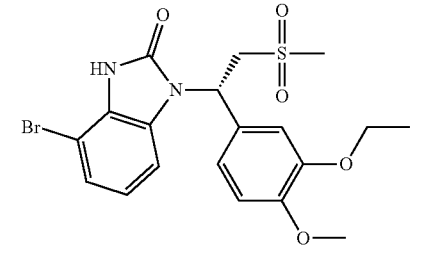
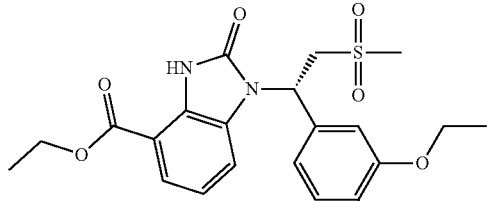
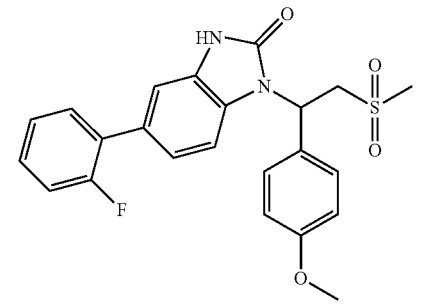
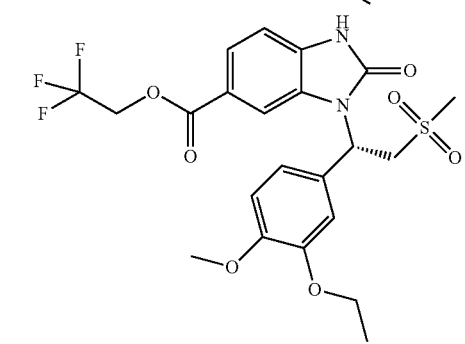

213
-continued
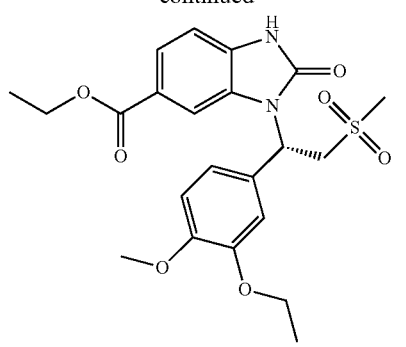
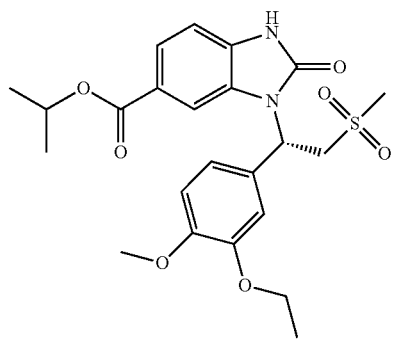
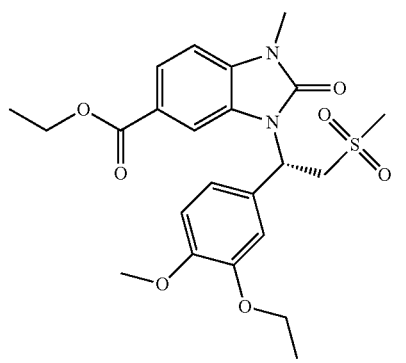
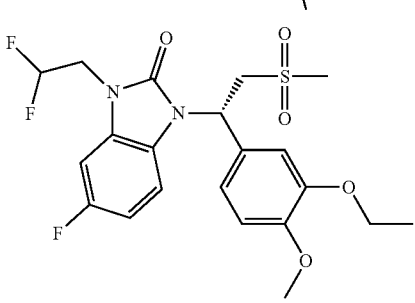
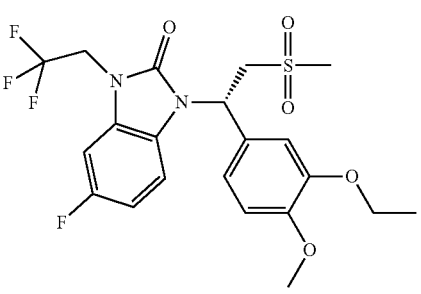
214
-continued
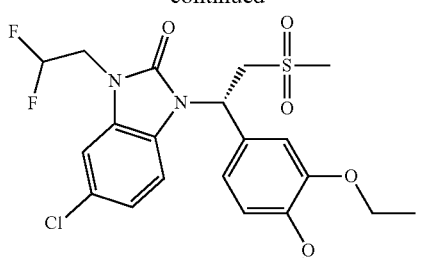
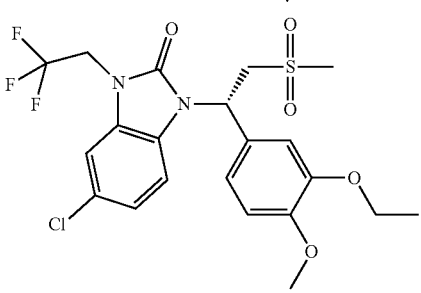
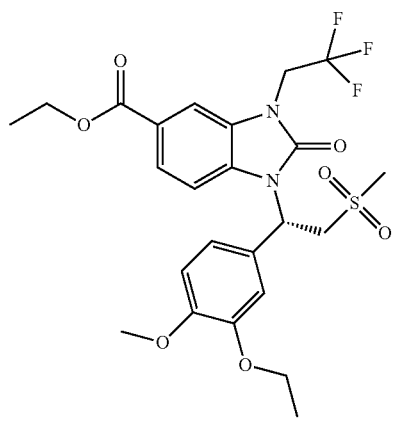
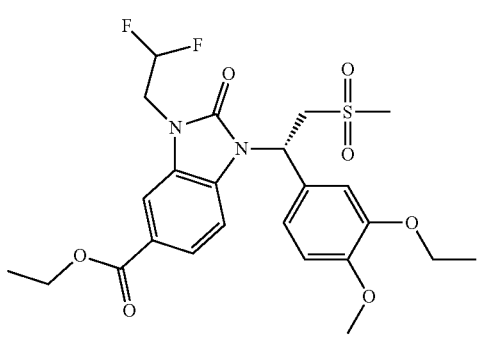
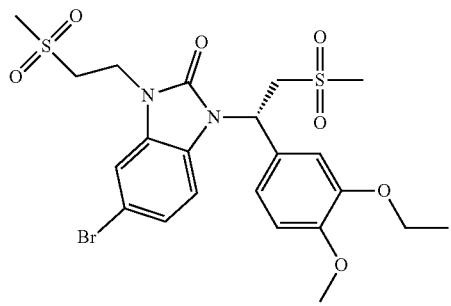

215
-continued
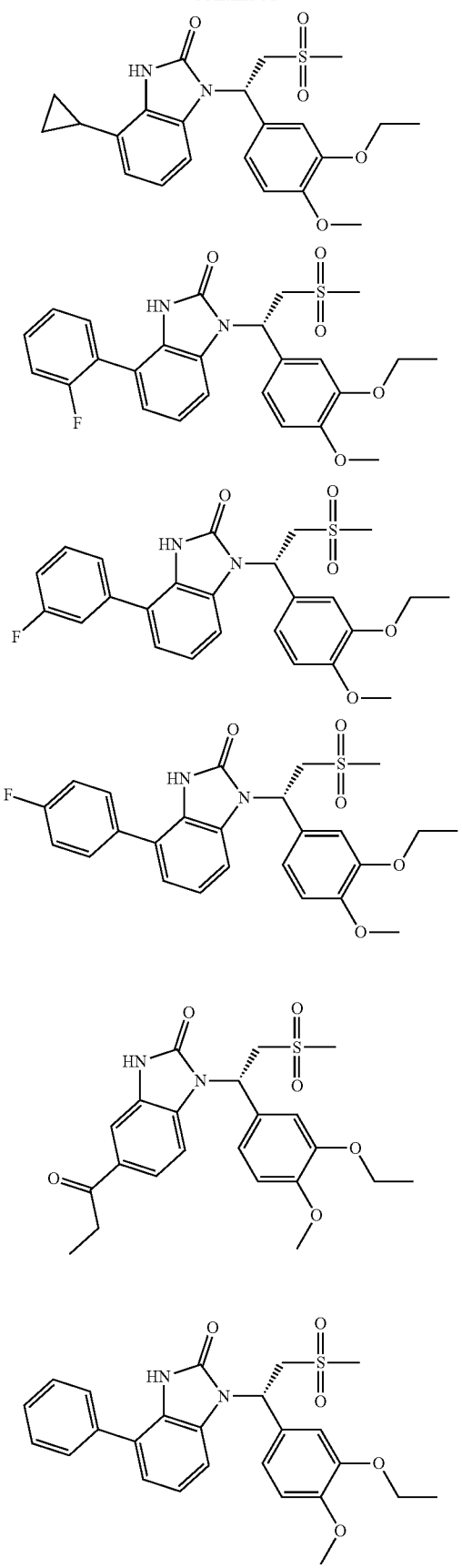
216
-continued
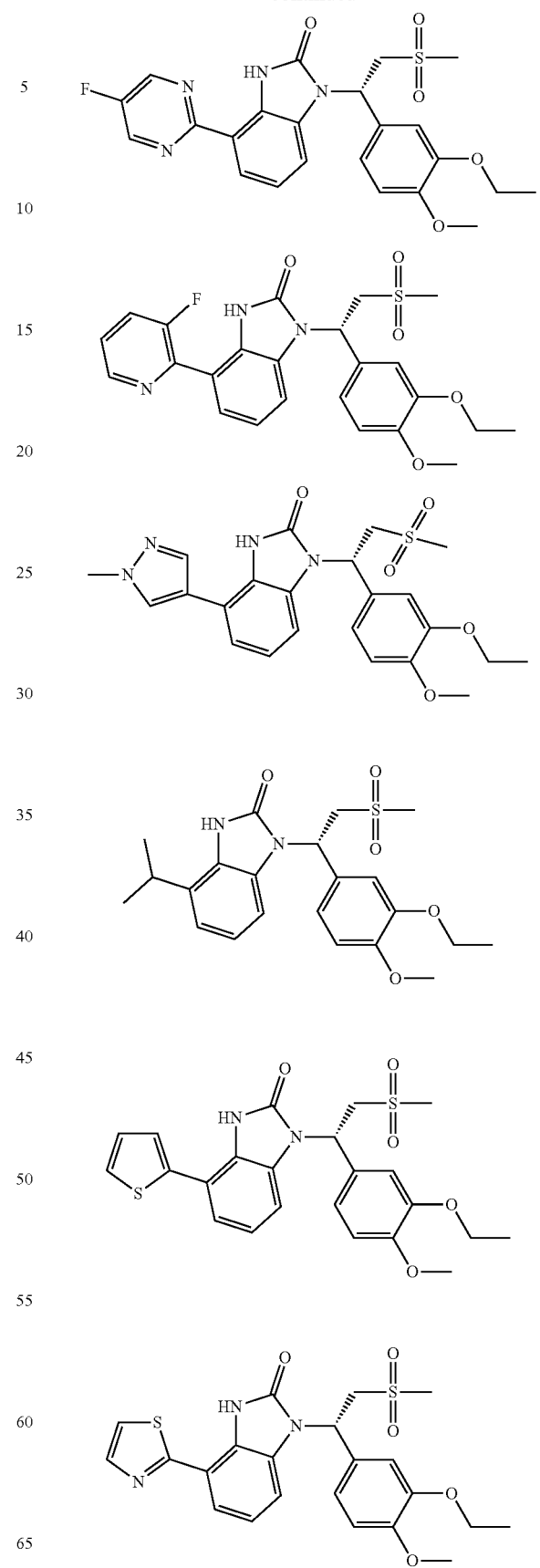

217
-continued
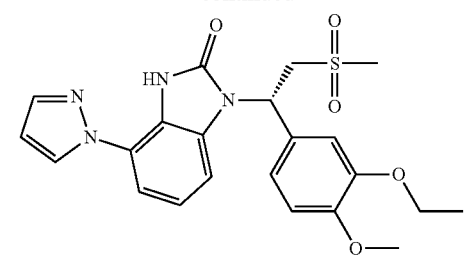
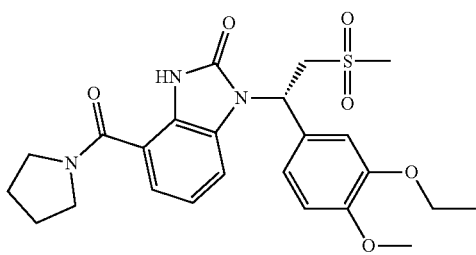
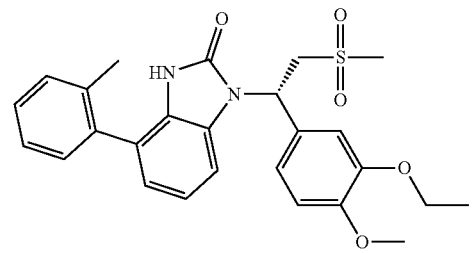
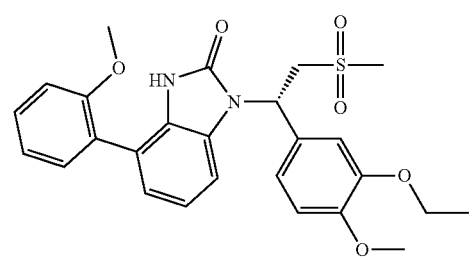
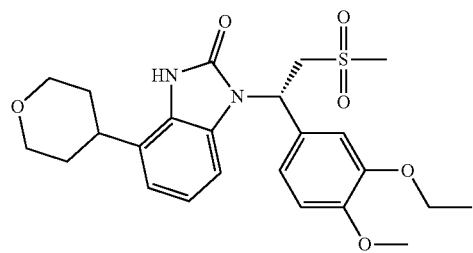
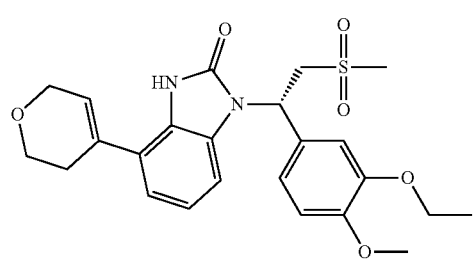
218
-continued
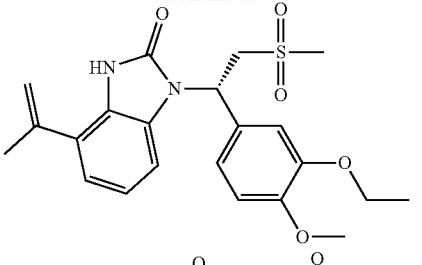
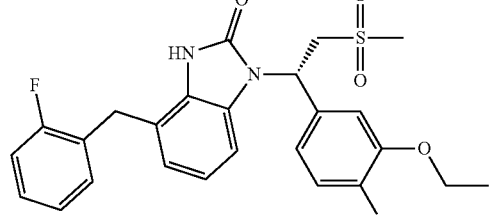
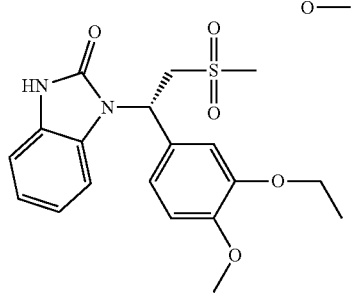
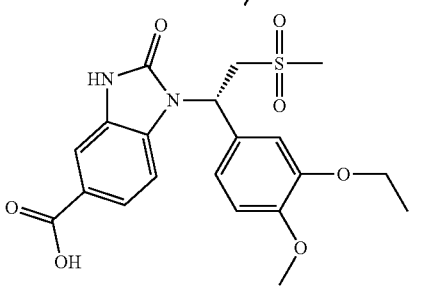
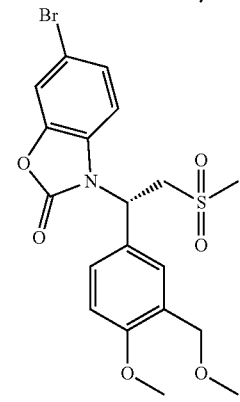
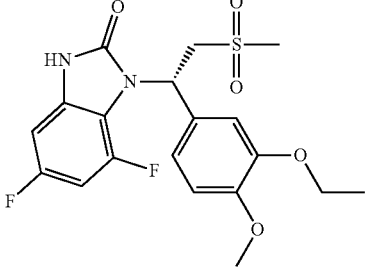

219
-continued
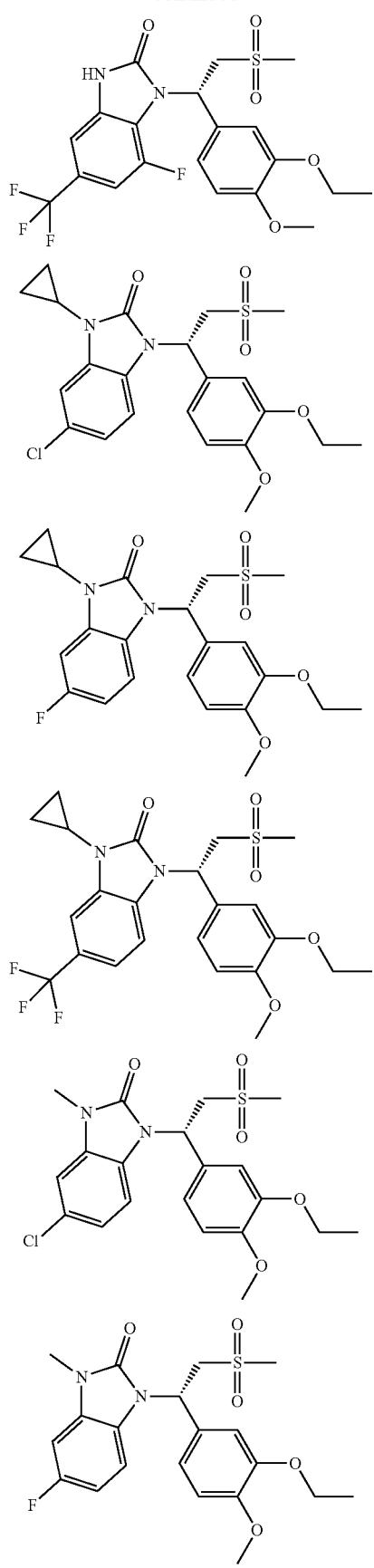
220
-continued
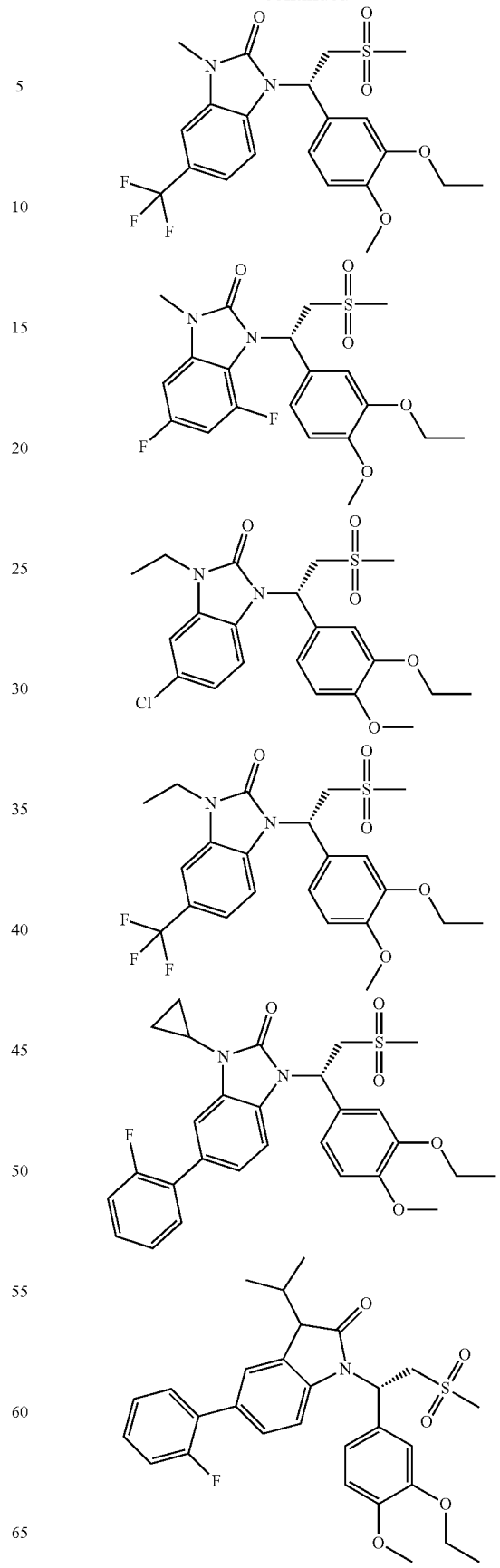

221
-continued
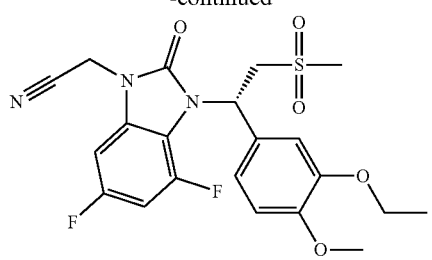
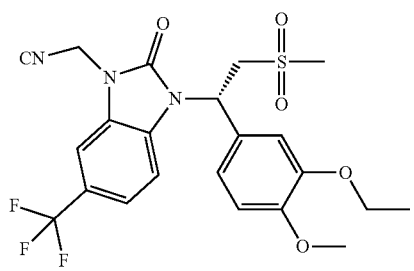
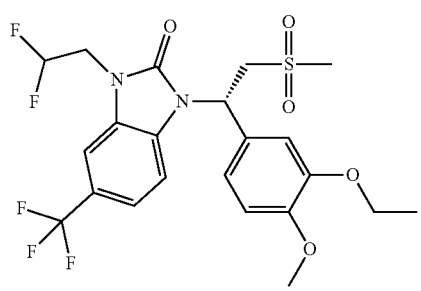
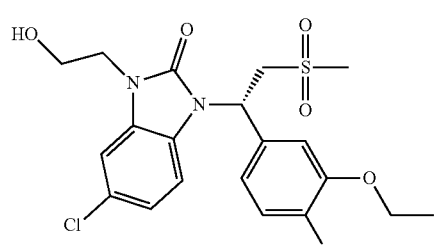
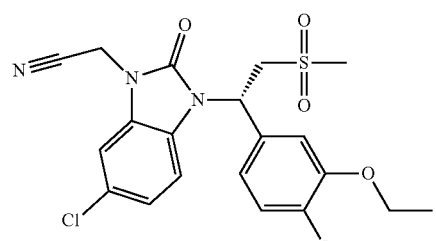
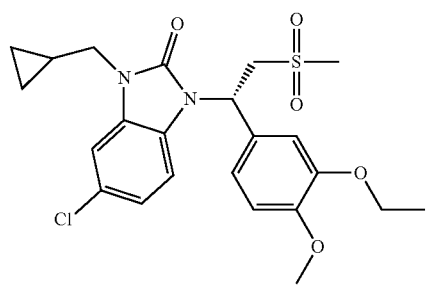
222
-continued
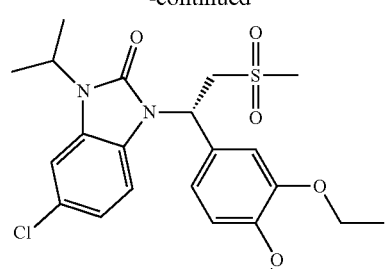
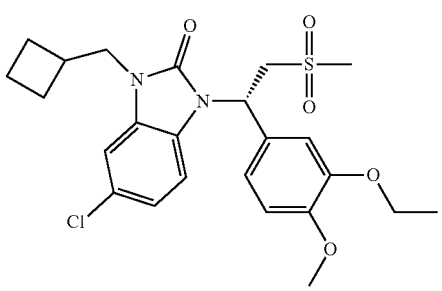
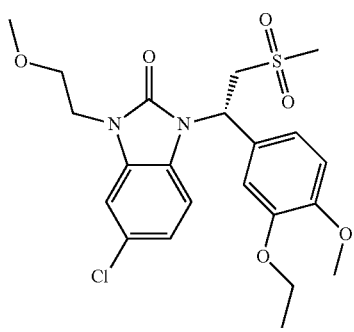
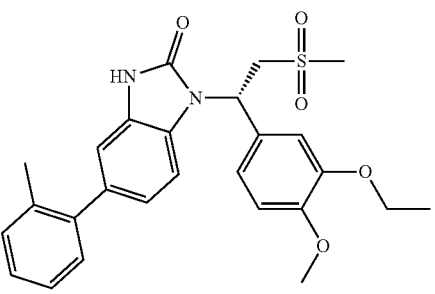
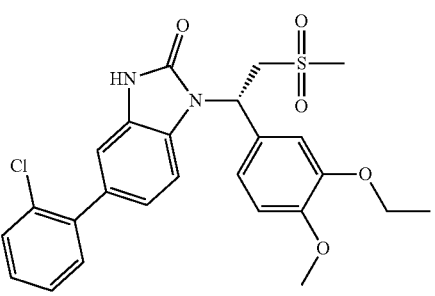

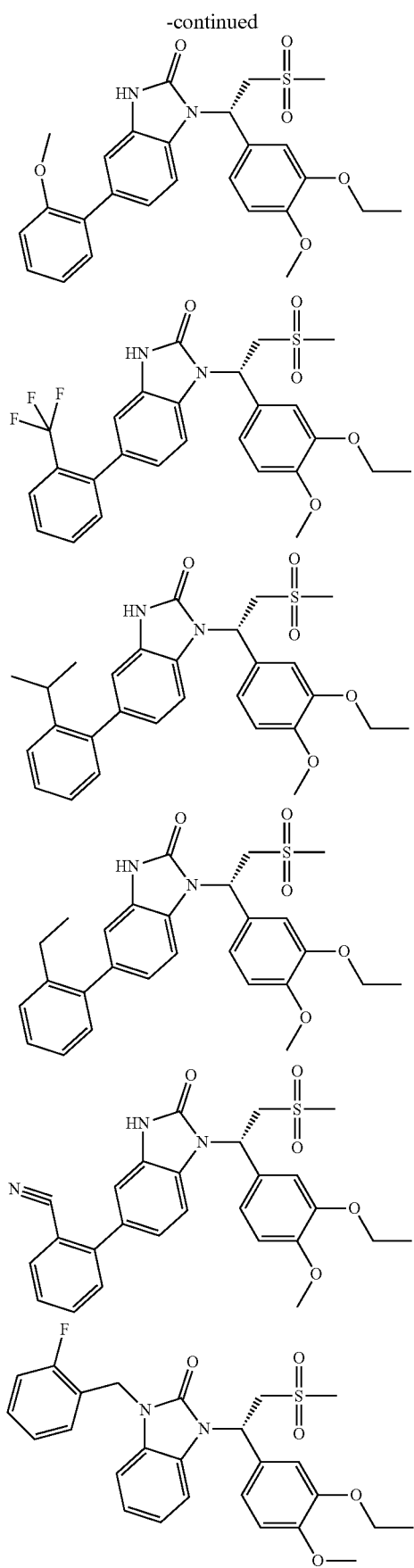
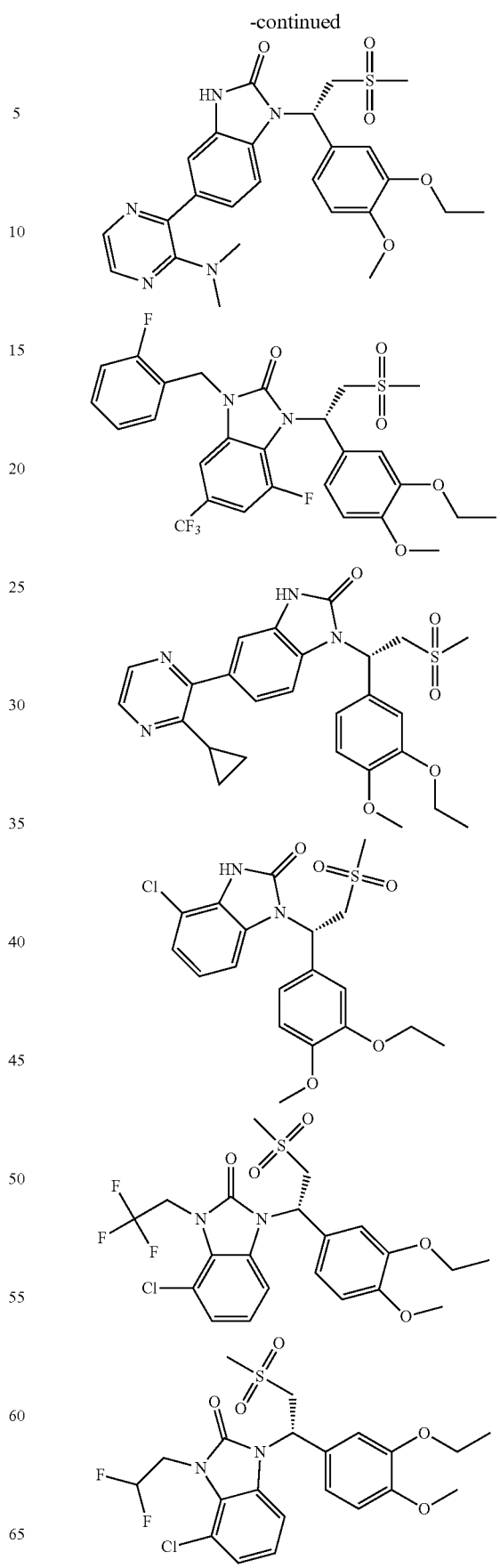

225
-continued
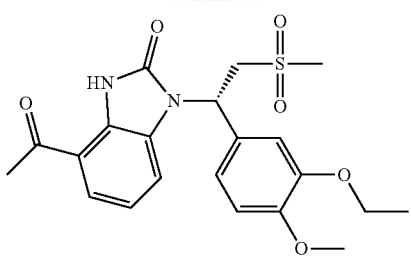
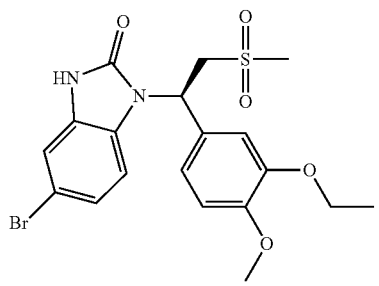
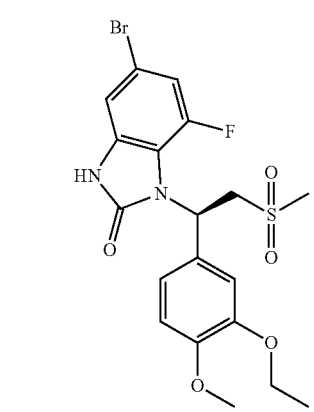
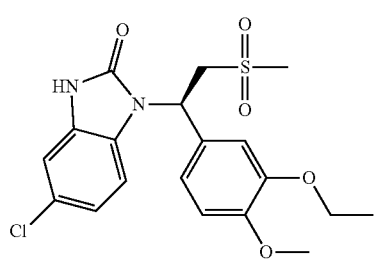
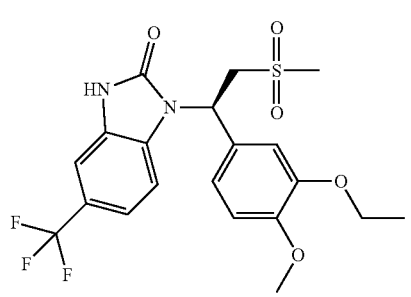
226
-continued
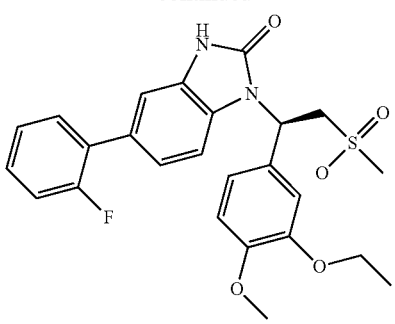
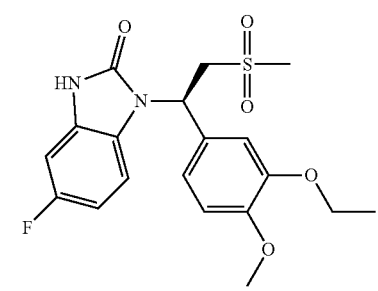
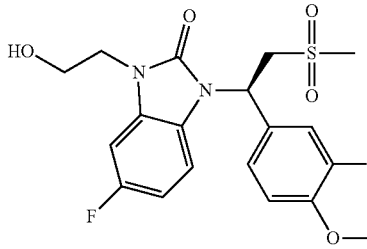
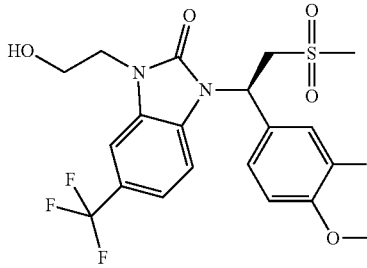
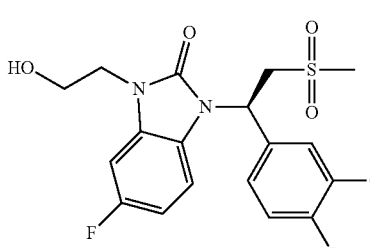
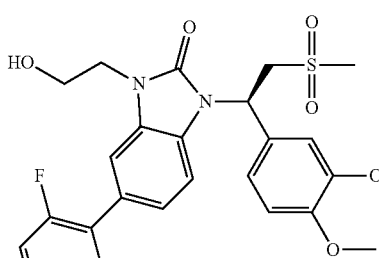

227
-continued
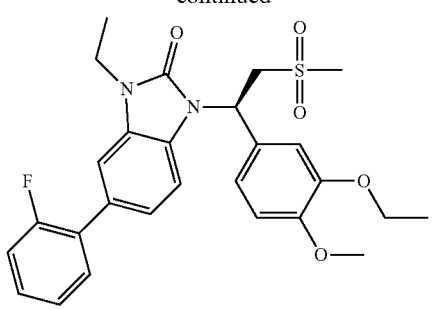
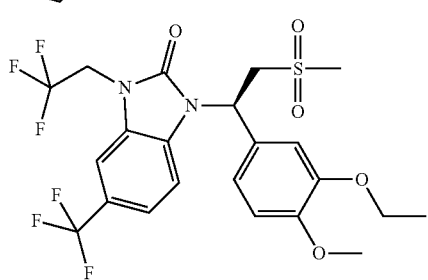
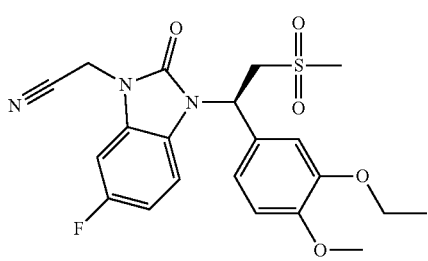
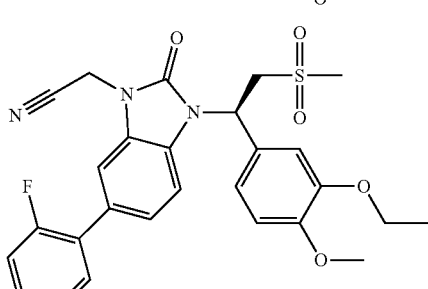
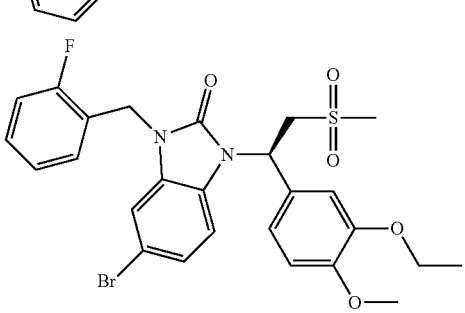
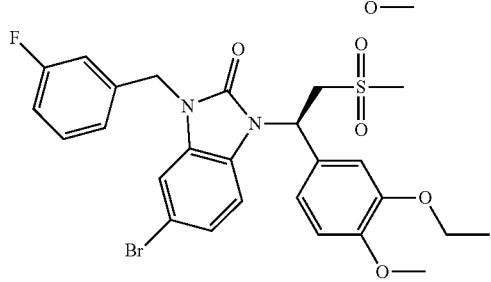
228
-continued
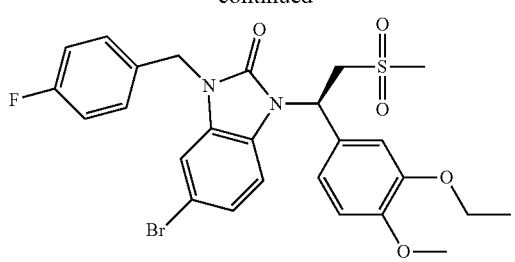
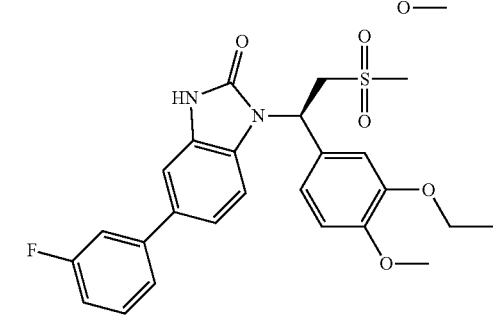
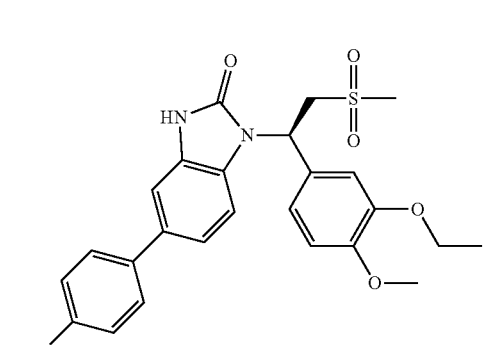
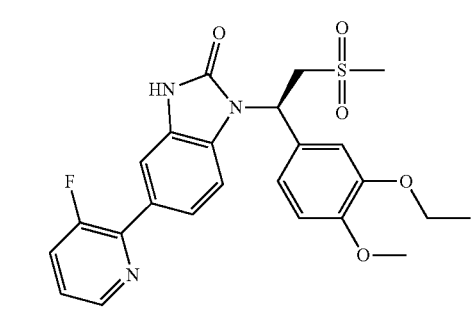
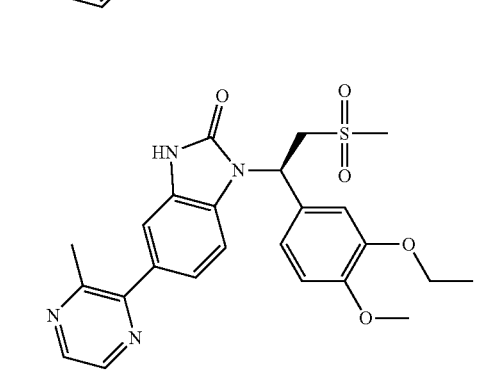

229
-continued
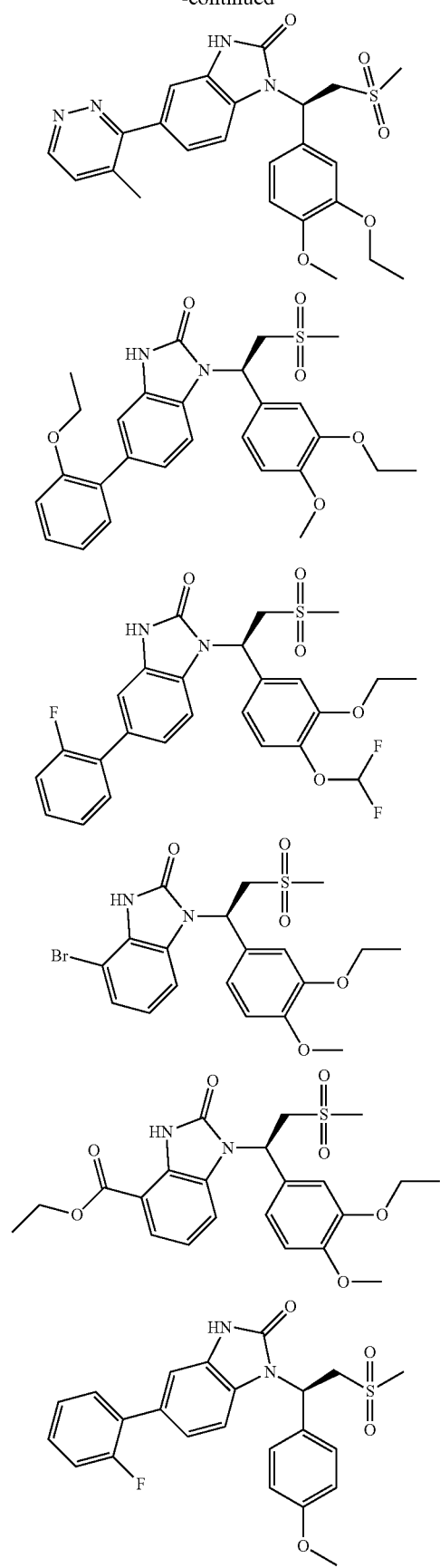
230
-continued
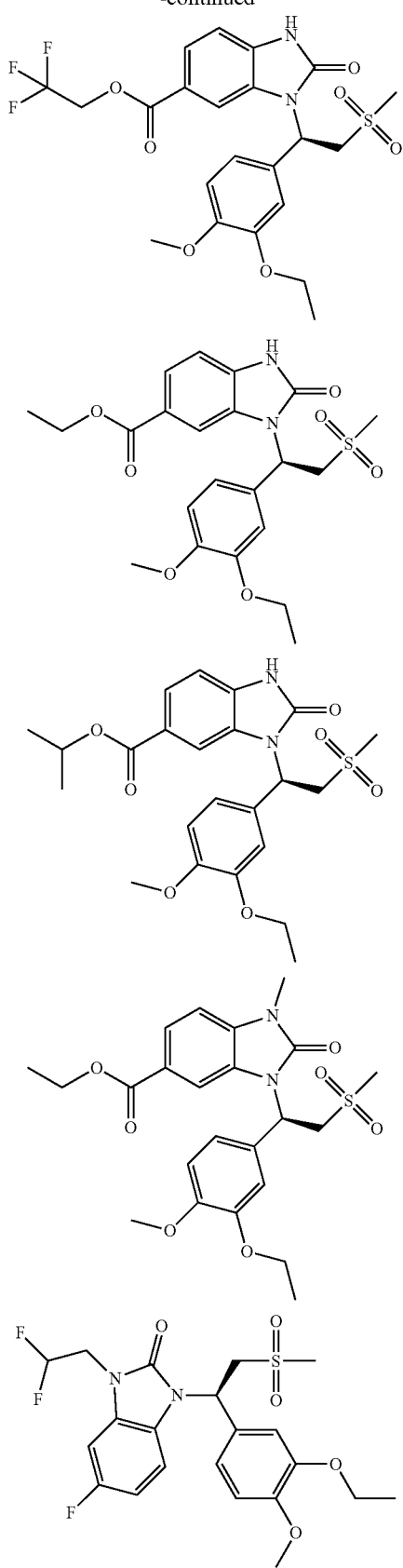

231
-continued
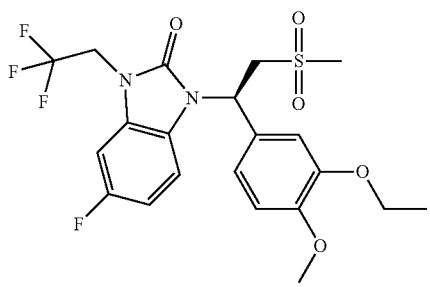
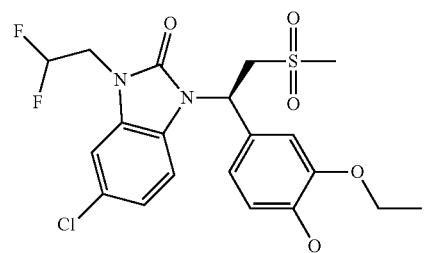
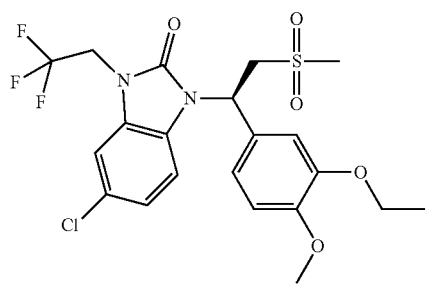
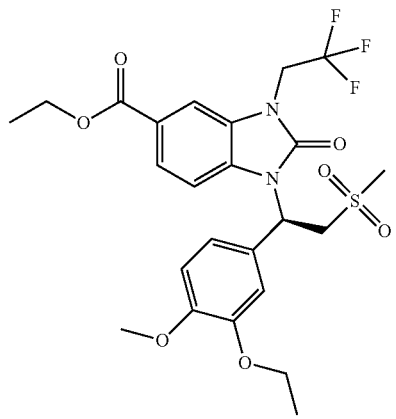
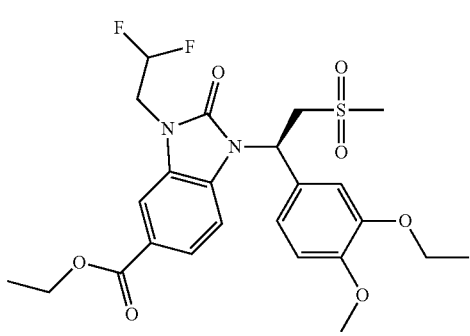
232
-continued
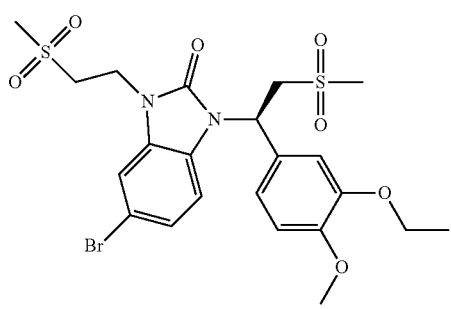
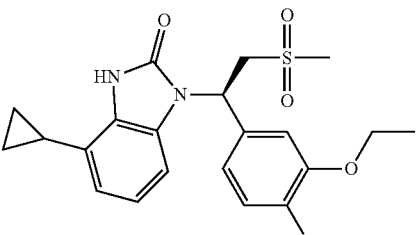
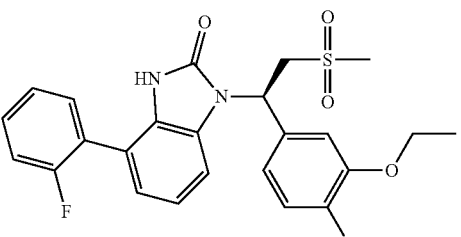
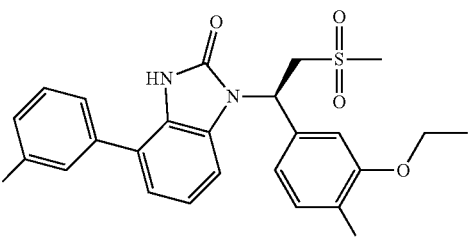
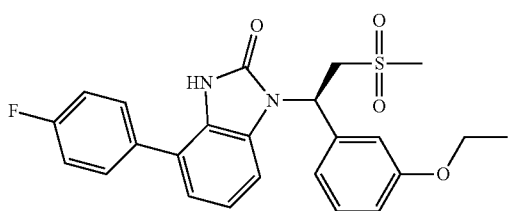
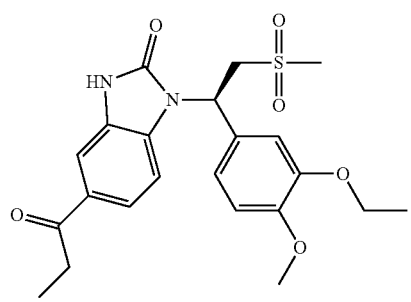

233
-continued
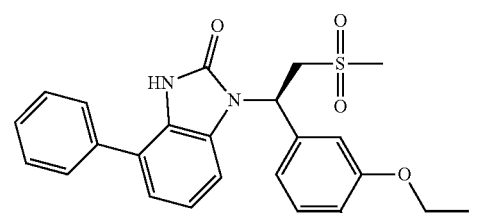
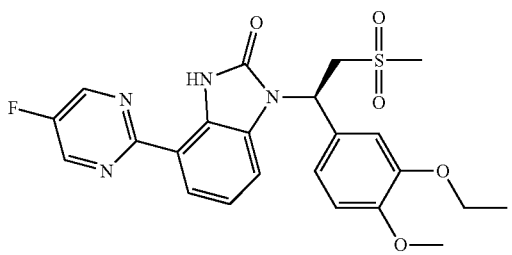
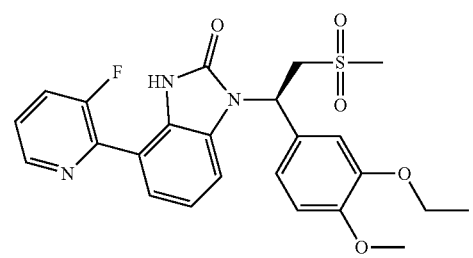
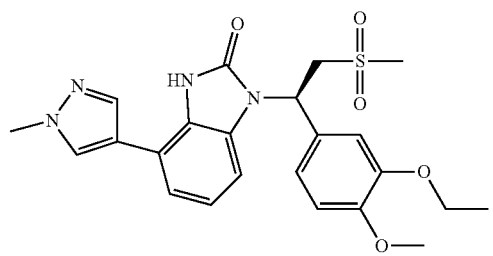
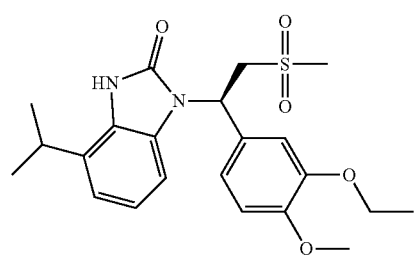
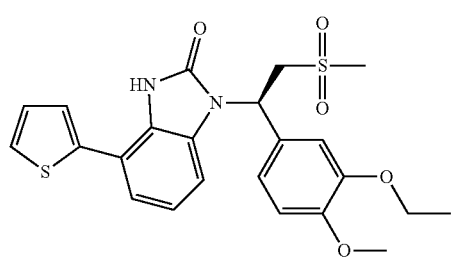
234
-continued
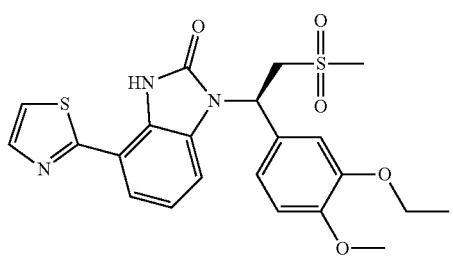
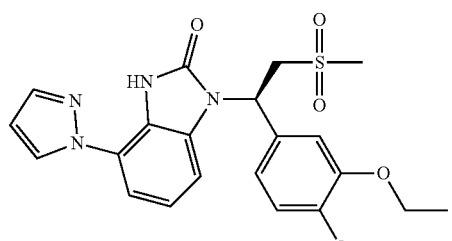
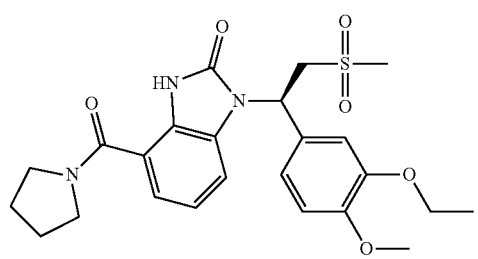
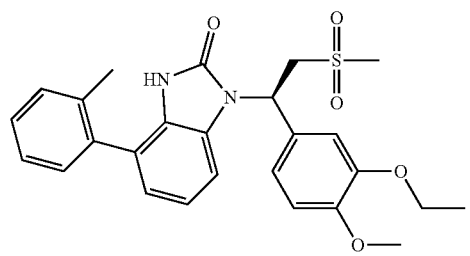
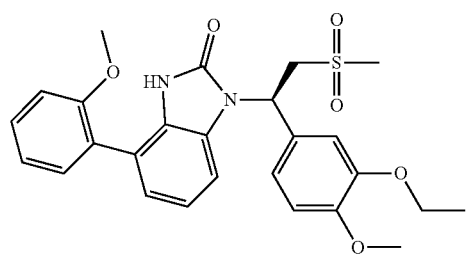
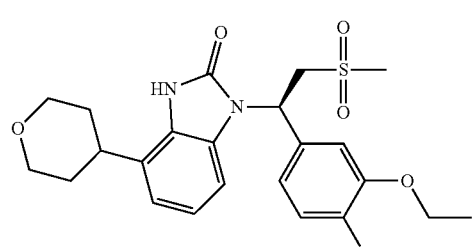

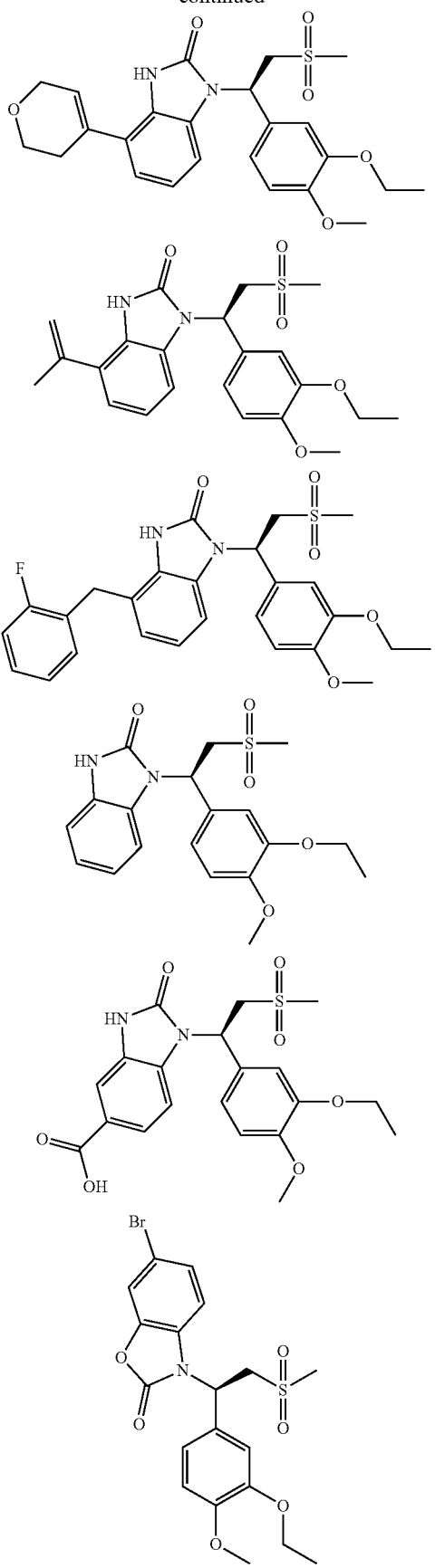
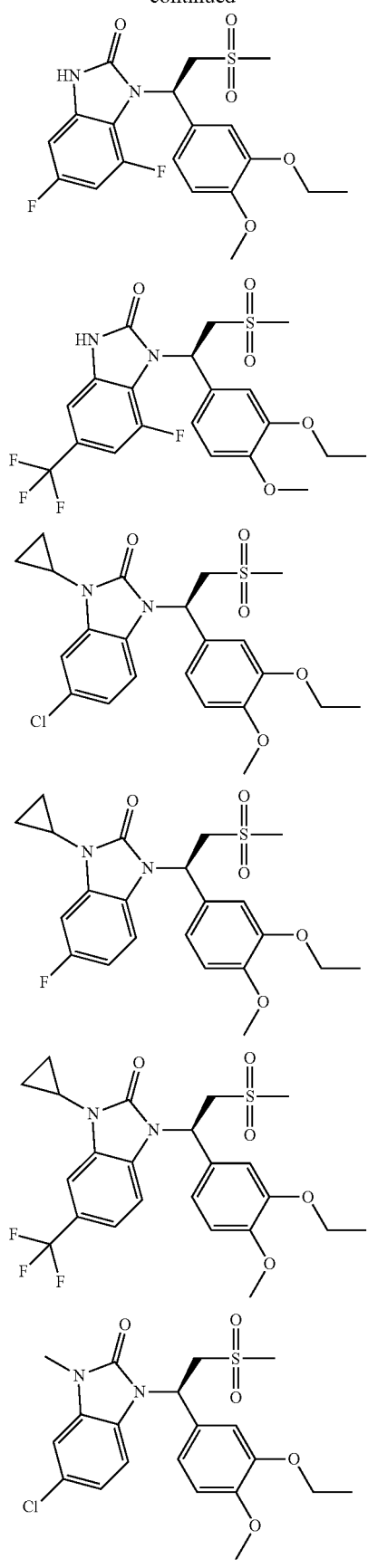

237
-continued
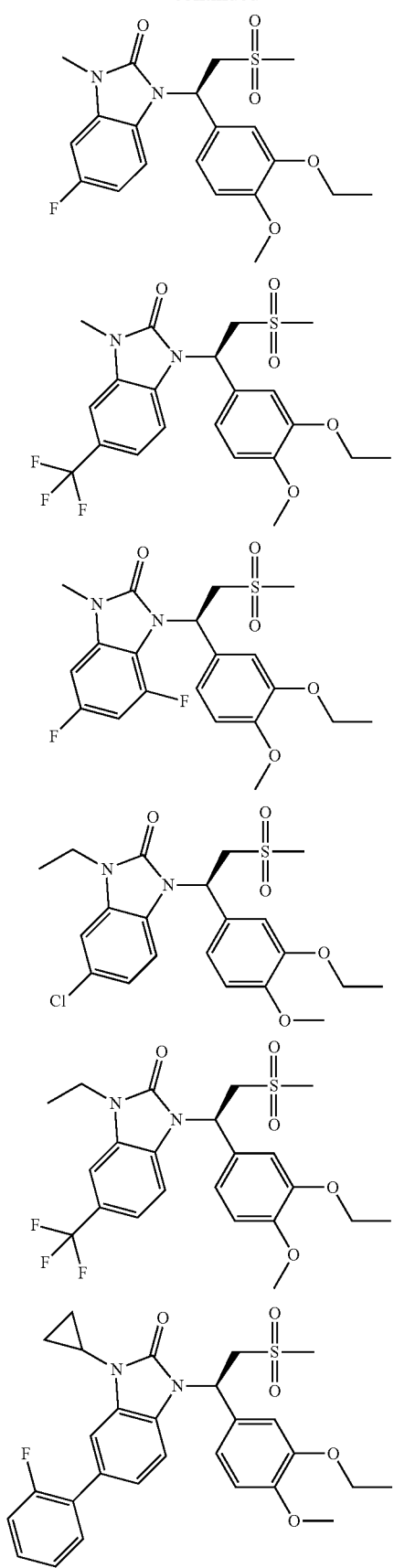
238
-continued
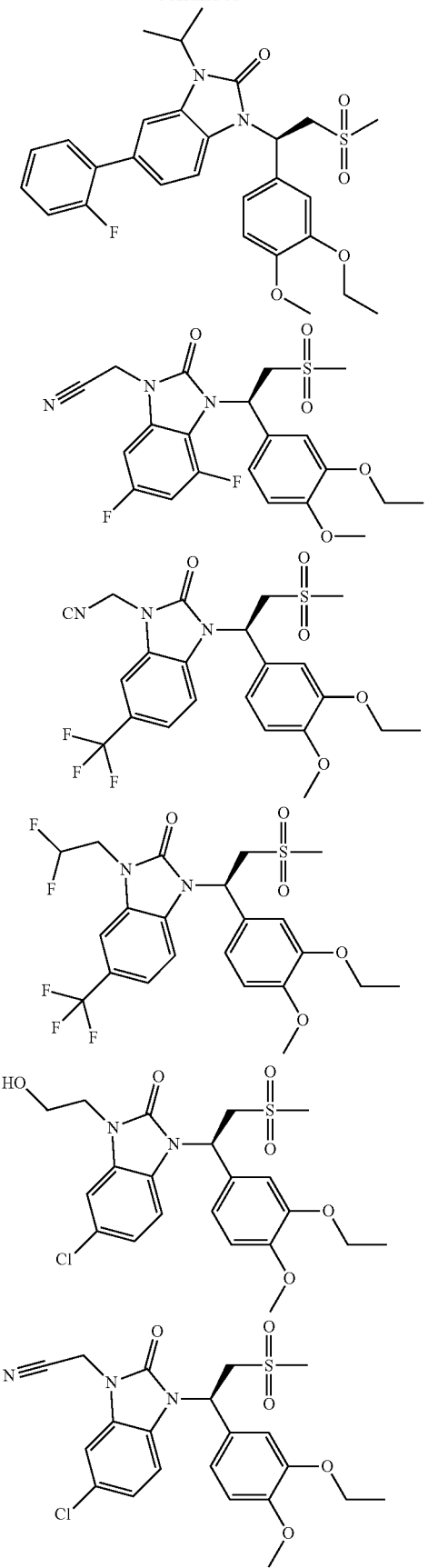

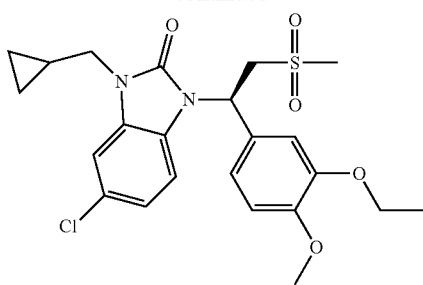
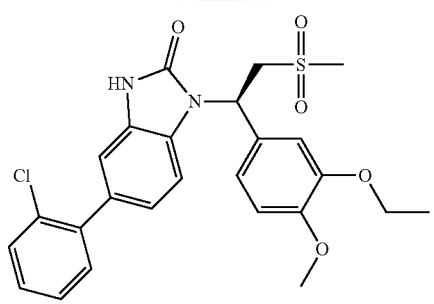
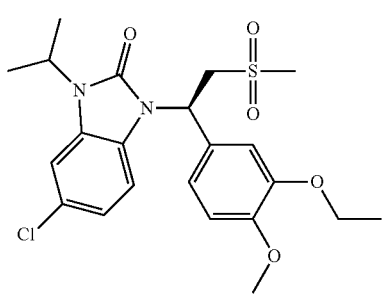
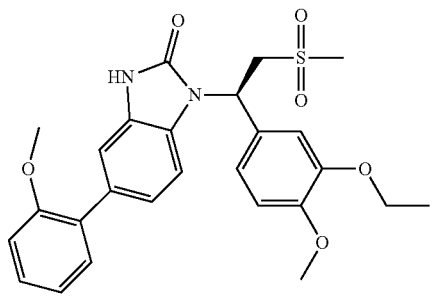
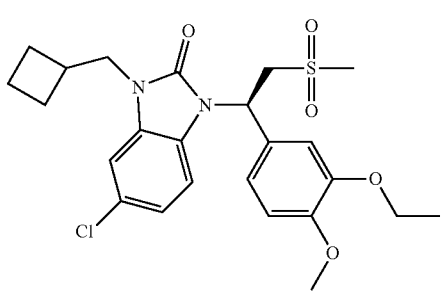
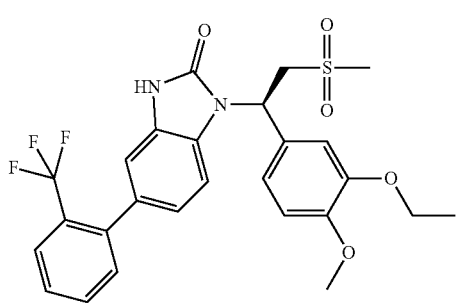
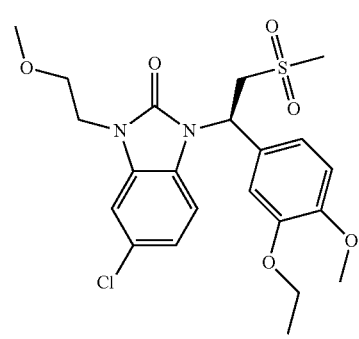
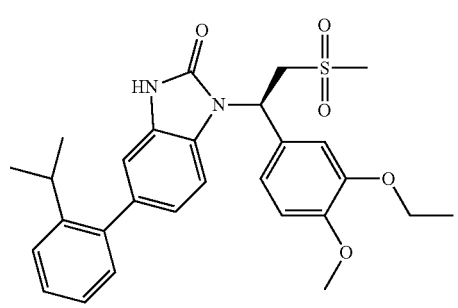
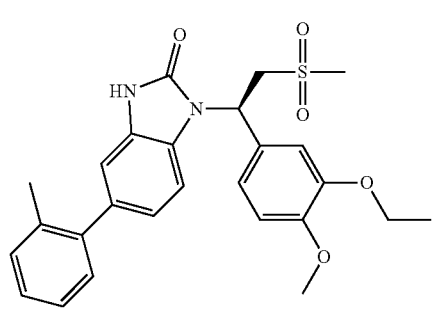
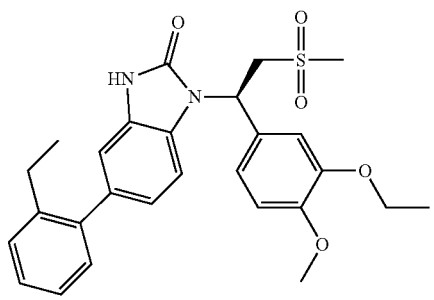

-continued

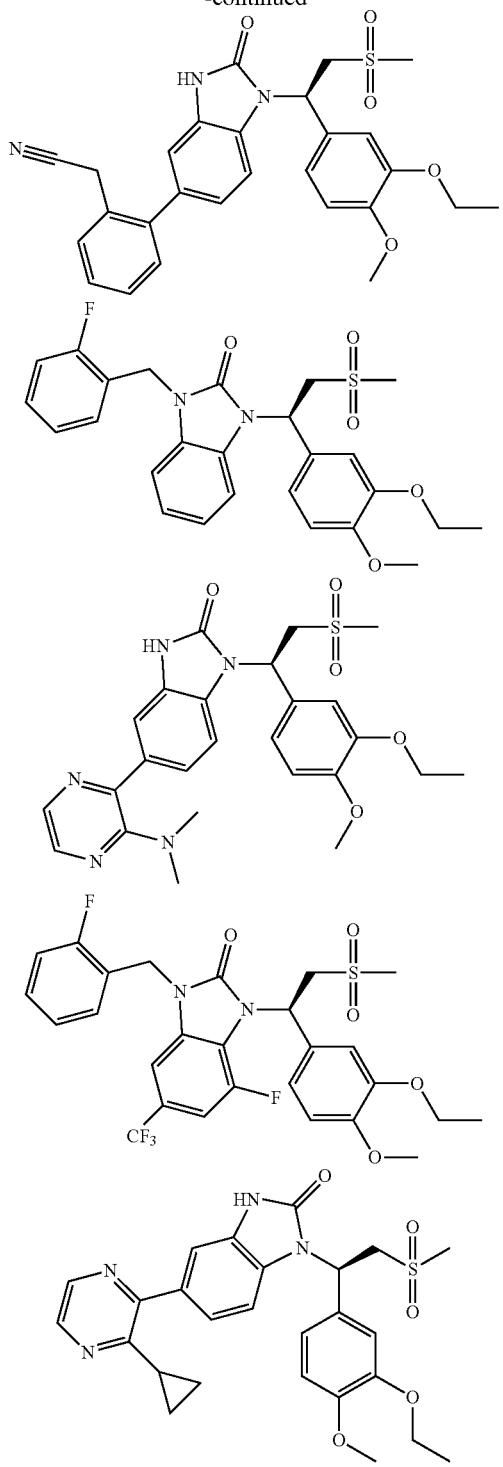

-continued

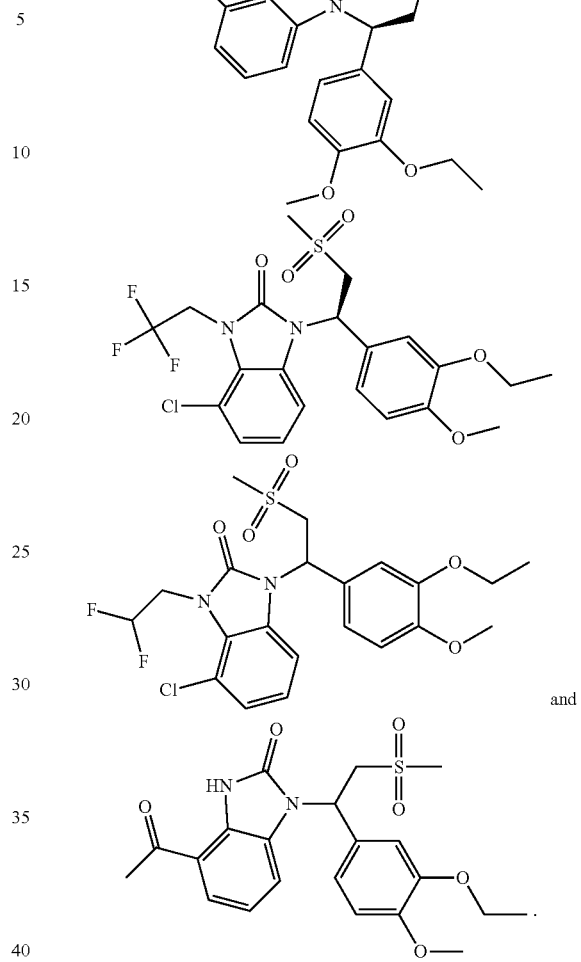

and

22. A pharmaceutical composition comprising a therapeutically effective amount of the compound or the pharmaceutically acceptable salt thereof according to claim 1 as the active ingredient and a pharmaceutically acceptable carrier.

23. A method for treating a disease related to PDE4 inhibition in a subject in need thereof, comprising administering an effective amount of the compound or the pharmaceutically acceptable salt thereof according to claim 1 to the subject.

24. A method for treating a disease related to PDE4 inhibition in a subject in need thereof, comprising administering an effective amount of the pharmaceutical composition according to claim 22 to the subject.

* * * * *